United States Patent
Vacca et al.

(10) Patent No.: US 11,945,784 B2
(45) Date of Patent: Apr. 2, 2024

(54) IRE1 SMALL MOLECULE INHIBITORS

(71) Applicant: Cornell University, Ithaca, NY (US)

(72) Inventors: Joseph P. Vacca, Telford, PA (US); Sarah Elizabeth Bettigole, New York, NY (US)

(73) Assignee: Cornell University, Ithaca, NY (US)

( * ) Notice: Subject to any disclaimer, the term of this patent is extended or adjusted under 35 U.S.C. 154(b) by 421 days.

(21) Appl. No.: 17/296,771

(22) PCT Filed: Dec. 2, 2019

(86) PCT No.: PCT/US2019/063920
§ 371 (c)(1),
(2) Date: May 25, 2021

(87) PCT Pub. No.: WO2020/117634
PCT Pub. Date: Jun. 11, 2020

(65) Prior Publication Data
US 2022/0024878 A1     Jan. 27, 2022

Related U.S. Application Data

(60) Provisional application No. 62/774,789, filed on Dec. 3, 2018.

(51) Int. Cl.
*C07D 239/42* (2006.01)
*C07D 213/76* (2006.01)
*C07D 401/06* (2006.01)
*C07D 403/06* (2006.01)

(52) U.S. Cl.
CPC ......... *C07D 239/42* (2013.01); *C07D 213/76* (2013.01); *C07D 401/06* (2013.01); *C07D 403/06* (2013.01)

(58) Field of Classification Search
CPC .. C07D 239/42; C07D 213/76; C07D 401/06; C07D 403/06
See application file for complete search history.

(56) References Cited

U.S. PATENT DOCUMENTS

| 2017/0253590 A1 | 9/2017 | Glimcher et al. |
| 2018/0265497 A1 | 9/2018 | Braun et al. |

FOREIGN PATENT DOCUMENTS

| JP | 2001261649 | * | 9/2001 |
| WO | WO-2014052669 A1 | | 4/2014 |
| WO | WO-2016022839 A1 | | 2/2016 |
| WO | WO-2018030466 A1 | | 2/2018 |
| WO | WO-2018102751 A1 | | 6/2018 |
| WO | WO-2020117634 A1 | | 6/2020 |

OTHER PUBLICATIONS

Morita, Cell Metabolism, Apr. 2017, 883-897. (Year: 2017).*
Wise, Cancers, 2022, vol. 14, 1-17. (Year: 2022).*
"International Application Serial No. PCT/US2019/063920, International Search Report dated Feb. 18, 2020", 5 pgs.
"International Application Serial No. PCT/US2019/063920, Written Opinion dated Feb. 18, 2020", 7 pgs.
Morita, Shuhei, et al., "Targeting ABL-IRE1a signaling spares ER-stressed pancreatic β- cells to reverse autoimmune diabetes", Cell Metabolism, Cell Press, United States, vol. 25, No. 4, (Apr. 4, 2017), 883.
"European Application Serial No. 19828387.1, Communication Pursuant to Article 94(3) EPC dated Jun. 30, 2022", 4 pgs.
"European Application Serial No. 19828387.1, Response filed Oct. 17, 22 to Communication Pursuant to Article 94(3) EPC dated Jun. 30, 2022", 154 pgs.
"European Application Serial No. 22209484.9, Extended European Search Report dated May 2, 2023", 12 pgs.
"European Application Serial No. 22209484.9, Response Filed Jul. 27, 23 to Extended European Search Report dated May 2, 2023", 23 pgs.
Morita, Shuhei, et al., "Targeting ABL-IRE1[alpha] Signaling Spares ER-Stressed Pancreatic [beta] Cells to Reverse Autoimmune Diabetes", Cell Metabolism, Cell Press, United States, vol. 25, No. 4, (Apr. 4, 2017), 883 pgs.

* cited by examiner

*Primary Examiner* — D Margaret M Seaman
(74) *Attorney, Agent, or Firm* — Schwegman Lundberg & Woessner, P.A.

(57) ABSTRACT

Provided herein are small molecule inhibitors for the targeting or IRE1 protein family members. Binding may be direct or indirect. Further provided herein are methods of using IRE1 small molecule inhibitors for use in treating or ameliorating cancer in a subject. Moreover, IRE1 small molecule inhibitors described herein are for the treatment of cancer, where the cancer is a solid or hematologic cancer.

22 Claims, 7 Drawing Sheets
Specification includes a Sequence Listing.

IRE1 SMALL MOLECULE INHIBITORS

CROSS-REFERENCE TO RELATED APPLICATIONS

This application is a U.S. national stage filing under 35 U.S.C. 371 from International Application No. PCT/US2019/063920, filed Dec. 2, 2019, and published as WO 2020/117634 A1 on Jun. 11, 2020, which claims the benefit of priority of U.S. Provisional Application No. 62/774,789, filed Dec. 3, 2018, which is hereby incorporated by reference in its entirety.

BACKGROUND

Aggressive tumors have evolved strategies that enable them to thrive under constant adverse conditions. For example, cancer cells respond to hypoxia, nutrient starvation, oxidative stress, and high metabolic demand by adjusting their protein folding capacity via the endoplasmic reticulum (ER) stress response pathway. There exists a need for improved methods and compositions to target cancer cells and counter their mechanisms of survival.

BRIEF SUMMARY

The present invention provides, inter alia, compounds and compositions that are IRE1 inhibitors. The invention further provides a process for the preparation of the compounds of the invention, pharmaceutical preparations comprising such compound and methods of using such compounds in the management of diseases and disorders associated with altered IRE1 signaling. In an exemplary embodiment, diseases treatable by the present methods include cancers. Cancers treatable by the present methods include those that will benefit from inhibition of IRE1 alpha. A subset of such cancers are those that exhibit ER stress. Adaptation to ER stress is achieved by activation of the UPR (Unfolded protein response). Without being bound by theory, inhibitors of IRE1 alpha are believed to alter the adaptation to ER stress and thereby act as anti-tumor agents Provided in one aspect is a compound of Formula (I), or a pharmaceutically acceptable salt, or solvate thereof:

Formula (I)

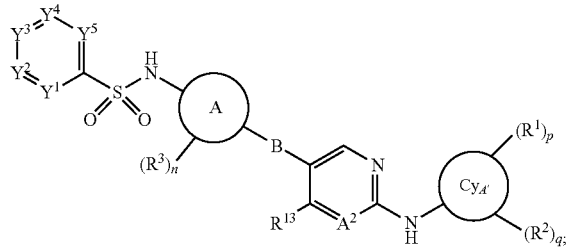

wherein,

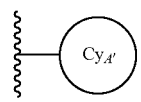

is $C_3$-$C_{10}$cycloalkyl;

each $R^1$ is independently —$OR^{6a}$, —$SR^{6a}$, —$S(=O)R^7$, —$S(=O)_2R^7$, or —$N(R^{6b})_2$;

each $R^2$ is independently halogen, —CN, —$OR^{8a}$, —$SR^{8a}$, —$S(=O)R^9$, —$S(=O)_2R^9$, —$S(=O)_2N(R^{8b})_2$, —$NR^{8a}S(=O)_2R^9$, —$C(=O)R^9$, —$OC(=O)R^9$, —$CO_2R^{8a}$, —$OCO_2R^9$, —$N(R^{8b})_2$, —$OC(=O)N(R^{8b})_2$, —$NR^{8a}C(=O)R^9$, —$NR^{8a}C(=O)OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$Y^5$ is $CR^4$;

$Y^1$, $Y^2$, $Y^3$, and $Y^4$ are each independently selected from N and $CR^5$ with the proviso that no more than two of $Y^1$, $Y^2$, $Y^3$, and $Y^4$ are N;

each $R^{6a}$ is independently H, optionally substituted $C_1$-$C_4$alkyl, optionally substituted $C_1$-$C_4$heteroalkyl, optionally substituted $C_1$-$C_4$fluoroalkyl, —X-optionally substituted $C_1$-$C_4$alkyl, —X-optionally substituted $C_1$-$C_4$heteroalkyl, —X-optionally substituted $C_1$-$C_4$fluoroalkyl, optionally substituted $C_3$-$C_6$cycloalkyl, optionally substituted $C_3$-$C_4$cycloalkyl$C_1$-$C_3$alkyl, optionally substituted $C_2$-$C_{10}$heterocycloalkyl, optionally substituted aryl, or optionally substituted heteroaryl;

each $R^{6b}$ is independently H, optionally substituted $C_1$-$C_4$alkyl, optionally substituted $C_1$-$C_4$heteroalkyl, optionally substituted $C_1$-$C_4$fluoroalkyl, —X-optionally substituted $C_1$-$C_4$alkyl, —X-optionally substituted $C_1$-$C_4$heteroalkyl, —X-optionally substituted $C_1$-$C_4$fluoroalkyl, optionally substituted $C_3$-$C_6$cycloalkyl, optionally substituted $C_3$-$C_4$cycloalkyl$C_1$-$C_3$alkyl, optionally substituted $C_2$-$C_{10}$heterocycloalkyl, optionally substituted aryl, or optionally substituted heteroaryl;

or two $R^{6b}$ are taken together with the N atom to which they are attached to form an optionally substituted heterocycle;

X is —C(=O)—;

each $R^7$ is independently optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

each $R^{8a}$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

each $R^{8b}$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

or two $R^{8b}$ are taken together with the N atom to which they are attached to form an optionally substituted heterocycle;

each $R^9$ is independently optionally substituted $C_1$-$C_4$alkyl, optionally substituted $C_1$-$C_4$heteroalkyl, or optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

$A^2$ is N or $CR^4$;

$R^4$ is H, halogen, optionally substituted $C_1$-$C_4$alkyl, optionally substituted $C_1$-$C_4$fluoroalkyl, optionally substituted aryl, or —$OR^{10}$;

$R^{41}$, $R^{42}$, $R^{43}$ and $R^{44}$ are each independently H, optionally substituted $C_1$-$C_4$alkyl, optionally substituted $C_1$-$C_4$fluoroalkyl, or optionally substituted aryl;

$R^{10}$ is independently H, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

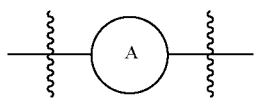

is phenylene or a 6-membered heteroarylene ring comprising 1 or 2 nitrogen atoms in the ring;

B is

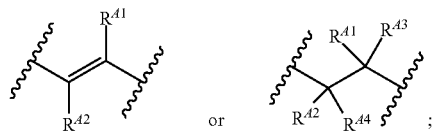

each $R^3$ is independently halogen, —CN, —$OR^{11}$, —$SR^{11}$, —$N(R^{11})_2$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

each $R^{11}$ is independently H, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

n is 0, 1, 2, 3, or 4;

p is 1, 2, or 3;

q is 0, 1, 2, or 3;

$R^4$ and each $R^5$ are each independently H, halogen, —CN, —$OR^{12}$, —$SR^{12}$, —$N(R^{12})_2$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

$R^{12}$ is independently H, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl; and $R^{13}$ is H or unsubstituted $C_1$-$C_4$alkyl.

In another aspect, provided herein is a pharmaceutical composition comprising any one of the compounds described herein, or a pharmaceutically acceptable salt or solvate thereof. In some embodiments, the pharmaceutical composition further comprises one or more pharmaceutically acceptable excipients.

In another aspect, provided herein is a method for treating or ameliorating the effects of a disease associated with altered IRE1 signaling, the method comprising administering to a subject in need thereof a pharmaceutical composition, wherein the pharmaceutical composition comprises the compound of any one of the compounds described herein. In some embodiments, the disease is cancer. In some embodiments, the cancer is a solid cancer or a hematologic cancer. In some embodiments, the cancer is ovarian cancer, breast cancer, or triple negative breast cancer (TNBC).

In another aspect, provided herein is a method for treating or ameliorating a cell proliferative disorder, the method comprising administering a pharmaceutical composition comprising a compound, or a pharmaceutically acceptable salt, or solvate thereof, that selectively binds to at least one amino acid residue of a IRE1 family protein comprising an RNase domain and kinase domain. In some embodiments, the IRE1 family protein is IRE1α. In some embodiments, the compound binds to an ATP-binding site of IRE1α. In some embodiments, the cell proliferative disorder is cancer. In some embodiments, the cancer is a solid cancer or a hematologic cancer.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Certain Terminology

Figure 1:
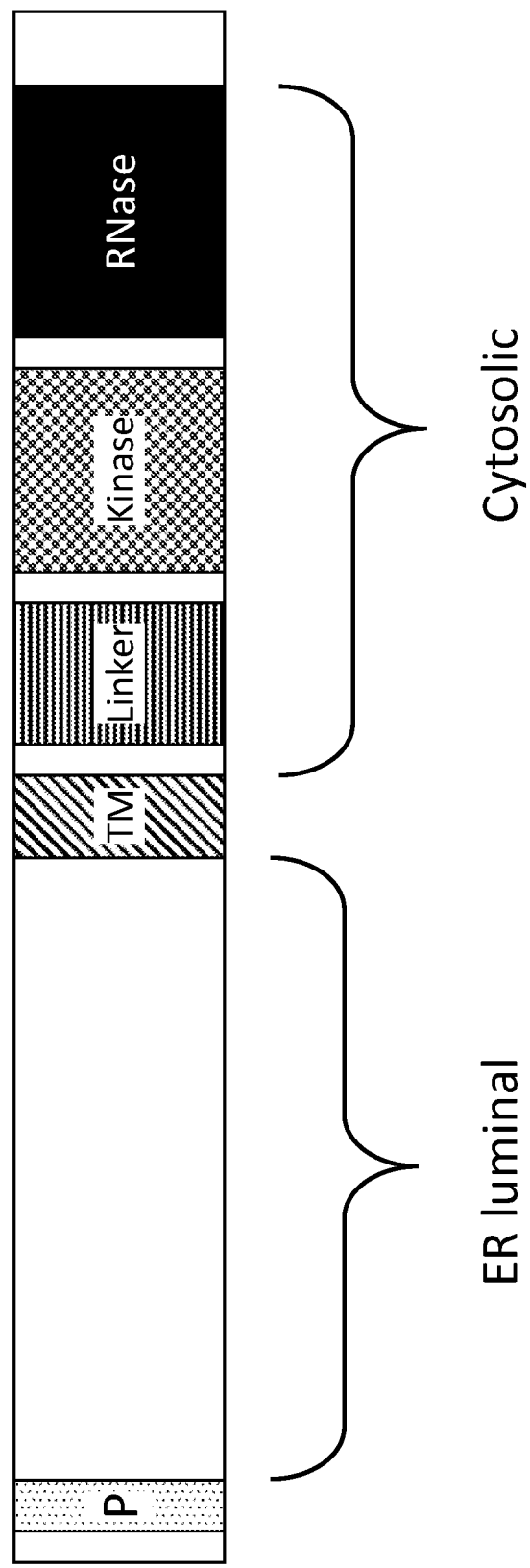
FIG. 1 shows an example diagram of the domain structure of IRE1a. A signal peptide (P) and transmembrane (TM) region are indicated.

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —NH$_2$ radical.

"Cyano" refers to the —CN radical.

"Nitro" refers to the —NO$_2$ radical.

"Oxa" refers to the —O— radical.

"Oxo" refers to the =O radical.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. Unless otherwise noted, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, 4 carbon atoms, 5 carbon atoms, 6 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers refers to a divalent alkyl radical. Any of the above mentioned monovalent alkyl groups may be an alkylene by abstraction of a second hydrogen atom from the alkyl. In some embodiments, an alkelene is a $C_1$-$C_6$alkylene. In other embodiments, an alkylene is a $C_1$-$C_4$alkylene. In certain embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises two carbon atoms (e.g., $C_2$ alkylene). In other embodiments, an alkylene comprises two to four carbon atoms (e.g., $C_2$-$C_4$ alkylene). Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

The term "alkenyl" refers to a type of alkyl group in which at least one carbon-carbon double bond is present. In one embodiment, an alkenyl group has the formula —C(R)=CR$_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=CH$_2$, —C(CH$_3$)=CH$_2$, —CH=CHCH$_3$, —C(CH$_3$)=CHCH$_3$, and —CH$_2$CH=CH$_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡CCH$_3$—C≡CCH$_2$CH$_3$, —CH$_2$C≡CH.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

The term "aromatic" refers to a planar ring having a delocalized π-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycle includes cycloalkyl and aryl.

As used herein, the term "aryl" refers to an aromatic ring wherein each of the atoms forming the ring is a carbon atom. In one aspect, aryl is phenyl or a naphthyl. In some embodiments, an aryl is a phenyl. Unless otherwise noted, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Unless otherwise noted, cycloalkyl groups include groups having from 3 to 10 ring atoms. In some embodiments, cycloalkyl groups include groups having from 3 to 6 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1] pentyl. In some embodiments, a cycloalkyl is a $C_3$-$C_6$cycloalkyl. In some embodiments, a cycloalkyl is a monocyclic cycloalkyl. Monocyclic cycloalkyls include, but are not limited to, cyclopropyl, cyclobutyl, cyclopentyl, cyclohexyl, cycloheptyl, and cyclooctyl. Polycyclic cycloalkyls include, for example, adamantyl, norbornyl (i.e., bicyclo[2.2.1]heptanyl), norbornenyl, decalinyl, 7,7-dimethyl-bicyclo[2.2.1]heptanyl, and the like.

The term "cycloalkylalkyl" refers to a moiety of the formula —$R_bR_d$ where $R_b$ is an alkylene group as defined herein and $R_d$ is a cycloalkyl moiety as defined herein. In some embodiments, a cycloalkylalkyl moiety is a $C_3$-$C_{10}$cycloalkylalkyl moiety. In such a case, the $C_3$-$C_{10}$cycloalkylalkyl includes a $C_3$-$C_{10}$cycloalkyl radical. In some embodiments, a cycloalkylalkyl moiety is a $C_3$-$C_4$cycloalkylalkyl moiety. In such a case, the $C_3$-$C_4$cycloalkylalkyl includes a $C_3$-$C_4$ cycloalkyl radical.

The term "cycloalkylene" refers to a monocyclic or polycyclic aliphatic, non-aromatic divalent radical, wherein each of the atoms forming the ring (i.e. skeletal atoms) is a carbon atom. In some embodiments, cycloalkylene are spirocyclic or bridged compounds. In some embodiments, cycloalkylenes are optionally fused with an aromatic ring, and the point of attachment is at a carbon that is not an aromatic ring carbon atom. In some embodiments, cycloalkylene groups include groups having from 3 to 10 ring atoms. In some embodiments, cycloalkylene groups include groups having from 3 to 6 ring atoms.

The term "halo" or, alternatively, "halogen" or "halide" means fluoro, chloro, bromo or iodo. In some embodiments, halo is fluoro, chloro, or bromo.

The term "haloalkyl" refers to an alkyl in which one or more hydrogen atoms are replaced by a halogen atom.

The term "fluoroalkyl" refers to an alkyl in which one or more hydrogen atoms are replaced by a fluorine atom. In one aspect, a fluoralkyl is a $C_1$-$C_6$fluoroalkyl. In some embodiments, a fluoroalkyl is selected from trifluoromethyl, difluoromethyl, fluoromethyl, 2,2,2-trifluoroethyl, 1-fluoromethyl-2-fluoroethyl, and the like.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "heteroalkylene" refers to an alkylene group in which one or more skeletal atoms of the alkylene are selected from an atom other than carbon, e.g., oxygen, nitrogen (e.g. —NH—, —N(alkyl)-, sulfur, or combinations thereof. In some embodiments, a heteroalkylene is attached to the rest of the molecule at a carbon atom of the heteroalkylene. In one aspect, a heteroalkylene is a $C_1$-$C_6$heteroalkylene.

As used herein, the term "heteroatom" refers to an atom of any element other than carbon or hydrogen. In some embodiments, the heteroatom is nitrogen, oxygen, or sulfur. In some embodiments, the heteroatom is nitrogen or oxygen. In some embodiments, the heteroatom is nitrogen.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. In some embodiments, heterocycles are monocyclic, bicyclic, polycyclic, spirocyclic or bridged compounds. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (═O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aromatic ring that includes carbon rings atoms and one or more ring heteroatoms selected from nitrogen, oxygen and sulfur. Unless otherwise noted, a heteroaryl has 5 to 10 atoms in its ring system wherein one to four of the ring atoms are heteroatoms and each heteroatom in the ring(s) is selected from O, S and N, with the proviso that any ring does not contain two adjacent O or S atoms. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. Unless otherwise noted, a heterocycloalkyl has 3 to 10 atoms in its ring system wherein one to four of the ring atoms are heteroatoms and each heteroatom in the ring(s) is selected from O, S and N, with the proviso that any ring does not contain two adjacent O, S, or N atoms In some embodiments, a heterocycloalkyl is a spirocyclic or bridged compound. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from D, halogen, —CN, —NH$_2$, —NH(alkyl), —CH$_2$N(alkyl)$_2$, —N(alkyl)$_2$, —OH, —CO$_2$H, —CO$_2$alkyl, —CH$_2$NH$_2$, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. Optional substituents can be independently selected from D, halogen, —CN, —NH$_2$, —NH(CH$_3$), —N(CH$_3$)$_2$, —OH, —CO$_2$H, —CO$_2$(C$_1$-C$_4$alkyl), —CH$_2$NH$_2$, —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. Alternatively, optional substituents can be independently selected from D, halogen, —CN, —NH$_2$, —OH, —NH(CH$_3$), —N(CH$_3$)$_2$, —CH$_3$, —CH$_2$CH$_3$, —CH$_2$NH$_2$, —CF$_3$, —OCH$_3$, —OCF$_2$H and —OCF$_3$. In some embodiments, substituted groups are substituted with one or two of the preceding groups. In some embodiments, an optional substituent on an aliphatic carbon atom (acyclic or cyclic) includes oxo (=O).

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

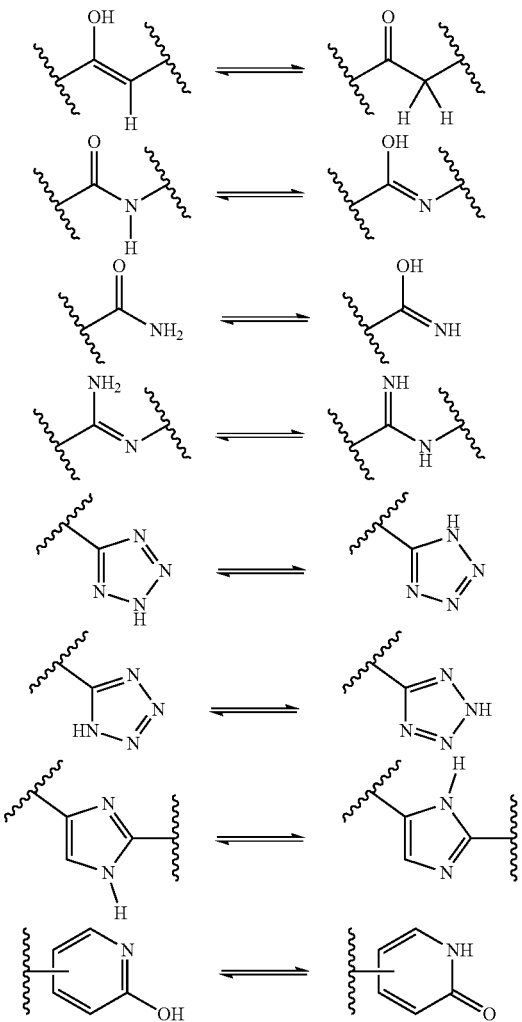

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the pyrazole compounds described herein is intended to encompass any and all pharmaceutically suitable salt forms.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methyl glucamine, glucosamine, methylglucamine, theobromine, purines, piperazine, piperidine, N-ethylpiperidine, polyamine resins and the like. See Berge et al., supra.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

Compounds

Compounds described herein, including pharmaceutically acceptable salts, and pharmaceutically acceptable solvates thereof, include those that modulate IRE1 mediated signaling, directly or indirectly.

Provided in one aspect is a compound of Formula (I), or a pharmaceutically acceptable salt, or solvate thereof:

Formula (I)

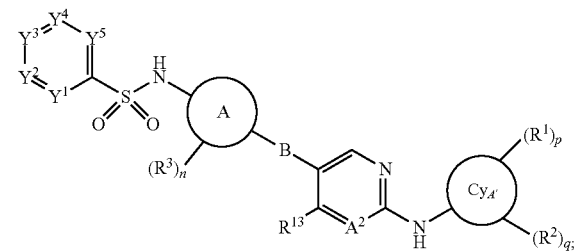

wherein,

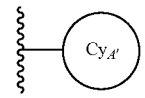

is $C_3$-$C_{10}$cycloalkyl;

each $R^1$ is independently —$OR^{6a}$, —$SR^{6a}$, —$S(=O)R^7$, —$S(=O)_2R^7$, or —$N(R^{6b})_2$;

each $R^2$ is independently halogen, —CN, —$OR^{8a}$, —$SR^{8a}$, —$S(=O)R^9$, —$S(=O)_2R^9$, —$S(=O)_2N(R^{8b})_2$, —$NR^{8a}S(=O)_2R^9$, —$C(=O)R^9$, —$OC(=O)R^9$, —$CO_2R^{8a}$, —$OCO_2R^9$, —$N(R^{8b})_2$, —$OC(=O)N(R^{8b})_2$, —$NR^{8a}C(=O)R^9$, —$NR^{8a}C(=O)OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$Y^5$ is $CR^4$;

$Y^1$, $Y^2$, $Y^3$, and $Y^4$ are each independently selected from N and $CR^5$ with the proviso that no more than two of $Y^1$, $Y^2$, $Y^3$, and $Y^4$ are N;

each $R^{6a}$ is independently H, optionally substituted $C_1$-$C_4$alkyl, optionally substituted $C_1$-$C_4$heteroalkyl, optionally substituted $C_1$-$C_4$fluoroalkyl, —X-optionally substituted $C_1$-$C_4$alkyl, —X-optionally substituted $C_1$-$C_4$heteroalkyl, —X-optionally substituted $C_1$-$C_4$fluoroalkyl, optionally substituted $C_3$-$C_6$cycloalkyl, optionally substituted $C_3$-$C_4$cycloalkyl$C_1$-$C_3$alkyl, optionally substituted $C_2$-$C_{10}$heterocycloalkyl, optionally substituted aryl, or optionally substituted heteroaryl;

each $R^{6b}$ is independently H, optionally substituted $C_1$-$C_4$alkyl, optionally substituted $C_1$-$C_4$heteroalkyl, optionally substituted $C_1$-$C_4$fluoroalkyl, —X-optionally substituted $C_1$-$C_4$alkyl, —X-optionally substituted $C_1$-$C_4$heteroalkyl, —X-optionally substituted $C_1$-$C_4$fluoroalkyl, optionally substituted $C_3$-$C_6$cycloalkyl, optionally substituted $C_3$-$C_4$cycloalkyl$C_1$-$C_3$alkyl, optionally substituted $C_2$-$C_{10}$heterocycloalkyl, optionally substituted aryl, or optionally substituted heteroaryl;

or two $R^{6b}$ are taken together with the N atom to which they are attached to form an optionally substituted heterocycle;

X is —C(=O)—;

each $R^7$ is independently optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

each $R^{8a}$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

each $R^{8b}$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

or two $R^{8b}$ are taken together with the N atom to which they are attached to form an optionally substituted heterocycle;

each $R^9$ is independently optionally substituted $C_1$-$C_4$alkyl, optionally substituted $C_1$-$C_4$heteroalkyl, or optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

$A^2$ is N or $CR^A$;

$R^A$ is H, halogen, optionally substituted $C_1$-$C_4$alkyl, optionally substituted $C_1$-$C_4$fluoroalkyl, optionally substituted aryl, or —$OR^{10}$;

$R^{A1}$, $R^{A2}$, $R^{A3}$ and $R^{A4}$ are each independently H, optionally substituted $C_1$-$C_4$alkyl, optionally substituted $C_1$-$C_4$fluoroalkyl, or optionally substituted aryl;

$R^{10}$ is independently H, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

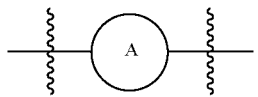

is phenylene or a 6-membered heteroarylene ring comprising 1 or 2 nitrogen atoms in the ring;

B is

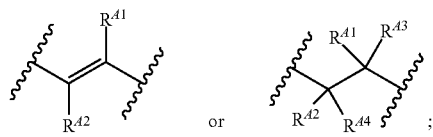

each $R^3$ is independently halogen, —CN, —$OR^{11}$, —$SR^{11}$, —$N(R^{11})_2$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

each $R^{11}$ is independently H, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

n is 0, 1, 2, 3, or 4;

p is 1, 2, or 3;

q is 0, 1, 2, or 3;

$R^4$ and each $R^5$ are each independently H, halogen, —CN, —$OR^{12}$, —$SR^{12}$, —$N(R^{12})_2$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

$R^{12}$ is independently H, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl; and $R^{13}$ is H or unsubstituted $C_1$-$C_4$alkyl.

Compounds of Formula (I), or a pharmaceutically acceptable salt, or solvate thereof include those wherein;

(i) $Y^5$ is —$CR^4$ and $R^4$ is H, halogen, —CN, —$OR^{12}$, —$SR^{12}$, —$N(R^{12})_2$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl; or (ii) $Y^5$ is —$CR^4$ and $R^4$ is hydrogen, halogen, —CN, or —$C_1$-$C_4$alkyl; or (iii) $Y^5$ is —$CR^4$ and $R^4$ is halogen, —CN, or —$C_1$-$C_4$alkyl; or (iv) $Y^5$ is —$CR^4$ and $R^4$ is, fluorine, chlorine, —CN, or —$CH_3$; and (v) $Y^1$, $Y^2$, $Y^3$, and $Y^4$ are each independently $CR^5$; or (vi) $Y^1$ is nitrogen and $Y^2$, $Y^3$, and $Y^4$ are each independently $CR^5$; or (vii) $Y^2$ is nitrogen and $Y^1$, $Y^3$, and $Y^4$ are each independently $CR^5$; or (viii) $Y^3$ is nitrogen and $Y^1$, $Y^2$, and $Y^4$ are each independently $CR^5$; or (ix) $Y^4$ is nitrogen and $Y^1$, $Y^2$, and $Y^3$ are each independently $CR^5$; or (x) $Y^1$ and $Y^2$ are nitrogen and $Y^3$ and $Y^4$ are each independently $CR^5$; or (xi) $Y^1$ and $Y^3$ are nitrogen and $Y^2$ and $Y^4$ are each independently $CR^5$; or (xii) $Y^1$ and $Y^4$ are nitrogen and $Y^2$ and $Y^3$ are each independently $CR^5$; or (xiii) $Y^2$ and $Y^3$ are nitrogen and $Y^1$ and $Y^4$ are each independently $CR^5$; or (xiv) $Y^3$ or $Y^4$ are nitrogen and $Y^1$ and $Y^2$ are each independently $CR^5$; or (xv) $Y^2$ and $Y^4$ are nitrogen and $Y^1$ and $Y^3$ are each independently $CR^5$; and (xvi) each $R^5$ is independently H, halogen, —CN, —$OR^{12}$, —$SR^{12}$, —$N(R^{12})_2$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl and $R^{12}$ is as described herein for compounds of Formula I; or (xvii) each $R^5$ is independently hydrogen, halogen, —CN, and —$C_1$-$C_4$alkyl; or (xviii) each $R^5$ is independently hydrogen, fluorine, chlorine, —CN, or —$CH_3$; and any combinations of Y5, $R^4$, $Y^1$, $Y^2$, $Y^3$, and $Y^4$ and $R^5$ are as provided in (i)-(xviii).

Compounds of Formula (I), or a pharmaceutically acceptable salt, or solvate thereof, include those wherein the variables B,

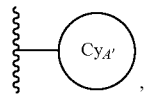

$Y^1$, $Y^2$, $Y^3$, $Y^4$, $Y^5$, $R^1$, $R^2$, $R^3$, $R^4$, $R^5$, $R^6$, $R^7$, $R^8$, $R^9$, $R^{10}$, $R^{11}$, $R^{12}$, $R^{13}$, X, $A^2$, $R^A$, $R^{A1}$, $R^{A2}$, $R^{A3}$, $R^{A4}$,

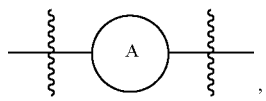

p, q, and n are as set forth for Compounds of Formula I above or are as set forth in any of the embodiments provided below. Any of the embodiments for B can be combined with any of the embodiments for the other variables and so forth for all of the variables provided that stable compounds are created.

In some embodiments, B is

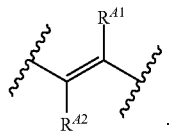

In some embodiments, B is

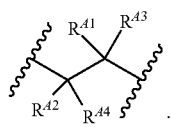

In some embodiments,

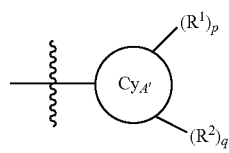

is substituted $C_4$-$C_7$ cycloalkyl that is substituted with 1-3$R^1$ and 0-3$R^2$ wherein each $R^1$ is —$N(R^{6b})_2$; each $R^2$ is independently halogen, —CN, —$OR^{8a}$, —$SR^{8a}$, —$S(=O)R^9$, —$S(=O)_2R^9$, —$S(=O)_2N(R^{8b})_2$, —$NR^{8a}S(=O)_2R^9$, —$C(=O)R^9$, —$OC(=O)R^9$, —$CO_2R^{8a}$, —$OCO_2R^9$, —$N(R^{8b})_2$, —$OC(=O)N(R^{8b})_2$, —$NR^{8a}C(=O)R^9$, —$NR^{8a}C(=O)OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl; each $R^{6b}$ is independently H, optionally substituted $C_1$-$C_4$alkyl, optionally substituted $C_1$-$C_4$heteroalkyl, optionally substituted $C_1$-$C_4$fluoroalkyl, —X-optionally substituted $C_1$-$C_4$alkyl, —X-optionally substituted $C_1$-$C_4$heteroalkyl, —X-optionally substituted $C_1$-$C_4$fluoroalkyl, optionally substituted $C_3$-$C_6$cycloalkyl, optionally substituted $C_3$-$C_4$cycloalkyl$C_1$-$C_3$alkyl, optionally substituted $C_2$-$C_{10}$heterocycloalkyl, optionally substituted aryl, or optionally substituted heteroaryl; or two $R^{6b}$ are taken together with the N atom to which they are attached to form an optionally substituted heterocycle; each $R^{8a}$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl; each $R^{8b}$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl; or two $R^{8b}$ are taken together with the N atom to which they are attached to form an optionally substituted heterocycle; and each $R^9$ is independently optionally substituted $C_1$-$C_4$alkyl, optionally substituted $C_1$-$C_4$heteroalkyl, or optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl. In some such embodiments, alternatively, each $R^{6b}$ can be independently H, optionally substituted $C_1$-$C_4$alkyl, optionally substituted $C_1$-$C_4$heteroalkyl, optionally substituted $C_1$-$C_4$fluoroalkyl, —X-optionally substituted $C_1$-$C_4$alkyl, —X-optionally substituted $C_1$-$C_4$heteroalkyl, or —X-optionally substituted $C_1$-$C_4$fluoroalkyl. X is as described herein for compounds of Formula I.

In some embodiments,

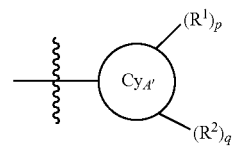

is substituted $C_4$-$C_7$ cycloalkyl that is substituted with 1-3$R^1$ and 0-3$R^2$ wherein each $R^1$ is —$N(R^{6b})_2$; each $R^2$ is, independently, optionally substituted $C_1$-$C_4$alkyl, optionally substituted $C_1$-$C_4$heteroalkyl, or optionally substituted $C_1$-$C_4$fluoroalkyl or $R^2$ is absent; and each $R^{6b}$ is independently H, optionally substituted $C_1$-$C_4$alkyl, optionally substituted $C_1$-$C_4$heteroalkyl, optionally substituted $C_1$-$C_4$fluoroalkyl, —X-optionally substituted $C_1$-$C_4$alkyl, —X-optionally substituted $C_1$-$C_4$heteroalkyl, —X-optionally substituted $C_1$-$C_4$fluoroalkyl, optionally substituted $C_3$-$C_6$cycloalkyl, optionally substituted $C_3$-$C_4$cycloalkyl$C_1$-

$C_3$alkyl, optionally substituted $C_2$-$C_{10}$heterocycloalkyl, optionally substituted aryl, or optionally substituted heteroaryl; or two $R^{6b}$ are taken together with the N atom to which they are attached to form an optionally substituted heterocycle. In some such embodiments, alternatively, each $R^{6b}$ can be independently H, optionally substituted $C_1$-$C_4$alkyl, optionally substituted $C_1$-$C_4$heteroalkyl, optionally substituted $C_1$-$C_4$fluoroalkyl, —X-optionally substituted $C_1$-$C_4$alkyl, —X-optionally substituted $C_1$-$C_4$heteroalkyl, or —X-optionally substituted $C_1$-$C_4$fluoroalkyl. X is as described herein for compounds of Formula I.

In some embodiments,

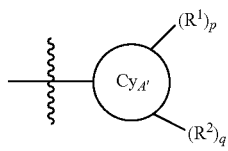

is

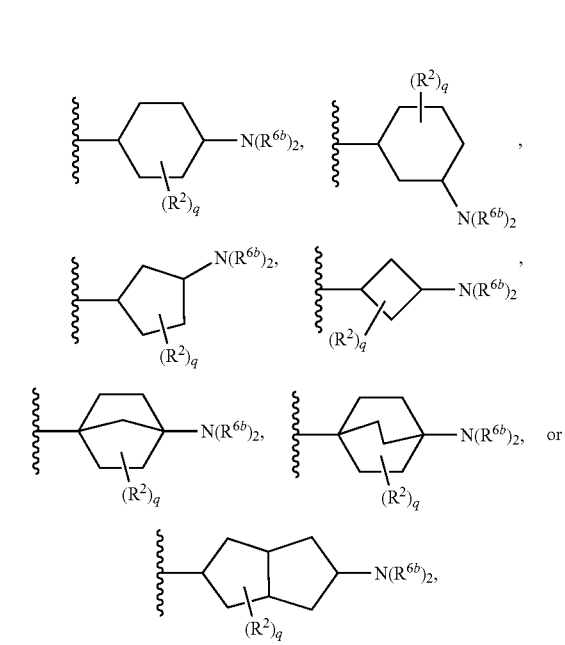

and q is 0, 1, 2, or 3; wherein $R^{6b}$ and $R^2$ are as described in any of the embodiments set forth herein.

In some embodiments,

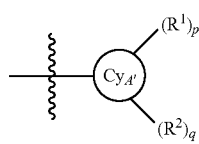

is

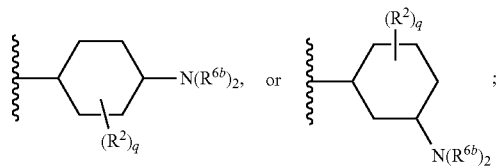

and q is 0, 1, 2, or 3 wherein $R^{6b}$ and $R^2$ are as described in any of the embodiments set forth herein.

In some embodiments,

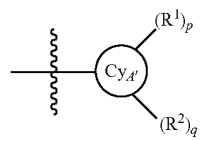

is

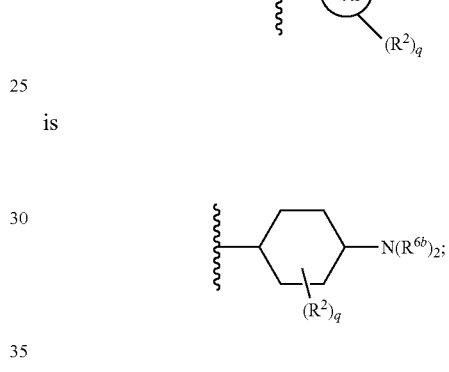

and q is 0, 1, 2, or 3; wherein $R^{6b}$ and $R^2$ are as described in any of the embodiments set forth herein.

In some embodiments, q is 0 or 1. In some embodiments, each $R^{6b}$ is independently H, optionally substituted $C_1$-$C_4$alkyl, optionally substituted $C_1$-$C_4$heteroalkyl, optionally substituted $C_1$-$C_4$fluoroalkyl, —X-optionally substituted $C_1$-$C_4$alkyl, —X-optionally substituted $C_1$-$C_4$heteroalkyl, or —X-optionally substituted $C_1$-$C_4$fluoroalkyl. In some embodiments, each $R^{6b}$ is independently H or $C_1$-$C_4$alkyl. In some embodiments, each $R^{6b}$ is independently H. In some embodiments, each $R^{6b}$ is independently methyl, ethyl, or propyl. In some embodiments, each $R^2$ is independently optionally substituted $C_1$-$C_4$alkyl, optionally substituted $C_1$-$C_4$heteroalkyl, or optionally substituted $C_1$-$C_4$fluoroalkyl or $R^2$ is absent. X is as described herein for compounds of Formula I.

In some embodiments,

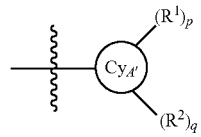

is

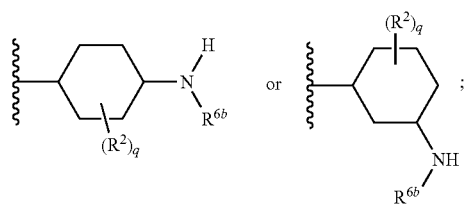

$R^{6b}$ is H, optionally substituted $C_1$-$C_4$alkyl, optionally substituted $C_1$-$C_4$heteroalkyl, optionally substituted $C_1$-$C_4$fluoroalkyl, —X-optionally substituted $C_1$-$C_4$alkyl, —X-optionally substituted $C_1$-$C_4$heteroalkyl, or —X-optionally substituted $C_1$-$C_4$fluoroalkyl; q is 0 or 1; and $R^2$ is optionally substituted $C_1$-$C_4$alkyl, optionally substituted $C_1$-$C_4$heteroalkyl, or optionally substituted $C_1$-$C_4$fluoroalkyl. X is as described herein for compounds of Formula I.

In some embodiments,

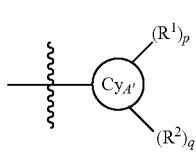

is

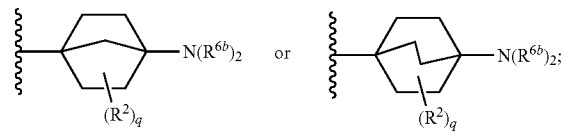

q is 0, 1, 2, or 3.

In some embodiments, q is 0 or 1. In some embodiments, each $R^{6b}$ is independently H, optionally substituted $C_1$-$C_4$alkyl, optionally substituted $C_1$-$C_4$heteroalkyl, optionally substituted $C_1$-$C_4$fluoroalkyl, —X-optionally substituted $C_1$-$C_4$alkyl, —X-optionally substituted $C_1$-$C_4$heteroalkyl, or —X-optionally substituted $C_1$-$C_4$fluoroalkyl. In some embodiments, each $R^{6b}$ is independently H. In some embodiments, each $R^2$ is independently optionally substituted $C_1$-$C_4$alkyl, optionally substituted $C_1$-$C_4$heteroalkyl, or optionally substituted $C_1$-$C_4$fluoroalkyl or $R^2$ is absent. X is as described herein for compounds of Formula I.

In some embodiments,

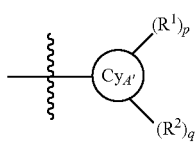

is

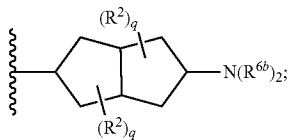

each q is independently 0, 1, 2, or 3.

In some embodiments, q is 0 or 1. In some embodiments, each $R^{6b}$ is independently H, optionally substituted $C_1$-$C_4$alkyl, optionally substituted $C_1$-$C_4$heteroalkyl, optionally substituted $C_1$-$C_4$fluoroalkyl, —X-optionally substituted $C_1$-$C_4$alkyl, —X-optionally substituted $C_1$-$C_4$heteroalkyl, or —X-optionally substituted $C_1$-$C_4$fluoroalkyl. In some embodiments, each $R^{6b}$ is independently H. In some embodiments, each $R^2$ is independently optionally substituted $C_1$-$C_4$alkyl, optionally substituted $C_1$-$C_4$heteroalkyl, or optionally substituted $C_1$-$C_4$fluoroalkyl or $R^2$ is absent. X is as described herein for compounds of Formula I.

In some embodiments, $R^{6b}$ is H. In some embodiments, $A^2$ is N. In some embodiments, $A^2$ is $CR^A$. In some embodiments, $R^A$ is H, halogen, optionally substituted $C_1$-$C_4$alkyl, optionally substituted $C_1$-$C_4$fluoroalkyl, optionally substituted $C_1$-$C_4$heteroalkyl, or —$OR^{10}$. In some embodiments, $R^A$ is H, optionally substituted $C_1$-$C_4$alkyl, or optionally substituted $C_1$-$C_4$fluoroalkyl. In some embodiments, $R^A$ is H. In some embodiments, $R^{A1}$ is H, optionally substituted $C_1$-$C_4$alkyl, optionally substituted $C_1$-$C_4$fluoroalkyl, or optionally substituted $C_1$-$C_4$heteroalkyl. In some embodiments, $R^{A1}$ is H, optionally substituted $C_1$-$C_4$alkyl, or optionally substituted $C_1$-$C_4$fluoroalkyl. In some embodiments, $R^{A1}$ is H. In some embodiments, $R^{A2}$ is H, optionally substituted $C_1$-$C_4$alkyl, optionally substituted $C_1$-$C_4$fluoroalkyl, or optionally substituted $C_1$-$C_4$heteroalkyl. In some embodiments, $R^{A2}$ is H, optionally substituted $C_1$-$C_4$alkyl, or optionally substituted $C_1$-$C_4$fluoroalkyl. In some embodiments, $R^{A2}$ is H. In some embodiments, $R^{A3}$ is H, optionally substituted $C_1$-$C_4$alkyl, optionally substituted $C_1$-$C_4$fluoroalkyl, or optionally substituted aryl. In some embodiments, $R^{A3}$ is H, optionally substituted $C_1$-$C_4$alkyl, optionally substituted $C_1$-$C_4$fluoroalkyl, or optionally substituted $C_1$-$C_4$heteroalkyl. In some embodiments, $R^{A3}$ is H, optionally substituted $C_1$-$C_4$alkyl, or optionally substituted $C_1$-$C_4$fluoroalkyl. In some embodiments, $R^{A3}$ is optionally substituted $C_{1-4}$heteroalkyl. In some embodiments, $R^{A3}$ is optionally substituted $C_1$-$C_4$alkyl. In some embodiments, $R^{A3}$ is methyl, ethyl, propyl or butyl. In some embodiments, $R^{A3}$ is H. In some embodiments, $R^{A4}$ is H, optionally substituted $C_1$-$C_4$alkyl, optionally substituted $C_1$-$C_4$fluoroalkyl, or optionally substituted aryl. In some embodiments, $R^{A4}$ is H, optionally substituted $C_1$-$C_4$alkyl, optionally substituted $C_1$-$C_4$fluoroalkyl, or optionally substituted $C_1$-$C_4$heteroalkyl. In some embodiments, $R^{A4}$ is H, optionally substituted $C_1$-$C_4$alkyl, or optionally substituted $C_1$-$C_4$fluoroalkyl. In some embodiments, $R^{A4}$ is optionally substituted $C_{1-4}$heteroalkyl. In some embodiments, $R^{A4}$ is optionally substituted $C_1$-$C_4$alkyl. In some embodiments, $R^{A4}$ is methyl, ethyl, propyl or butyl. In some embodiments, $R^{A4}$ is H.

In some embodiments,

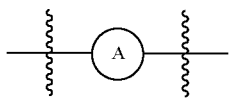

is phenylene.

In some embodiments,

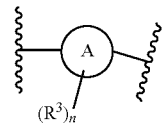

is

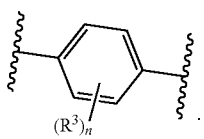

In some embodiments,

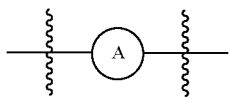

is a monocyclic 6-membered heteroarylene selected from pyridinylene, pyrimidinylene, pyrazinylene, and pyridazinylene. In some embodiments,

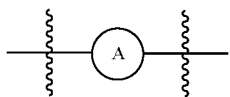

is pyridinylene.

In some embodiments,

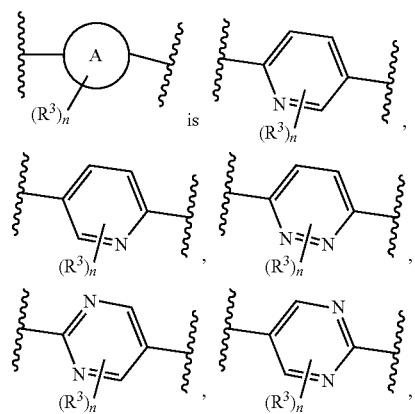

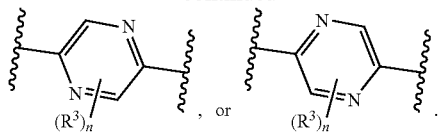

In some embodiments,

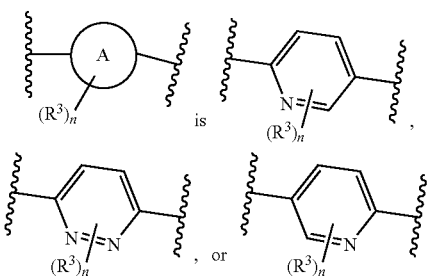

The substitution pattern for $R^3$ can be, for example, as follows:

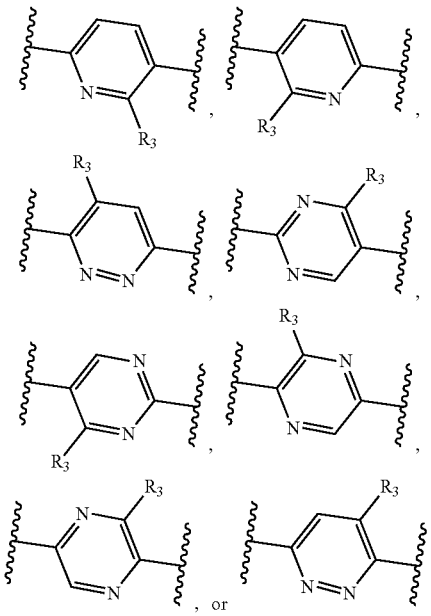

In some embodiments, each $R^3$ is independently H, halogen, —CN, —OR$^{11}$, —SR$^{11}$, optionally substituted $C_1$-$C_4$alkyl, or optionally substituted $C_1$-$C_4$fluoroalkyl; and n is 1, 2, or 3. In some embodiments, $R^3$ is halogen. In some embodiments, $R^3$ is —Cl, —Br, —F, or —I. In some embodiments, $R^3$ is —Cl. In some embodiments, $R^3$ is —Br. In some embodiments, $R^3$ is —F. In some embodiments, $R^3$ is optionally substituted $C_1$-$C_4$alkyl.

In some embodiments, $R^3$ is methyl, ethyl, propyl, or butyl. In some embodiments, $R^3$ is —OR$^{11}$. In some embodiments, $R^{11}$ is H, optionally substituted $C_1$-$C_4$alkyl, or optionally substituted $C_1$-$C_4$fluoroalkyl. In some embodiments, $R^{11}$ is methyl, ethyl, propyl, or butyl. In some embodiments, $R^{11}$ is —CF$_3$ or —CH$_2$CF$_3$. In some embodiments, $R^4$ is H, halogen, —CN, —OR$^{12}$, —SR$^{12}$, —N(R$^{12}$)$_2$, optionally substituted $C_1$-$C_4$alkyl, or optionally substituted $C_1$-$C_4$fluoroalkyl. In some embodiments, $R^4$ is H. In some embodiments, $R^4$ is halogen. In some embodiments, $R^4$ is —Cl, —Br, —F, or —I. In some embodiments, $R^4$ is —Cl. In some embodiments, $R^4$ is —Br. In some embodiments, $R^4$ is —F. In some embodiments, $R^4$ is —I. In some embodiments, $R^4$ is —$OR^{12}$. In some embodiments, $R^{12}$ is H, optionally substituted $C_1$-$C_4$alkyl, or optionally substituted $C_1$-$C_4$fluoroalkyl. In some embodiments, $R^4$ is optionally substituted $C_1$-$C_4$alkyl. In some embodiments, $R^4$ is methyl, ethyl, propyl, or butyl. In some embodiments, $R^4$ is optionally substituted $C_1$-$C_4$fluoroalkyl. In some embodiments, $R^4$ is —$CF_3$ or —$CH_2CF_3$. In some embodiments, each $R^5$ is independently H, halogen, —CN, —$OR^{12}$, —$SR^{12}$, —$N(R^{12})_2$, optionally substituted $C_1$-$C_4$alkyl, or optionally substituted $C_1$-$C_4$fluoroalkyl. In some embodiments, each $R^5$ is H. In some embodiments, each $R^5$ is independently H or halogen. In some embodiments, each $R^5$ is independently H, —Cl, —Br, —F, or —I. In some embodiments, each $R^5$ is independently H or —$OR^{12}$. In some embodiments, $R^{12}$ is H, optionally substituted $C_1$-$C_4$alkyl, or optionally substituted $C_1$-$C_4$fluoroalkyl. In some embodiments, each $R^5$ is independently H or optionally substituted $C_1$-$C_4$alkyl. In some embodiments, each $R^5$ is independently H, methyl, ethyl, propyl, or butyl. In some embodiments, each $R^5$ is independently H or optionally substituted $C_1$-$C_4$fluoroalkyl. In some embodiments, each $R^5$ is independently H, —$CF_3$ or —$CH_2CF_3$.

In some embodiments, $R^{13}$ is H or unsubstituted $C_1$-$C_4$alkyl. In some embodiments, $R^{13}$ is hydrogen, methyl, ethyl, propyl, or butyl.

Compounds of Formula (I), or a pharmaceutically acceptable salt, or solvate thereof include those compounds having the structures of formulas (Ia)-(In) or a pharmaceutically acceptable salt or solvate thereof:

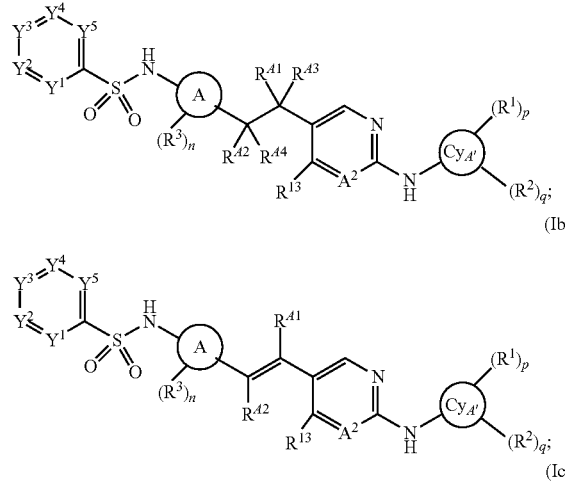

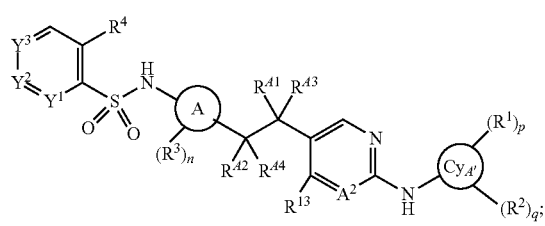

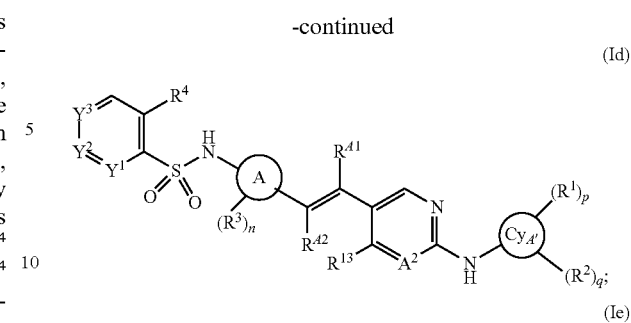

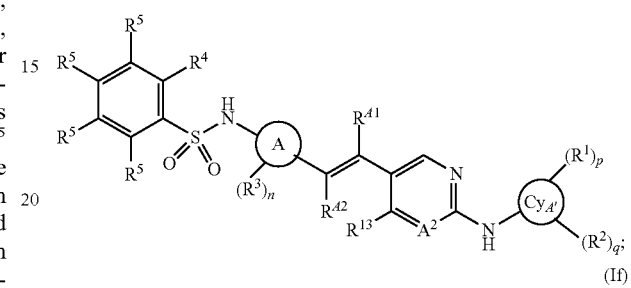

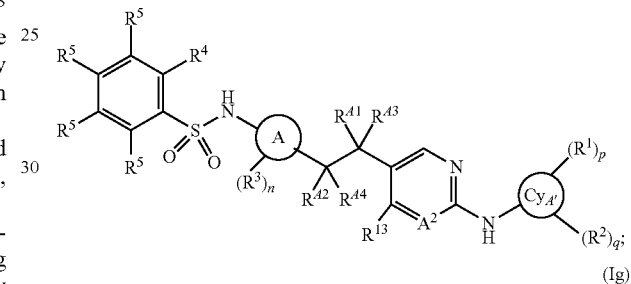

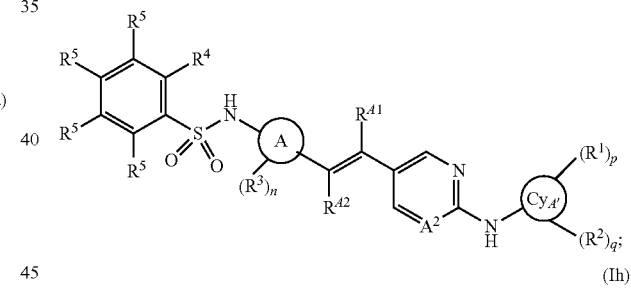

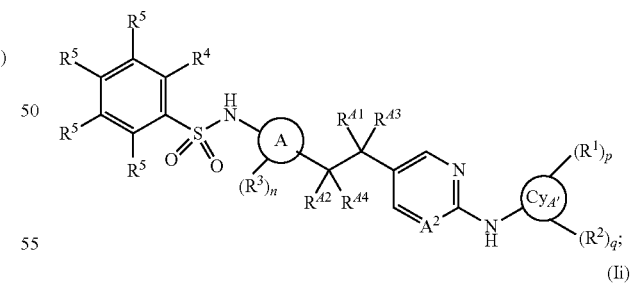

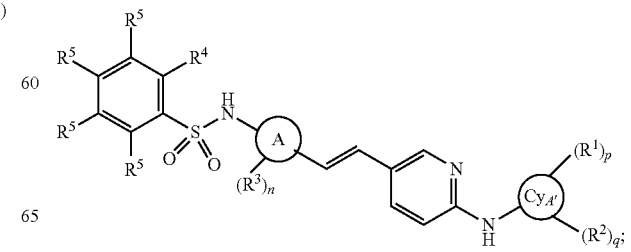

-continued

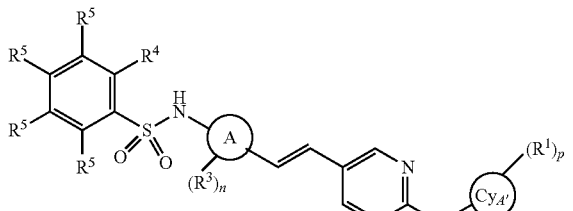
(Ij)

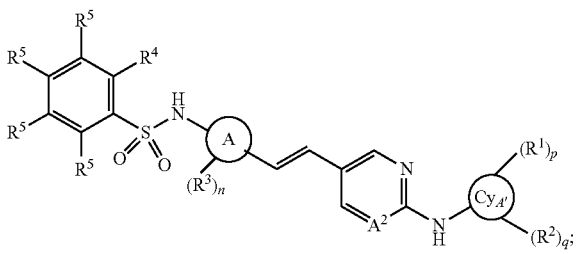
(Ik)

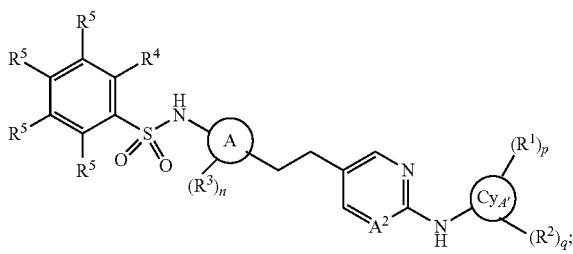
(Il)

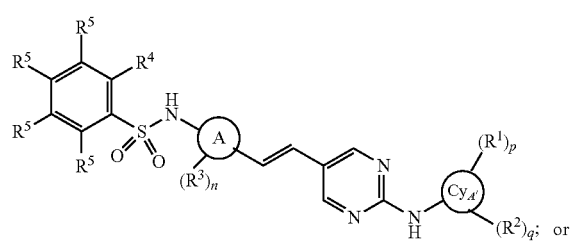
(Im)

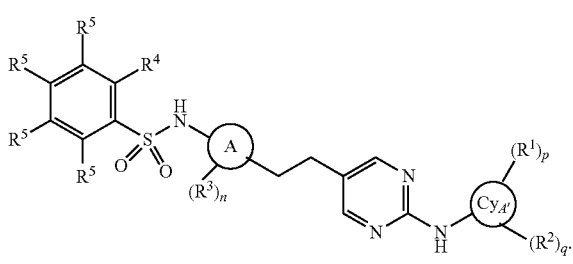
(In)

The variables for formulas (Ia)-(In) are as set forth in Formula I or in any of the embodiments set forth herein. In some embodiments,

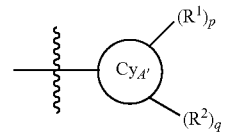

is

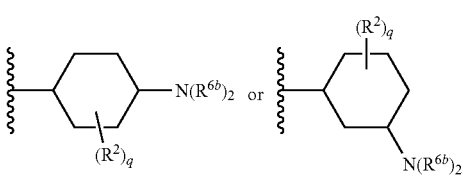

and each $R^{6b}$ is independently H, optionally substituted $C_1$-$C_4$alkyl, optionally substituted $C_1$-$C_4$heteroalkyl, optionally substituted $C_1$-$C_4$fluoroalkyl, —X-optionally substituted $C_1$-$C_4$alkyl, —X-optionally substituted $C_1$-$C_4$heteroalkyl, optionally substituted $C_3$-$C_4$cycloalkyl$C_1$-$C_3$alkyl, or —X-optionally substituted $C_1$-$C_4$fluoroalkyl; or each $R^{6b}$ is independently H, methyl, ethyl, or propyl; or each $R^{6b}$ is independently H, optionally substituted $C_1$-$C_5$alkyl, optionally substituted $C_1$-$C_4$fluoroalkyl, optionally substituted $C_1$-$C_3$heteroalkyl, or optionally substituted $C_3$-$C_4$cyclooalkyl-$C_1$-$C_3$alkyl; or each $R^{6b}$ is independently H, —$CH_2CH_2CH_3$, —$CH_2CH_3$, or —$CH_3$. In some further embodiments, q is 0 or 1; and $R^2$ is as set forth herein. X is as set forth herein for Compounds of Formula I.

In some such embodiments,
(i) each $R^2$ is independently optionally substituted $C_1$-$C_4$alkyl, optionally substituted $C_1$-$C_4$heteroalkyl, or optionally substituted $C_1$-$C_4$fluoroalkyl or $R^2$ is absent;
(ii) $A^2$ is N; or
(iii) $A^2$ is $CR^A$ wherein $R^A$ is H, optionally substituted $C_1$-$C_4$alkyl, or optionally substituted $C_1$-$C_4$fluoroalkyl; or
(iv) $A^2$ is $CR^A$ wherein $R^A$ is H;
(v) $R^{A1}$ is H, optionally substituted $C_1$-$C_4$alkyl, or optionally substituted $C_1$-$C_4$fluoroalkyl; or
(vi) $R^{A1}$ is H;
(viii) $R^{A2}$ is H, optionally substituted $C_1$-$C_4$alkyl, or optionally substituted $C_1$-$C_4$fluoroalkyl; or
(viiii) $R^{A2}$ is H;
(ix) $R^{A3}$ is H, optionally substituted $C_1$-$C_4$alkyl, optionally substituted $C_1$-$C_4$fluoroalkyl, or optionally substituted aryl; or
(x) $R^{A3}$ is H, optionally substituted $C_1$-$C_4$alkyl, or optionally substituted $C_1$-$C_4$fluoroalkyl; or
(xi) $R^{A3}$ is H; or
(xii) $R^{A3}$ is optionally substituted $C_1$-$C_4$alkyl; or
(xiii) $R^{A3}$ is methyl, ethyl, propyl, or butyl; or
(xiv) $R^{A3}$ is ethyl or $R^{A3}$ is H;
(xv) $R^{A4}$ is H, optionally substituted $C_1$-$C_4$alkyl, optionally substituted $C_1$-$C_4$fluoroalkyl, or optionally substituted aryl; or
(xvi) $R^{A4}$ is H, optionally substituted $C_1$-$C_4$alkyl, or optionally substituted $C_1$-$C_4$fluoroalkyl; or (xvii) $R^{44}$ is H; or
(xviii) $R^{44}$ is optionally substituted $C_1$-$C_4$alkyl; or,
(xix) $R^{44}$ is methyl, ethyl, propyl, or butyl; or
(xx) $R^{44}$ is ethyl; or
(xxi) $R^{44}$ is H;

(xxii)

~~~~~~~~~~~A~~~~~~~~~~~ is phenylene; or (xxiii)

~~~~~~~~~~~A~~~~~~~~~~~ is a monocyclic 6-membered heteroarylene selected from pyridinylene, pyrimidinylene, pyrazinylene, and pyridazinylene; or (xxiv)

~~~~~~~~~~~A~~~~~~~~~~~ is pyridinylene;

(xxv) $R^3$ is independently —$OR^{11}$, optionally substituted $C_1$-$C_4$alkyl, or optionally substituted $C_1$-$C_4$fluoroalkyl; and n is 0, 1, 2, or 3;

(xxvi) $R^{11}$ is H, optionally substituted $C_1$-$C_4$alkyl, or optionally substituted $C_1$-$C_4$fluoroalkyl;

(xxvii) $R^4$ and each $R^5$ are each independently H, halogen, —CN, —$OR^{12}$, —$SR^{12}$, —$N(R^{12})_2$, optionally substituted $C_1$-$C_4$alkyl, or optionally substituted $C_1$-$C_4$fluoroalkyl;

(xxviii) $R^4$ and each $R^5$ are each independently H, halogen, or optionally substituted $C_1$-$C_4$alkyl (xxix) $R^4$ is halogen and each $R^5$ is independently H, halogen, or optionally substituted $C_1$-$C_4$alkyl;

(xxx) $R^4$ is chlorine and each $R^5$ is independently H, halogen, or optionally substituted $C_1$-$C_4$alkyl;

(xxxi) $R^{13}$ is H or unsubstituted $C_1$-$C_4$alkyl;

(xxxii) $Y^1$ is nitrogen and $Y^2$ and $Y^3$ are independently $CR^5$;

(xxxiii) $Y^2$ is nitrogen and $Y^1$ and $Y^3$ are independently $CR^5$;

(xxxiv) $Y^3$ is nitrogen and $Y^1$ and $Y^2$ are independently $CR^5$;

(xxxv) $Y^1$ is nitrogen and $Y^2$ and $Y^3$ are independently $CR^5$;

(xxxvi) two of $Y^1$, $Y^2$, and $Y^3$ are nitrogen and the other of $Y^1$, $Y^2$, and $Y^3$ are $CR^5$; and any combinations thereof of (i)-(xxxvi).

Compounds of Formula (I), or a pharmaceutically acceptable salt, or solvate thereof include those compounds having the structures formulas (Io) and (Ip) or a pharmaceutically acceptable salt or solvate thereof:

(Io)

[chemical structure of formula (Io) with $R_5$, $R^4$, sulfonamide, ring A with $(R^3)_n$, vinyl linker to pyrimidine, NH-cyclohexyl-$N(R^{6b})_2$]

or (Ip)

[chemical structure of formula (Ip) with $R_5$, $R^4$, sulfonamide, ring A with $(R^3)_n$, ethylene linker to pyrimidine, NH-cyclohexyl-$N(R^{6b})_2$]

In some embodiments of the present invention, compounds of the present invention are in the trans-configuration. The trans-configuration for formulas (Io) and (Ip), for example are as shown below for formulas (Io') and (Ip'):

(Io')

[chemical structure of formula (Io') - trans configuration]

or (Ip')

[chemical structure of formula (Ip') - trans configuration]

The variables for formulas (Io)-(Ip) are as set forth in Formula I or in any of the embodiments set forth herein. In some embodiments (i)

~~~~~~~~~~~A~~~~~~~~~~~ is phenylene, pyridinylene, pyrimidinylene, pyrazinylene, and pyridazinylene; or

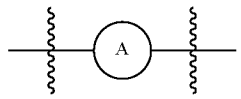

is phenylene; or

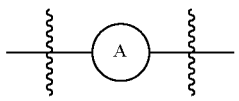

(ii)

is pyridinylene; or

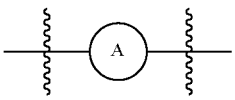

(iii)

is pyridazinylene; or

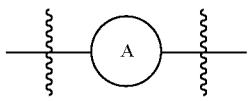

(iv)

is pyrimidinylene; or

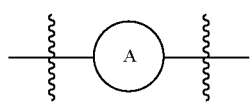

(v)

is pyrazinylene;

(vi) each $R^3$ is independently halogen, —$OR^{11}$, optionally substituted $C_1$-$C_4$alkyl, or optionally substituted $C_1$-$C_4$fluoroalkyl or $R^3$ is absent (i.e., n is 0);

(vii) n is 0, 1, 2, or 3; or (viii) n is 0, 1 or 2;

(ix) n is 0; or (x) $R^3$ is halogen; or (xi) $R^3$ is F; or (xii) $R^3$ is Cl; or (xiii) $R^3$ is —$OR^{11}$; or (xiv) $R^3$ is —OMe; or (xv) $R^3$ is —OEt; or (xvi) $R^3$ is —$OCF_3$; or (xvii) $R^3$ is optionally substituted $C_1$-$C_4$alkyl; or (xviii) $R^3$ is methyl, ethyl, n-propyl, iso-propyl, n-butyl, iso-butyl, sec-butyl, or tert-butyl; or (xix) $R^3$ is methyl or ethyl; or (xx) $R^3$ is optionally substituted $C_1$-$C_4$fluoroalkyl; or (xxi) $R^3$ is $CF_3$;

(xxii) $R^4$ and $R^5$ are each independently H, halogen, —CN, —$OR^{12}$, —$SR^{12}$, —$N(R^{12})_2$, optionally substituted $C_1$-$C_4$alkyl, or optionally substituted $C_1$-$C_4$fluoroalkyl; or (xxiii) $R^4$ is halogen and $R^5$ is H; or (xxiv) $R^4$ is F; or (xxv) $R^4$ is Cl;

(xxvi) each $R^{6b}$ is hydrogen or optionally substituted $C_1$-$C_4$alkyl; or (xxvii) each $R^{6b}$ is hydrogen, methyl, or unsubstituted $C_1$-$C_4$alkyl; or (xxviii) each $R^{6b}$ is hydrogen, methyl, or ethyl; or (xxix) each $R^{6b}$ is methyl or ethyl; or (xxx) each $R^{6b}$ is methyl; and any combinations thereof of (i)-(xxx).

In some embodiments, a compound described herein is selected from any one of the compounds from Table 1.

TABLE 1

| Compound No. | Structure | Compound Name |
|---|---|---|
| 1 | 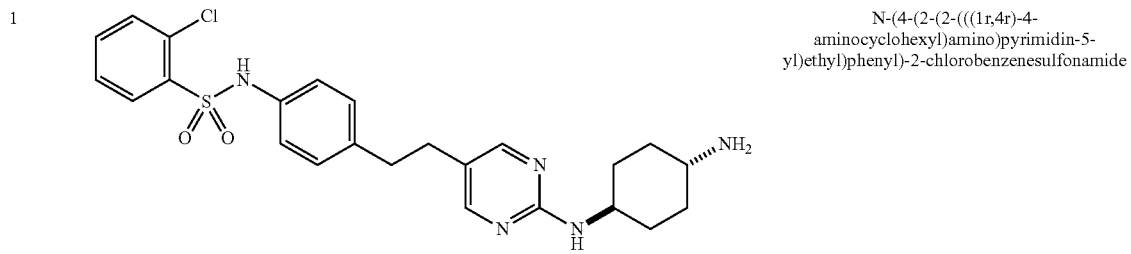 | N-(4-(2-(2-(((1r,4r)-4-aminocyclohexyl)amino)pyrimidin-5-yl)ethyl)phenyl)-2-chlorobenzenesulfonamide |

TABLE 1-continued

| Compound No. | Structure | Compound Name |
|---|---|---|
| 2 | 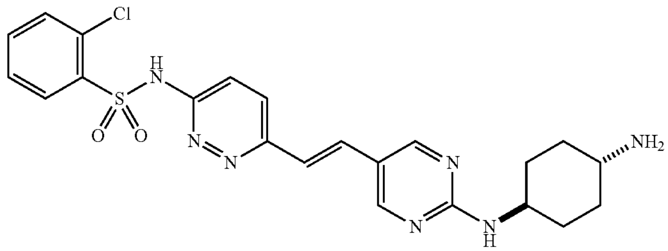 | N-(6-((E)-2-(2-(((1r,4r)-4-aminocyclohexyl)amino)pyrimidin-5-yl)vinyl)pyridazin-3-yl)-2-chlorobenzenesulfonamide |
| 3 | 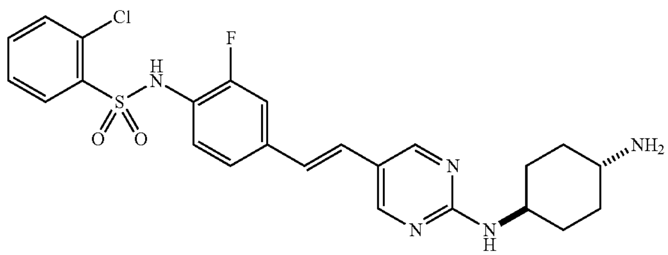 | N-(4-((E)-2-(2-(((1r,4r)-4-aminocyclohexyl)amino)pyrimidin-5-yl)vinyl)-2-fluorophenyl)-2-chlorobenzenesulfonamide |
| 4 | 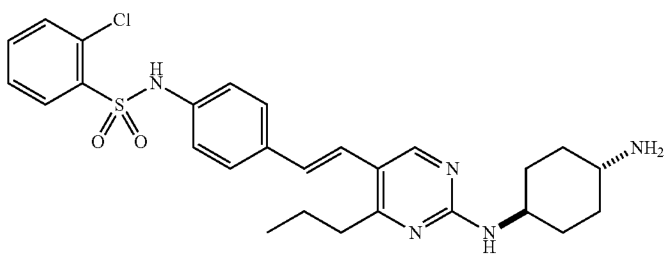 | N-(4-((E)-2-(2-(((1r,4r)-4-aminocyclohexyl)amino)-4-propylpyrimidin-5-yl)vinyl)phenyl)-2-chlorobenzenesulfonamide |
| 5 | 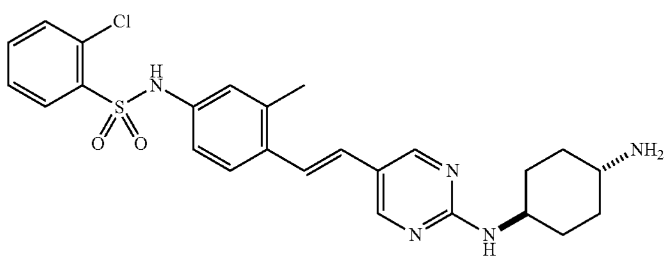 | N-(4-((E)-2-(2-(((1r,4r)-4-aminocyclohexyl)amino)pyrimidin-5-yl)vinyl)-3-methylphenyl)-2-chlorobenzenesulfonamide |
| 6 | 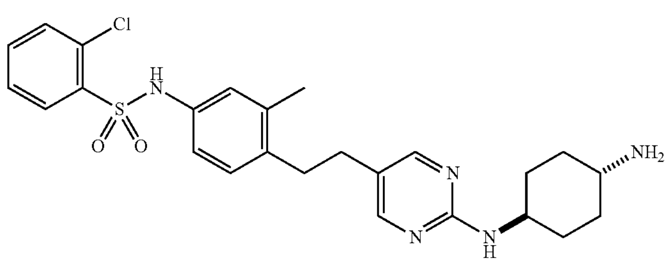 | N-(4-(2-(2-(((1r,4r)-4-aminocyclohexyl)amino)pyrimidin-5-yl)ethyl)-3-methylphenyl)-2-chlorobenzenesulfonamide |
| 7 | 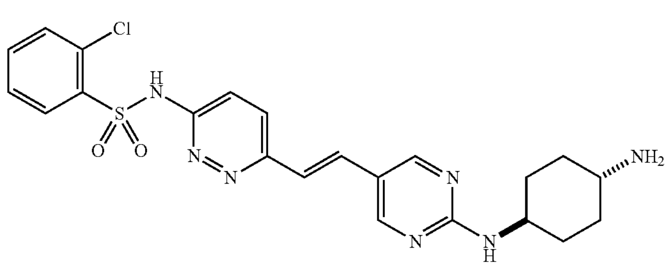 | N-(6-(2-(2-(((1r,4r)-4-aminocyclohexyl)amino)pyrimidin-5-yl)ethyl)pyridazin-3-yl)-2-chlorobenzenesulfonamide |

TABLE 1-continued

| Compound No. | Structure | Compound Name |
|---|---|---|
| 8 | 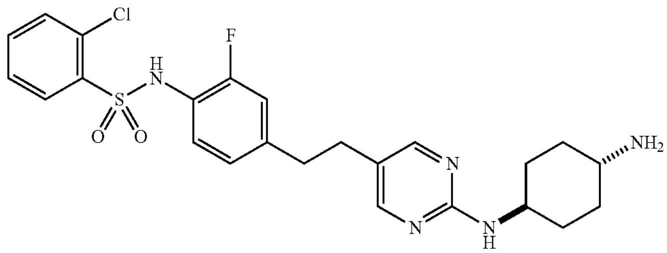 | N-(4-(2-(2-(((1r,4r)-4-aminocyclohexyl)amino)pyrimidin-5-yl)ethyl)-2-fluorophenyl)-2-chlorobenzenesulfonamide |
| 9 | 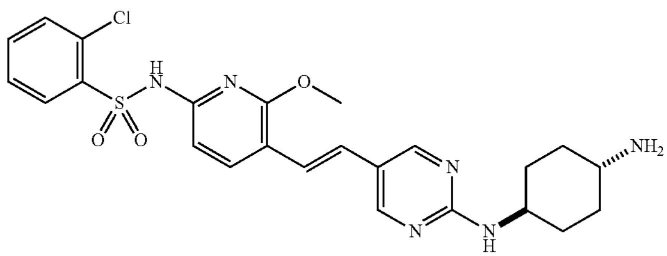 | N-(5-((E)-2-(2-(((1r,4r)-4-aminocyclohexyl)amino)pyrimidin-5-yl)vinyl)-6-methoxypyridin-2-yl)-2-chlorobenzenesulfonamide |
| 10 | 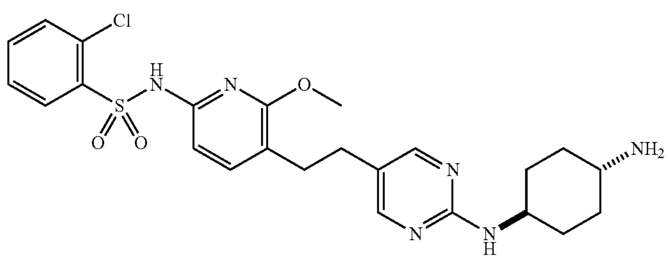 | N-(5-(2-(2-(((1r,4r)-4-aminocyclohexyl)amino)pyrimidin-5-yl)ethyl)-6-methoxypyridin-2-yl)-2-chlorobenzenesulfonamide |
| 11 | 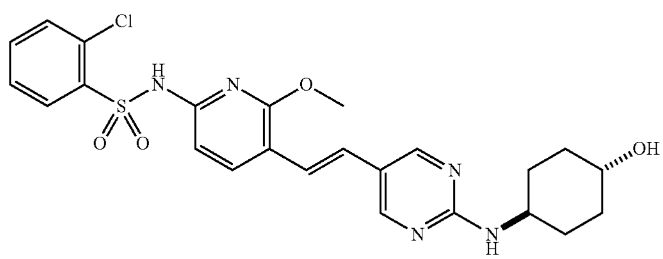 | 2-chloro-N-(5-((E)-2-(2-(((1r,4r)-4-hydroxycyclohexyl)amino)pyrimidin-5-yl)vinyl)-6-methoxypyridin-2-yl)benzenesulfonamide |
| 12 | 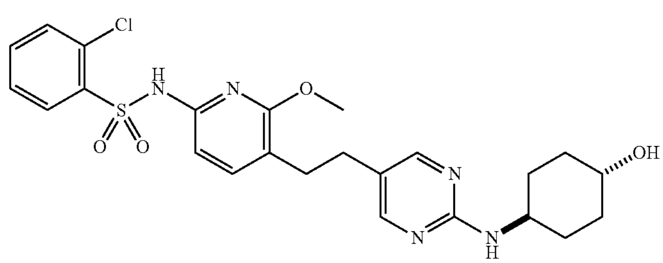 | 2-chloro-N-(5-(2-(2-(((1r,4r)-4-hydroxycyclohexyl)amino)pyrimidin-5-yl)ethyl)-6-methoxypyridin-2-yl)benzenesulfonamide |
| 13 | 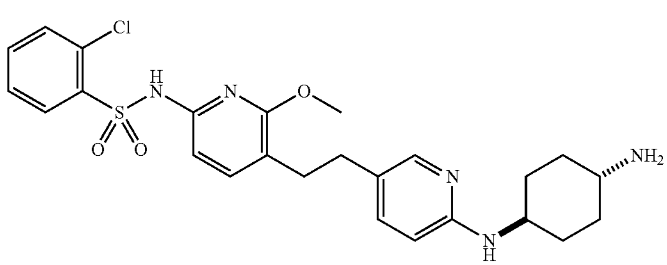 | N-(5-(2-(6-(((1r,4r)-4-aminocyclohexyl)amino)pyridin-3-yl)ethyl)-6-methoxypyridin-2-yl)-2-chlorobenzenesulfonamide |

TABLE 1-continued

| Compound No. | Structure | Compound Name |
|---|---|---|
| 14 | 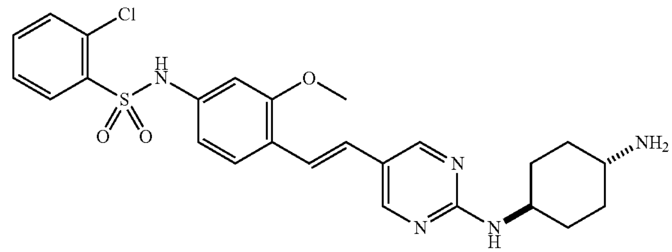 | N-(4-((E)-2-(2-(((1r,4r)-4-aminocyclohexyl)amino)pyrimidin-5-yl)vinyl)-3-methoxyphenyl)-2-chlorobenzenesulfonamide |
| 15 | 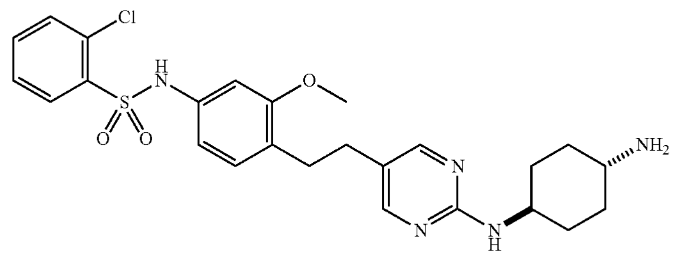 | N-(4-(2-(2-(((1r,4r)-4-aminocyclohexyl)amino)pyrimidin-5-yl)ethyl)-3-methoxyphenyl)-2-chlorobenzenesulfonamide |
| 16 | 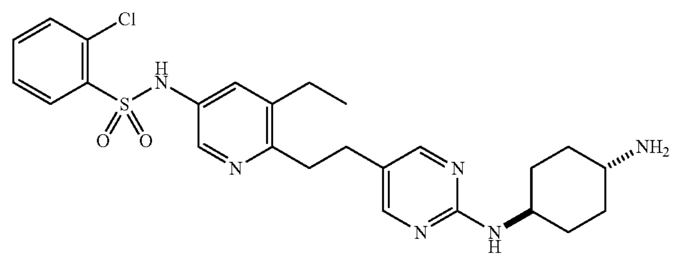 | N-(6-(2-(2-(((1r,4r)-4-aminocyclohexyl)amino)pyrimidin-5-yl)ethyl)-5-ethylpyridin-3-yl)-2-chlorobenzenesulfonamide |
| 17 | 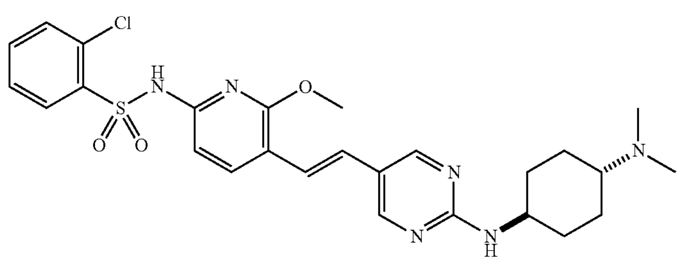 | 2-chloro-N-(5-((E)-2-(2-(((1r,4r)-4-(dimethylamino)cyclohexyl)amino)pyrimidin-5-yl)vinyl)-6-methoxypyridin-2-yl)benzenesulfonamide |
| 18 | 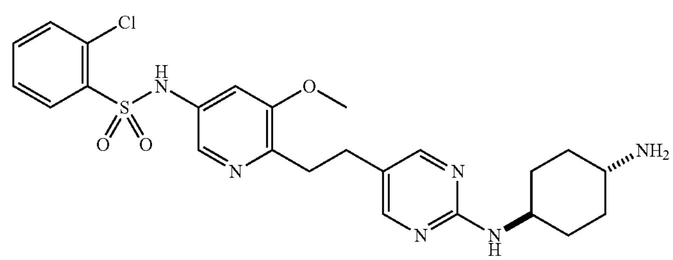 | N-(6-(2-(2-(((1r,4r)-4-aminocyclohexyl)amino)pyrimidin-5-yl)ethyl)-5-methoxypyridin-3-yl)-2-chlorobenzenesulfonamide |
| 19 | 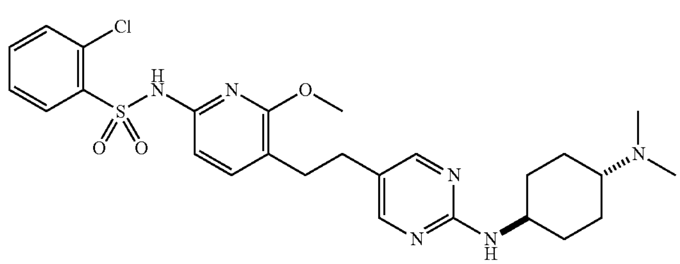 | 2-chloro-N-(5-(2-(2-(((1r,4r)-4-(dimethylamino)cyclohexyl)amino)pyrimidin-5-yl) ethyl)-6-methoxypyridin-2-yl)benzenesulfonamide |

TABLE 1-continued

| Compound No. | Structure | Compound Name |
|---|---|---|
| 20 | 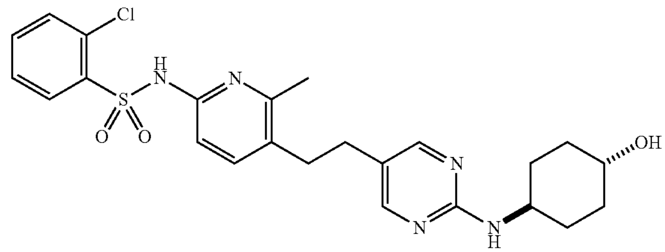 | 2-chloro-N-(5-(2-(2-(((1r,4r)-4-hydroxycyclohexyl)amino)pyrimidin-5-yl)ethyl)-6-methylpyridin-2-yl)benzenesulfonamide |
| 21 | 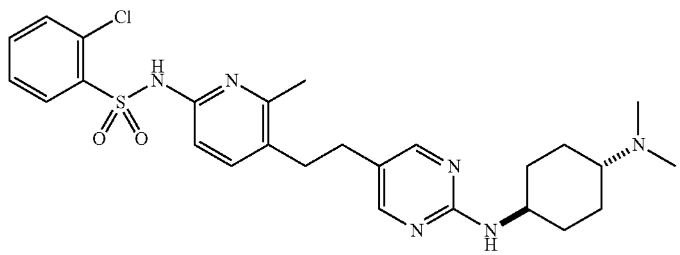 | 2-chloro-N-(5-(2-(2-(((1r,4r)-4-(dimethylamino)cyclohexyl)amino)pyrimidin-5-yl)ethyl)-6-methylpyridin-2-yl)benzenesulfonamide |
| 22 | 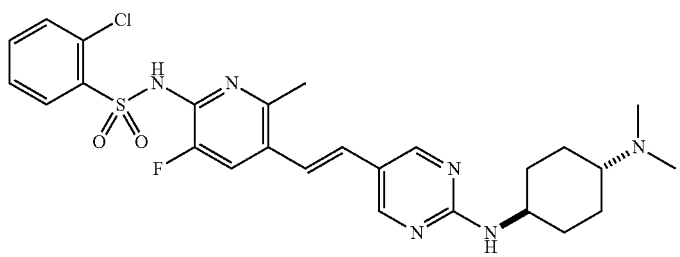 | 2-chloro-N-(5-((E)-2-(2-(((1r,4r)-4-(dimethylamino)cyclohexyl)amino)pyrimidin-5-yl)vinyl)-3-fluoro-6-methylpyridin-2-yl)benzenesulfonamide |
| 23 | 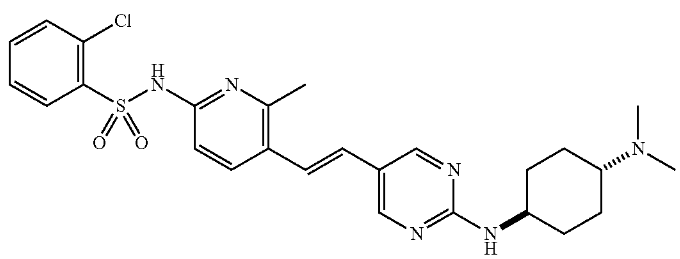 | 2-chloro-N-(5-((E)-2-(2-(((1r,4r)-4-(dimethylamino)cyclohexyl)amino)pyrimidin-5-yl)vinyl)-6-methylpyridin-2-yl)benzenesulfonamide |
| 24 | 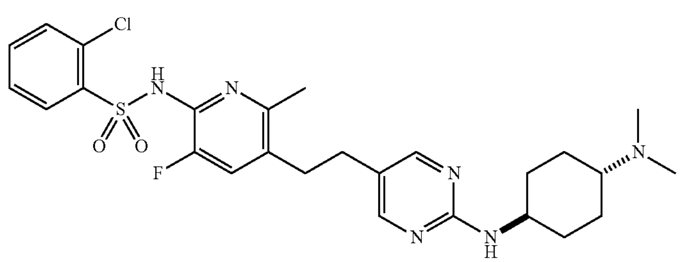 | 2-chloro-N-(5-(2-(2-(((1r,4r)-4-(dimethylamino)cyclohexyl)amino)pyrimidin-5-yl)ethyl)-3-fluoro-6-methylpyridin-2-yl)benzenesulfonamide |
| 25 | 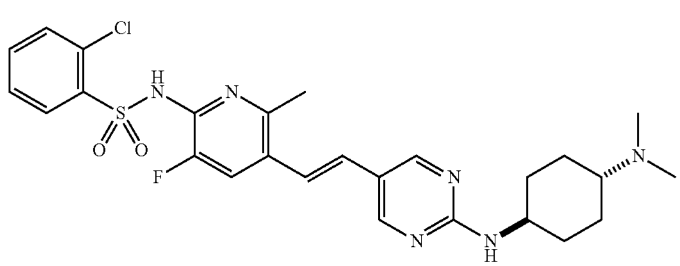 | 2-chloro-N-(5-((E)-2-(2-(((1r,4r)-4-(dimethylamino)cyclohexyl)amino)pyrimidin-5-yl)vinyl)-3-fluoro-6-methylpyridin-2-yl)benzenesulfonamide |

TABLE 1-continued

| Compound No. | Structure | Compound Name |
|---|---|---|
| 26 | 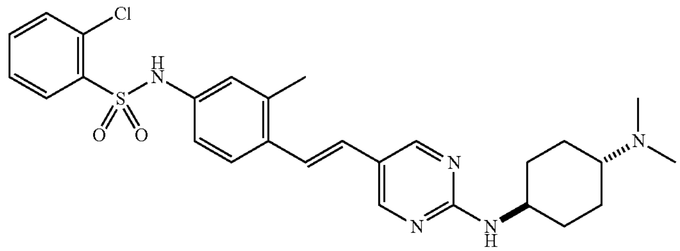 | 2-chloro-N-(4-((E)-2-(2-(((1r,4r)-4-(dimethylamino)cyclohexyl)amino)pyrimidin-5-yl)vinyl)-3-methylphenyl)benzenesulfonamide |
| 27 | 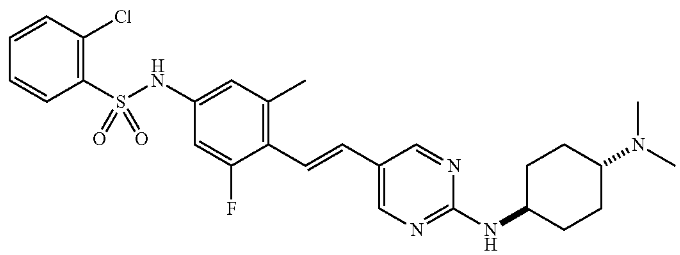 | 2-chloro-N-(4-((E)-2-(2-(((1r,4r)-4-(dimethylamino)cyclohexyl)amino)pyrimidin-5-yl)vinyl)-3-fluoro-5-methylphenyl)benzenesulfonamide |
| 28 | 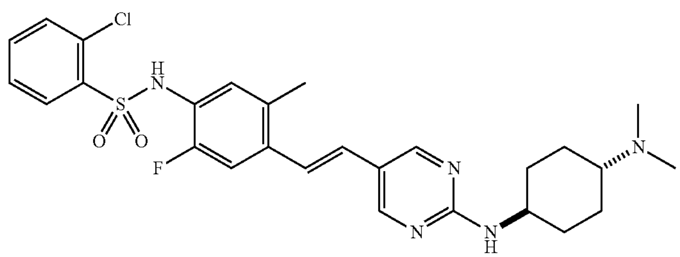 | 2-chloro-N-(4-((E)-2-(2-(((1r,4r)-4-(dimethylamino)cyclohexyl)amino)pyrimidin-5-yl)vinyl)-2-fluoro-5-methylphenyl)benzenesulfonamide |
| 29 | 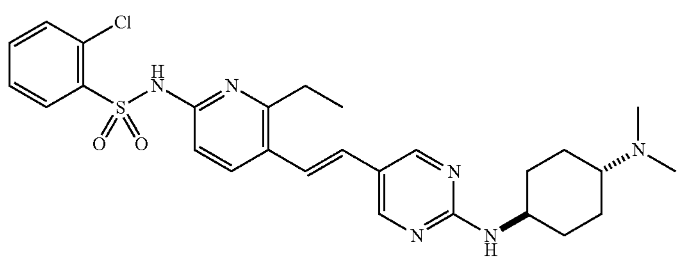 | 2-chloro-N-(5-((E)-2-(2-(((1r,4r)-4-(dimethylamino)cyclohexyl)amino)pyrimidin-5-yl)vinyl)-6-ethylpyridin-2-yl)benzenesulfonamide |
| 30 | 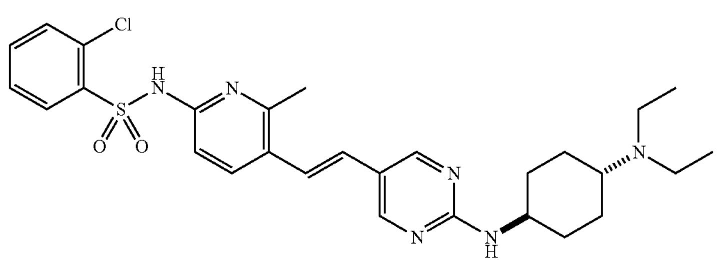 | 2-chloro-N-(5-((E)-2-(2-(((1r,4r)-4-(diethylamino)cyclohexyl)amino)pyrimidin-5-yl)vinyl)-6-methylpyridin-2-yl)benzenesulfonamide |
| 31 | 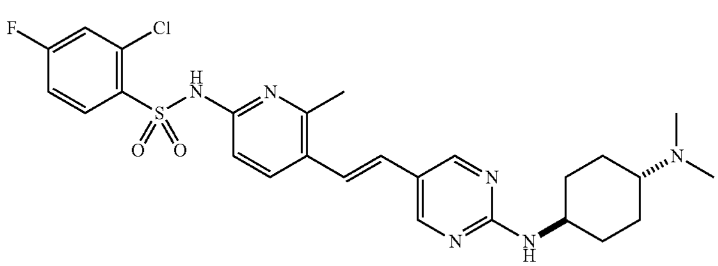 | 2-chloro-N-(5-((E)-2-(2-(((1r,4r)-4-(dimethylamino)cyclohexyl)amino)pyrimidin-5-yl)vinyl)-6-methylpyridin-2-yl)-4-fluorobenzenesulfonamide |

TABLE 1-continued

| Compound No. | Structure | Compound Name |
|---|---|---|
| 32 | 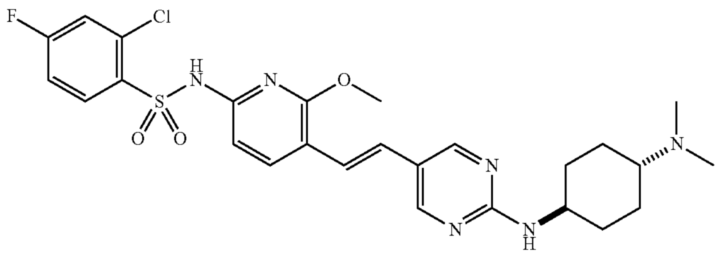 | 2-chloro-N-(5-((E)-2-(2-(((1r,4r)-4-(dimethylamino)cyclohexyl)amino)pyrimidin-5-yl)vinyl)-6-methoxypyridin-2-yl)-4-fluorobenzenesulfonamide |
| 33 | 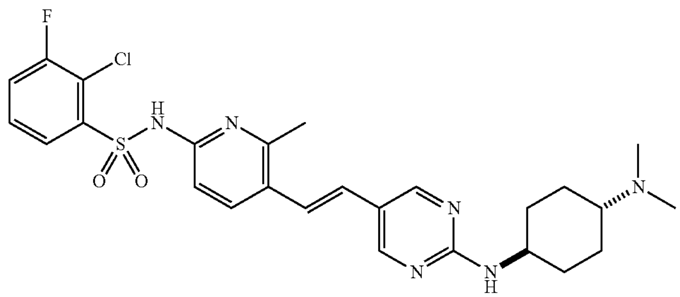 | 2-chloro-N-(5-((E)-2-(2-(((1r,4r)-4-(dimethylamino)cyclohexyl)amino)pyrimidin-5-yl)vinyl)-6-methylpyridin-2-yl)-3-fluorobenzenesulfonamide |
| 34 | 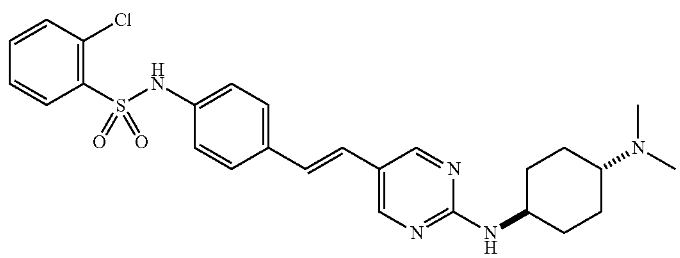 | 2-chloro-N-(4-((E)-2-(2-(((1r,4r)-4-(dimethylamino)cyclohexyl)amino)pyrimidin-5-yl)vinyl)phenyl)benzenesulfonamide |
| 35 | 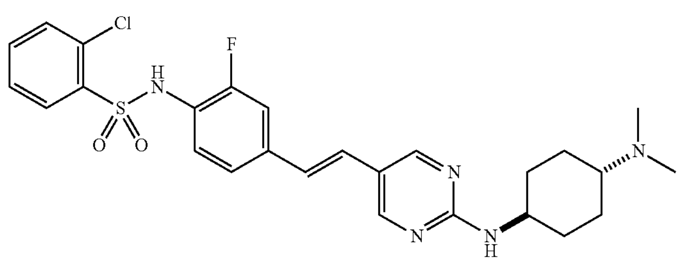 | 2-chloro-N-(4-((E)-2-(2-(((1r,4r)-4-(dimethylamino)cyclohexyl)amino)pyrimidin-5-yl)vinyl)-2-fluorophenyl)benzenesulfonamide |
| 36 | 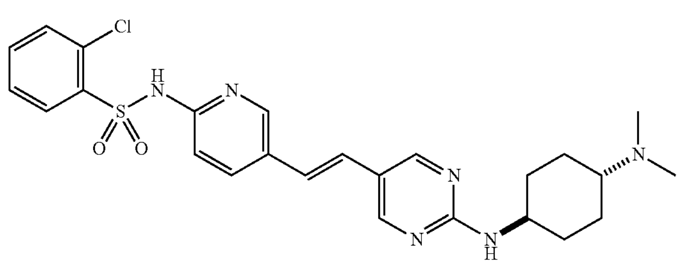 | 2-chloro-N-(5-((E)-2-(2-(((1r,4r)-4-(dimethylamino)cyclohexyl)amino)pyrimidin-5-yl)vinyl)pyridin-2-yl)benzenesulfonamide |
| 37 | 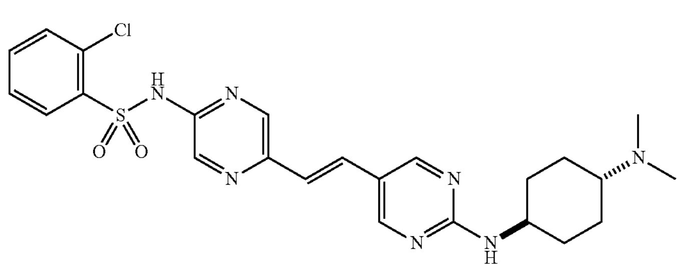 | 2-chloro-N-(5-((E)-2-(2-(((1r,4r)-4-(dimethylamino)cyclohexyl)amino)pyrimidin-5-yl)vinyl)pyrazin-2-yl)benzenesulfonamide |

TABLE 1-continued

| Compound No. | Structure | Compound Name |
|---|---|---|
| 38 | 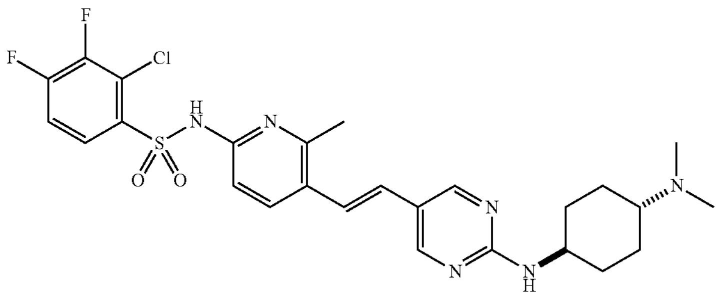 | 2-chloro-N-(5-((E)-2-(2-(((1r,4r)-4-(dimethylamino)cyclohexyl)amino)pyrimidin-5-yl)vinyl)-6-methylpyridin-2-yl)-3,4-difluorobenzenesulfonamide |
| 39 | 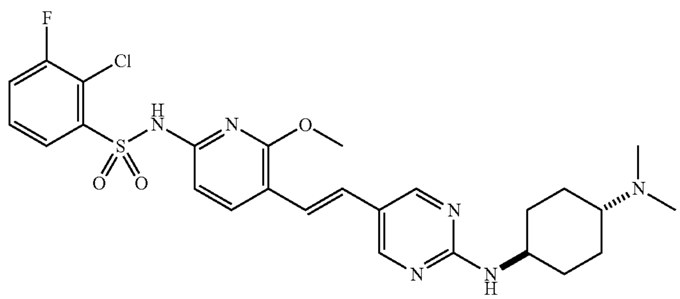 | 2-chloro-N-(5-((E)-2-(2-(((1r,4r)-4-(dimethylamino)cyclohexyl)amino)pyrimidin-5-yl)vinyl)-6-methoxypyridin-2-yl)-3-fluorobenzenesulfonamide |
| 40 | 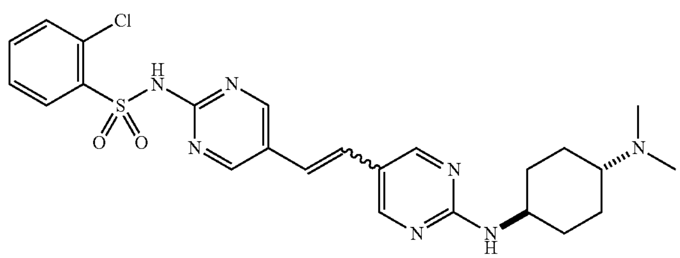 | 2-chloro-N-(5-(2-(2-(((1r,4r)-4-(dimethylamino)cyclohexyl)amino)pyrimidin-5-yl)vinyl)pyrimidin-2-yl)benzenesulfonamide |
| 41 | 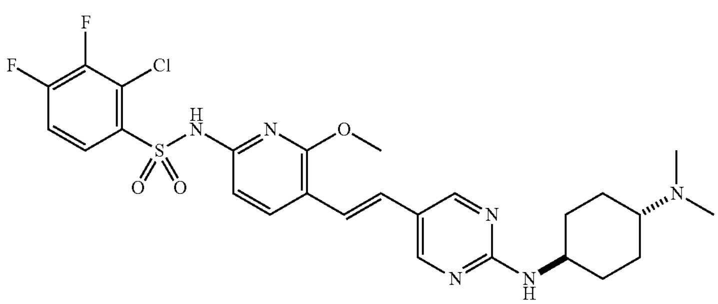 | 2-chloro-N-(5-((E)-2-(2-(((1r,4r)-4-(dimethylamino)cyclohexyl)amino)pyrimidin-5-yl)vinyl)-6-methoxypyridin-2-yl)-3,4-difluorobenzenesulfonamide |
| 42 | 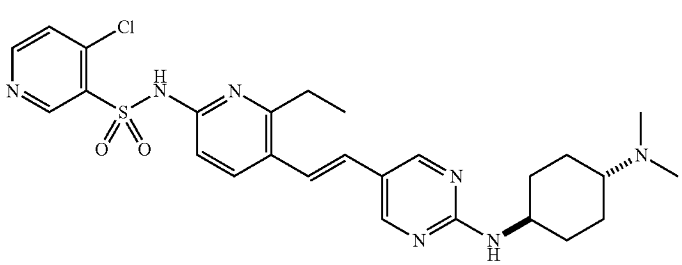 | 4-chloro-N-(5-((E)-2-(2-(((1r,4r)-4-(dimethylamino)cyclohexyl)amino)pyrimidin-5-yl)vinyl)-6-ethylpyridin-2-yl)pyridine-3-sulfonamide |

TABLE 1-continued

| Compound No. | Structure | Compound Name |
|---|---|---|
| 43 | 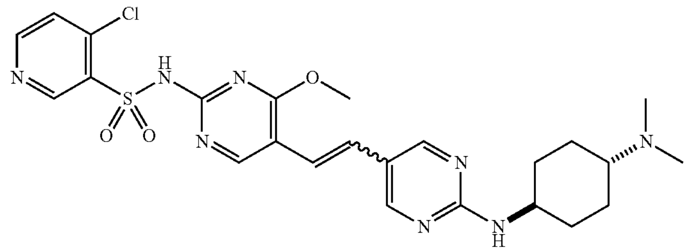 | 4-chloro-N-(5-(2-(2-(((1r,4r)-4-(dimethylamino)cyclohexyl)amino)pyrimidin-5-yl)vinyl)-4-methoxypyrimidin-2-yl)pyridine-3-sulfonamide |
| 44 | 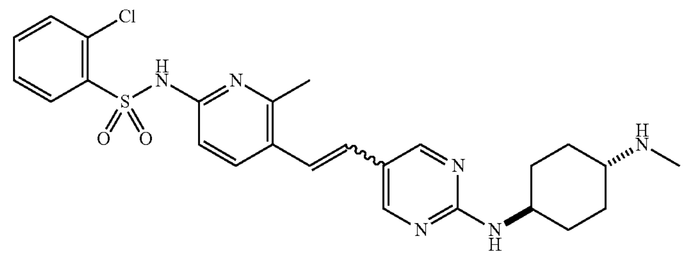 | 2-chloro-N-(6-methyl-5-(2-(2-(((1r,4r)-4-(methylamino)cyclohexyl)amino)pyrimidin-5-yl)vinyl)pyridin-2-yl)benzenesulfonamide |
| 45 | 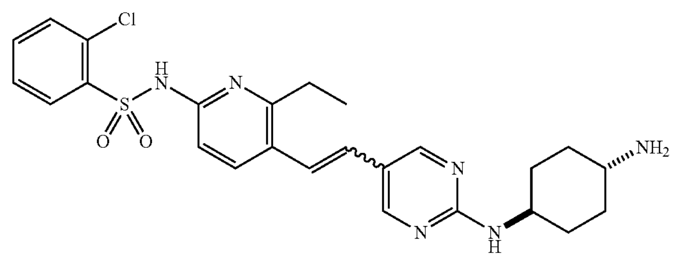 | N-(5-(2-(2-(((1r,4r)-4-aminocyclohexyl)amino)pyrimidin-5-yl)vinyl)-6-ethylpyridin-2-yl)-2-chlorobenzenesulfonamide |
| 46 | 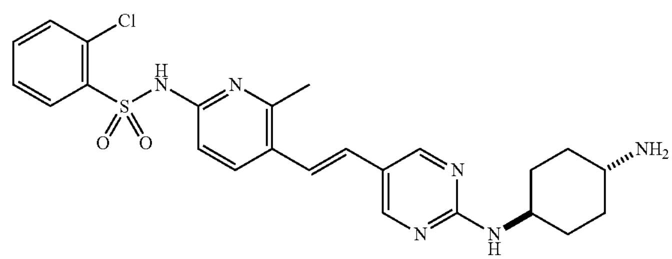 | N-(5-((E)-2-(2-(((1r,4r)-4-aminocyclohexyl)amino)pyrimidin-5-yl)vinyl)-6-methylpyridin-2-yl)-2-chlorobenzenesulfonamide |
| 47 | 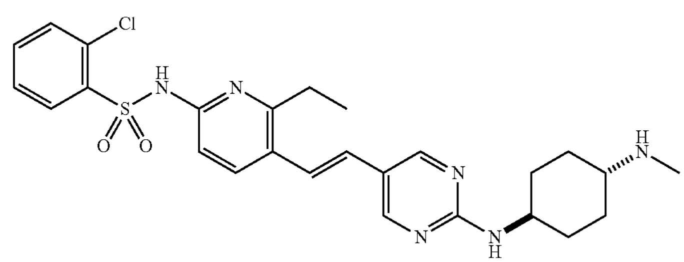 | 2-chloro-N-(6-ethyl-5-((E)-2-(2-(((1r,4r)-4-(methylamino)cyclohexyl)amino)pyrimidin-5-yl)vinyl)pyridin-2-yl)benzenesulfonamide |
| 48 | 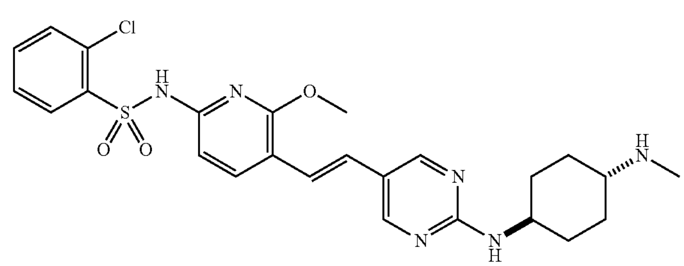 | 2-chloro-N-(6-methoxy-5-((E)-2-(2-(((1r,4r)-4-(methylamino)cyclohexyl)amino)pyrimidin-5-yl)vinyl)pyridin-2-yl)benzenesulfonamide |

TABLE 1-continued

| Compound No. | Structure | Compound Name |
|---|---|---|
| 49 | 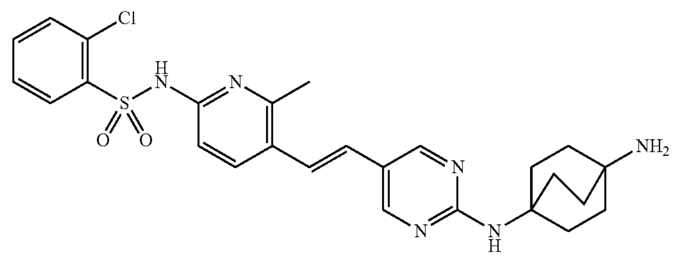 [SMILES: Cc1nc(NS(=O)(=O)c2ccccc2Cl)ccc1/C=C/c1cnc(NC23CCC(N)(CC2)CC3)nc1] | (E)-N-(5-(2-(2-((4-aminobicyclo[2.2.2]octan-1-yl)amino)pyrimidin-5-yl)vinyl)-6-methylpyridin-2-yl)-2-chlorobenzenesulfonamide |
| 50 | 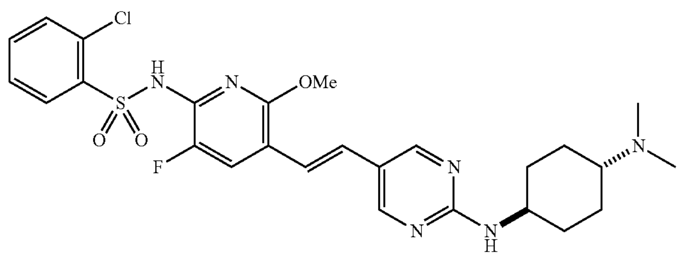 | 2-chloro-N-(5-((E)-2-(2-(((1r,4r)-4-(dimethylamino)cyclohexyl)amino)pyrimidin-5-yl)vinyl)-3-fluoro-6-methoxypyridin-2-yl)benzenesulfonamide |
| 51 | 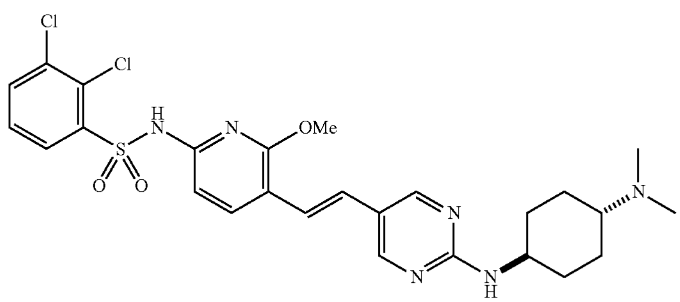 | 2,3-dichloro-N-(5-((E)-2-(2-(((1r,4r)-4-(dimethylamino)cyclohexyl)amino)pyrimidin-5-yl)vinyl)-6-methoxypyridin-2-yl)benzenesulfonamide |
| 52 | 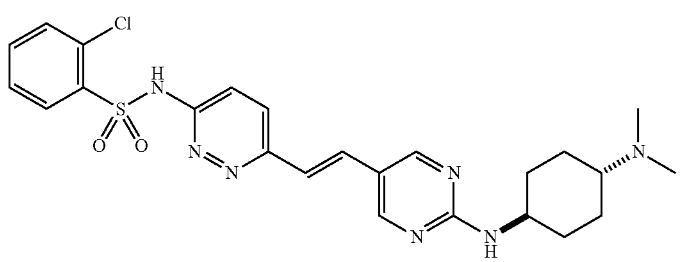 | 2-chloro-N-(6-((E)-2-(2-(((1r,4r)-4-(dimethylamino)cyclohexyl)amino)pyrimidin-5-yl)vinyl)pyridazin-3-yl)benzenesulfonamide |
| 53 | 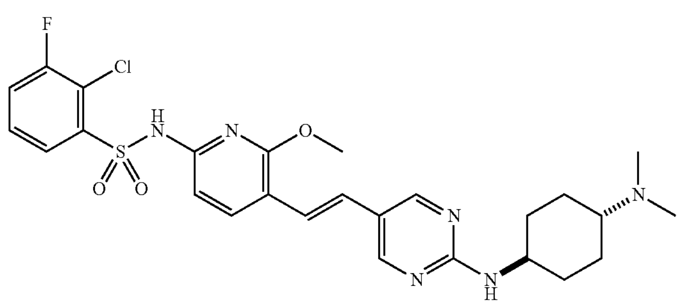 | 2-chloro-N-(5-((E)-2-(2-(((1r,4r)-4-(dimethylamino)cyclohexyl)amino)pyrimidin-5-yl)vinyl)-6-methoxypyridin-2-yl)-3-fluorobenzenesulfonamide |

TABLE 1-continued

| Compound No. | Structure | Compound Name |
|---|---|---|
| 54 | 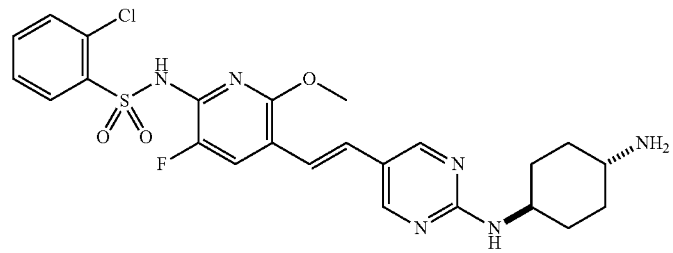 | N-(5-((E)-2-(2-(((1r,4r)-4-aminocyclohexyl)amino)pyrimidin-5-yl)vinyl)-3-fluoro-6-methoxypyridin-2-yl)-2-chlorobenzenesulfonamide |
| 55 | 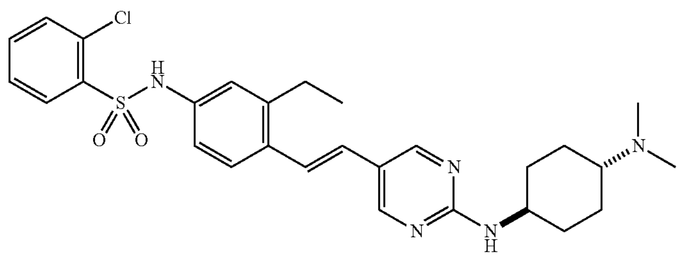 | 2-chloro-N-(4-((E)-2-(2-(((1r,4r)-4-(dimethylamino)cyclohexyl)amino)pyrimidin-5-yl)vinyl)-3-methoxyphenyl)benzenesulfonamide |
| 56 | 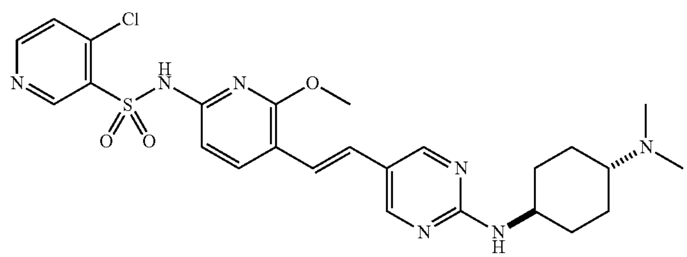 | 4-chloro-N-(5-((E)-2-(2-(((1r,4r)-4-(dimethylamino)cyclohexyl)amino)pyrimidin-5-yl)vinyl)-6-methoxypyridin-2-yl)pyridine-3-sulfonamide |
| 57 | 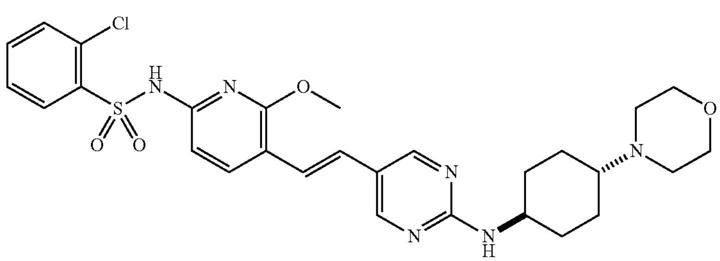 | 2-chloro-N-(6-methoxy-5-((E)-2-(2-(((1r,4r)-4-morpholinocyclohexyl)amino)pyrimidin-5-yl)vinyl)pyridin-2-yl)benzenesulfonamide |
| 58 | 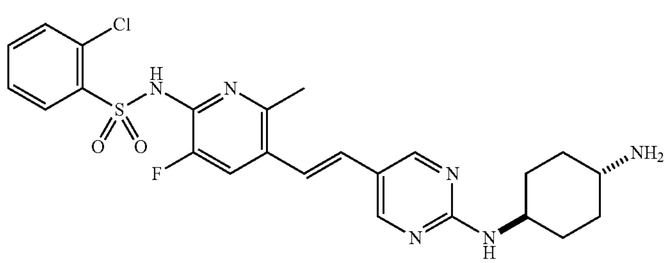 | N-(5-((E)-2-(2-(((1r,4r)-4-aminocyclohexyl)amino)pyrimidin-5-yl)vinyl)-3-fluoro-6-methylpyridin-2-yl)-2-chlorobenzenesulfonamide |
| 59 | 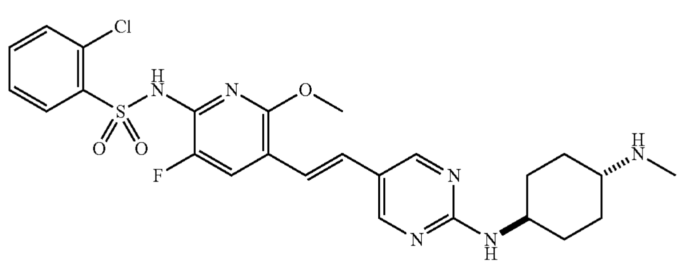 | 2-chloro-N-(3-fluoro-6-methoxy-5-((E)-2-(2-(((1r,4r)-4-(methylamino)cyclohexyl)amino)pyrimidin-5-yl)vinyl)pyridin-2-yl)benzenesulfonamide |

TABLE 1-continued

| Compound No. | Structure | Compound Name |
|---|---|---|
| 60 | 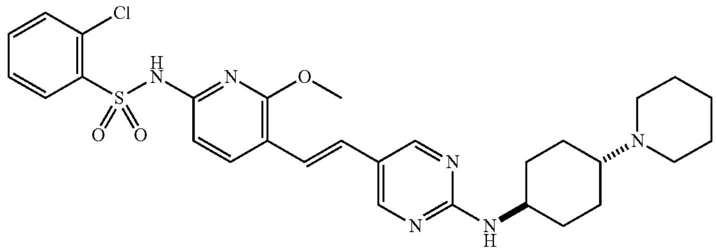 | 2-chloro-N-(6-methoxy-5-((E)-2-(2-(((1r,4r)-4-(piperidin-1-yl)cyclohexyl)amino)pyrimidin-5-yl)vinyl)pyridin-2-yl)benzenesulfonamide |
| 61 | 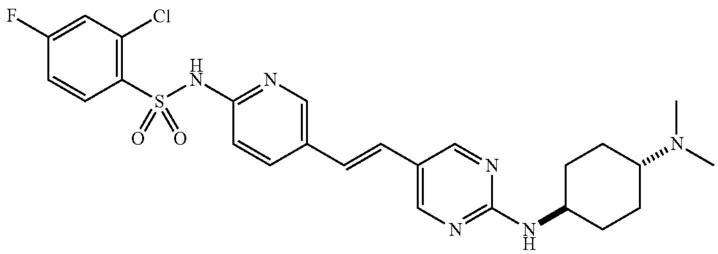 | 2-chloro-N-(5-((E)-2-(2-(((1r,4r)-4-(dimethylamino)cyclohexyl)amino)pyrimidin-5-yl)vinyl)pyridin-2-yl)-4-fluorobenzenesulfonamide |
| 62 | 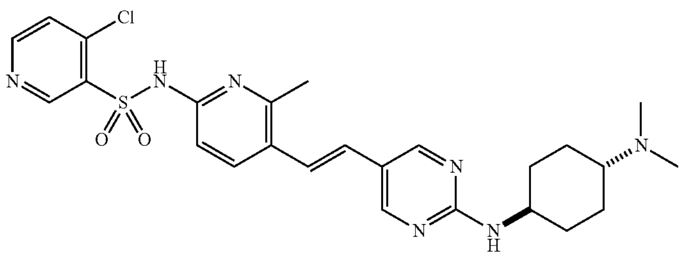 | 4-chloro-N-(5-((E)-2-(2-(((1r,4r)-4-(dimethylamino)cyclohexyl)amino)pyrimidin-5-yl)vinyl)-6-methylpyridin-2-yl)pyridine-3-sulfonamide |
| 63 | 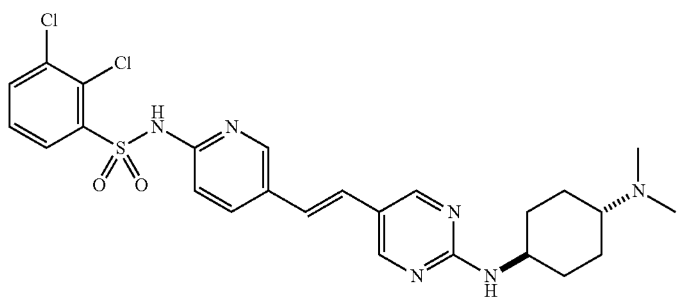 | 2,3-dichloro-N-(5-((E)-2-(2-(((1r,4r)-4-(dimethylamino)cyclohexyl)amino)pyrimidin-5-yl)vinyl)pyridin-2-yl)benzenesulfonamide |
| 64 | 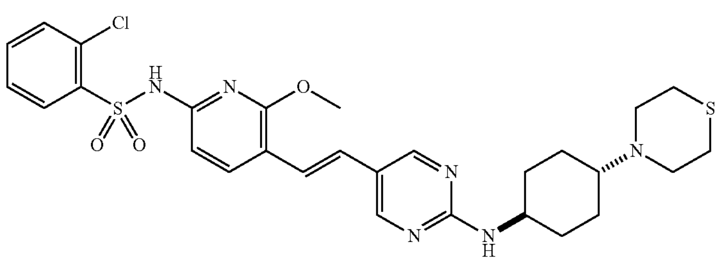 | 2-chloro-N-(6-methoxy-5-((E)-2-(2-(((1r,4r)-4-thiomorpholinocyclohexyl)amino)pyrimidin-5-yl)vinyl)pyridin-2-yl)benzenesulfonamide |
| 65 | 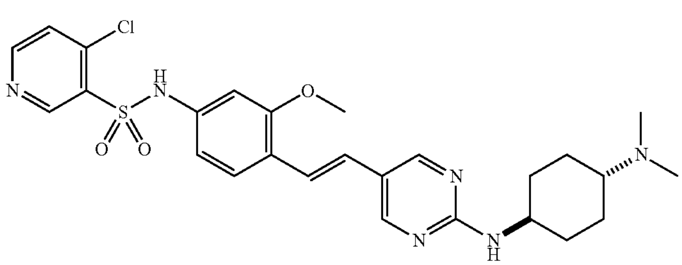 | 4-chloro-N-(4-((E)-2-(2-(((1r,4r)-4-(dimethylamino)cyclohexyl)amino)pyrimidin-5-yl)vinyl)-3-methoxyphenyl)pyridine-3-sulfonamide |

TABLE 1-continued

| Compound No. | Structure | Compound Name |
|---|---|---|
| 66 | 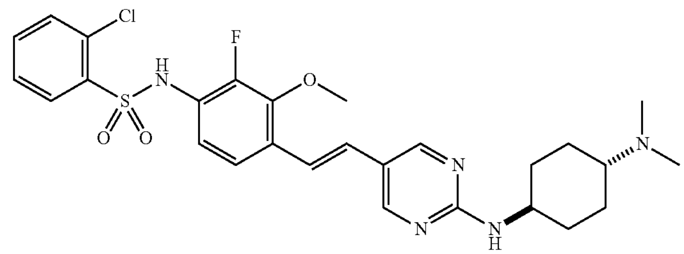 | 2-chloro-N-(4-((E)-2-(2-(((1r,4r)-4-(dimethylamino)cyclohexyl)amino)pyrimidin-5-yl)vinyl)-2-fluoro-3-methoxyphenyl)benzenesulfonamide |
| 67 | 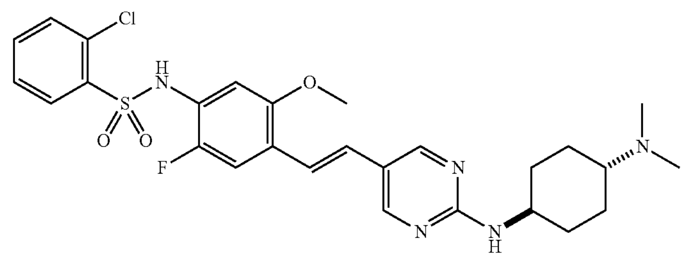 | 2-chloro-N-(4-((E)-2-(2-(((1r,4r)-4-(dimethylamino)cyclohexyl)amino)pyrimidin-5-yl)vinyl)-2-fluoro-5-methoxyphenyl)benzenesulfonamide |
| 68 | 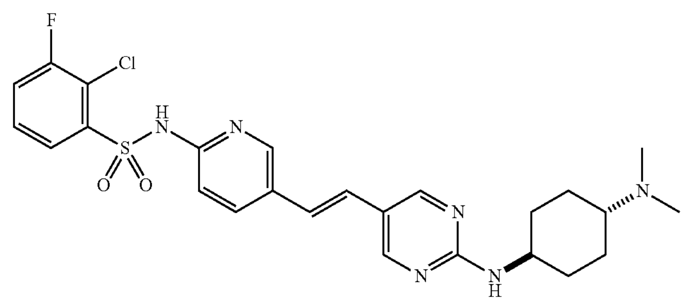 | 2-chloro-N-(5-((E)-2-(2-(((1r,4r)-4-(dimethylamino)cyclohexyl)amino)pyrimidin-5-yl)vinyl)pyridin-2-yl)-3-fluorobenzenesulfonamide |
| 69 | 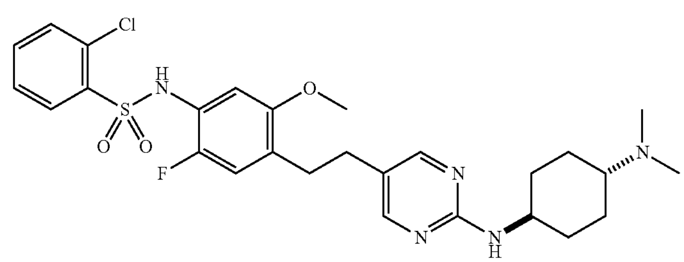 | 2-chloro-N-(4-(2-(2-(((1r,4r)-4-(dimethylamino)cyclohexyl)amino)pyrimidin-5-yl)ethyl)-2-fluoro-5-methoxyphenyl)benzenesulfonamide |
| 70 | 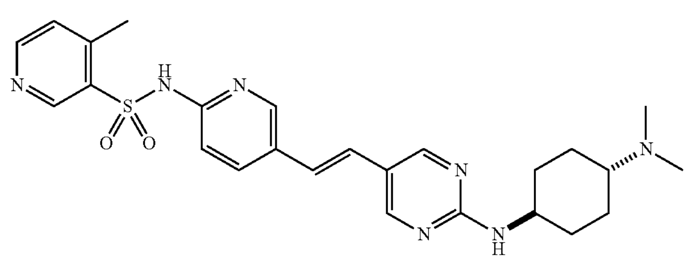 | N-(5-((E)-2-(2-(((1r,4r)-4-(dimethylamino)cyclohexyl)amino)pyrimidin-5-yl)vinyl)pyridin-2-yl)-4-methylpyridine-3-sulfonamide |

TABLE 1-continued

| Compound No. | Structure | Compound Name |
| --- | --- | --- |
| 71 | 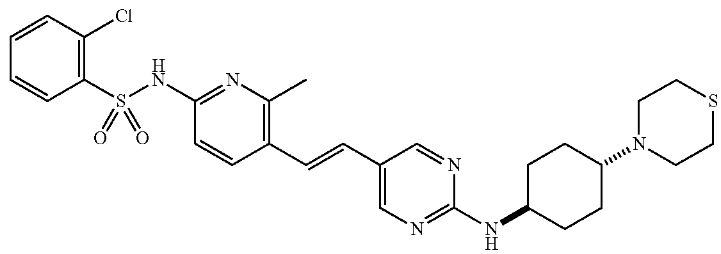 | 2-chloro-N-(6-methyl-5-((E)-2-(2-(((1r,4r)-4-thiomorpholinocyclohexyl)amino)pyrimidin-5-yl)vinyl)pyridin-2-yl)benzenesulfonamide |
| 72 | 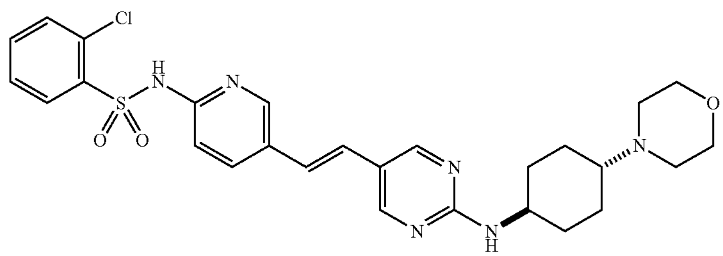 | 2-chloro-N-(5-((E)-2-(2-(((1r,4r)-4-morpholinocyclohexyl)amino)pyrimidin-5-yl)vinyl)pyridin-2-yl)benzenesulfonamide |

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^3H$ and $^{14}C$ are incorporated, are useful in drug and/or substrate tissue distribution assays. Tritiated, i. e., $^3H$ and carbon-14, i. e., $^{14}C$, isotopes are particularly preferred for their ease of preparation and detectability. Further, substitution with heavy isotopes such as deuterium, i.e., $^2H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or MeOH. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. Also described herein are methods of treating diseases by administering such prodrugs. Further described herein are methods of treating diseases by administering such prodrugs as pharmaceutical compositions.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds described herein. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound described herein.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In some embodiments, compounds having free amino, amido, hydroxy or carboxylic groups are converted into prodrugs. For instance, free carboxyl groups are derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

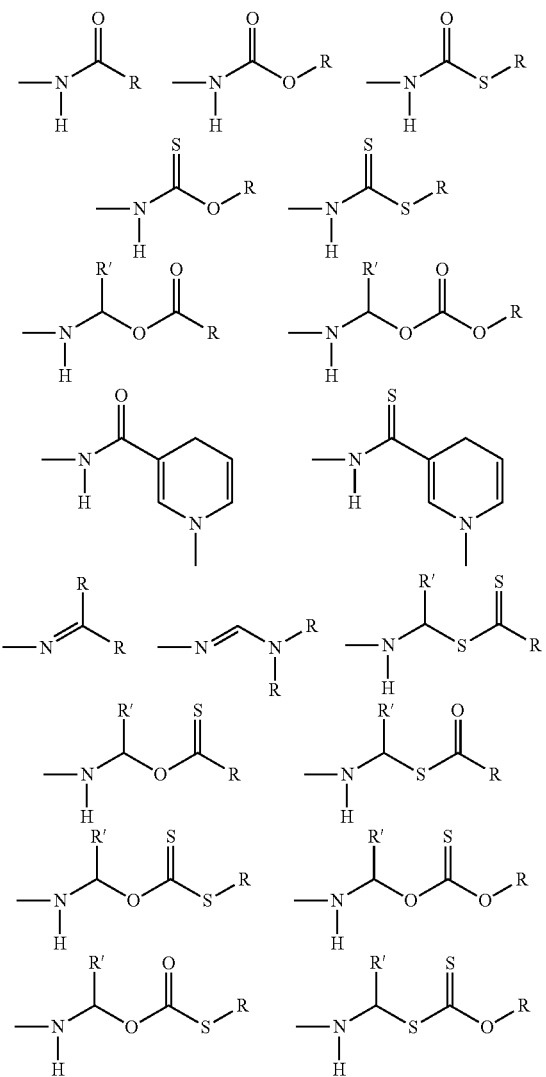

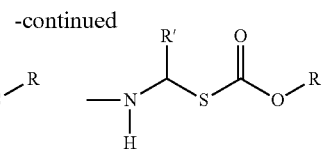

as well as sulfonamides and phosphonamides.

In certain instances, sites on any aromatic ring portions are susceptible to various metabolic reactions, therefore incorporation of appropriate substituents on the aromatic ring structures, reduce, minimize or eliminate this metabolic pathway.

IRE1-Like Family of Proteins

In some embodiments, a compound disclosed herein selectively binds to a protein of the IRE1 family of proteins. Exemplary IRE1 family proteins include IRE1, IRE1α, or ERN1. Other exemplary IRE1 family proteins include IRE1 homologues or orthologues in other organisms. Exemplary organisms include human, non-human primate, mouse, rat, chicken, fruit fly, yeast, and others listed in Table 2. In some embodiments, the IRE1 protein is human IRE1α.

TABLE 2

| Organism | Accession # |
| --- | --- |
| Homo sapiens | NP_001424.3 |
| Mus musculus | NP_076402.1 |
| Rattus norvegicus | XP_006247696.1 |

Figure 2:
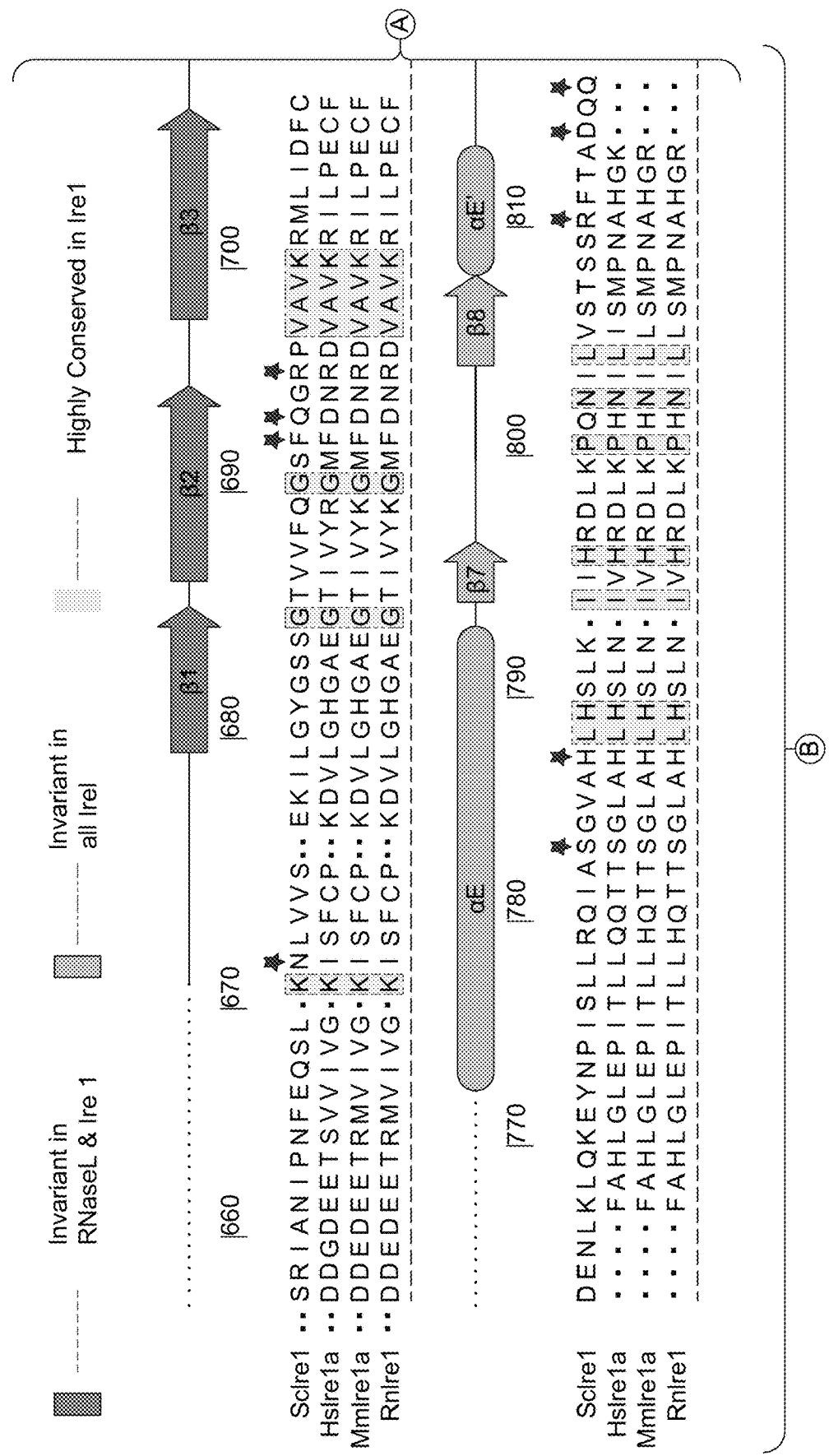
FIG. 2 shows an example alignment of the C-terminal half IRE1 orthologues from yeast (ScIre1), human (HsIre1), mouse (MmIre1), and rat (RnIRE1). Stars indicate kinase domain dimer interface residues. Circles indicate Kinase extension nuclease (KEN) domain dimer interface residues. Triangles indicate putative nuclease active site residues.
Figure 2:
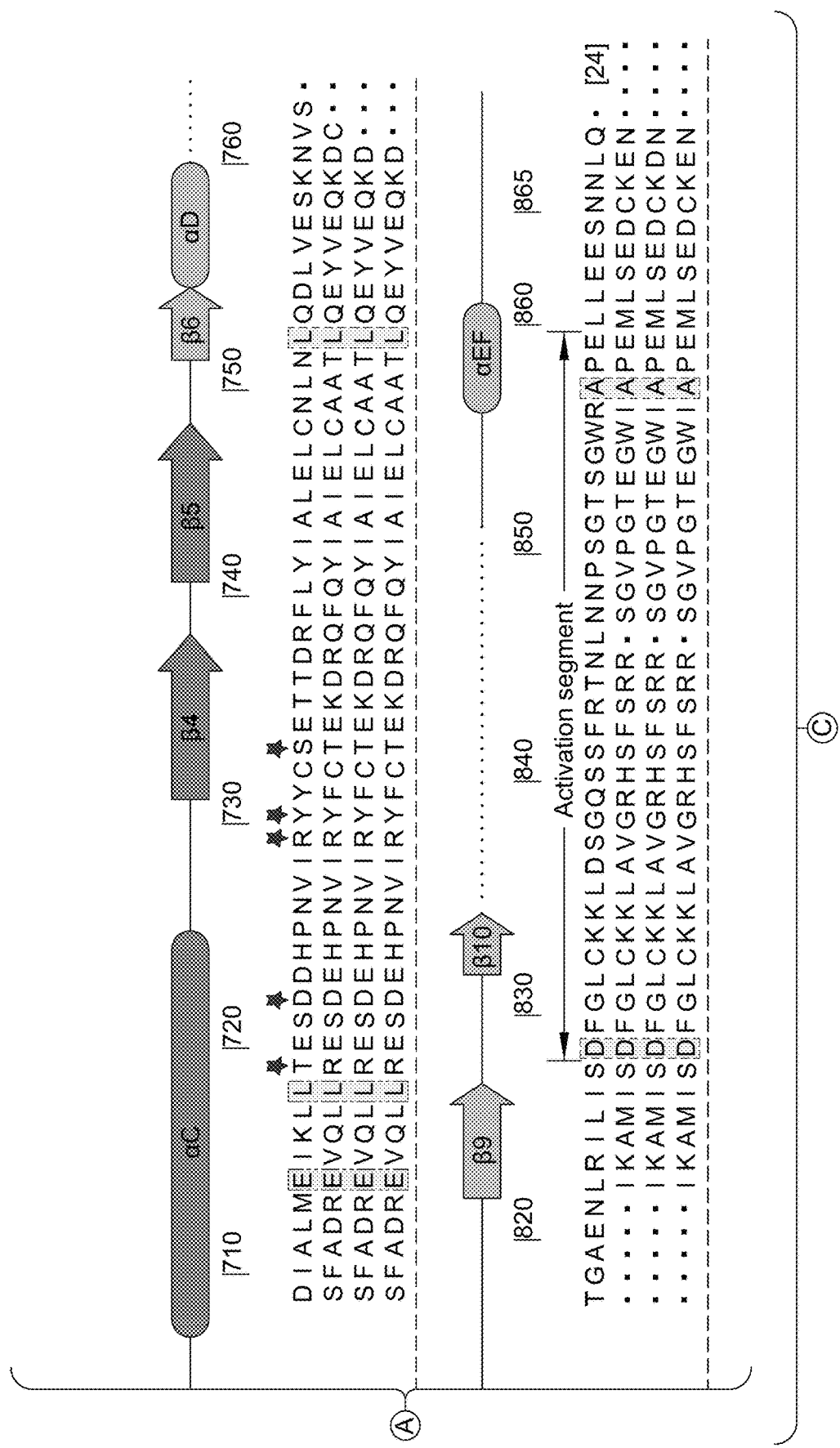
Figure 2:
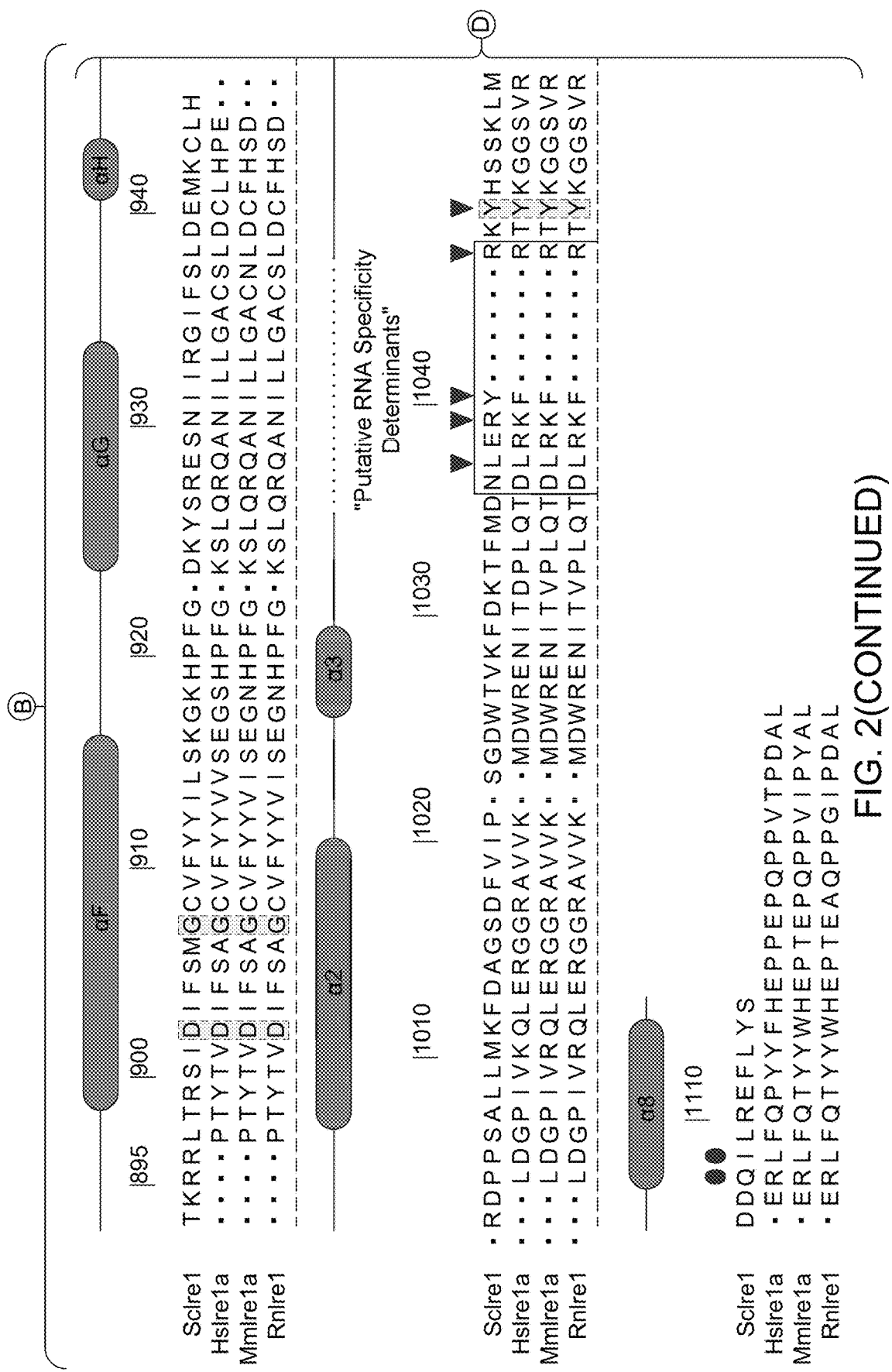
Figure 2:
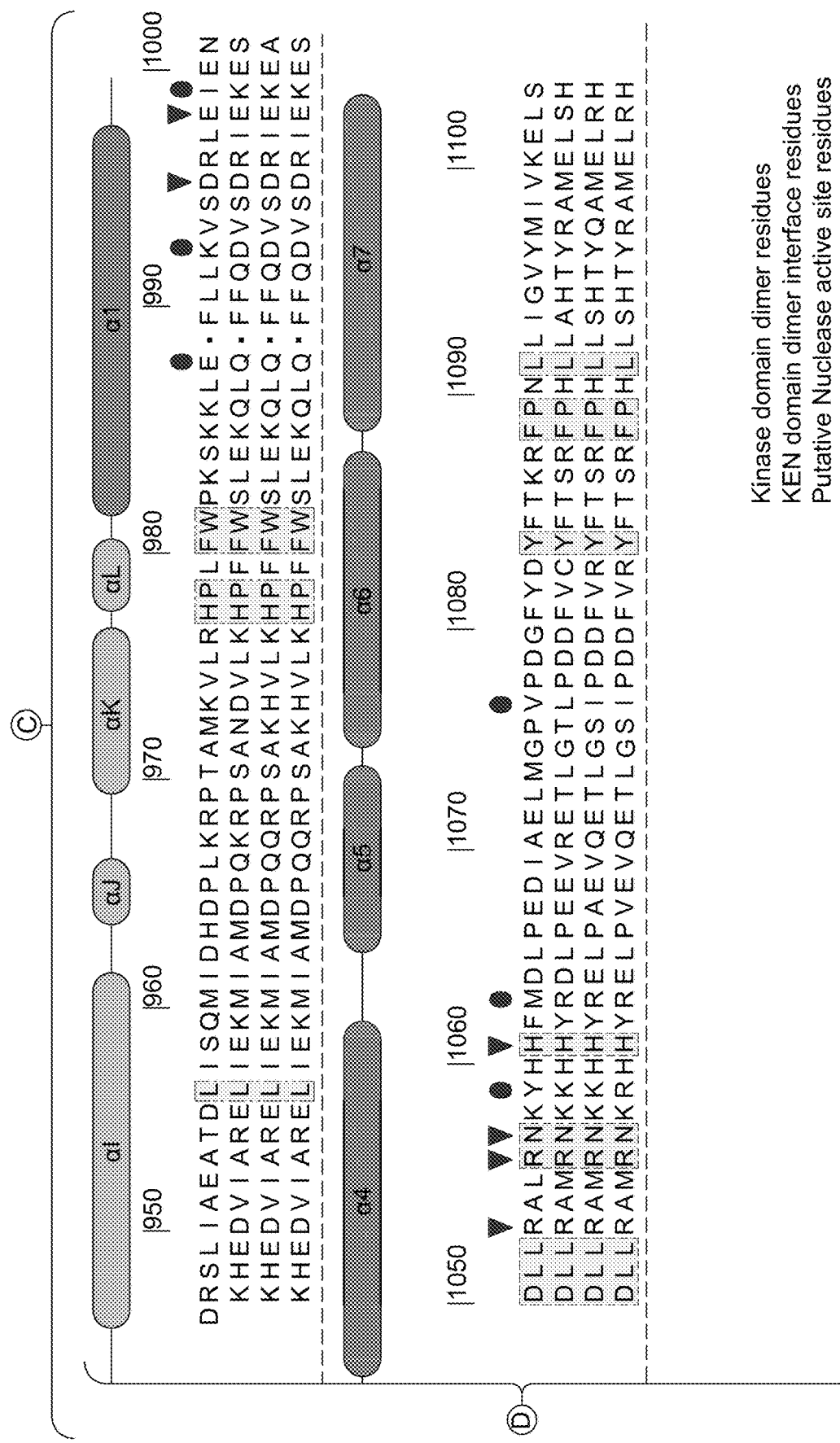

In some embodiments, a compound disclosed herein selectively binds to an IRE1 family protein comprising a kinase domain and/or an RNase domain. In some embodiments, the kinase domain is a trans-autophosphorylation kinase domain. In some embodiments, the IRE1 family protein is IRE1α. An example arrangement of domains within an IRE1a protein is depicted in FIG. 1. An example alignment of IRE1 family protein orthologues is depicted in FIG. 2.

In some embodiments, a compound disclosed herein selectively binds to a trans-autophosphorylation kinase domain region of IRE1α. In some embodiments, a compound disclosed herein selectively binds to a trans-autophosphorylation kinase domain region of IRE1α, for example within amino acid residues 568-833 of SEQ ID NO: 1, or equivalent amino acid residues thereof.

In some embodiments, a compound disclosed herein selectively binds to an ATP-binding pocket within a trans-autophosphorylation kinase domain region of IRE1α. In some embodiments, a compound disclosed herein selectively binds to an ATP-binding pocket within a trans-autophosphorylation kinase domain region of IRE1α, for example, one or more of amino acid resides 577-711, 577-586, 597, 599, 626, 642-643, 645, 648, 688, 692-693, 695, or 711 of SEQ ID NO: 1, or equivalent amino acid residues thereof.

In some embodiments, a compound disclosed herein selectively binds to an activation loop within a trans-autophosphorylation kinase domain region of IRE1α. In some embodiments, a compound disclosed herein selectively binds to an activation loop within a trans-autophosphorylation kinase domain region of IRE1α, for example, one or more of amino acid residues 710-736, 710-725, or 729-736 of SEQ ID NO: 1, or equivalent amino acid residues thereof.

In some embodiments, a compound disclosed herein selectively binds to an RNase domain region of IRE1α. In some embodiments, a compound disclosed herein selectively binds to an RNase domain region of IRE1α, for example within amino acid residues 835-963 of SEQ ID NO: 1, or equivalent amino acid residues thereof.

In some embodiments, a compound disclosed herein selectively binds to a kinase domain dimer interface amino acid residue. In some embodiments, a compound disclosed herein selectively binds to a kinase domain dimer interface amino acid residue, such as one or more of amino acid residues 569-701, 569, 591, 592, 594, 617, 620, 627, 628, 631, 674, 678, or 701 of SEQ ID NO: 1.

In some embodiments, a compound disclosed herein selectively binds to a first IRE1a and blocks dimerization between kinase domain dimer interface amino acid residues of the first IRE1a and a second IRE1α. In some embodiments, a compound disclosed herein selectively binds to a first IRE1α, and inhibit dimerization at one or more of amino acid residues 569-701, 569, 591, 592, 594, 617, 620, 627, 628, 631, 674, 678, or 701 of SEQ ID NO: 1.

In some embodiments, a compound disclosed herein selectively binds to a kinase-extension nuclease (KEN) domain dimer interface amino acid residue of an IRE1α. In some embodiments, a compound disclosed herein selectively binds to a KEN domain dimer interface amino acid residue, such as one or more of amino acid residues 840-925, 840, 844, 851, 908, 912, or 925 of SEQ ID NO: 1.

In some embodiments, a compound disclosed herein selectively binds to amino acid residues of a nuclease active site. In some embodiments, a compound disclosed herein selectively binds to amino acid residues of a nuclease active site, such as one or more of amino acid residues 847-910, 847, 850, 886, 888, 889, 890, 892, 902, 905, 906, or 910 of SEQ ID NO: 1.

In some embodiments, a compound disclosed herein selectively binds to an RNase domain and a trans-autophosphorylation kinase domain region of IRE1α. In some embodiments, a compound disclosed herein selectively binds to an RNase domain and an ATP-binding pocket within a trans-autophosphorylation kinase domain region of IRE1α. In some embodiments, a compound disclosed herein selectively binds to an RNase domain and an activation loop within a trans autophosphorylation kinase domain region of IRE1α.

In some embodiments, a compound disclosed herein selectively binds to IRE1a at two sites located in an RNase domain, trans-autophosphorylation kinase domain region, ATP-binding pocket, activation loop, or any combination thereof. In some embodiments, a compound disclosed herein selectively binds to IRE1a at two or more sites. In some embodiments, a compound disclosed herein selectively binds to IRE1a at two or more sites located in an RNase domain, trans-autophosphorylation kinase domain region, ATP-binding pocket, activation loop, or any combination thereof. In some embodiments, a compound disclosed herein selectively binds to IRE1a at three sites located in an RNase domain, trans-autophosphorylation kinase domain region, ATP-binding pocket, activation loop, or any combination thereof.

In some embodiments, a compound disclosed herein selectively binds to IRE1a at a first site located in an RNase domain, trans-autophosphorylation kinase domain region, ATP-binding pocket, or activation loop. In some embodiments, a first site comprises one or more of any amino acid residue within amino acid residues 465-977 of SEQ ID NO: 1. In some embodiments, a compound disclosed herein selectively binds to IRE1a at a second site located in an RNase domain, trans-autophosphorylation kinase domain region, ATP-binding pocket, or activation loop. In some examples, the first site is located within the same domain or region as the second site. In some examples, the first site is located within a different domain or region as the second site.

In some embodiments, a compound disclosed herein selectively binds to first IRE1α, thereby blocking dimerization of the first IRE1a to a second IRE1α. In some embodiments, a compound disclosed herein selectively binds to first IRE1α, thereby blocking auto-transphosphorylation of the first IRE1a or a second IRE1a to which the first IRE1a is dimerized. In some embodiments, a compound disclosed herein selectively binds to a first IRE1α, thereby blocking activation of the first IRE1a or a second IRE1a to which the first IRE1a is dimerized. In some embodiments, a compound disclosed herein selectively binds to a first IRE1α, thereby blocking kinase activity of the first IRE1a or a second IRE1a to which the first IRE1a is dimerized. In some embodiments, a compound disclosed herein selectively binds to a first IRE1α, thereby blocking RNase activity of the first IRE1a or a second IRE1a to which the first IRE1a is dimerized.

In some embodiments, a compound disclosed herein selectively binds to IRE1a when in a homo-dimerized conformation. In some embodiments, a compound disclosed herein selectively binds to IRE1a when in an oligomerized conformation. In some embodiments, a compound disclosed herein selectively binds to IRE1a when in a non-oligomerized or non-dimerized conformation. In some embodiments, a compound disclosed herein selectively binds to IRE1a when in an ATP-bound state. In some embodiments, a compound disclosed herein selectively binds to a IRE1 family protein when in a non-ATP-bound state. In some embodiments, the compound is a pharmaceutically acceptable salt, or solvate thereof.

IRE1 Signaling Pathway

In some embodiments, a compound disclosed herein selectively binds to an IRE1 family protein and alters a downstream signaling pathway. In some embodiments, a compound disclosed herein selectively binds to an IRE1 family protein and alters signaling of immunoglobulin heavy-chain binding protein (BIP), protein kinase R (PKR)-like endoplasmic reticulum kinase (PERK), glucose regulate protein 78 (Grp78), eukaryotic translation initiation factor 2α (eIF2α), X-box binding protein 1 (XBP1), activating transcription factor 6α (ATF6α), C/EBP homologous protein (CHOP), growth arrest and DNA damage-inducible protein 34 (GADD34), tumor necrosis factor receptor-associated factor 2 (TRAF2), JUN N-terminal kinase (JNK), regulated IRE1-dependent decay (RIDD), transcriptionally active XBP1 (XBP1s), or unspliced XBP1 (XBP1u). In some embodiments, a compound disclosed herein selectively binds to an IRE1 family protein and alters a downstream cellular process. In some embodiments, an IRE1 family protein is IRE1, IRE1α, or ERN1.

In some embodiments, a compound disclosed herein selectively binds to an IRE1 family protein and decreases or blocks a downstream signaling pathway. In some embodiments, a compound disclosed herein selectively binds to an IRE1 family protein and decreases or blocks activity or signaling of TXNIP, Caspase 1, Interleukin 1-beta, JNK, Bim, cytochrome C, Caspase 3, Caspase 8, mRNA degradation, miRNA degradation, apoptotosis-inducing proteins, or inflammation-inducing proteins. In some embodiments, a compound disclosed herein selectively binds to an IRE1 family protein and decreases XBP1 mRNA levels. In some embodiments, a compound disclosed herein selectively binds to an IRE1 family protein and decreases transcriptionally active XBP1 (XBP1s) mRNA levels. In some embodiments, a compound disclosed herein selectively binds to an IRE1 family protein and decreases spliced XBP1 mRNA levels. In some embodiments, an IRE1 family protein is IRE1, IRE1α, or ERN1.

In some embodiments, a compound disclosed herein selectively binds to an IRE1 family protein and increases, activates, or removes a block of a downstream signaling pathway. In some embodiments, a compound disclosed herein selectively binds to an IRE1 family protein and increases, activates, or removes a block of activity or signaling of Bcl2, Bcl-XL, Mcl-1, Bax, Bak, other anti-apoptotic proteins, or an mRNA translocon proteins. In some embodiments, an IRE1 family protein is IRE1, IRE1α, or ERN1.

In some embodiments, a compound disclosed herein selectively binds to an IRE1family protein and disrupts binding with an effector protein. In some cases, the effector protein binds to the IRE1 family protein when in a dimerized or oligomerized state. In some cases, the effector protein binds to the IRE1 family protein when in a non-dimerized or non-oligomerized state. In some cases, the effector protein is immunoglobulin heavy-chain binding protein (BIP), protein kinase R (PKR)-like endoplasmic reticulum kinase (PERK), glucose regulate protein 78 (Grp78), tumor necrosis factor receptor-associated factor 2 (TRAF2), JUN N-terminal kinase (JNK), transcriptionally active XBP1 (XBP1s), unspliced XBP1 (XBP1u), regulated IRE1-dependent decay (RIDD), Heat shock protein 90 kDa alpha (HSP 90-alpha), or misfolded protein. In some embodiments, an IRE1 family protein is IRE1, IRE1α, or ERN1.

In some embodiments, a compound disclosed herein selectively binds to an IRE1 family protein and alters activity of a cellular process or cellular function, such as regulated IRE1-dependent decay (RIDD), RNA decay, translation, autophagy, cell survival, ER protein folding, ERAD, reactive oxygen species generation, transport, ER-associated protein degradation (ERAD), protein synthesis, or apoptosis. In some embodiments, where an altered or lack of a cellular process or cellular function is associate with a disease state, selective binding of a compound disclosed herein results in inhibiting or alleviating the disease state, or inhibiting a deleterious activity associated with the disease state. In some embodiments, an IRE1 family protein is IRE1, IRE1α, or ERN1.

Diseases Associated with Altered IRE1 Pathway Signaling

In some cases, a compound disclosed herein is used to treat or ameliorate a disease associated with altered IRE1α pathway signaling when administered to a subject in need thereof. In some cases, a compound disclosed herein is used to treat or ameliorate the effects of a disease associated with altered IRE1α pathway signaling when administered to a subject in need thereof. Exemplary disease associated with altered IRE1α signaling include cancer. In some cases, a compound disclosed herein is used to treat or ameliorate a cancer when administered to a subject in need thereof. Exemplary cancers include tumors, solid and hematologic cancers. In some cases, a compound disclosed herein is used to treat or ameliorate a cell proliferative disorder when administered to a subject in need thereof. In some cases, the cell proliferative disorder is a cancer. In some cases, the solid cancer is ovarian cancer, breast cancer, bladder cancer, or triple negative breast cancer (TNBC). In some cases, the hematological cancer is a leukemia, lymphoma, and multiple myeloma.

An IRE1α pathway can be involved in a variety of pathological conditions, including neurodegenerative diseases, inflammation, metabolic disorders, liver dysfunction, brain ischemia, heart ischemia, autoimmune diseases, and cancer. In some cases, modulation of this pathway provides therapeutic methods useful for treatment of such diseases.

In some instances, a compound disclosed herein is used to reinforce anti-tumor mechanisms. In some cases, an anti-tumor mechanism comprises direct inhibition of tumor growth. In some cases, an anti-tumor mechanism comprises induction of anti-tumor immunity. In some cases, anti-tumor mechanisms comprise direct inhibition of tumor growth and simultaneous induction of anti-tumor immunity. In some cases, a compound disclosed herein can prevent lipid accumulation in myeloid cells exposed to ovarian cancer-derived ascites supernatants. In some cases, a compound disclosed herein can block myeloid cell immunosuppression mediated by tumor-associated factors. In some cases, a compound disclosed herein can be employed as therapeutic compound that enhances dendritic cell and T cell anti-tumor activity in mammals. For example, the compounds disclosed herein can be used to treat murine and human ovarian cancers.

Exemplary compounds of the present invention have a mean $EC_{50}$ of about 0.01 nm to about 100, more preferably from about 0.01 nm to about 50 nm and even more preferably from about 0.01 nm to about 5 nm or even from about 0.01 nm to about 2 nm in an in vitro luciferase assay as described in example 2.

Exemplary compounds have a mean EC50 of about 2 nM to about 100 nM in a XBP1 slicing assay as described in Example 6.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from administration of any one of the compounds disclosed. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (e.g., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%), 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg to 5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the LD50 and the ED50. The dose ratio between the toxic and therapeutic effects is the therapeutic index and it is expressed as the ratio between LD50 and ED50. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the ED50 with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day, e.g., two, three, four or more times daily.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents. In one embodiment, the therapeutic effectiveness of one of the compounds described herein is enhanced by administration of an adjuvant {i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

Representative Illustrative Embodiments

In a first embodiment, provided is a compound of Formula (I), or a pharmaceutically acceptable salt, or solvate thereof:

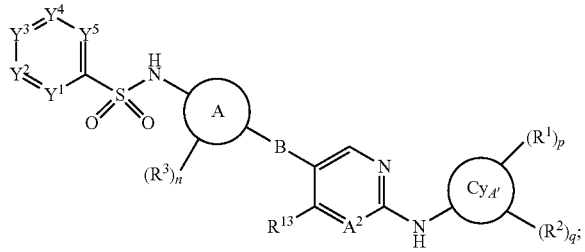

Formula (I)

wherein,

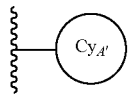

is $C_3$-$C_{10}$cycloalkyl;

each $R^1$ is independently —$OR^{6a}$, —$SR^{6a}$, —$S(=O)R^7$, —$S(=O)_2R^7$, or —$N(R^{6b})_2$;

each $R^2$ is independently halogen, —CN, —$OR^{8a}$, —$SR^{8a}$, —$S(=O)R^9$, —$S(=O)_2R^9$, —$S(=O)_2N(R^{8b})_2$, —$NR^{8a}S(=O)_2R^9$, —$C(=O)R^9$, —$OC(=O)R^9$, —$CO_2R^{8a}$, —$OCO_2R^9$, —$N(R^{8b})_2$, —OC (=O)N(R$^{8b}$)$_2$, —NR$^{8a}$C(=O)R$^9$, —NR$^{8a}$C(=O)OR$^9$, optionally substituted C$_1$-C$_4$alkyl, optionally substituted C$_1$-C$_4$fluoroalkyl, optionally substituted C$_1$-C$_4$heteroalkyl, optionally substituted C$_3$-C$_6$cycloalkyl, optionally substituted aryl, or optionally substituted heteroaryl;

Y$^5$ is CR$^4$;

Y$^1$, Y$^2$, Y$^3$, and Y$^4$ are each independently selected from N and CR$^5$ with the proviso that no more than two of Y$^1$, Y$^2$, Y$^3$, and Y$^4$ are N;

each R$^{6a}$ is independently H, optionally substituted C$_1$-C$_4$alkyl, optionally substituted C$_1$-C$_4$heteroalkyl, optionally substituted C$_1$-C$_4$fluoroalkyl, —X-optionally substituted C$_1$-C$_4$alkyl, —X-optionally substituted C$_1$-C$_4$heteroalkyl, —X-optionally substituted C$_1$-C$_4$fluoroalkyl, optionally substituted C$_3$-C$_6$cycloalkyl, optionally substituted C$_3$-C$_4$cycloalkylC$_1$-C$_3$alkyl, optionally substituted C$_2$-C$_{10}$heterocycloalkyl, optionally substituted aryl, or optionally substituted heteroaryl;

each R$^{6b}$ is independently H, optionally substituted C$_1$-C$_4$alkyl, optionally substituted C$_1$-C$_4$heteroalkyl, optionally substituted C$_1$-C$_4$fluoroalkyl, —X-optionally substituted C$_1$-C$_4$alkyl, —X-optionally substituted C$_1$-C$_4$heteroalkyl, —X-optionally substituted C$_1$-C$_4$fluoroalkyl, optionally substituted C$_3$-C$_6$cycloalkyl, optionally substituted C$_3$-C$_4$cycloalkylC$_1$-C$_3$alkyl, optionally substituted C$_2$-C$_{10}$heterocycloalkyl, optionally substituted aryl, or optionally substituted heteroaryl;

or two R$^{6b}$ are taken together with the N atom to which they are attached to form an optionally substituted heterocycle;

X is —C(=O)—;

each R$^7$ is independently optionally substituted C$_1$-C$_4$alkyl, optionally substituted C$_1$-C$_4$heteroalkyl, optionally substituted C$_1$-C$_4$fluoroalkyl, optionally substituted C$_3$-C$_6$cycloalkyl, optionally substituted C$_2$-C$_{10}$heterocycloalkyl, optionally substituted aryl, or optionally substituted heteroaryl;

each R$^{8a}$ is independently H, optionally substituted C$_1$-C$_4$alkyl, optionally substituted C$_1$-C$_4$heteroalkyl, optionally substituted C$_1$-C$_4$fluoroalkyl, optionally substituted C$_3$-C$_6$cycloalkyl, optionally substituted C$_2$-C$_{10}$heterocycloalkyl, optionally substituted aryl, or optionally substituted heteroaryl;

each R$^{8b}$ is independently H, optionally substituted C$_1$-C$_4$alkyl, optionally substituted C$_1$-C$_4$heteroalkyl, optionally substituted C$_1$-C$_4$fluoroalkyl, optionally substituted C$_3$-C$_6$cycloalkyl, optionally substituted C$_2$-C$_{10}$heterocycloalkyl, optionally substituted aryl, or optionally substituted heteroaryl;

or two R$^{8b}$ are taken together with the N atom to which they are attached to form an optionally substituted heterocycle;

each R$^9$ is independently optionally substituted C$_1$-C$_4$alkyl, optionally substituted C$_1$-C$_4$heteroalkyl, or optionally substituted C$_1$-C$_4$fluoroalkyl, optionally substituted C$_3$-C$_6$cycloalkyl, optionally substituted C$_2$-C$_{10}$heterocycloalkyl, optionally substituted aryl, or optionally substituted heteroaryl;

A$^2$ is N or CR$^4$;

R$^4$ is H, halogen, optionally substituted C$_1$-C$_4$alkyl, optionally substituted C$_1$-C$_4$fluoroalkyl, optionally substituted aryl, or —OR$^{10}$;

R$^{41}$, R$^{42}$, R$^{43}$ and R$^{44}$ are each independently H, optionally substituted C$_1$-C$_4$alkyl, optionally substituted C$_1$-C$_4$fluoroalkyl, or optionally substituted aryl;

R$^{10}$ is independently H, optionally substituted C$_1$-C$_4$alkyl, optionally substituted C$_1$-C$_4$fluoroalkyl, optionally substituted C$_1$-C$_4$heteroalkyl, optionally substituted C$_3$-C$_6$cycloalkyl, optionally substituted C$_2$-C$_{10}$heterocycloalkyl, optionally substituted aryl, or optionally substituted heteroaryl;

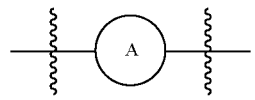

is phenylene or a 6-membered heteroarylene ring comprising 1 or 2 nitrogen atoms in the ring;

B is

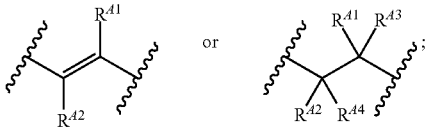

each R$^3$ is independently halogen, —CN, —OR$^{11}$, —SR$^{11}$, —N(R$^{11}$)$_2$, optionally substituted C$_1$-C$_4$alkyl, optionally substituted C$_1$-C$_4$fluoroalkyl, optionally substituted C$_1$-C$_4$heteroalkyl, optionally substituted C$_3$-C$_6$cycloalkyl, optionally substituted C$_2$-C$_{10}$heterocycloalkyl, optionally substituted aryl, or optionally substituted heteroaryl;

each R$^{11}$ is independently H, optionally substituted C$_1$-C$_4$alkyl, optionally substituted C$_1$-C$_4$fluoroalkyl, optionally substituted C$_1$-C$_4$heteroalkyl, optionally substituted C$_3$-C$_6$cycloalkyl, optionally substituted C$_2$-C$_{10}$heterocycloalkyl, optionally substituted aryl, or optionally substituted heteroaryl;

n is 0, 1, 2, 3, or 4;

p is 1, 2, or 3;

q is 0, 1, 2, or 3;

R$^4$ and each R$^5$ are each independently H, halogen, —CN, —OR$^{12}$, —SR$^{12}$, —N(R$^{12}$)$_2$, optionally substituted C$_1$-C$_4$alkyl, optionally substituted C$_1$-C$_4$fluoroalkyl, optionally substituted C$_1$-C$_4$heteroalkyl, optionally substituted C$_3$-C$_6$cycloalkyl, optionally substituted C$_2$-C$_{10}$heterocycloalkyl, optionally substituted aryl, or optionally substituted heteroaryl;

R$^{12}$ is independently H, optionally substituted C$_1$-C$_4$alkyl, optionally substituted C$_1$-C$_4$fluoroalkyl, optionally substituted C$_1$-C$_4$heteroalkyl, optionally substituted C$_3$-C$_6$cycloalkyl, optionally substituted C$_2$-C$_{10}$heterocycloalkyl, optionally substituted aryl, or optionally substituted heteroaryl; and R$^{13}$ is H or unsubstituted C$_1$-C$_4$alkyl.

In a second embodiment, provided are the compounds of the first embodiment, or a pharmaceutically acceptable salt, or solvate thereof, wherein B is

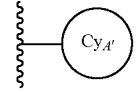

In a third embodiment, provided are the compounds of the first embodiment, or a pharmaceutically acceptable salt, or solvate thereof, wherein B is

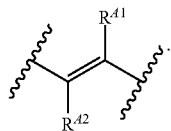

In a fourth embodiment, provided are any of the compounds of embodiment 3, or a pharmaceutically acceptable salt, or solvate thereof, wherein $R^{A3}$ is H, optionally substituted $C_1$-$C_4$alkyl, or optionally substituted $C_1$-$C_4$fluoroalkyl.

In a fifth embodiment, provided are any of the compounds of embodiment 4, or a pharmaceutically acceptable salt, or solvate thereof, wherein $R^{A3}$ is H.

In a sixth embodiment, provided are any of the compounds of embodiment 4 or 5, or a pharmaceutically acceptable salt, or solvate thereof, wherein $R^{A4}$ is H, optionally substituted $C_1$-$C_4$alkyl, or optionally substituted $C_1$-$C_4$fluoroalkyl.

In a seventh embodiment, provided are any of the compounds of embodiment 6, or a pharmaceutically acceptable salt, or solvate thereof, wherein $R^{A4}$ is H.

In an eighth embodiment, provided are any of the compounds of embodiments 1-7, or a pharmaceutically acceptable salt, or solvate thereof, wherein $R^{A1}$ is H, optionally substituted $C_1$-$C_4$alkyl, or optionally substituted $C_1$-$C_4$fluoroalkyl.

In a ninth embodiment, provided are any of the compounds of embodiment 8, or a pharmaceutically acceptable salt, or solvate thereof, wherein $R^{A1}$ is H.

In a tenth embodiment, provided are any of the compounds of embodiments 1-9, or a pharmaceutically acceptable salt, or solvate thereof, wherein $R^{A2}$ is H, optionally substituted $C_1$-$C_4$alkyl, or optionally substituted $C_1$-$C_4$fluoroalkyl.

In an eleventh embodiment, provided are any of the compounds of embodiment 10, or a pharmaceutically acceptable salt, or solvate thereof, wherein $R^{A2}$ is H.

In a twelfth embodiment, provided are any of the compounds of embodiments 1-11, or or a pharmaceutically acceptable salt, or solvate thereof, wherein

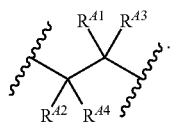

is $C_4$-$C_7$ cycloalkyl.

In a thirteenth embodiment, provided are any of the compounds of embodiments 1-12, or a pharmaceutically acceptable salt, or solvate thereof, wherein each $R^1$ is —N($R^{6b}$)$_2$.

In a fourteenth embodiment, provided are any of the compounds of embodiments 1-13, or a pharmaceutically acceptable salt, or solvate thereof, wherein each p is 1.

In a fifteenth embodiment, provided are any of the compounds of embodiments 1-14, or a pharmaceutically acceptable salt, or solvate thereof, wherein

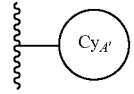

is

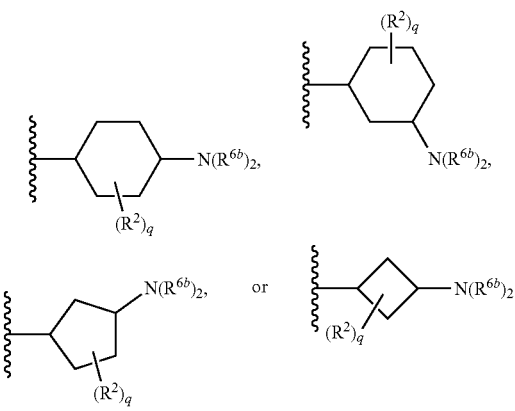

In a sixteenth embodiment, provided are any of the compounds of embodiments 1-15, or a pharmaceutically acceptable salt, or solvate thereof, wherein

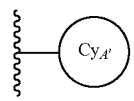

is

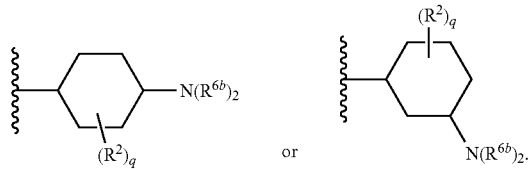

In an seventeenth embodiment, provided are any of the compounds of embodiments 1-16, wherein q is 0 or 1.

In a eighteenth embodiment, provided are any of the compounds of embodiments 1-17, or a pharmaceutically acceptable salt, or solvate thereof, wherein each $R^{6b}$ is independently H, optionally substituted $C_1$-$C_4$alkyl, optionally substituted $C_1$-$C_4$heteroalkyl, optionally substituted $C_1$-$C_4$fluoroalkyl, —X-optionally substituted $C_1$-$C_4$alkyl, —X-optionally substituted $C_1$-$C_4$heteroalkyl, or —X-optionally substituted $C_1$-$C_4$fluoroalkyl.

In a nineteenth embodiment, provided are any of the compounds of embodiments 1-18, or a pharmaceutically acceptable salt, or solvate thereof, wherein each $R^{6b}$ is independently H, optionally substituted $C_1$-$C_3$alkyl, optionally substituted $C_1$-$C_3$fluoroalkyl, optionally substituted $C_1$-$C_3$heteroalkyl, or optionally substituted $C_3$-$C_4$cyclooalkyl-$C_1$-$C_3$alkyl.

In an twentieth embodiment, provided are any of the compounds of embodiment 19, or a pharmaceutically acceptable salt, or solvate thereof, wherein each $R^{6b}$ is independently H, —CH$_2$CH$_2$CH$_3$, —CH$_2$CH$_3$, or —CH$_3$.

In a twenty-first embodiment, provided are any of the compounds of embodiment 19, or a pharmaceutically acceptable salt, or solvate thereof, wherein each $R^{6b}$ is independently hydrogen or optionally substituted C$_1$-C$_3$alkyl.

In a twenty-second embodiment, provided are any of the compounds of embodiment 21, or a pharmaceutically acceptable salt, or solvate thereof, wherein each $R^{6b}$ is hydrogen.

In a twenty-third embodiment, provided are any of the compounds of embodiment 21, or a pharmaceutically acceptable salt, or solvate thereof, wherein each $R^{6b}$ is optionally substituted C$_1$-C$_3$alkyl.

In a twenty-fourth embodiment, provided are any of the compounds of embodiments 1-16, or a pharmaceutically acceptable salt, or solvate thereof, wherein two $R^{6b}$ are taken together with the N atom to which they are attached to form an optionally substituted heterocycle.

In a twenty-fifth embodiment, provided are any of the compounds of embodiment 24, or a pharmaceutically acceptable salt, or solvate thereof, wherein two $R^{6b}$ are taken together with the N atom to which they are attached to form an optionally substituted heterocycle selected from piperidinyl, morpholinyl, and thiomorpholinyl.

In a twenty-sixth embodiment, provided are any of the compounds of embodiments 1-25, or a pharmaceutically acceptable salt, or solvate thereof, wherein each $R^2$ is independently optionally substituted C$_1$-C$_4$alkyl, optionally substituted C$_1$-C$_4$heteroalkyl, optionally substituted C$_1$-C$_4$fluoroalkyl.

In a twenty-seventh embodiment, provided are any of the compounds of embodiments 1-26, or a pharmaceutically acceptable salt, or solvate thereof, wherein each $R^2$ is independently halogen, —CN, optionally substituted C$_1$-C$_4$alkyl, optionally substituted C$_1$-C$_4$heteroalkyl, or optionally substituted C$_1$-C$_4$fluoroalkyl or optionally substituted C$_3$-C$_6$cycloalkyl.

In a twenty-eighth embodiment, provided are any of the compounds of embodiments 1-27, or a pharmaceutically acceptable salt, or solvate thereof, wherein each $R^2$ is independently halogen, —CN, optionally substituted C$_1$-C$_4$alkyl, optionally substituted C$_1$-C$_4$fluoroalkyl, optionally substituted C$_1$-C$_4$heteroalkyl, optionally substituted C$_3$-C$_6$cycloalkyl, optionally substituted aryl, or optionally substituted heteroaryl.

In a twenty-ninth embodiment, provided are any of the compounds of embodiments 1-28, or a pharmaceutically acceptable salt, or solvate thereof, wherein q is 0.

In a thirtieth embodiment, provided are any of the compounds of embodiments 1-29, or a pharmaceutically acceptable salt, or solvate thereof, wherein $A^2$ is N.

In a thirty-first embodiment, provided are any of the compounds of embodiments 1-29, or a pharmaceutically acceptable salt, or solvate thereof, wherein $A^2$ is $CR^4$.

In a thirty-second embodiment, provided are any of the compounds of embodiment 31, or a pharmaceutically acceptable salt, or solvate thereof, wherein $R^4$ is H, optionally substituted C$_1$-C$_4$alkyl, or optionally substituted C$_1$-C$_4$fluoroalkyl.

In a thirty-third embodiment, provided are any of the compounds of embodiment 32, or a pharmaceutically acceptable salt, or solvate thereof, wherein $R^4$ is H.

In a thirty-fourth embodiment, provided are any of the compounds of embodiments 1-33, or a pharmaceutically acceptable salt, or solvate thereof, wherein

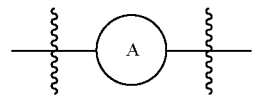

is pyridinylene, pyrimidinylene, pyrazinylene, and pyridazinylene.

In a thirty-fifth embodiment, provided are any of the compounds of embodiments 1-33, or a pharmaceutically acceptable salt, or solvate thereof, wherein

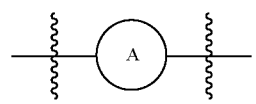

is phenylene.

In a thirty-sixth embodiment, provided are any of the compounds of embodiment 35, or a pharmaceutically acceptable salt, or solvate thereof, wherein:

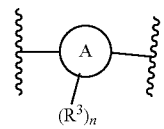

is

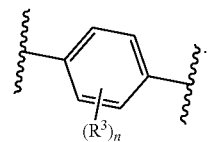

In a thirty-seventh embodiment, provided are any of the compounds of embodiment 34, or a pharmaceutically acceptable salt, or solvate thereof, wherein

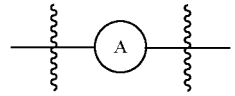

is pyridinylene.

In a thirty-eighth embodiment, provided are any of the compounds of embodiment 34, or a pharmaceutically acceptable salt, or solvate thereof, wherein:

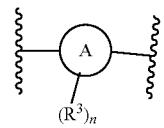

is

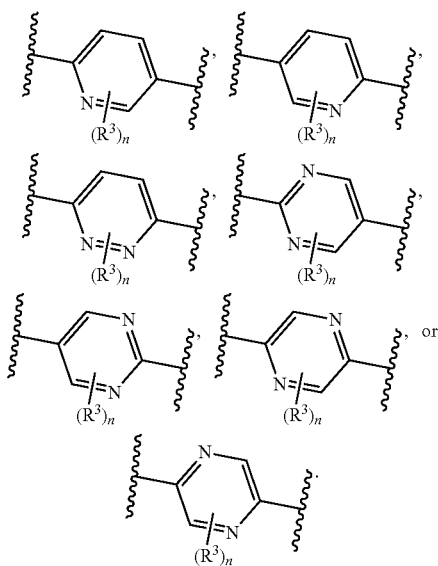

In a thirty-ninth embodiment, provided are any of the compounds of embodiment 34, or a pharmaceutically acceptable salt, or solvate thereof, wherein:

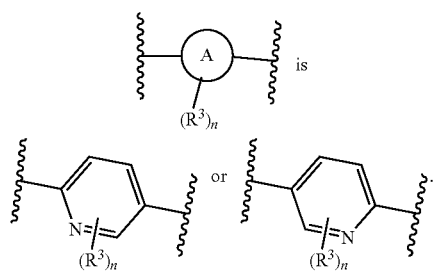

In a fortieth embodiment, provided are any of the compounds of embodiments 1-39, or a pharmaceutically acceptable salt, or solvate thereof, wherein n is 1.

In a forty-first embodiment, provided are any of the compounds of embodiment 38, or a pharmaceutically acceptable salt, or solvate thereof, wherein:

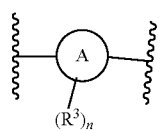

is

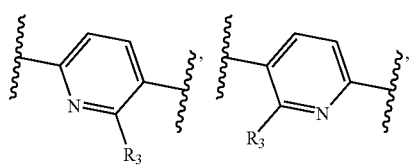

-continued

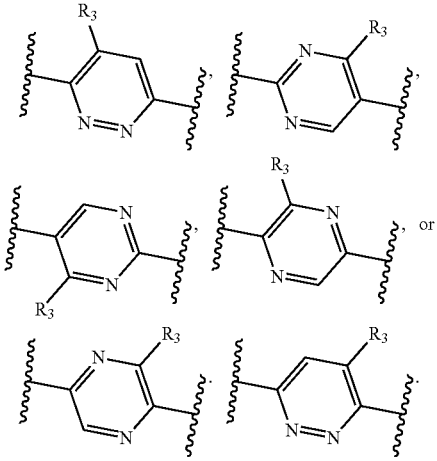

In a forty-second embodiment, provided are any of the compounds of embodiments 1-41, or a pharmaceutically acceptable salt, or solvate thereof, wherein each $R^3$ is independently halogen, —CN, —OR$^{11}$, —SR$^{11}$, optionally substituted $C_1$-$C_4$alkyl, or optionally substituted $C_1$-$C_4$fluoroalkyl.

In a forty-third embodiment, provided are any of the compounds of embodiment 42, or a pharmaceutically acceptable salt, or solvate thereof, wherein each $R^3$ is independently halogen, —CN, optionally substituted $C_1$-$C_4$alkyl, or optionally substituted $C_1$-$C_4$fluoroalkyl.

In a forty-fourth embodiment, provided are any of the compounds of embodiment 42, or a pharmaceutically acceptable salt, or solvate thereof, wherein each $R^3$ is independently —OR$^{11}$, optionally substituted $C_1$-$C_4$alkyl, or optionally substituted $C_1$-$C_4$fluoroalkyl.

In a forty-fifth embodiment, provided are any of the compounds of embodiment 44, or a pharmaceutically acceptable salt, or solvate thereof, wherein $R^3$ is optionally substituted $C_1$-$C_4$alkyl.

In a forty-sixth embodiment, provided are any of the compounds of embodiment 45, or a pharmaceutically acceptable salt, or solvate thereof, wherein $R^3$ is methyl, ethyl, propyl, or butyl.

In a forty-seventh embodiment, provided are any of the compounds of embodiment 44, or a pharmaceutically acceptable salt, or solvate thereof, wherein $R^3$ is —OR$^{11}$.

In a forty-eighth embodiment, provided are any of the compounds of embodiments 1-47, or a pharmaceutically acceptable salt, or solvate thereof, wherein $R^{11}$ is H, optionally substituted $C_1$-$C_4$alkyl, or optionally substituted $C_1$-$C_4$fluoroalkyl.

In a forty-ninth embodiment, provided are any of the compounds of embodiment 48, or a pharmaceutically acceptable salt, or solvate thereof, wherein $R^{11}$ is methyl, ethyl, propyl, or butyl.

In a fiftieth embodiment, provided are any of the compounds of embodiment 48, or a pharmaceutically acceptable salt, or solvate thereof, wherein $R^{11}$ is —CF$_3$ or —CH$_2$CF$_3$.

In a fifty-first embodiment, provided are any of the compounds of embodiments 1-39, or a pharmaceutically acceptable salt, or solvate thereof, wherein n is 0.

In a fifty-second embodiment, provided are any of the compounds of embodiments 1-51, or a pharmaceutically acceptable salt, or solvate thereof, wherein $R^4$ is H, halogen, —CN, —OR$^{12}$, —SR$^{12}$, —N(R$^{12}$)$_2$, optionally substituted $C_1$-$C_4$alkyl, or optionally substituted $C_1$-$C_4$fluoroalkyl.

In a fifty-third embodiment, provided are any of the compounds of embodiment 52, or a pharmaceutically acceptable salt, or solvate thereof, wherein $R^4$ is H, halogen, —CN, optionally substituted $C_1$-$C_4$alkyl, or optionally substituted $C_1$-$C_4$fluoroalkyl.

In a fifty-fourth embodiment, provided are any of the compounds of embodiment 53, or a pharmaceutically acceptable salt, or solvate thereof, wherein $R^4$ is H, halogen, or optionally substituted $C_1$-$C_4$alkyl.

In a fifty-fifth embodiment, provided are any of the compounds of embodiment 54, or a pharmaceutically acceptable salt, or solvate thereof, wherein $R^4$ is H.

In a fifty-sixth embodiment, provided are any of the compounds of embodiment 54, or a pharmaceutically acceptable salt, or solvate thereof, wherein $R^4$ is halogen.

In a fifty-seventh embodiment, provided are any of the compounds of embodiment 56, or a pharmaceutically acceptable salt, or solvate thereof, wherein $R^4$ is —Cl.

In a fifty-eighth embodiment, provided are any of the compounds of embodiment 52, or a pharmaceutically acceptable salt, or solvate thereof, wherein $R^4$ is —$OR^{12}$.

In a fifty-ninth embodiment, provided are any of the compounds of embodiment 58, or a pharmaceutically acceptable salt, or solvate thereof, wherein $R^{12}$ is H, optionally substituted $C_1$-$C_4$alkyl, or optionally substituted $C_1$-$C_4$fluoroalkyl.

In a sixtieth embodiment, provided are any of the compounds of embodiment 54, or a pharmaceutically acceptable salt, or solvate thereof, wherein $R^4$ is optionally substituted $C_1$-$C_4$alkyl.

In a sixty-first embodiment, provided are any of the compounds of embodiment 60, or a pharmaceutically acceptable salt, or solvate thereof, wherein $R^4$ is methyl, ethyl, propyl, or butyl.

In a sixty-second embodiment, provided are any of the compounds of embodiment 53, or a pharmaceutically acceptable salt, or solvate thereof, wherein $R^4$ is optionally substituted $C_1$-$C_4$fluoroalkyl.

In a sixty-third embodiment, provided are any of the compounds of embodiment 62, or a pharmaceutically acceptable salt, or solvate thereof, wherein $R^4$ is —$CF_3$ or —$CH_2CF_3$.

In a sixty-fourth embodiment, provided are any of the compounds of embodiments 1-63, or a pharmaceutically acceptable salt, or solvate thereof, wherein each $R^5$ is independently H, halogen, —CN, —$OR^{12}$, —$SR^{12}$, —$N(R^{12})_2$, optionally substituted $C_1$-$C_4$alkyl, or optionally substituted $C_1$-$C_4$fluoroalkyl.

In a sixty-fifth embodiment, provided are any of the compounds of embodiments 1-64, or a pharmaceutically acceptable salt, or solvate thereof, wherein each $R^5$ is independently H, halogen, —CN, -optionally substituted $C_1$-$C_4$alkyl, or optionally substituted $C_1$-$C_4$fluoroalkyl.

In a sixty-sixth embodiment, provided are any of the compounds of embodiments 1-65, or a pharmaceutically acceptable salt, or solvate thereof, wherein each $R^5$ is independently H, halogen, or optionally substituted $C_1$-$C_4$alkyl.

In a sixty-seventh embodiment, provided are any of the compounds of embodiment 66, or a pharmaceutically acceptable salt, or solvate thereof, wherein each $R^5$ is H.

In a sixty-eighth embodiment, provided are any of the compounds of embodiment 66, or a pharmaceutically acceptable salt, or solvate thereof, wherein each $R^5$ is independently H or halogen.

In a sixty-ninth embodiment, provided are any of the compounds of embodiment 68, or a pharmaceutically acceptable salt, or solvate thereof, wherein each $R^5$ is independently H or —Cl.

In a seventieth embodiment, provided are any of the compounds of embodiment 64, or a pharmaceutically acceptable salt, or solvate thereof, wherein each $R^5$ is independently H or —$OR^{12}$.

In a seventy-first embodiment, provided are any of the compounds of embodiment 66, or a pharmaceutically acceptable salt, or solvate thereof, wherein each $R^5$ is independently H or optionally substituted $C_1$-$C_4$alkyl.

In a seventy-second embodiment, provided are any of the compounds of embodiment 71, or a pharmaceutically acceptable salt, or solvate thereof, wherein each $R^5$ is independently H or methyl, ethyl, propyl, or butyl.

In a seventy-third embodiment, provided are any of the compounds of embodiment 65, or a pharmaceutically acceptable salt, or solvate thereof, wherein each $R^5$ is independently H or optionally substituted $C_1$-$C_4$fluoroalkyl.

In a seventy-fourth embodiment, provided are any of the compounds of embodiment 73, or a pharmaceutically acceptable salt, or solvate thereof, wherein each $R^5$ is independently H, —$CF_3$, or —$CH_2CF_3$.

In a seventy-fifth embodiment, provided are any of the compounds of embodiments 1-74, or a pharmaceutically acceptable salt, or solvate thereof, wherein one of $Y^1$, $Y^2$, $Y^3$, and $Y^4$ is N.

In a seventy-sixth embodiment, provided are any of the compounds of embodiments 1-74, or a pharmaceutically acceptable salt, or solvate thereof, wherein two of $Y^1$, $Y^2$, $Y^3$, and $Y^4$ are N.

In a seventy-seventh embodiment, provided are any of the compounds of embodiments 1-74, or a pharmaceutically acceptable salt, or solvate thereof, wherein none of $Y^1$, $Y^2$, $Y^3$, and $Y^4$ is N.

In a seventy-eighth embodiment, provided are any of the compounds of embodiments 1-77, or a pharmaceutically acceptable salt, or solvate thereof, wherein $R^{13}$ is H.

In a seventy-ninth embodiment, provided are any of the compounds of embodiments 1-77, or a pharmaceutically acceptable salt, or solvate thereof, wherein the compound has the structure of any one of formula (Ia)-(Ip) set forth herein.

In an eightieth embodiment, provided are any of the compounds of embodiment 79, or a pharmaceutically acceptable salt, or solvate thereof, wherein one, two, three, or four of $R^5$ is hydrogen.

In an eighty-first embodiment, provided are any of the compounds of embodiments 79 or 80, or a pharmaceutically acceptable salt, or solvate thereof, having the Formula (Io) or (Ip) wherein $R^4$ is chlorine; each $R^{6b}$ is independently selected from hydrogen, —$CH_3$, or —$CH_2CH_3$; each $R^5$ is independently selected from hydrogen, fluorine, or chlorine; each $R^3$ is independently selected from —$CH_3$, —$OCH_3$, —$CH_2CH_3$, or fluorine;

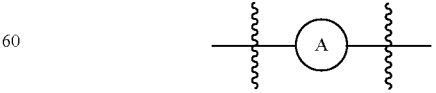

is phenylene, pyridazinyl, pyrimidinyl, pyrazinyl, or pyridinyl; and n is 0, 1, or 2.

In an eight-second embodiment, provided are any of the compounds of embodiment 81, or a pharmaceutically acceptable salt, or solvate thereof, wherein each $R^{6b}$ is hydrogen; each $R^{6b}$ is —$CH_3$; or one of $R^{6b}$ is —$CH_3$ or —$CH_2CH_3$ and the other is hydrogen.

In an eighty-third embodiment, provided are any of the compounds of embodiments 79-82, or a pharmaceutically acceptable salt, or solvate thereof, wherein each $R^3$ is independently selected from —$CH_3$ or —$OCH_3$, and n is 1.

In an eighty-fourth embodiment, provided are any of the compounds of embodiments 79-83, or a pharmaceutically acceptable salt, or solvate thereof, wherein:

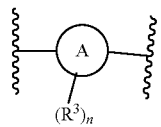

is

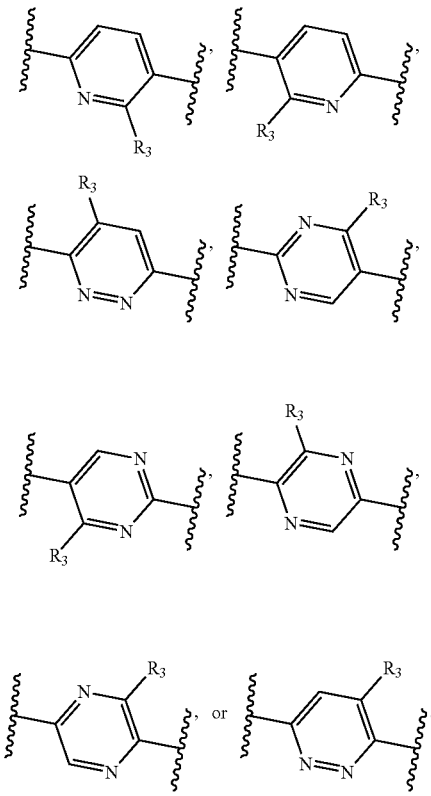

In an eighty-fifth embodiment, provided are any of the compounds of embodiment 84, or a pharmaceutically acceptable salt, or solvate thereof, wherein:

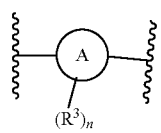

is

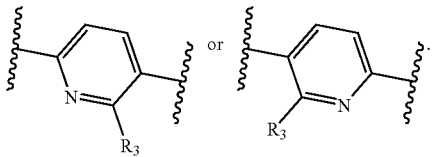

In an eighty-sixth embodiment, provided are any of the compounds of embodiments 79 or 80, or a pharmaceutically acceptable salt, or solvate thereof, wherein

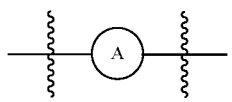

is phenylene, R is fluorine or —$CH_3$, and n is 1 or 2; or

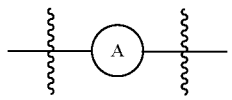

is pyridnyl, R is —$OCH_3$, $CH_3$, —$CH_2CH_3$, or fluorine, and n is 1 or 2.

In an eighty-seventh embodiment, provided are any of the compounds of embodiments 79-86, or a pharmaceutically acceptable salt, or solvate thereof, wherein one or two of $R^5$ is chlorine or fluorine and the rest of $R^5$ are hydrogen.

In an eighty-eighth embodiment, provided are any of the compounds of embodiments 79-86, or a pharmaceutically acceptable salt, or solvate thereof, wherein each $R^5$ is hydrogen.

In an eighty-ninth embodiment, provided are any of the compounds of embodiments 79 or 80, or a pharmaceutically acceptable salt, or solvate thereof, having the Formula (Ic) or (Id), wherein $Y^1$ and $Y^3$ are $CR^5$ and $Y^2$ is nitrogen.

In a ninetieth embodiment, provided are any of the compounds of embodiments 1-89, or a pharmaceutically acceptable salt, or solvate thereof, wherein when optional substituents are present, the optional substituents are selected from D, halogen, —CN, —$NH_2$, —NH($CH_3$), —N($CH_3$)$_2$, —OH, —$CO_2H$, —$CO_2(C_1$-$C_4$alkyl), —$CH_2NH_2$, —C(=O)$NH_2$, —C(=O)NH($C_1$-$C_4$alkyl), —C(=O)N($C_1$-$C_4$alkyl)$_2$, —S(=O)$_2NH_2$, —S(=O)$_2$NH($C_1$-$C_4$alkyl), —S(=O)$_2$N($C_1$-$C_4$alkyl)$_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —$SC_1$-$C_4$alkyl, —S(=O)$C_1$-$C_4$alkyl, and —S(=O)$_2C_1$-$C_4$alkyl.

In a ninety-first embodiment, provided are any of the compounds of embodiments 1-89, or a pharmaceutically acceptable salt, or solvate thereof, wherein when optional substituents are present, the optional substituents are selected from D, halogen, —CN, —$NH_2$, —OH, —NH($CH_3$), —N($CH_3$)$_2$, —$CH_3$, —$CH_2CH_3$, —$CH_2NH_2$, —$CF_3$, —$OCH_3$, —$OCF_2H$ and —$OCF_3$.

In a ninety-second embodiment, provided are any of the compounds of embodiments 1-89, or a pharmaceutically acceptable salt, or solvate thereof, wherein there are no optional substituents.

In a ninety-third embodiment, provided are any of the compounds 1-72 shown in Table 1, or a pharmaceutically acceptable salt or solvate thereof.

In a ninety-fourth embodiment, provided are any of the compounds of embodiments 1-93, or a pharmaceutically acceptable salt, or solvate thereof, wherein the compound or pharmaceutically acceptable salt, or solvate thereof, selectively binds to IRE1α at one or more binding sites.

In a ninety-fifth embodiment, provided are any of the compounds of embodiment 93, wherein the IRE1α comprises an RNase domain, a kinase domain, or any combination thereof.

In a ninety-sixth embodiment, provided are any of the compounds of embodiments 94 or 95, wherein the kinase domain comprises an ATP-binding pocket.

In a ninety-seventh embodiment, provided are pharmaceutical compositions comprising any of the compounds of embodiments 1-96, or a pharmaceutically acceptable salt or solvate thereof.

In a ninety-eighth embodiment, provided are pharmaceutical compositions comprising any of the compounds of embodiments 1-96, or a pharmaceutically acceptable salt or solvate thereof, and one or more pharmaceutically acceptable excipients.

In a ninety-ninth embodiment, provided are methods for treating or ameliorating the effects of a disease associated with altered IRE1 signaling, the method comprising administering to a subject in need thereof a pharmaceutical composition, wherein the pharmaceutical composition comprises any of the compounds of embodiments 1-96, or a pharmaceutically acceptable salt or solvate thereof, or a pharmaceutical composition of embodiments 97 or 98. The disease can be for example, cancer. The cancer can be, for example, a solid cancer or a hematologic cancer. The cancer can be, for example, ovarian cancer, breast cancer, or triple negative breast cancer (TNBC).

In a one-hundredth embodiment, provided are any of the compounds of embodiments 1-96, or a pharmaceutically acceptable salt or solvate thereof, for use as a medicament, for example for use in the treatment of cancer.

EXAMPLES

I. Chemical Synthesis

In some embodiments, the compounds that modulate IRE1 mediated signaling disclosed herein are synthesized according to the following examples. As used below, and throughout the description of the invention, the following abbreviations, unless otherwise indicated, shall be understood to have the following meanings:
° C. degrees Celsius
$δ_H$ chemical shift in parts per million downfield from tetramethylsilane
ACN acetonitrile
n-Bu normal butyl
t-Bu tert-butyl
Boc tert-butyloxycarbonyl
Cy cyclohexyl
dba dibenzylideneacetone
dppf bis(diphenylphosphino)ferrocene
DCM dichloromethane ($CH_2Cl_2$)
DIEA N,N-diisopropylethylamine
DMSO dimethylsulfoxide
EA ethyl acetate
Et ethyl
FA formic acid
g gram(s)
h hour(s)
HPLC high performance liquid chromatography
Hz hertz
J coupling constant (in NMR spectrometry)
LCMS liquid chromatography mass spectrometry
μ/u micro
m multiplet (spectral); meter(s); milli
M molar
$M^+$ parent molecular ion
Me methyl
MHz megahertz
min minute(s)
mol mole(s); molecular (as in mol wt)
mL milliliter
MS mass spectrometry
NBS N-bromosuccinimide
NCS N-chlorosuccinimide
nm nanometer(s)
NMR nuclear magnetic resonance
pH potential of hydrogen; a measure of the acidity or basicity of an aqueous solution
PE petroleum ether
Py pyridine
RT room temperature
s singlet (spectral)
t triplet (spectral)
T temperature
TEA triethylamine
TFA trifluoroacetic acid
THF tetrahydrofuran The following examples are intended to illustrate but not limit the disclosed embodiments.

Example 1A: Synthesis of 2-nitrobenzenesulfonohydrazide

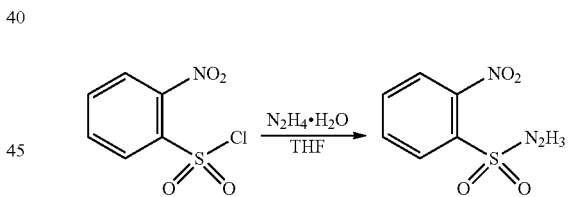

To a solution of 2-nitrobenzenesulfonyl chloride (1.0 g, 4.5 mmol) in THF (5.0 mL) was added hydrazine hydrate (576 mg, 11.3 mmol, 559.5 uL) at −30° C. The mixture was stirred at 25° C. for 10 min. Ethyl acetate (10.0 mL) and petroleum ether (20.0 mL) were added to the reaction mixture and the mixture was filtered. The filtered cake was washed with petroleum ether (10 mL×3) to afford 2-nitrobenzenesulfonohydrazide (900 mg).

Example 2A: Synthesis of N-(6-bromo-5-methoxy-pyridin-3-yl)-2-chlorobenzenesulfonamide

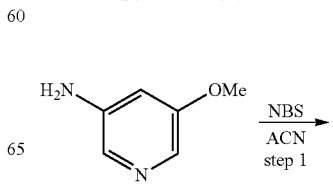

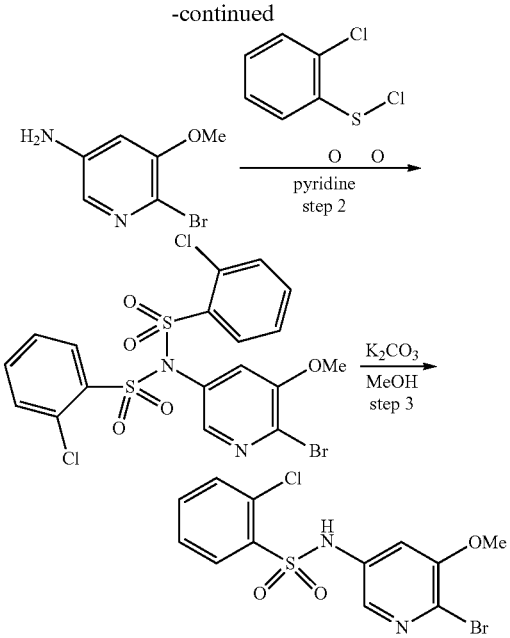

Step 1:

To a solution 5-methoxypyridin-3-amine (2.0 g, 16.1 mmol) in ACN (50.0 mL) at 0° C. for 1 h, and then added NBS (2.9 g, 16.1 mmol) at 0° C. slowly. The mixture was stirred at 20° C. for 2 h. The reaction mixture was concentrated under reduced pressure. The residue was purified by column chromatography ($SiO_2$) to afford 6-bromo-5-methoxypyridin-3-amine (1.4 g, 24.4% yield). $^1$H NMR (400 MHz, DMSO-$d_6$) δ 7.30 (d, J=2.2 Hz, 1H), 6.65 (d, J=2.2 Hz, 1H), 5.54 (s, 2H), 3.76 (s, 3H).

Step 2:

To a solution of 6-bromo-5-methoxypyridin-3-amine (1.4 g, 6.9 mmol) in pyridine (20.0 mL) was added 2-chlorobenzenesulfonyl chloride (1.8 g, 8.3 mmol, 1.1 mL). The mixture was stirred at 45° C. for 12 h. The reaction mixture was concentrated under reduced pressure to give a crude N-(6-bromo-5-methoxypyridin-3-yl)-2-chloro-N-((2-chlorophenyl)sulfonyl)benzenesulfonamide (3.8 g).

Step 3:

To a solution of N-(6-bromo-5-methoxypyridin-3-yl)-2-chloro-N-((2-chlorophenyl)sulfonyl) benzenesulfonamide in MeOH (20.0 mL) was added $K_2CO_3$ (2.8 g, 20.6 mmol). The mixture was stirred at 60° C. for 12 h. The reaction mixture was concentrated under reduced pressure. The residue was diluted with $H_2O$ (20.0 mL) and extracted with ethyl acetate (20.0 mL×3). The combined organic layers were washed with brine (50.0 mL), dried over $Na_2SO_4$, filtered and concentrated under reduced pressure to give a residue. The residue was purified by column chromatography ($SiO_2$) to give N-(6-bromo-5-methoxypyridin-3-yl)-2-chlorobenzenesulfonamide (720 mg, 26.9% yield). M+H$^+$=379.0 (LCMS).

Example 1: Synthesis of N-(4-((E)-2-(2-(((1r,4r)-4-aminocyclohexyl)amino)pyrimidin-5-yl)vinyl)-3-methylphenyl)-2-chlorobenzenesulfonamide (Compound 5)

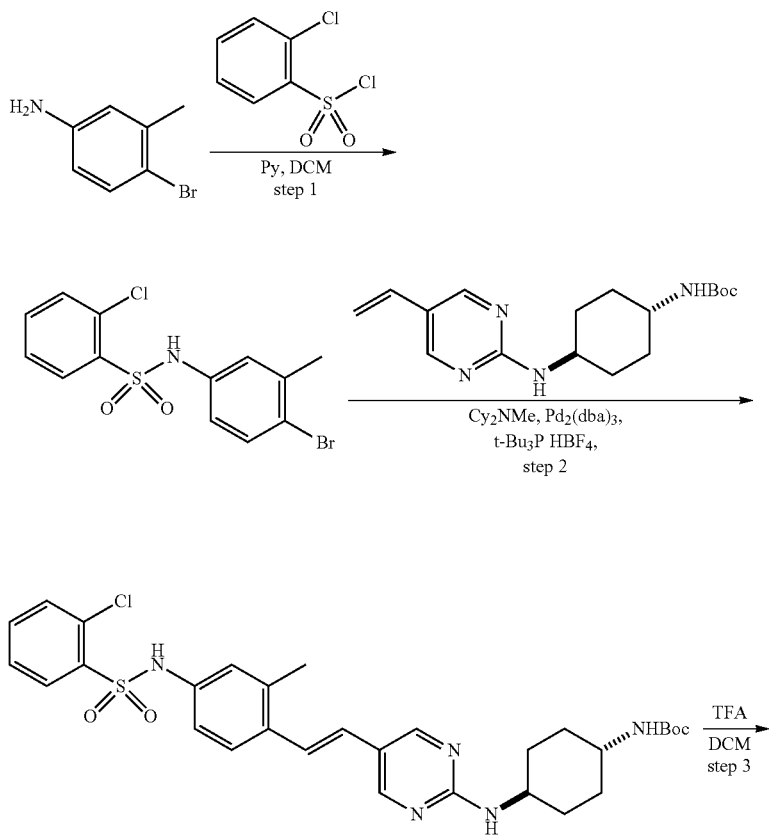

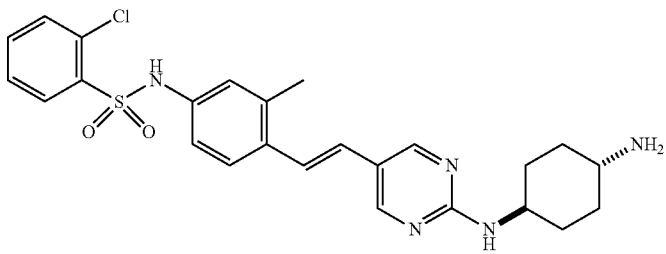

Step 1:

To a solution of 4-bromo-3-methylaniline (1.0 g, 5.3 mmol) and 2-chlorobenzene-1-sulfonyl chloride (1.4 g, 6.4 mmol, 878.3 uL) in DCM (20.0 mL) was added pyridine (1.3 g, 16.1 mmol, 1.3 mL). The mixture was stirred at 45° C. for 12 h. The reaction mixture was concentrated under reduced pressure to give a residue. The residue was purified by column chromatography (SiO$_2$) to give N-(4-bromo-3-methylphenyl)-2-chlorobenzenesulfonamide (1.8 g, 90.5% yield). M−H$^+$=359.9 (LCMS).

Step 2

A mixture of N-(4-bromo-3-methylphenyl)-2-chlorobenzenesulfonamide (150 mg, 415.9 umol), tert-butyl ((1r,4r)-4-((5-vinylpyrimidin-2-yl)amino)cyclohexyl)carbamate (158 mg, 499.0 umol), Cy$_2$NMe (243 mg, 1.2 mmol, 264.6 uL), t-Bu$_3$P HBF$_4$, (24 mg, 83.1 umol), and Pd$_2$(dba)$_3$ (76 mg, 83.1 umol) in dioxane (4.0 mL) was degassed and purged with N$_2$ three times, and then the mixture was stirred at 100° C. for 12 h under N$_2$ atmosphere. The reaction mixture was concentrated under reduced pressure to give a residue. The residue was purified by prep-TLC (SiO$_2$) to give tert-butyl ((1r,4r)-4-((5-((E)-4-(2-chlorophenylsulfonamido)-2-methylstyryl)pyrimidin-2-yl)amino)cyclohexyl)carbamate (30 mg, 10.7% yield). M+H$^+$=598.4 (LCMS); $^1$H NMR (400 MHz, CHLOROFORM-d) S 8.44-8.32 (m, 2H), 8.07-8.00 (m, 1H), 7.56-7.31 (m, 4H), 7.05-6.89 (m, 4H), 6.72-6.61 (m, 1H), 5.16 (br s, 1H), 4.41 (br s, 1H), 3.80 (br s, 1H), 3.47 (br s, 1H), 2.37-2.25 (m, 3H), 2.21-2.00 (m, 6H), 1.61 (br s, 2H), 1.39-1.19 (m, 6H).

Step 3:

To a solution of tert-butyl ((1r,4r)-4-((5-((E)-4-(2-chlorophenylsulfonamido)-2-methylstyryl)pyrimidin-2-yl)amino)cyclohexyl)carbamate (30 mg, 50.1 umol) in DCM (2.0 mL) was added TFA (1.5 g, 13.5 mmol, 1.0 mL). The mixture was stirred at 25° C. for 0.5 h. The mixture was concentrated under reduced pressure to give a residue. The residue was dissolved in MeOH (2.0 mL) and basified pH to 8 with NH$_3$·H$_2$O (25% solution), concentrated to give a residue. The residue was purified by pre-HPLC (FA condition) to give N-(4-((E)-2-(2-(((1r,4r)-4-aminocyclohexyl)amino)pyrimidin-5-yl)vinyl)-3-methylphenyl)-2-chlorobenzenesulfonamide (10.0 mg, 35.0% yield, formic acid salt (FA)). M+H$^+$=498.1 (LCMS); $^1$H NMR (400 MHz, METHANOL-d$_4$) δ 8.49 (br s, 1H), 8.45 (s, 2H), 8.09-8.03 (m, 1H), 7.57-7.49 (m, 2H), 7.46-7.37 (m, 2H), 7.13 (d, J=16.3 Hz, 1H), 7.02-6.92 (m, 2H), 6.74 (d, J=16.3 Hz, 1H), 3.86-3.72 (m, 1H), 3.12 (tt, J=3.8, 11.6 Hz, 1H), 2.29 (s, 3H), 2.21-2.04 (m, 4H), 1.63-1.35 (m, 4H).

Example 2: Synthesis of N-(6-(2-(2-(((1r,4r)-4-aminocyclohexyl)amino)pyrimidin-5-yl)ethyl)pyridazin-3-yl)-2-chlorobenzenesulfonamide (Compound 7)

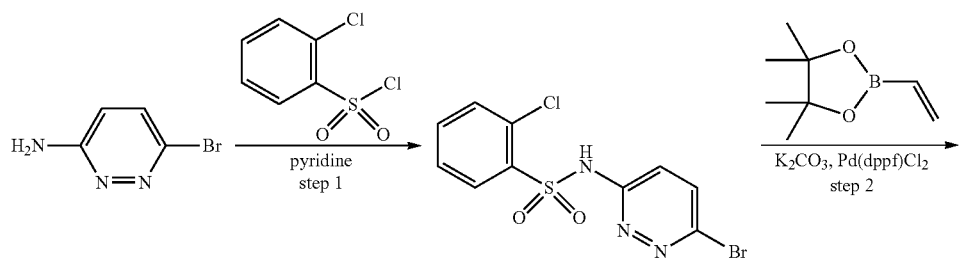

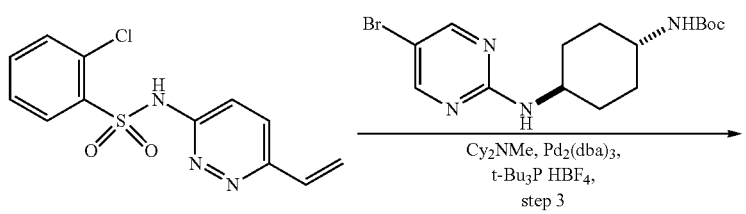

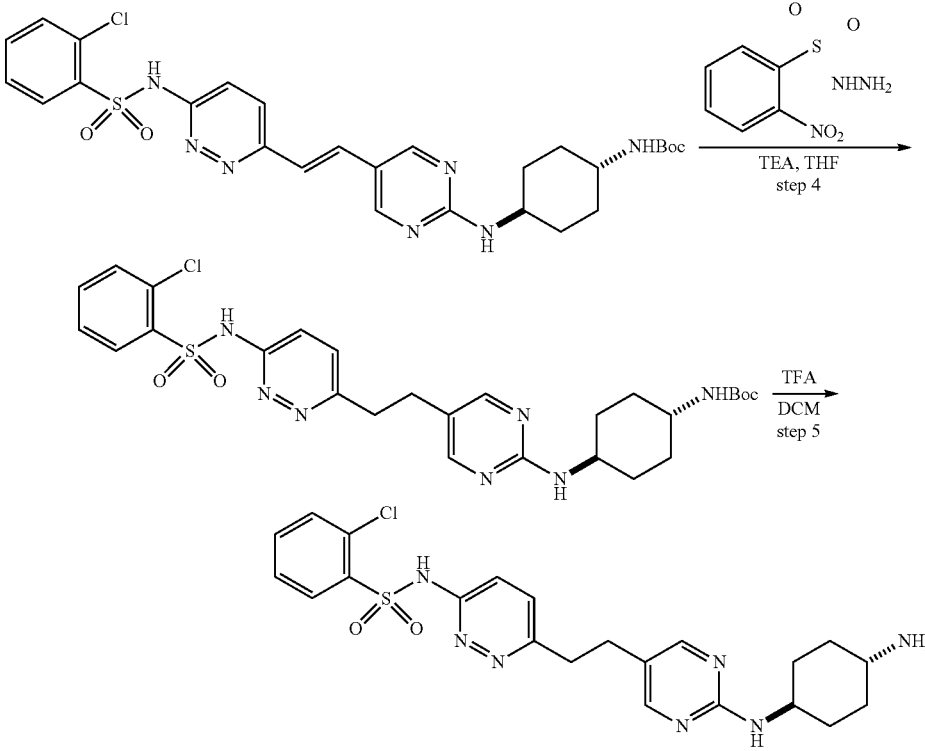

Step 1:
To a solution of 6-bromopyridazin-3-amine (4.0 g, 22.9 mmol) and 2-chlorobenzenesulfonyl chloride (5.8 g, 27.5 mmol, 3.7 mL) in pyridine (40.0 mL) was stirred at 45° C. for 12 h. The reaction mixture was concentrated under reduced pressure. The residue was purified by column chromatography ($SiO_2$) to afford N-(6-bromopyridazin-3-yl)-2-chlorobenzenesulfonamide (7.0 g, 72.1% yield). $M+H^+$=350.0 (LCMS).

Step 2:
A mixture of N-(6-bromopyridazin-3-yl)-2-chlorobenzenesulfonamide (500 mg, 1.4 mmol) and 4,4,5,5-tetramethyl-2-vinyl-1,3,2-dioxaborolane (265 mg, 1.7 mmol, 291.9 uL), $K_2CO_3$ (317 mg, 2.2 mmol), and $Pd(dppf)Cl_2$ (104 mg, 143.4 umol) in dioxane (10.0 mL) and $H_2O$ (1.0 mL) was degassed and purged with $N_2$ three times, and then the mixture was stirred at 90° C. for 12 h under $N_2$ atmosphere. The reaction mixture was concentrated under reduced pressure. The residue was purified by column chromatography ($SiO_2$) to afford 2-chloro-N-(6-vinylpyridazin-3-yl)benzenesulfonamide (400 mg, 77.0% yield). $M+H^+$=295.9 (LCMS).

Step 3:
A mixture of 2-chloro-N-(6-vinylpyridazin-3-yl)benzenesulfonamide (200 mg, 676.2 umol), tert-butyl ((1r,4r)-4-((5-bromopyrimidin-2-yl)amino)cyclohexyl)carbamate (209 mg, 563.5 umol), $Pd_2(dba)_3$ (103 mg, 112.7 umol), N-cyclohexyl-N-methyl-cyclohexanamine (330 mg, 1.6 mmol, 358.59 uL), and tritert-butylphosphonium; tetrafluoroborate (32 mg, 112.7 umol) in dioxane (3.0 mL) was degassed and purged with $N_2$ three times, and then the mixture was stirred at 100° C. for 12 h under $N_2$ atmosphere. The reaction mixture was concentrated under reduced pressure. The residue was purified by column chromatography ($SiO_2$) to afford tert-butyl ((1r,4r)-4-((5-((E)-2-(6-(2-chlorophenylsulfonamido)pyridazin-3-yl)vinyl)pyrimidin-2-yl)amino)cyclohexyl)carbamate (230 mg).

Step 4:
To a solution of tert-butyl ((1r,4r)-4-((5-((E)-2-(6-(2-chlorophenylsulfonamido)pyridazin-3-yl)vinyl)pyrimidin-2-yl)amino)cyclohexyl)carbamate (50 mg, 85.3 umol) and 2-nitrobenzenesulfonohydrazide (185 mg, 853.0 umol) in THF (4.0 mL) was added TEA (172 mg, 1.7 mmol, 237.4 uL). The mixture was stirred at 60° C. for 12 h. The reaction mixture was concentrated under reduced pressure. The residue was purified by prep-TLC ($SiO_2$) to afford tert-butyl((1r,4r)-4-((5-(2-(6-(2-chlorophenylsulfonamido)pyridazin-3-yl)ethyl)pyrimidin-2-yl)amino)cyclohexyl)carbamate (20 mg).

Step 5:
To a solution of tert-butyl((1r,4r)-4-((5-(2-(6-(2-chlorophenylsulfonamido)pyridazin-3-yl)ethyl)pyrimidin-2-yl)amino)cyclohexyl)carbamate (50 mg, 85.0 umol) in DCM (2.0 mL) was added TFA (1.5 g, 13.5 mmol, 1.0 mL). The mixture was stirred at 25° C. for 0.5 h. The reaction mixture was concentrated under reduced pressure. The residue was diluted with MeOH (2.0 mL), then used the ammonium hydroxide (25% solution) to adjust the pH to 7~8, then filtered. The residue was purified by prep-HPLC (FA condition) to afford N-(6-(2-(2-(((1r,4r)-4-aminocyclohexyl)amino)pyrimidin-5-yl)ethyl)pyridazin-3-yl)-2-chlorobenzenesulfonamide (3.9 mg, 8.7% yield, FA). $M+H^+$=488.1 (LCMS); $^1$H NMR (METHANOL-$d_4$, 400 MHz) δ 8.61 (br s, 1H), 8.18 (d, J=7.2 Hz, 1H), 8.13 (s, 2H), 7.84 (d, J=9.7 Hz, 1H), 7.59-7.52 (m, 3H), 7.52-7.45 (m, 1H), 3.79-3.68 (m, 1H), 3.18-3.08 (m, 1H), 3.04-2.97 (m, 2H), 2.91-2.84 (m, 2H), 2.12 (br t, J=14.5 Hz, 4H), 1.63-1.49 (m, 2H), 1.48-1.35 (m, 2H).

Example 3: Synthesis of N-(4-(2-(2-(((1r,4r)-4-aminocyclohexyl)amino)pyrimidin-5-yl)ethyl)-3-methylphenyl)-2-chlorobenzenesulfonamide (Compound 6)

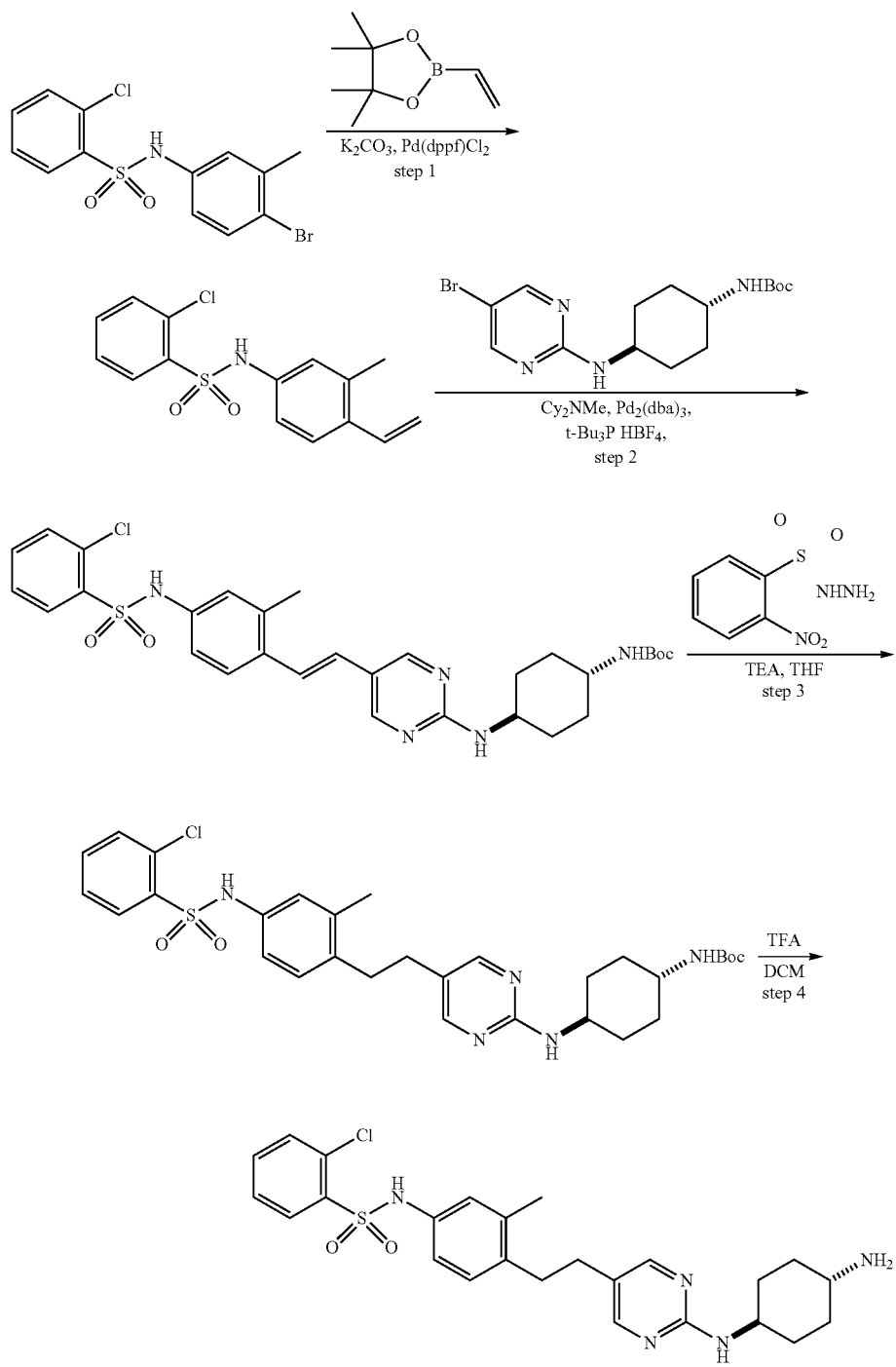

N-(4-(2-(2-(((1r,4r)-4-aminocyclohexyl)amino)pyrimidin-5-yl)ethyl)-3-methylphenyl)-2-chlorobenzenesulfonamide was synthesized according to the synthetic procedure reported for the preparation of N-(6-(2-(2-(((1r,4r)-4-aminocyclohexyl)amino)pyrimidin-5-yl)ethyl)pyridazin-3-yl)-2-chlorobenzenesulfonamide (4.5 mg, 19.5% yield, FA). $M+H^+$=500.0 (LCMS); $^1$H NMR (400 MHz, METHANOL-$d_4$) δ 8.53 (br s, 1H), 8.00 (d, J=8.4 Hz, 1H), 7.90 (s, 2H), 7.59-7.48 (m, 2H), 7.45-7.37 (m, 1H), 6.93-6.81 (m, 3H), 3.71 (brt, J=11.4 Hz, 1H), 3.18-3.06 (m, 1H), 2.77-2.56 (m, 4H), 2.18-2.03 (m, 7H), 1.62-1.32 (m, 4H).

Example 4: Synthesis of N-(4-(2-(2-(((1r,4r)-4-aminocyclohexyl)amino)pyrimidin-5-yl)ethyl)-2-fluorophenyl)-2-chlorobenzenesulfonamide (Compound 8)

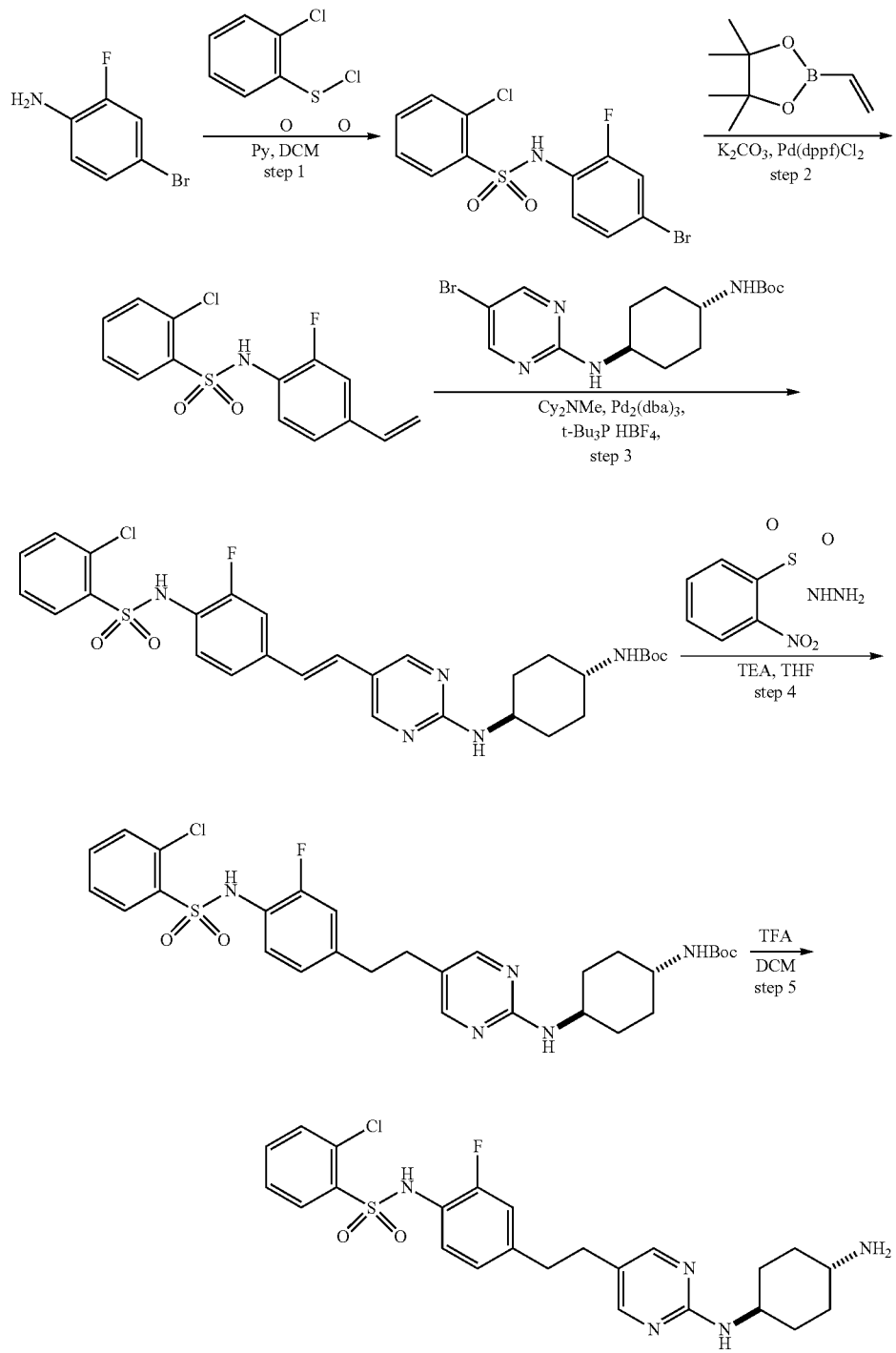

N-(4-(2-(2-(((1r,4r)-4-aminocyclohexyl)amino)pyrimidin-5-yl)ethyl)-2-fluorophenyl)-2-chlorobenzenesulfonamide was synthesized according to the synthetic procedure reported for the preparation of N-(6-(2-(2-(((1r,4r)-4-aminocyclohexyl)amino)pyrimidin-5-yl)ethyl)pyridazin-3-yl)-2-chlorobenzenesulfonamide (8.5 mg, 20.0% yield, FA). M+H$^+$=504.1 (LCMS); $^1$H NMR (400 MHz, METHANOL-d$_4$) δ 8.55 (br s, 1H), 7.99-7.88 (m, 3H), 7.60-7.48 (m, 2H), 7.43-7.35 (m, 1H), 7.23 (t, J=8.3 Hz, 1H), 6.89-6.77 (m, 2H), 3.77-3.64 (m, 1H), 3.14-3.02 (m, 1H), 2.82-2.64 (m, 4H), 2.09 (br t, J=16.0 Hz, 4H), 1.59-1.31 (m, 4H).

Example 5: Synthesis of tert-butyl ((1r,4r)-4-((6-(6-(2-chlorophenylsulfonamido)-4-ethylpyridazin-3-yl)-8-ethylquinazolin-2-yl)amino)cyclohexyl)carbamate and N-(5-((E)-2-(2-(((1r,4r)-4-aminocyclohexyl)amino)pyrimidin-5-yl)vinyl)-6-methoxypyridin-2-yl)-2-chlorobenzenesulfonamide (Compound 9)

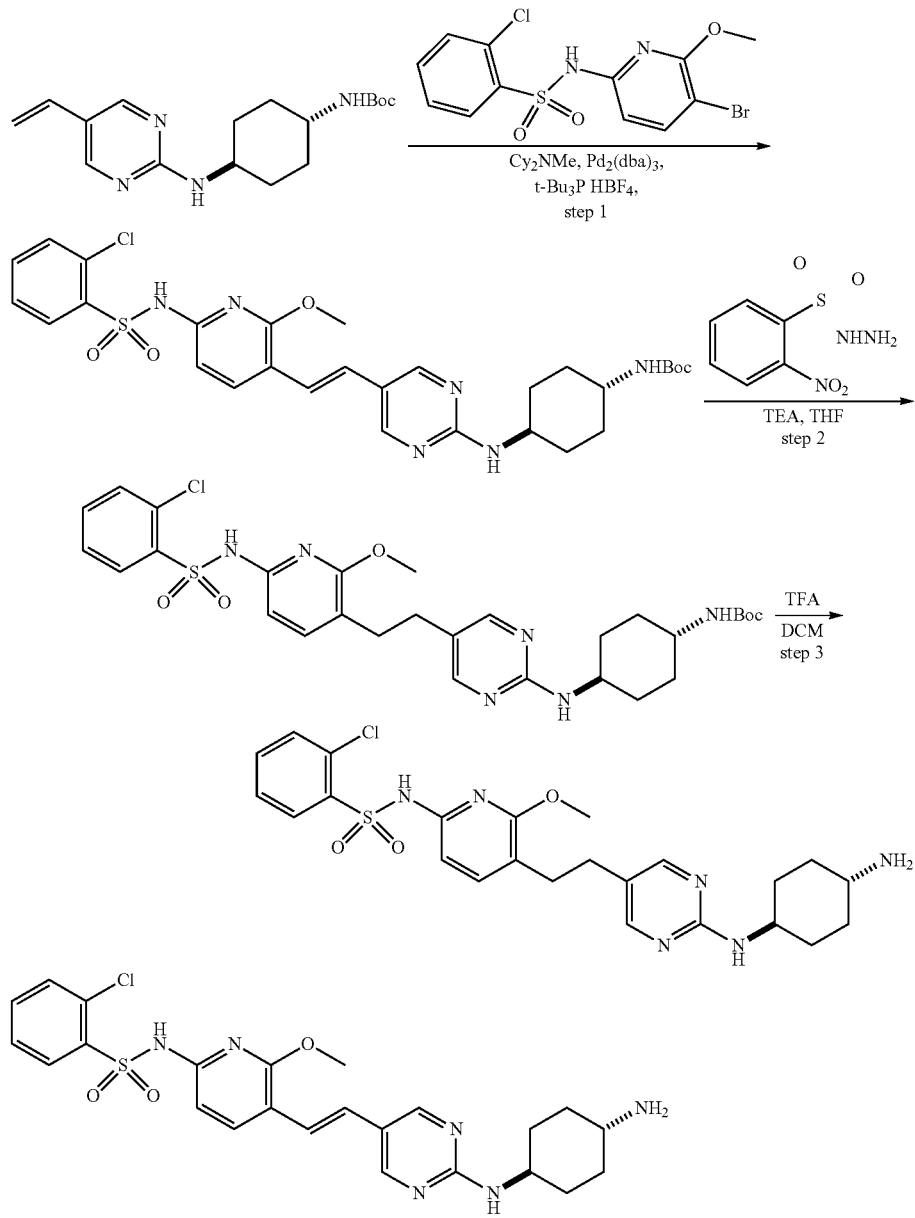

Step 1:

A mixture of N-(5-bromo-6-methoxypyridin-2-yl)-2-chlorobenzenesulfonamide (150 mg, 397.2 umol), tert-butyl ((1r,4r)-4-((5-vinylpyrimidin-2-yl)amino)cyclohexyl)carbamate (127 mg, 397.2 umol), N-cyclohexyl-N-methylcyclohexanamine (233 mg, 1.2 mmol, 252.7 uL), tritert-butylphosphonium; tetrafluoroborate (12 mg, 39.7 umol), and (1E,4E)-1,5-diphenylpenta-1,4-dien-3-one palladium (37 mg, 39.7 umol) in dioxane (3.0 mL) was degassed and purged with $N_2$ three times, and then the mixture was stirred at 100° C. for 12 h under $N_2$ atmosphere. The reaction was concentrated to give a residue. The residue was purified by prep-TLC ($SiO_2$) to afford tert-butyl ((1r,4r)-4-((5-((E)-2-(6-(2-chlorophenylsulfonamido)-2-methoxypyridin-3-yl)vinyl)pyrimidin-2-yl)amino)cyclohexyl)carbamate (200 mg).

Step 2:

To a solution of tert-butyl ((1r,4r)-4-((5-((E)-2-(6-(2-chlorophenylsulfonamido)-2-methoxypyridin-3-yl)vinyl)pyrimidin-2-yl)amino)cyclohexyl)carbamate (100 mg, 162.6 umol) in THF (4.0 mL) was added TEA (329 mg, 3.3 mmol, 452.5 uL) and 2-nitrobenzenesulfonohydrazide (353 mg, 1.6 mmol). The mixture was stirred at 60° C. for 12 h. The reaction was concentrated to give a residue. The residue was purified by prep-TLC ($SiO_2$) to afford tert-butyl ((1r,4r)-4-((5-(2-(6-(2-chlorophenylsulfonamido)-2-methoxypyridin- 3-yl)ethyl)pyrimidin-2-yl)amino)cyclohexyl)carbamate and tert-butyl ((1r,4r)-4-((5-((E)-2-(6-(2-chlorophenylsulfonamido)-2-methoxypyridin-3-yl)vinyl)pyrimidin-2-yl)amino)cyclohexyl)carbamate (60 mg) as a mixture.

Step 3:

To a solution of the mixture of tert-butyl ((1r,4r)-4-((5-(2-(6-(2-chlorophenylsulfonamido)-2-methoxypyridin-3-yl)ethyl)pyrimidin-2-yl)amino)cyclohexyl)carbamate and tert-butyl ((1r,4r)-4-((5-((E)-2-(6-(2-chlorophenylsulfonamido)-2-methoxypyridin-3-yl)vinyl)pyrimidin-2-yl)amino)cyclohexyl)carbamate (60 mg, 97.5 umol) in DCM (2.0 mL) was added TFA (1.0 mL). The mixture was stirred at 20° C. for 10 min. The reaction was concentrated to give a residue. The residue was dissolved in MeOH (2.0 mL) and basified to pH 7 with NH$_3$·H$_2$O (25% solution). The residue was purified by prep-HPLC (FA condition) to afford tert-butyl ((1r,4r)-4-((6-(6-(2-chlorophenylsulfonamido)-4-ethylpyridazin-3-yl)-8-ethylquinazolin-2-yl)amino)cyclohexyl)carbamate (4.4 mg, 7.8% yield, FA). M+H$^+$=517.2 (LCMS); $^1$H NMR (400 MHz, METHANOL-d$_4$) δ 8.62-8.41 (m, 1H), 8.25 (dd, J=1.2, 7.8 Hz, 1H), 7.95 (s, 2H), 7.62-7.54 (m, 2H), 7.53-7.47 (m, 1H), 7.24 (d, J=7.8 Hz, 1H), 6.45 (d, J=7.8 Hz, 1H), 3.77-3.65 (m, 1H), 3.59 (s, 3H), 3.14 (dq, J=3.7, 7.9 Hz, 1H), 2.71-2.58 (m, 4H), 2.19-2.03 (m, 4H), 1.62-1.49 (m, 2H), 1.47-1.33 (m, 2H); and N-(5-((E)-2-(2-(((1r,4r)-4-aminocyclohexyl)amino)pyrimidin-5-yl)vinyl)-6-methoxypyridin-2-yl)-2-chlorobenzenesulfonamide (13.6 mg, 23.1 umol, 23.8% yield, FA). M+H$^+$=515.1 (LCMS); $^1$H NMR (400 MHz, METHANOL-d$_4$) δ 8.42 (s, 3H), 8.30 (dd, J=1.3, 7.9 Hz, 1H), 7.77 (d, J=8.2 Hz, 1H), 7.62-7.49 (m, 3H), 7.07-6.99 (m, 1H), 6.97-6.87 (m, 1H), 6.56 (d, J=8.1 Hz, 1H), 3.85-3.76 (m, 1H), 3.71 (s, 3H), 3.19-3.10 (m, 1H), 2.21-2.05 (m, 4H), 1.65-1.36 (m, 4H).

Example 6: Synthesis of N-(5-(2-(6-(((1r,4r)-4-aminocyclohexyl)amino)pyridin-3-yl)ethyl)-6-methoxypyridin-2-yl)-2-chlorobenzenesulfonamide (Compound 10)

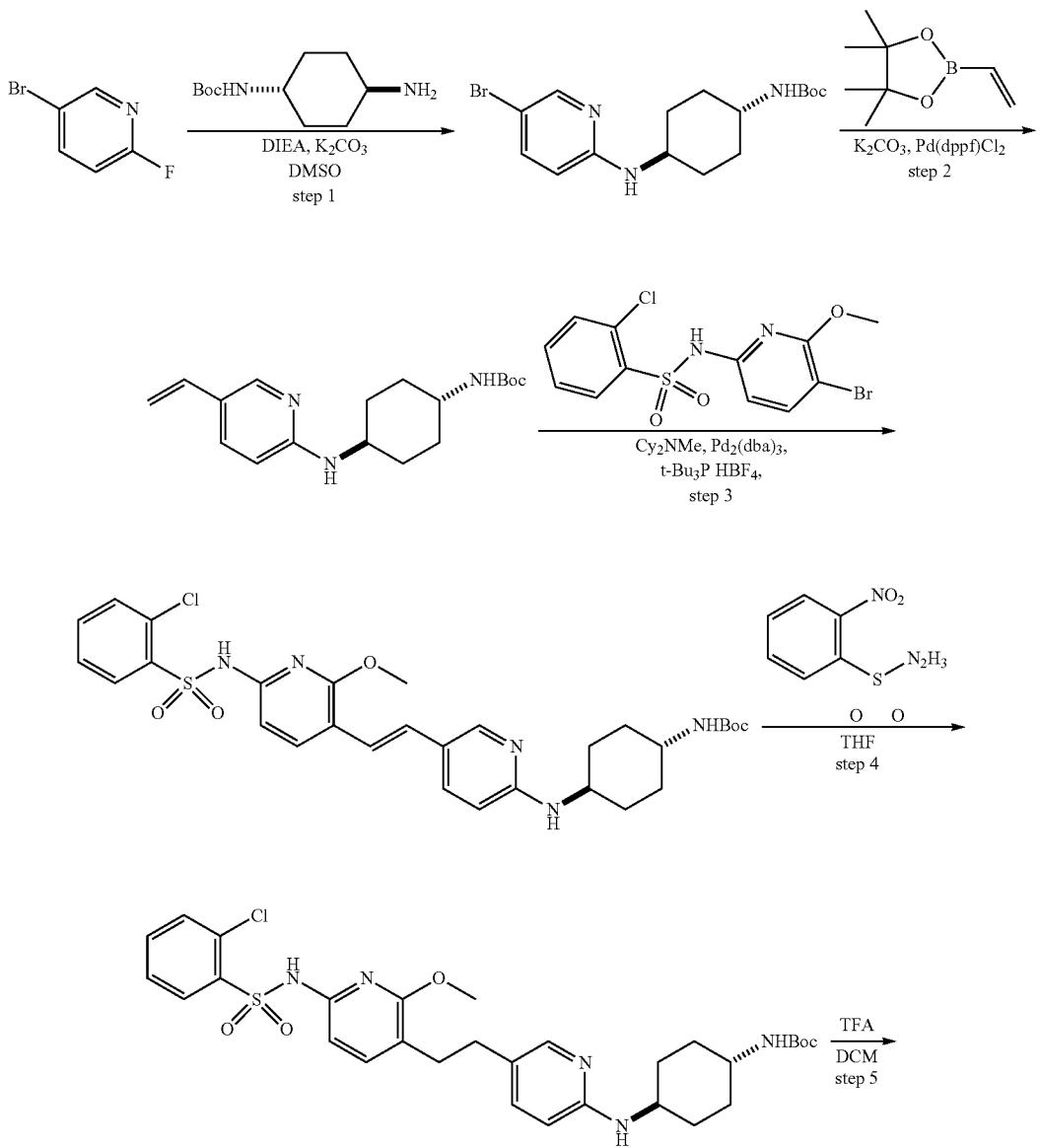

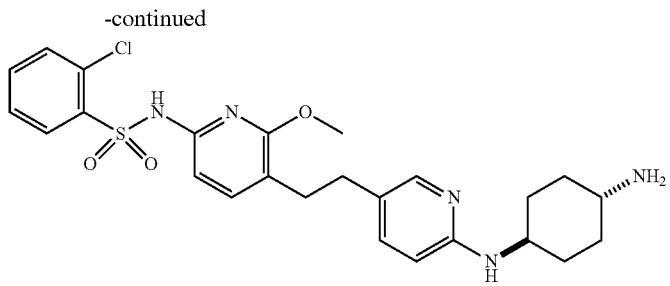

Step 1:

To a solution of 5-bromo-2-fluoropyridine (1.0 g, 605.1 uL) in DMSO (15.0 mL) was added tert-butyl ((1r,4r)-4-((5-bromopyridin-2-yl)amino)cyclohexyl)carbamate (0.6 g, 2.9 mmol), DIEA (760 mg, 5.9 mmol, 1.0 mL), and $K_2CO_3$ (813 mg, 5.9 mmol). The mixture was stirred at 130° C. for 2 h. The reaction mixture was partitioned between $H_2O$ (20.0 mL) the mixture was extracted with ethyl acetate (10.0 mL×3). The combined organic layers were washed with brine (10.0 mL×3), dried over $Na_2SO_4$, filtered, and concentrated under reduced pressure to give tert-butyl ((1r,4r)-4-((5-bromopyridin-2-yl)amino)cyclohexyl)carbamate (1.0 g).

Step 2:

A mixture of tert-butyl ((1r,4r)-4-((5-bromopyridin-2-yl)amino)cyclohexyl)carbamate (500 mg, 1.4 mmol), 4,4,5,5-tetramethyl-2-vinyl-1,3,2-dioxaborolane (250 mg, 1.6 mmol, 274.8 uL), $K_2CO_3$ (560 mg, 4.1 mmol), and Pd(dppf)$Cl_2$ (99 mg, 135 umol) in dioxane (10.0 mL) and $H_2O$ (1.0 mL) was degassed and purged with $N_2$ three times, and then the mixture was stirred at 90° C. for 12 h under $N_2$ atmosphere. The reaction mixture was concentrated under reduced pressure. The residue was purified by column chromatography ($SiO_2$) to afford tert-butyl ((1r,4r)-4-((5-vinylpyridin-2-yl)amino)cyclohexyl)carbamate (164 mg, 22.2% yield). M+H$^+$=318.4 (LCMS).

Step 3:

A mixture of N-(5-bromo-6-methoxypyridin-2-yl)-2-chlorobenzenesulfonamide (234 mg, 620.0 umol), tert-butyl ((1r,4r)-4-((5-vinylpyridin-2-yl)amino)cyclohexyl)carbamate (164 mg, 516.66 umol), N-cyclohexyl-N-methyl-cyclohexanamine (303 mg, 1.5 mmol, 328.7 uL), tritert-butylphosphonium; tetrafluoroborate (30 mg, 103.3 umol), and $Pd_2(dba)_3$ (95 mg, 103.3 umol) in dioxane (8.0 mL) was degassed and purged with $N_2$ three times, and then the mixture was stirred at 100° C. for 12 h under $N_2$ atmosphere. The reaction mixture was concentrated under reduced pressure. The residue was purified by prep-TLC ($SiO_2$) to give tert-butyl ((1r,4r)-4-((5-((E)-2-(6-(2-chlorophenylsulfonamido)-2-methoxypyridin-3-yl)vinyl)pyridin-2-yl)amino)cyclohexyl)carbamate (160 mg, 32.3% yield). M+H$^+$=614.2 (LCMS).

Step 4:

A mixture of tert-butyl ((1r,4r)-4-((5-((E)-2-(6-(2-chlorophenylsulfonamido)-2-methoxypyridin-3-yl)vinyl)pyridin-2-yl)amino)cyclohexyl)carbamate (160 mg, 260.5 umol), 2-nitrobenzenesulfonohydrazide (565 mg, 2.6 mmol), and TEA (527 mg, 5.2 mmol, 725.2 uL) in THF (5.0 mL) was stirred at 60° C. for 12 h. The reaction mixture was concentrated under reduced pressure. The residue was purified by prep-TLC ($SiO_2$) to afford tert-butyl ((1r,4r)-4-((5-(2-(6-(2-chlorophenylsulfonamido)-2-methoxypyridin-3-yl)ethyl)pyridin-2-yl)amino)cyclohexyl)carbamate (74 mg, 27.20% yield). M+H$^+$=616.2 (LCMS).

Step 5:

To a solution of tert-butyl ((1r,4r)-4-((5-(2-(6-(2-chlorophenylsulfonamido)-2-methoxypyridin-3-yl)ethyl)pyridin-2-yl)amino)cyclohexyl)carbamate (74 mg, 120.1 umol) in DCM (2.0 mL) was added TFA (1.5 g, 13.5 mmol, 1.0 mL). The mixture was stirred at 25° C. for 0.5 h. The reaction mixture was concentrated under reduced pressure. To the residue was added methanol (2.0 mL) and $NH_3 \cdot H_2O$ (25% solution) to pH 7, and then the mixture was concentrated under reduced pressure. The residue was purified by prep-HPLC (basic condition) to give N-(5-(2-(6-(((1r,4r)-4-aminocyclohexyl)amino)pyridin-3-yl)ethyl)-6-methoxypyridin-2-yl)-2-chlorobenzenesulfonamide (2.1 mg, 3.5% yield). M+H$^+$=516.1 (LCMS); $^1$H NMR (400 MHz, METHANOL-$d_4$) δ 8.21 (d, J=13 Hz, 1H), 7.58-7.48 (m, 3H), 7.47-7.39 (m, 1H), 7.17-7.09 (m, 2H), 6.37 (dd, J=8.2, 17.0 Hz, 2H), 3.61-3.51 (m, 4H), 3.00 (br t, J=11.5 Hz, 1H), 2.68-2.53 (m, 4H), 2.13-1.98 (m, 4H), 1.56-1.37 (m, 2H), 1.37-1.21 (m, 2H).

Example 7: Synthesis N-(6-(2-(2-(((1r,4r)-4-aminocyclohexyl)amino)pyrimidin-5-yl)ethyl)-5-methoxypyridin-3-yl)-2-chlorobenzenesulfonamide (Compound 18)

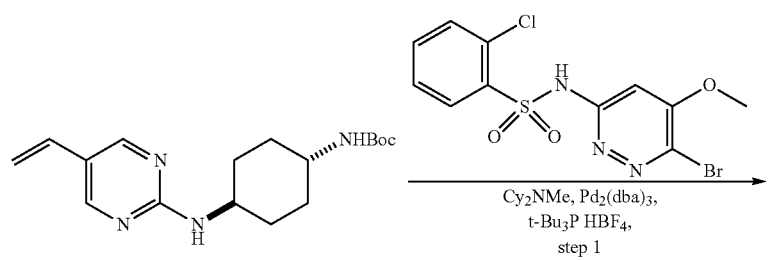

-continued

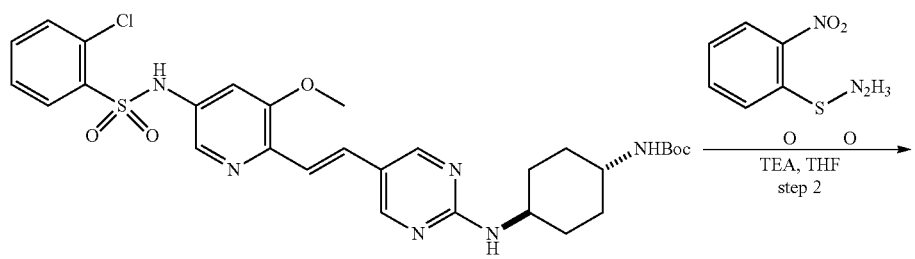

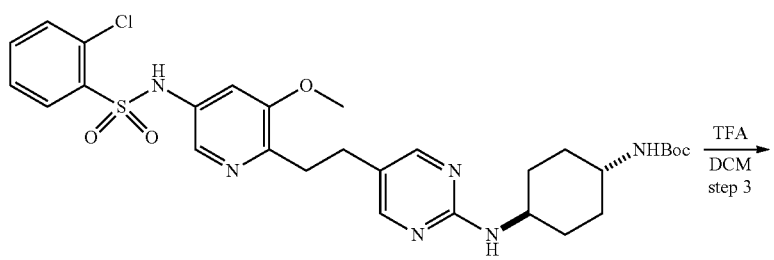

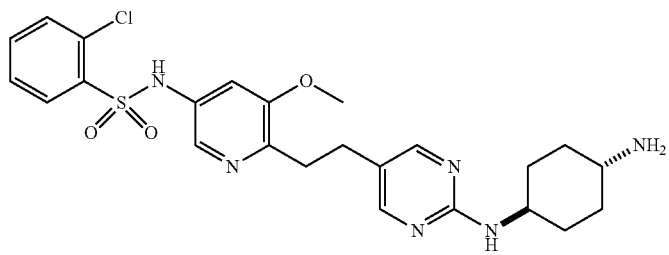

N-(6-(2-(2-(((1r,4r)-4-aminocyclohexyl)amino)pyrimidin-5-yl)ethyl)-5-methoxypyridin-3-yl)-2-chlorobenzenesulfonamide was synthesized according to the synthetic procedure reported for the preparation of N-(5-(2-(6-(((1r,4r)-4-aminocyclohexyl)amino)pyridin-3-yl)ethyl)-6-methoxypyridin-2-yl)-2-chlorobenzenesulfonamide (45.6 mg, 56.4% yield, FA). M+H$^+$=517.2 (LCMS); $^1$H NMR (400 MHz, METHANOL-d$_4$) δ 8.45 (br s, 1H), 8.07 (d, J=7.5 Hz, 1H), 7.90 (s, 2H), 7.78 (d, J=2.2 Hz, 1H), 7.59-7.53 (m, 2H), 7.51-7.39 (m, 1H), 7.12 (d, J=2.0 Hz, 1H), 3.74-3.64 (m, 4H), 3.12 (ddd, J=3.7, 8.0, 11.6 Hz, 1H), 2.93-2.83 (m, 2H), 2.74-2.64 (m, 2H), 2.10 (br t, J=10.4 Hz, 4H), 1.60-1.44 (m, 2H), 1.44-1.27 (m, 2H).

Example 8: N-(4-((E)-2-(2-(((1r,4r)-4-aminocyclohexyl)amino)pyrimidin-5-yl)vinyl)-3-methoxyphenyl)-2-chlorobenzenesulfonamide (Compound 14)

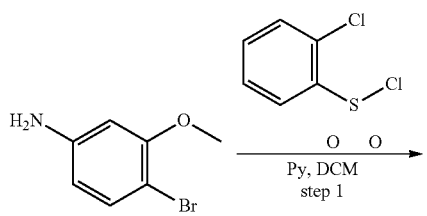

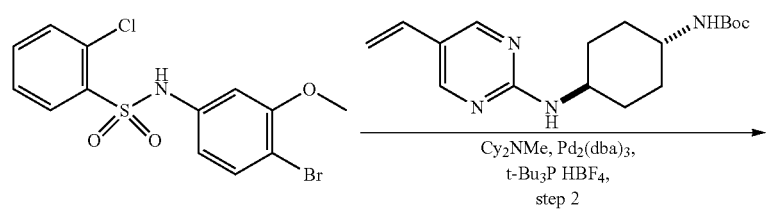

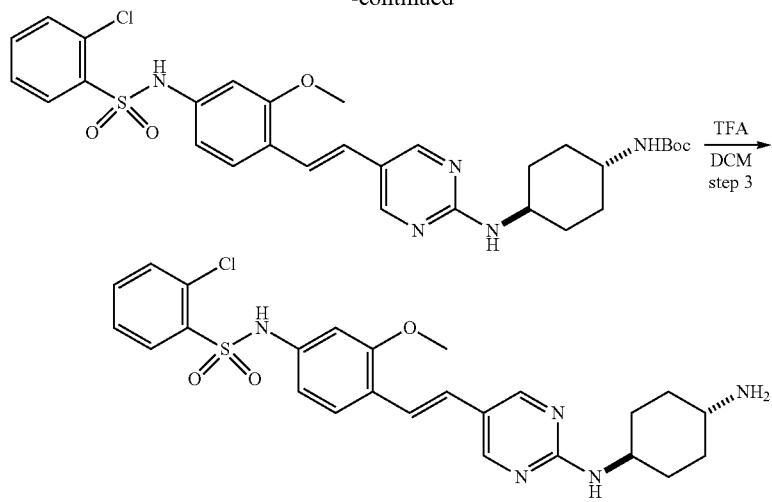

Step 1:
To a solution of 4-bromo-3-methoxy-aniline (100 mg, 494.9 umol) in DCM (2.0 mL) was added pyridine (117 mg, 1.4 mmol, 119.8 uL) and 2-chlorobenzenesulfonyl chloride (125 mg, 593.9 umol, 80.8 uL). The mixture was stirred at 45° C. for 12 h. The reaction mixture was concentrated. The residue was purified by column chromatography (SiO₂) to afford N-(4-bromo-3-methoxyphenyl)-2-chlorobenzenesulfonamide (180 mg).

Step 2:
A mixture of N-(4-bromo-3-methoxyphenyl)-2-chlorobenzenesulfonamide (50 mg, 157.0 umol), tert-butyl ((1r,4r)-4-((5-vinylpyrimidin-2-yl)amino)cyclohexyl)carbamate (70 mg, 188.4 umol), Pd₂(dba)₃ (28 mg, 31.4 umol), N-cyclohexyl-N-methylcyclohexanamine (92 mg, 471.0 umol, 99.9 uL), and tritert-butylphosphonium tetrafluoroborate (9 mg, 31.4 umol) in dioxane (2.0 mL) was degassed and purged with N₂ three times, and then the mixture was stirred at 100° C. for 12 h under N₂ atmosphere. The reaction mixture was concentrated under reduced pressure. The residue was purified by prep-TLC (SiO₂) to afford tert-butyl ((1r,4r)-4-((5-((E)-4-(2-chlorophenylsulfonamido)-2-methoxystyryl) pyrimidin-2-yl)amino)cyclohexyl)carbamate (58 mg, 43.9% yield). M+H⁺=614.4 (LCMS).

Step 3:
To a solution of tert-butyl ((1r,4r)-4-((5-((E)-4-(2-chlorophenylsulfonamido)-2-methoxystyryl) pyrimidin-2-yl)amino)cyclohexyl)carbamate (50 mg, 81.4 umol) in DCM (2.0 mL) was added TFA (1.0 mL). The mixture was stirred at 25° C. for 0.5 h. The reaction mixture was concentrated under reduced pressure. To the residue was added dichloromethane (2.0 mL) and NH₃·H₂O (25% solution) to pH 7, and the mixture was concentrated under reduced pressure. The residue was purified by prep-HPLC (FA condition) to give N-(4-((E)-2-(2-(((1r,4r)-4-aminocyclohexyl)amino)pyrimidin-5-yl)vinyl)-3-methoxy phenyl)-2-chlorobenzenesulfonamide (12.6 mg, 27.4% yield, FA). M+H⁺=514.2 (LCMS); ¹H NMR (400 MHz, METHANOL-d₄) δ 8.53 (br s, 1H), 8.38 (s, 2H), 8.10 (br d, J=1.9 Hz, 1H), 7.60-7.48 (m, 2H), 7.48-7.39 (m, 1H), 7.35 (br d, J=8.3 Hz, 1H), 7.14 (br d, J=16.7 Hz, 1H), 6.89-6.74 (m, 2H), 6.70 (br d, J=8.3 Hz, 1H), 3.77 (s, 4H), 3.12 (br t, J=11.2 Hz, 1H), 2.12 (br t, J=15.8 Hz, 4H), 1.62-1.48 (m, 2H), 1.48-1.34 (m, 2H).

Example 9: Synthesis N-(4-(2-(2-(((1r,4r)-4-aminocyclohexyl)amino)pyrimidin-5-yl)ethyl)-3-methoxyphenyl)-2-chlorobenzenesulfonamide (Compound 15)

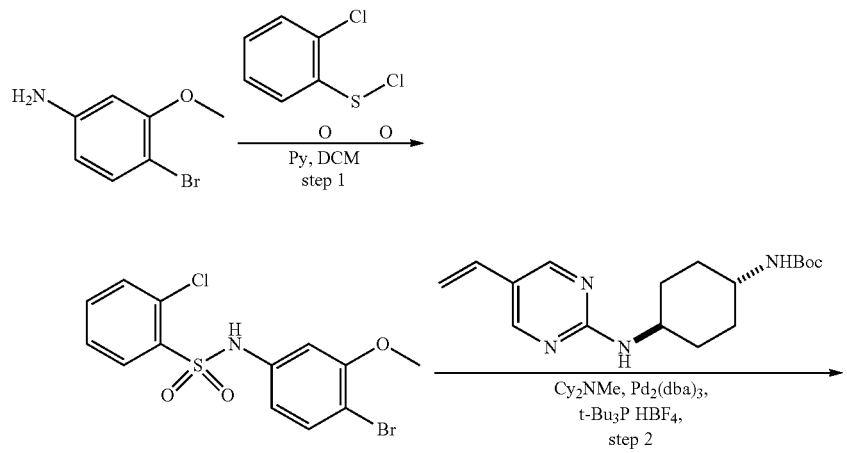

-continued

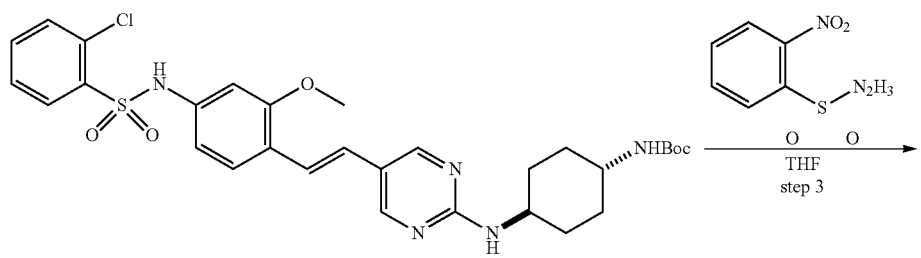

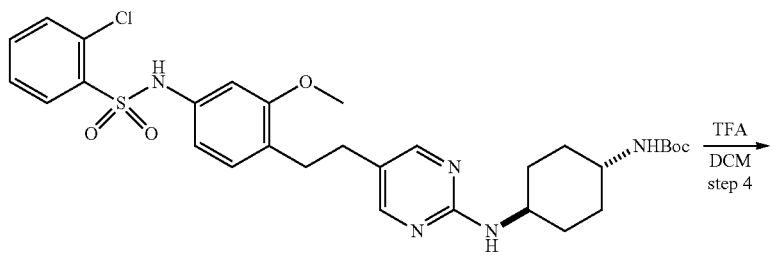

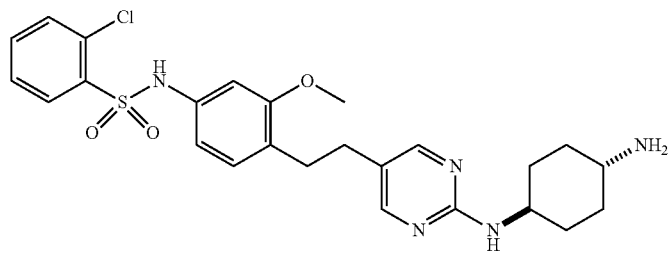

Step 1:

To a solution of 4-bromo-3-methoxy-aniline (0.4 g, 1.9 mmol) in DCM (5.0 mL) was added pyridine (469 mg, 5.9 mmol, 479.3 uL) and 2-chlorobenzenesulfonyl chloride (626 mg, 2.9 mmol, 404.3 uL). The mixture was stirred at 45° C. for 12 h. The reaction mixture was concentrated under reduced pressure. The residue was purified by column chromatography ($SiO_2$) to afford N-(4-bromo-3-methoxyphenyl)-2-chlorobenzenesulfonamide (0.7 g, 75.1% yield). M+H$^+$=378.1 (LCMS).

Step 2:

A mixture of N-(4-bromo-3-methoxyphenyl)-2-chlorobenzenesulfonamide (200 mg, 628.1 umol), tert-butyl ((1r,4r)-4-((5-vinylpyrimidin-2-yl)amino)cyclohexyl)carbamate (283 mg, 753.7 umol), $Pd_2(dba)_3$ (115 mg, 125.6 umol), N-cyclohexyl-N-methylcyclohexanamine (368 mg, 1.8 mmol, 399.6 uL), and tri-tert-butylphosphonium tetrafluoroborate (36 mg, 125.6 umol) in dioxane (2.0 mL) was degassed and purged with $N_2$ three times, and then the mixture was stirred at 100° C. for 12 h under $N_2$ atmosphere. The reaction mixture was concentrated under reduced pressure. The residue was purified by column chromatography ($SiO_2$) to afford tert-butyl ((1r,4r)-4-((5-((E)-4-(2-chlorophenylsulfonamido)-2-methoxystyryl) pyrimidin-2-yl)amino)cyclohexyl)carbamate (0.2 g, 12.9% yield). M+H$^+$=614.4 (LCMS).

Step 3:

To a solution of tert-butyl ((1r,4r)-4-((5-((E)-4-(2-chlorophenylsulfonamido)-2-methoxystyryl) pyrimidin-2-yl)amino)cyclohexyl)carbamate (0.2 g, 293.0 umol) in THF (10.0 mL) was added TEA (593 mg, 5.8 mmol, 815.8 uL) and 2-nitrobenzenesulfonohydrazide (636 mg, 2.9 mmol). The mixture was stirred at 60° C. for 12 h. The reaction mixture was concentrated under reduced pressure. The residue was purified by column chromatography ($SiO_2$) to afford tert-butyl ((1r,4r)-4-((5-(4-(2-chlorophenylsulfonamido)-2-methoxyphenethyl) pyrimidin-2-yl)amino)cyclohexyl)carbamate (180 mg, 46.8% yield). M+H$^+$=616.4 (LCMS).

Step 4:

To a solution of tert-butyl ((1r,4r)-4-((5-(4-(2-chlorophenylsulfonamido)-2-methoxyphenethyl) pyrimidin-2-yl)amino)cyclohexyl)carbamate (180 mg, 292 umol) in DCM (2.0 mL) was added TFA (1.0 mL). The mixture was stirred at 25° C. for 0.5 h. The reaction mixture was concentrated under reduced pressure. To the residue was added dichloromethane (2.0 mL) and $NH_3 \cdot H_2O$ (25% solution) to pH 7, and the mixture was concentrated under reduced pressure. The residue was purified by prep-HPLC (FA condition) to give N-(4-(2-(2-(((1r,4r)-4-aminocyclohexyl)amino)pyrimidin-5-yl)ethyl)-3-methoxyphenyl)-2-chlorobenzenesulfonamide (25.3 mg, 14.7% yield, FA). M+H$^+$=516.2 (LCMS); $^1$H NMR (400 MHz, METHANOL-$d_4$) δ 8.41 (br s, 1H), 8.02 (d, J=7.5 Hz, 1H), 7.85 (s, 2H), 7.57-7.47 (m, 2H), 7.46-7.36 (m, 1H), 6.79 (d, J=7.9 Hz, 1H), 6.69 (d, J=1.8 Hz, 1H), 6.58 (dd, J=2.0, 8.1 Hz, 1H), 3.78-3.61 (m, 4H), 3.20-3.05 (m, 1H), 2.72-2.64 (m, 2H), 2.62-2.53 (m, 2H), 2.10 (br t, J=11.6 Hz, 4H), 1.63-1.48 (m, 2H), 1.45-1.31 (m, 2H).

Example 10: Synthesis of N-(6-(2-(2-(((1r,4r)-4-aminocyclohexyl)amino)pyrimidin-5-yl)ethyl)-5-ethylpyridin-3-yl)-2-chlorobenzenesulfonamide (Compound 16)

Step 2:

To a solution of 5-vinylpyridin-3-amine (0.9 g, 7.4 mmol) in MeOH (20.0 mL) and $NH_3 \cdot H_2O$ (1.0 mL, 25% solution) was added Pd/C (0.1 g, 10% Pd base) under $N_2$ atmosphere. The suspension was degassed and purged with $H_2$ three

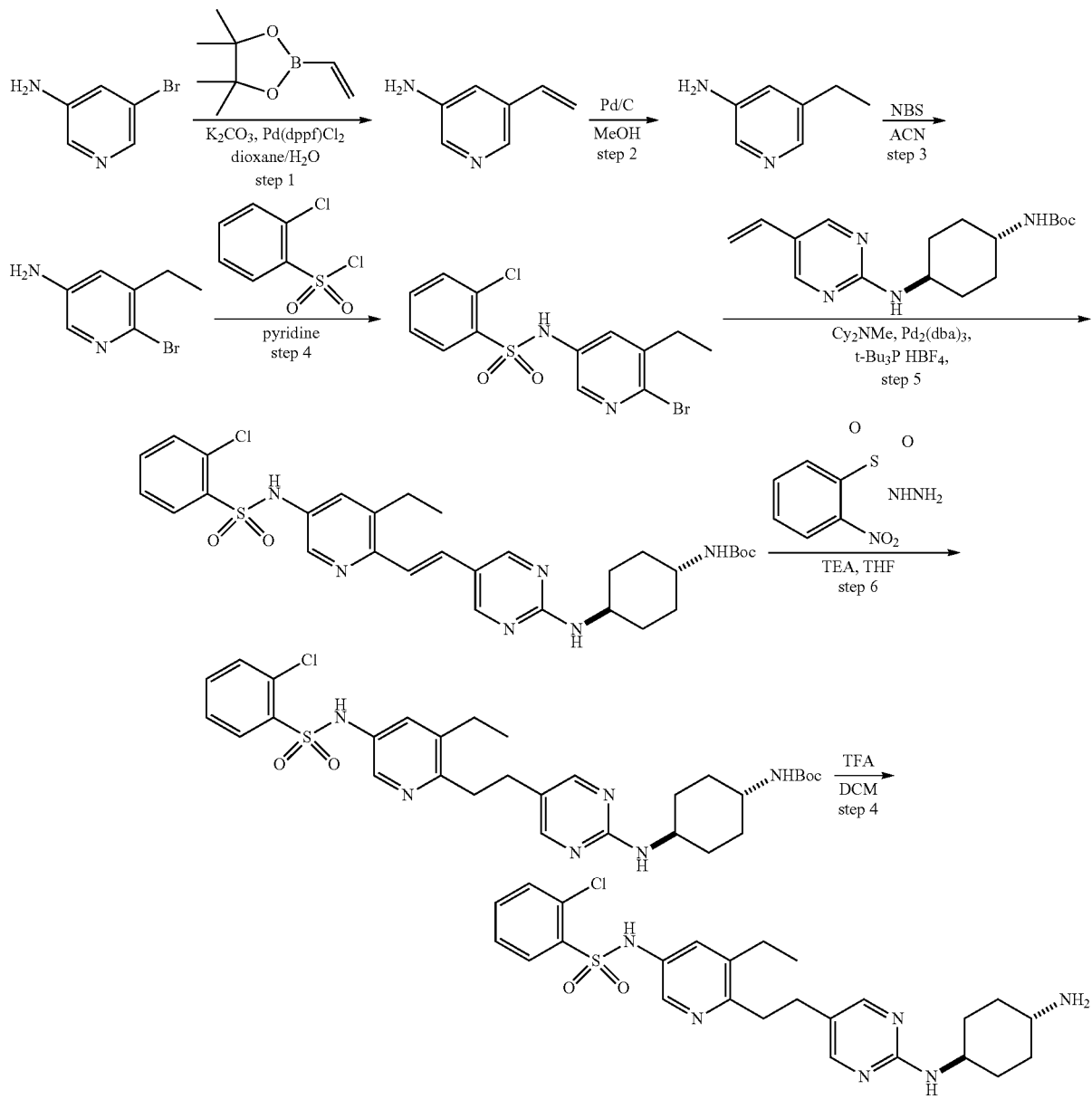

Step 1:

To a solution of 5-bromopyridin-3-amine (2.0 g, 11.5 mmol) and $K_2CO_3$ (4.7 g, 34.6 mmol) in dioxane (60.0 mL) and $H_2O$ (6.0 mL) were added 4,4,5,5-tetramethyl-2-vinyl-1,3,2-dioxaborolane (3.5 g, 23.1 mmol, 3.9 mL) and $Pd(dppf)Cl_2$ (845 mg, 1.1 mmol). The mixture was stirred at 80° C. for 12 h under $N_2$. The mixture was concentrated to give a residue. The residue was purified by column chromatography ($SiO_2$) to afford 5-vinylpyridin-3-amine (0.9 g, 46.0% yield). $M+H^+$=121.2 (LCMS); $^1H$ NMR (CHLOROFORM-d, 400 MHz): δ 8.10-7.94 (m, 2H), 7.02 (s, 1H), 6.64 (dd, J=10.9, 17.7 Hz, 1H), 5.77 (d, J=17.6 Hz, 1H), 5.34 (d, J=10.9 Hz, 1H), 3.69 (br s, 2H).

times. The mixture was stirred under $H_2$ (15 Psi) at 20° C. for 10 min. The reaction mixture was filtered and concentrated under reduced pressure to give 5-ethylpyridin-3-amine (0.8 g).

Step 3:

A solution of 5-ethylpyridin-3-amine (0.7 g, 5.7 mmol) in ACN (20.0 mL) was added NBS (1.0 g, 5.7 mmol). The mixture was stirred at 20° C. for 12 h. The mixture was concentrated to give a residue. The residue was purified by column chromatography ($SiO_2$) to afford 6-bromo-5-ethylpyridin-3-amine (0.8 g). $^1H$ NMR (METHANOL-$d_4$, 400 MHz) δ 7.59 (d, J=2.9 Hz, 1H), 7.00 (d, J=2.9 Hz, 1H), 2.65-2.57 (m, 2H), 1.22-1.16 (m, 3H).

Step 4:

To a solution of 6-bromo-5-ethylpyridin-3-amine (0.4 g, 1.9 mmol) in pyridine (10.0 mL) was added 2-chlorobenzenesulfonyl chloride (503 mg, 2.3 mmol, 325.0 uL). The mixture was stirred at 45° C. for 12 h. The mixture was concentrated to give a residue. The residue was purified by column chromatography ($SiO_2$) to afford N-(6-bromo-5-ethylpyridin-3-yl)-2-chlorobenzenesulfonamide (0.3 g, 32.1% yield). $^1$H NMR (CHLOROFORM-d, 400 MHz): δ 8.04-7.99 (m, 1H), 7.97 (d, J=2.7 Hz, 1H), 7.54-7.51 (m, 2H), 7.44 (d, J=2.7 Hz, 2H), 7.40-7.34 (m, 1H), 2.65 (q, J=7.6 Hz, 2H), 1.20-1.11 (m, 3H).

Step 5:

To a solution of N-(6-bromo-5-ethylpyridin-3-yl)-2-chlorobenzenesulfonamide (0.3 g, 798.5 umol) and N-cyclohexyl-N-methyl-cyclohexanamine (467 mg, 2.4 mmol, 508.1 uL) in dioxane (20.0 mL) was added tert-butyl ((1r, 4r)-4-((5-vinylpyrimidin-2-yl)amino)cyclohexyl)carbamate (305 mg, 958.2 umol), tritert-butylphosphonium; tetrafluoroborate (46 mg, 159.7 umol), and (1E,4E)-1,5-diphenylpenta-1,4-dien-3-one; palladium (146 mg, 159.7 umol). The mixture was stirred at 100° C. for 12 h under $N_2$. The mixture was concentrated to give a residue. The residue was purified by prep-TLC ($SiO_2$) to afford tert-butyl ((1r,4r)-4-((5-((E)-2-(5-(2-chlorophenylsulfonamido)-3-ethylpyridin-2-yl)vinyl)pyrimidin-2-yl)amino)cyclohexyl)carbamate (0.2 g).

Step 6:

To a solution of tert-butyl ((1r,4r)-4-((5-((E)-2-(5-(2-chlorophenylsulfonamido)-3-ethylpyridin-2-yl)vinyl)pyrimidin-2-yl)amino)cyclohexyl)carbamate (0.2 g, 326.1 umol) in THF (6.0 mL) was added 2-nitrobenzenesulfonohydrazide (708 mg, 3.2 mmol) and TEA (99 mg, 978.5 umol, 136.2 uL). The mixture was stirred at 65° C. for 12 h. The mixture was concentrated to give a residue. The residue was purified by column chromatography ($SiO_2$). The residue was further purified by prep-TLC ($SiO_2$) to afford tert-butyl ((1r,4r)-4-((5-(2-(5-(2-chlorophenylsulfonamido)-3-ethylpyridin-2-yl)ethyl)pyrimidin-2-yl)amino)cyclohexyl)carbamate (15 mg).

Step 7:

A solution of tert-butyl ((1r,4r)-4-((5-(2-(5-(2-chlorophenylsulfonamido)-3-ethylpyridin-2-yl)ethyl)pyrimidin-2-yl)amino)cyclohexyl)carbamate (25 mg, 40.6 umol) in DCM (2.0 mL) and TFA (1.0 mL) was stirred at 25° C. for 10 min. The mixture was concentrated to give a residue. The residue was dissolved in MeOH (2.0 mL), basified pH to 8 with $NH_3 \cdot H_2O$ (25% solution), and concentrated to give a residue. The residue was purified by prep-HPLC (FA condition) to afford N-(6-(2-(2-(((1r,4r)-4-aminocyclohexyl)amino)pyrimidin-5-yl)ethyl)-5-ethylpyridin-3-yl)-2-chlorobenzenesulfonamide (9.0 mg, 39.2% yield, FA). M+H$^+$=515.3 (LCMS); $^1$H NMR (METHANOL-d$_4$, 400 MHz) δ 8.53 (br s, 1H), 8.10 (d, J=2.4 Hz, 1H), 8.07-8.01 (m, 1H), 7.95 (s, 2H), 7.61-7.53 (m, 2H), 7.49-7.41 (m, 1H), 7.37 (d, J=2.4 Hz, 1H), 3.80-3.64 (m, 1H), 3.20-3.06 (m, 1H), 2.97-2.86 (m, 2H), 2.79-2.69 (m, 2H), 2.49 (q, J=7.5 Hz, 2H), 2.10 (br t, J=13.1 Hz, 4H), 1.63-1.47 (m, 2H), 1.46-1.31 (m, 2H), 1.05 (t, J=7.5 Hz, 3H).

Example 11: Synthesis of 2-chloro-N-(5-(2-(2-(((1r, 4r)-4-hydroxycyclohexyl)amino)pyrimidin-5-yl) ethyl)-6-methylpyridin-2-yl)benzenesulfonamide (Compound 20)

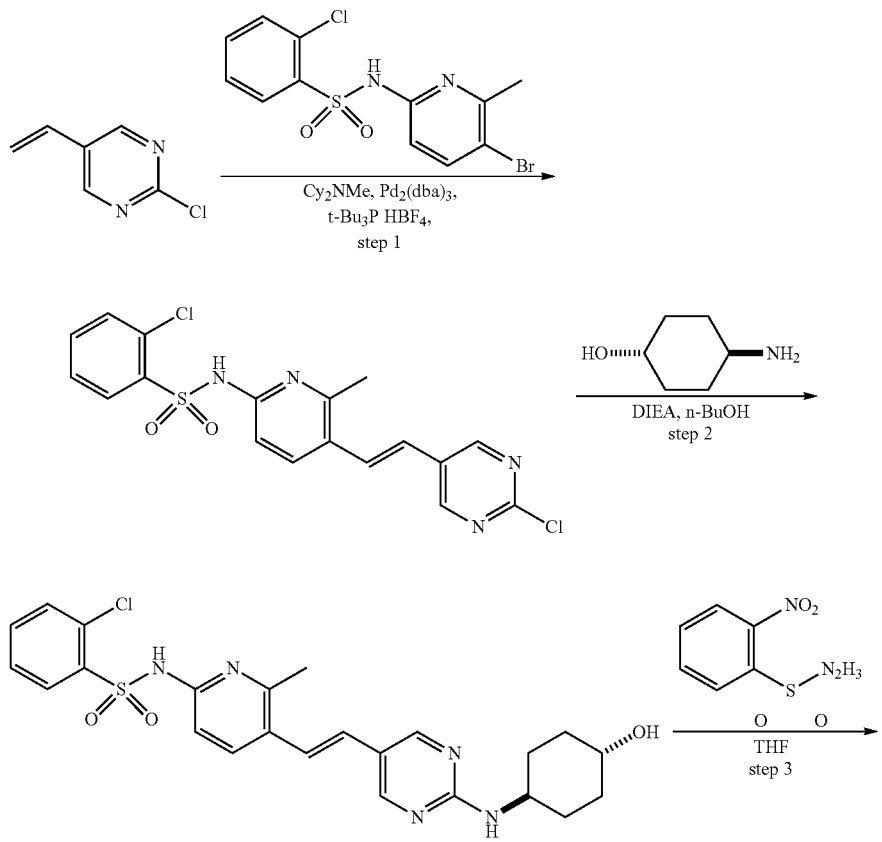

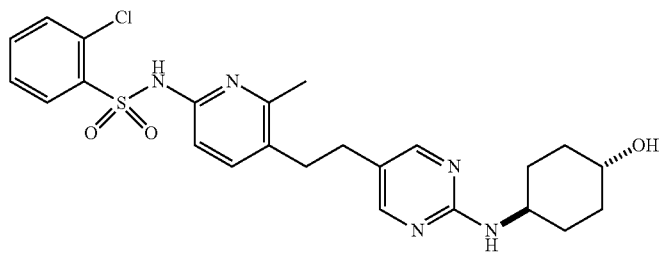

Step 1:

A mixture of 2-chloro-5-vinylpyrimidine (330 mg, 2.4 mmol), N-(5-bromo-6-methylpyridin-2-yl)-2-chlorobenzenesulfonamide (1.0 g, 2.8 mmol), N-cyclohexyl-N-methyl-cyclohexanamine (1.4 g, 7.0 mmol, 1.5 mL), tri-tert-butylphosphonium tetrafluoroborate (136 mg, 469.5 umol), and (1E,4E)-1,5-diphenylpenta-1,4-dien-3-one palladium (430 mg, 469.5 umol) in dioxane (30.0 mL) was degassed and purged with $N_2$ three times, and then the mixture was stirred at 100° C. for 12 h under $N_2$ atmosphere. The reaction mixture was concentrated under reduced pressure. The residue was purified by column chromatography ($SiO_2$) to afford (E)-2-chloro-N-(5-(2-(2-chloropyrimidin-5-yl)vinyl)-6-methylpyridin-2-yl)benzene sulfonamide (510 mg, 27.8% yield). $M+H^+$=420.9 (LCMS).

Step 2:

To a solution of (E)-2-chloro-N-(5-(2-(2-chloropyrimidin-5-yl)vinyl)-6-methylpyridin-2-yl)benzene sulfonamide (200 mg, 474.7 umol) in n-BuOH (4.0 mL) was added DIEA (184 mg, 1.4 mmol, 248.1 uL) and 4-aminocyclohexanol (109 mg, 949.4 umol). The mixture was stirred at 100° C. for 12 h. The reaction mixture was concentrated under reduced pressure. The residue was added ethyl acetate (5.0 mL) and methanol (5.0 mL). The reaction mixture was concentrated by filtration. The filter cake was product, and the filtrate was concentrated under reduced pressure. The residue was purified by prep-TLC ($SiO_2$) to afford 2-chloro-N-(5-((E)-2-(2-(((1r,4r)-4-hydroxycyclohexyl)amino)pyrimidin-5-yl)vinyl)-6-methylpyridin-2-yl)benzenesulfonamide (110 mg, 32.4% yield). M+H+=500.1 (LCMS).

Step 3:

To a solution of 2-chloro-N-(5-((E)-2-(2-(((1r,4r)-4-hydroxycyclohexyl)amino)pyrimidin-5-yl)vinyl)-6-methylpyridin-2-yl)benzenesulfonamide (110 mg, 220.0 umol) in THF (5.0 mL) was added TEA (445 mg, 4.4 mmol, 612.4 uL) and 2-nitrobenzenesulfonohydrazide (477 mg, 2.2 mmol). The mixture was stirred at 60° C. for 12 h. Additional 2-nitrobenzenesulfonohydrazide (470 mg) was added to the reaction mixture and the resulting mixture was stirred at 60° C. for another 12 h. The reaction mixture was concentrated under reduced pressure. The residue was purified by prep-HPLC (FA condition) to give 2-chloro-N-(5-(2-(2-(((1r,4r)-4-hydroxycyclohexyl)amino)pyrimidin-5-yl)ethyl)-6-methylpyridin-2-yl)benzenesulfonamide (6.4 mg, 5.0% yield, FA). $M+H^+$=502.1 (LCMS); $^1H$ NMR (400 MHz, METHANOL-$d_4$) δ 8.18-8.13 (m, 1H), 8.01 (s, 2H), 7.55-7.41 (m, 4H), 7.08 (d, J=8.8 Hz, 1H), 3.73-3.62 (m, 1H), 3.62-3.51 (m, 1H), 2.77-2.70 (m, 2H), 2.68-2.60 (m, 2H), 2.28 (s, 3H), 1.99 (brt, J=14.8 Hz, 4H), 1.49-1.19 (m, 4H).

Example 12: Synthesis of 2-chloro-N-(5-(2-(2-(((1r,4r)-4-(dimethylamino)cyclohexyl)amino) pyrimidin-5-yl)ethyl)-6-methylpyridin-2-yl)benzenesulfonamide (Compound 21)

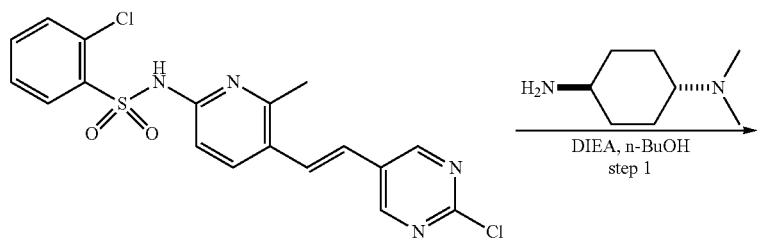

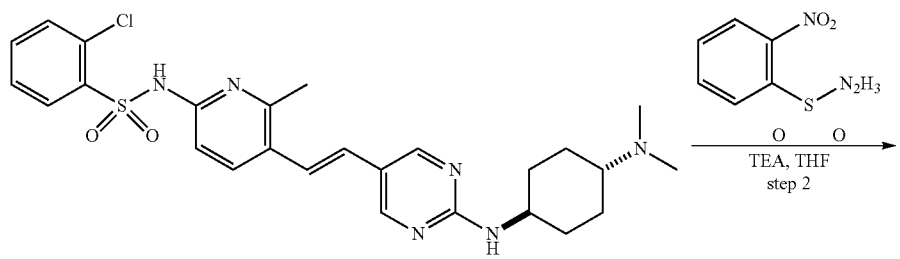

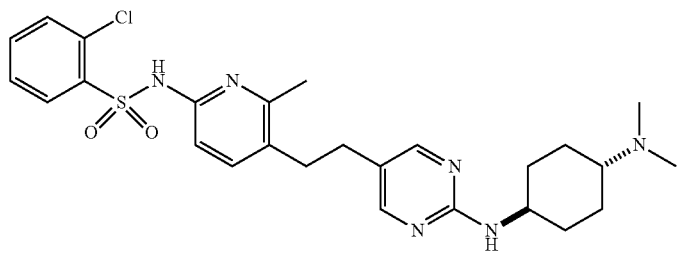

2-Chloro-N-(5-(2-(2-(((1r,4r)-4-(dimethylamino)cyclohexyl)amino) pyrimidin-5-yl)ethyl)-6-methylpyridin-2-yl)benzenesulfonamide was synthesized according to the synthetic procedure reported for the preparation of 2-chloro-N-(5-(2-(2-(((1r,4r)-4-hydroxycyclohexyl)amino)pyrimidin-5-yl)ethyl)-6-methylpyridin-2-yl)benzenesulfonamide (11.8 mg, 13.1% yield, FA). M+H⁺=529.2 (LCMS); ¹H NMR (400 MHz, METHANOL-$d_4$) δ 8.48 (br s, 1H), 8.15 (d, J=7.4 Hz, 1H), 8.03 (s, 2H), 7.53-7.41 (m, 4H), 7.07 (d, J=9.0 Hz, 1H), 3.72 (tt, J=3.7, 11.4 Hz, 1H), 3.28-3.16 (m, 1H), 2.84 (s, 6H), 2.77-2.69 (m, 2H), 2.68-2.61 (m, 2H), 2.27 (s, 3H), 2.24-2.08 (m, 4H), 1.75-1.54 (m, 2H), 1.49-1.31 (m, 2H).

Example 13: Synthesis of 2-chloro-N-(5-((E)-2-(2-(((1r,4r)-4-(dimethylamino)cyclohexyl)amino)pyrimidin-5-yl)vinyl)-6-methylpyridin-2-yl)benzenesulfonamide (Compound 23)

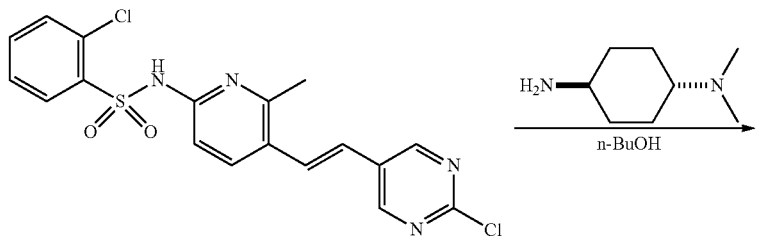

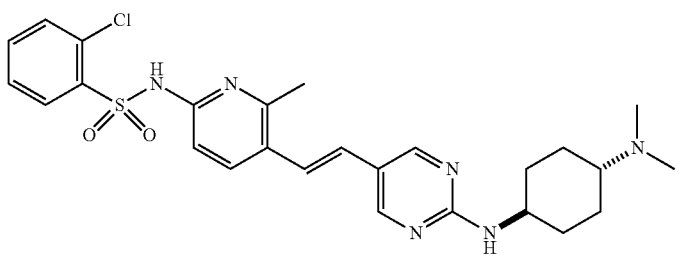

2-Chloro-N-(5-((E)-2-(2-(((1r,4r)-4-(dimethylamino)cyclohexyl)amino)pyrimidin-5-yl)vinyl)-6-methylpyridin-2-yl)benzenesulfonamide was synthesized according to the synthetic procedure reported for the preparation of 2-chloro-N-(5-(2-(2-(((1r,4r)-4-hydroxycyclohexyl)amino)pyrimidin-5-yl)ethyl)-6-methylpyridin-2-yl)benzenesulfonamide (27.4 mg, 17.3% yield, FA). M+H$^+$=527.1 (LCMS); $^1$H NMR (400 MHz, METHANOL-d$_4$) δ 8.51 (s, 1H), 8.40 (br s, 1H), 8.25-8.18 (m, 1H), 8.05-7.99 (m, 1H), 7.57-7.44 (m, 4H), 7.19 (d, J=9.0 Hz, 1H), 7.13-7.01 (m, 1H), 6.86 (d, J=16.4 Hz, 1H), 3.89-3.78 (m, 1H), 3.31-3.28 (m, 1H), 2.89-2.87 (m, 6H), 2.50 (s, 3H), 2.25 (br d, J=13.6 Hz, 2H), 2.17 (br d, J=12.0 Hz, 2H), 1.70 (q, J=12.6 Hz, 2H), 1.46 (br d, J=11.4 Hz, 2H).

Example 14: Synthesis of 2-chloro-N-(5-((E)-2-(2-(((1r,4r)-4-(dimethylamino)cyclohexyl)amino)pyrimidin-5-yl)vinyl)-6-methoxypyridin-2-yl)benzenesulfonamide (Compound 17)

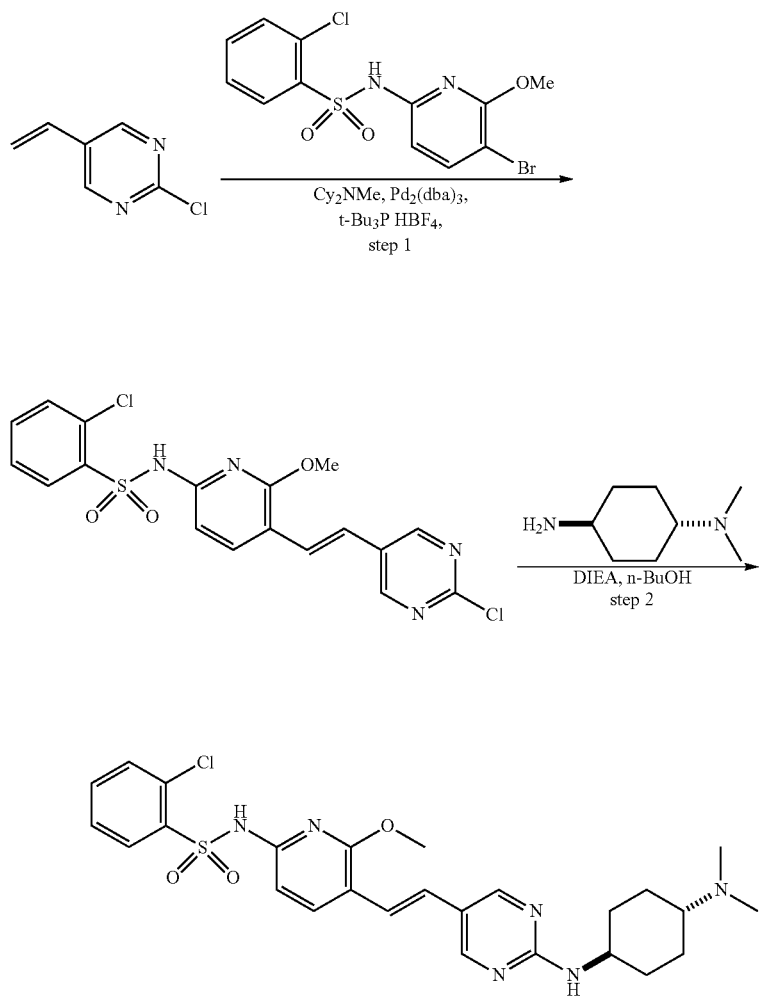

2-Chloro-N-(5-((E)-2-(2-(((1r,4r)-4-(dimethylamino)cyclohexyl)amino)pyrimidin-5-yl)vinyl)-6-methoxypyridin-2-yl)benzenesulfonamide was synthesized according to the synthetic procedure reported for the preparation of 2-chloro-N-(5-(2-(2-(((1r,4r)-4-hydroxycyclohexyl)amino)pyrimidin-5-yl)ethyl)-6-methylpyridin-2-yl)benzenesulfonamide (3.8 mg, 13.5% yield, FA). M+H$^+$=543.3 (LCMS); $^1$H NMR (400 MHz, METHANOL-d$_4$) δ 8.54 (br s, 1H), 8.39 (s, 2H), 8.27 (d, J=7.5 Hz, 1H), 7.73 (d, J=8.2 Hz, 1H), 7.60-7.45 (m, 3H), 7.05-6.95 (m, 1H), 6.94-6.84 (m, 1H), 6.52 (d, J=7.9 Hz, 1H), 3.84-3.71 (m, 1H), 3.67 (s, 3H), 2.99 (br t, J=11.9 Hz, 1H), 2.76-2.64 (m, 6H), 2.24-2.03 (m, 4H), 1.68-1.51 (m, 2H), 1.49-1.30 (m, 2H).

Example 15: Synthesis of 2-chloro-N-(5-(2-(2-(((1r,4r)-4-(dimethylamino)cyclohexyl)amino) pyrimidin-5-yl)ethyl)-6-methoxypyridin-2-yl)benzenesulfonamide (Compound 19)

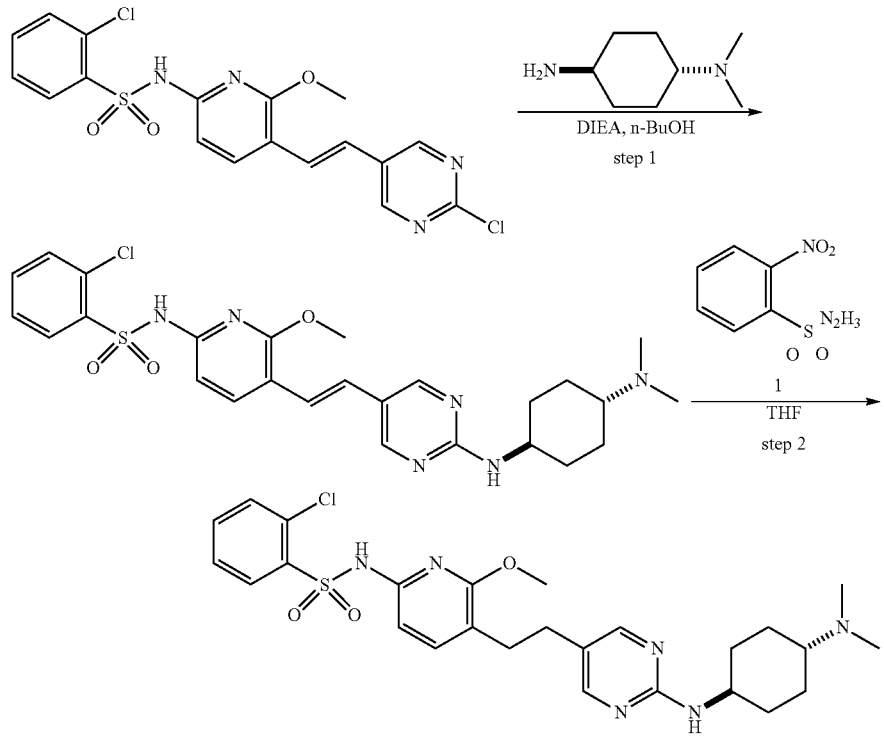

2-Chloro-N-(5-(2-(2-(((1r,4r)-4-(dimethylamino)cyclohexyl)amino) pyrimidin-5-yl)ethyl)-6-methoxypyridin-2-yl)benzenesulfonamide was synthesized according to the synthetic procedure reported for the preparation of 2-chloro-N-(5-(2-(2-(((1r,4r)-4-hydroxycyclohexyl)amino)pyrimidin-5-yl)ethyl)-6-methylpyridin-2-yl)benzenesulfonamide (6.4 mg, 19.7% yield, FA). M+H$^+$=545.2 (LCMS); $^1$H NMR (400 MHz, METHANOL-d$_4$) δ 8.53 (br s, 1H), 8.28-8.21 (m, 1H), 7.96 (s, 2H), 7.62-7.54 (m, 2H), 7.53-7.47 (m, 1H), 7.24 (d, J=7.8 Hz, 1H), 6.45 (d, J=7.7 Hz, 1H), 3.81-3.66 (m, 1H), 3.59 (s, 3H), 3.28-3.16 (m, 1H), 2.86 (s, 6H), 2.75-2.54 (m, 4H), 2.28-2.08 (m, 4H), 1.77-1.56 (m, 2H), 1.50-1.33 (m, 2H).

Example 16: Synthesis of 2-chloro-N-(5-((E)-2-(2-(((1r,4r)-4-(dimethylamino)cyclohexyl)amino)pyrimidin-5-yl)vinyl)-3-fluoro-6-methylpyridin-2-yl)benzenesulfonamide (Compound 25)

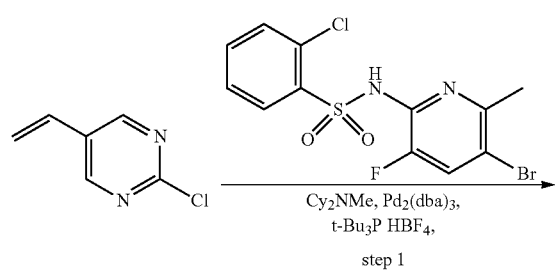

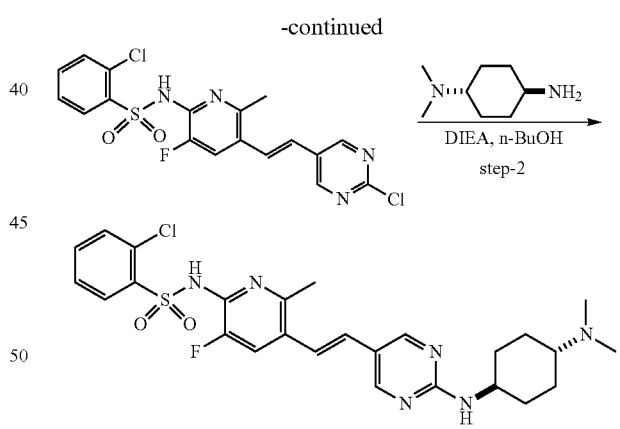

Step 1:

A mixture of 2-chloro-5-vinylpyrimidine (100 mg, 711.3 umol), N-(5-bromo-3-fluoro-6-methylpyridin-2-yl)-2-chlorobenzenesulfonamide (405 mg, 1.0 mmol), Pd$_2$(dba)$_3$ (130 mg, 142.2 umol), N-cyclohexyl-N-methyl-cyclohexanamine (416 mg, 2.1 mmol, 452.6 uL) and tritert-butylphosphonium; tetrafluoroborate (41 mg, 142.2 umol) in dioxane (2.0 mL) was degassed and purged with N$_2$ three times, and then the mixture was stirred at 100° C. for 12 h under N$_2$ atmosphere. The reaction mixture was concentrated under reduced pressure. The residue was purified by column chromatography (SiO$_2$) and prep-TLC (SiO$_2$) to afford (E)-

2-chloro-N-(5-(2-(2-chloropyrimidin-5-yl)vinyl)-3-fluoro-6-methylpyridin-2-yl)benzenesulfonamide (86 mg, 17.3% yield) as a yellow solid.

Step 2:

(E)-2-chloro-N-(5-(2-(2-chloropyrimidin-5-yl)vinyl)-3-fluoro-6-methylpyridin-2-yl)benzenesulfonamide (130 mg, 295.9 umol), (1r,4r)-N'N'-dimethylcyclohexane-1,4-diamine (528 mg, 2.9 mmol, HCl) and DIEA (114 mg, 887.8 umol, 154.6 uL) were taken up into a microwave tube in n-BuOH (3.0 mL). The sealed tube was heated at 150° C. for 2 h under microwave. The reaction mixture was concentrated under reduced pressure. The residue was purified by pre-HPLC (FA condition) to afford 2-chloro-N-(5-((E)-2-(2-(((1r,4r)-4-(dimethylamino)cyclohexyl)amino)pyrimidin-5-yl)vinyl)-3-fluoro-6-methylpyridin-2-yl)benzenesulfonamide (47 mg, 25.3% yield, FA) as a yellow solid. M+H$^+$=545.1 (LCMS); $^1$H NMR (400 MHz, METHANOL-d$_4$) δ 8.50 (s, 2H), 8.30 (d, J=7.7 Hz, 1H), 7.74 (d, J=11.5 Hz, 1H), 7.64-7.45 (m, 3H), 7.10-7.00 (m, 1H), 6.89-6.83 (m, 1H), 3.84 (brt, J=11.4 Hz, 1H), 3.27-3.13 (m, 1H), 2.94-2.80 (m, 6H), 2.31-2.25 (m, 3H), 2.24-2.10 (m, 4H), 1.79-1.60 (m, 2H), 1.53-1.39 (m, 2H).

Example 17: Synthesis of 2-chloro-N-(5-((E)-2-(2-(((1r,4r)-4-hydroxycyclohexyl)amino) pyrimidin-5-yl)vinyl)-6-methoxypyridin-2-yl)benzenesulfonamide (Compound 11)

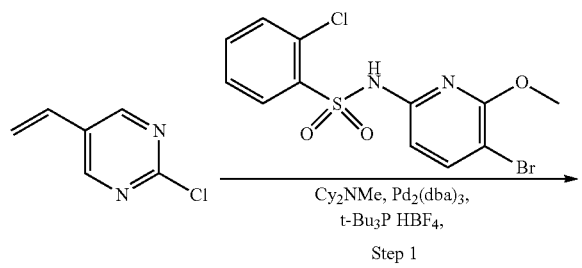

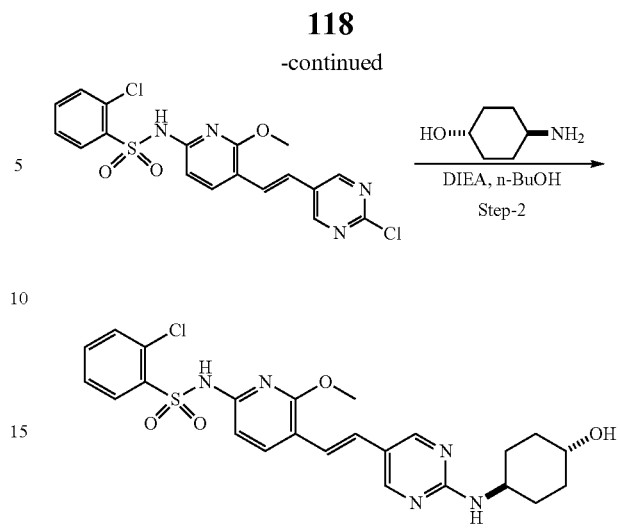

2-chloro-N-(5-((E)-2-(2-(((1r,4r)-4-hydroxycyclohexyl)amino) pyrimidin-5-yl)vinyl)-6-methoxypyridin-2-yl)benzenesulfonamide was synthesized according to the synthetic procedure reported for the preparation of 2-chloro-N-(5-(2-(2-(((1r,4r)-4-hydroxycyclohexyl)amino)pyrimidin-5-yl)ethyl)-6-methylpyridin-2-yl)benzenesulfonamide (3.1 mg, 5.5 umol, 5.7% yield, FA). M+H$^+$=516.2 (LCMS); $^1$H NMR (400 MHz, METHANOL-d$_4$) δ 8.39 (s, 2H), 8.28 (dd, J=1.3, 7.9 Hz, 1H), 7.75 (d, J=8.2 Hz, 1H), 7.62-7.46 (m, 3H), 7.04-6.95 (m, 1H), 6.93-6.85 (m, 1H), 6.53 (d, J=8.1 Hz, 1H), 3.80-3.66 (m, 4H), 3.63-3.51 (m, 1H), 2.07-1.92 (m, 4H), 1.48-1.27 (m, 4H).

Example 18: Synthesis of 2-chloro-N-(5-(2-(2-(((1r,4r)-4-(dimethylamino)cyclohexyl)amino) pyrimidin-5-yl)ethyl)-3-fluoro-6-methylpyridin-2-yl)benzenesulfonamide (Compound 24)

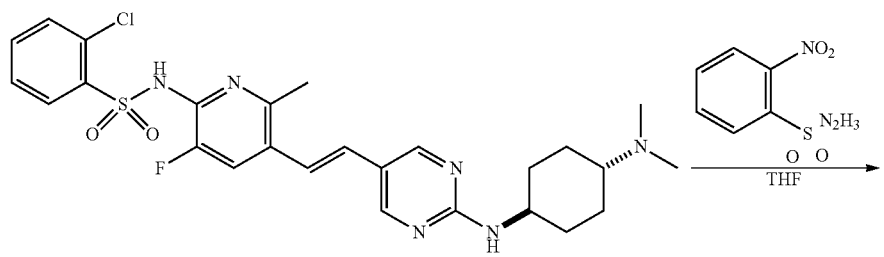

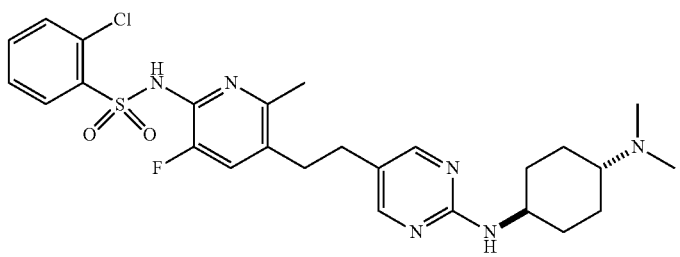

To a solution of 2-chloro-N-(5-((E)-2-(2-(((1r,4r)-4-(dimethylamino)cyclohexyl)amino)pyrimidin-5-yl)vinyl)-3-fluoro-6-methylpyridin-2-yl)benzenesulfonamide (Example 16) (40 mg, 73.3 umol) in THF (3.0 mL) was added TEA (148 mg, 1.4 mmol, 204.2 uL) and 2-nitrobenzenesulfonohydrazide (159 mg, 733.8 umol). The mixture was stirred at 60° C. for 12 h. The reaction mixture was concentrated under reduced pressure to give a residue. The residue was purified by pre-HPLC (FA condition) and further purified by pre-HPLC (basic condition) to give 2-chloro-N-(5-(2-(2-(((1r,4r)-4-(dimethylamino)cyclohexyl)amino) pyrimidin-5-yl)ethyl)-3-fluoro-6-methylpyridin-2-yl)benzenesulfonamide (3.9 mg, 9.7% yield) as a white solid. M+H$^+$=547.2 (LCMS); $^1$H NMR (400 MHz, METHANOL-d$_4$) δ 8.22 (d, J=7.3 Hz, 1H), 8.00 (s, 2H), 7.51-7.37 (m, 3H), 7.08 (d, J=11.0 Hz, 1H), 3.74-3.61 (m, 1H), 2.75-2.58 (m, 5H), 2.53 (s, 6H), 2.19-1.98 (m, 7H), 1.58-1.43 (m, 2H), 1.40-1.27 (m, 2H).

Example 19: Synthesis of 2-chloro-N-(6-methoxy-5-((E)-2-(2-(((1r,4r)-4-(methylamino)cyclohexyl)amino)pyrimidin-5-yl)vinyl)pyridin-2-yl)benzenesulfonamide (Compound 48)

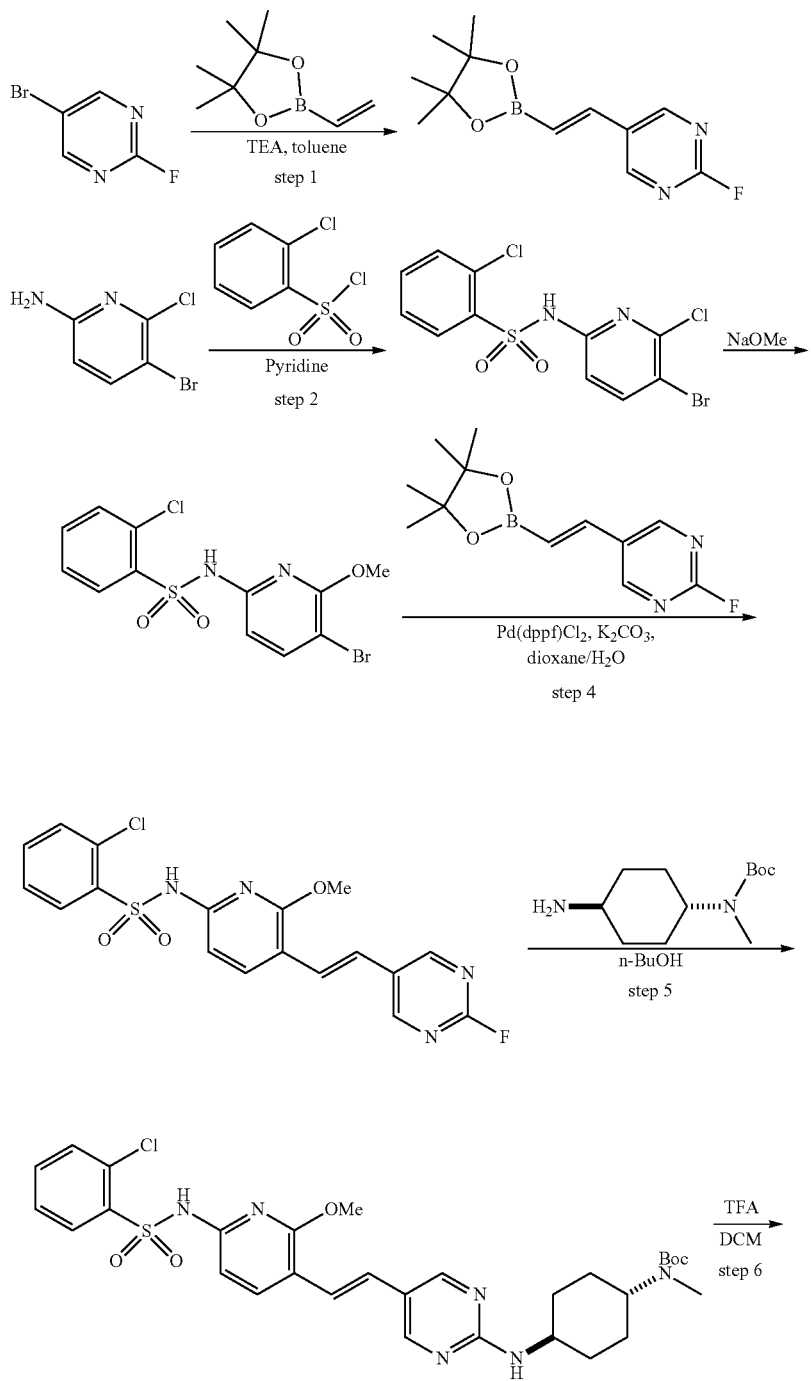

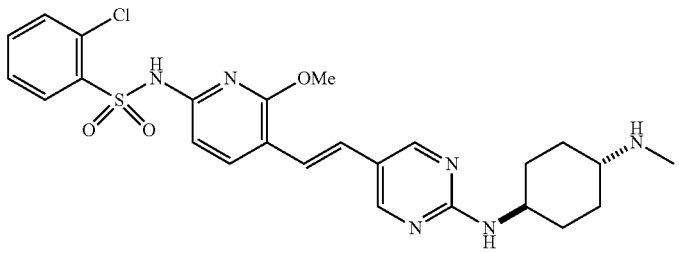

Step 1:
A mixture of 5-bromo-2-fluoropyrimidine (25.0 g, 141.2 mmol), 4,4,5,5-tetramethyl-2-vinyl-1,3,2-dioxaborolane (32.6 g, 211.9 mmol, 35.9 mL), TEA (28.5 g, 282.5 mmol, 39.3 mL), Pd(t-Bu$_3$P)$_2$ (3.6 g, 7.0 mmol) in toluene (500 mL) was degassed and purged with N$_2$ three times, and then the mixture was stirred at 80° C. for 12 h under N$_2$ atmosphere. The reaction mixture was concentrated under reduced pressure. The residue was purified by column chromatography (SiO$_2$) to give (E)-2-fluoro-5-(2-(4,4,5,5-tetramethyl-1,3,2-dioxaborolan-2-yl)vinyl)pyrimidine (30.0 g, 89.9 mmol, 63.6% yield) as a white solid. $^1$H NMR (400 MHz, CHLOROFORM-d) δ 8.69 (d, J=1.3 Hz, 2H), 7.37-7.19 (m, 1H), 6.26 (d, J=18.5 Hz, 1H), 1.30 (s, 12H).

Step 2:
To a solution of 5-bromo-6-chloropyridin-2-amine (32.0 g, 154.2 mmol) in pyridine (250.0 mL) was added 2-chlorobenzene-1-sulfonyl chloride (48.8 g, 231.3 mmol, 31.5 mL). The mixture was stirred at 45° C. for 24 h. The reaction mixture was concentrated under reduced pressure to give a residue. The residue was purified by flash silica gel chromatography to afford N-(5-bromo-6-chloropyridin-2-yl)-2-chlorobenzenesulfonamide (50.0 g) as a yellow solid. $^1$H NMR (400 MHz, METHANOL-d$_4$) δ 8.33-8.21 (m, 1H), 7.84 (d, J=8.6 Hz, 1H), 7.62-7.46 (m, 3H), 6.88 (d, J=8.6 Hz, 1H).

Step 3:
A solution of N-(5-bromo-6-chloropyridin-2-yl)-2-chlorobenzenesulfonamide (40.0 g, 104.7 mmol) in NaOMe (400.0 mL, 30% purity) was stirred at 80° C. for 12 h. The reaction mixture was quenched by addition H$_2$O (500 mL) at 25° C., and extracted with ethyl acetate (500 mL×3). The combined organic layers were washed with saturated NaCl (50.0 mL×3), dried over Na$_2$SO$_4$, filtered and concentrated under reduced pressure to give a residue. The residue was diluted with EtOAc (200 mL) and filtered. The cake was washed with EtOAc (100 mL) to give N-(5-bromo-6-methoxypyridin-2-yl)-2-chlorobenzenesulfonamide (45 g) as a white solid. $^1$H NMR (400 MHz, DMSO-d$_6$) δ 8.19-7.84 (m, 1H), 7.53-7.11 (m, 4H), 6.02 (d, J=8.4 Hz, 1H), 3.36 (br s, 3H).

Step 4:
A mixture of N-(5-bromo-6-methoxypyridin-2-yl)-2-chlorobenzenesulfonamide (1.5 g, 4.0 mmol), (E)-2-fluoro-5-(2-(4,4,5,5-tetramethyl-1,3,2-dioxaborolan-2-yl)vinyl)pyrimidine (1.0 g, 4.0 mmol), K$_2$CO$_3$ (1.6 g, 12.0 mmol), and Pd(dppf)Cl$_2$ (292 mg, 399.8 umol) in dioxane (40.0 mL) and H$_2$O (4.0 mL) was degassed and purged with N$_2$ three times, and then the mixture was stirred at 90° C. for 12 h under N$_2$ atmosphere. The reaction was concentrated under reduced pressure to give a residue. The residue was diluted with H$_2$O (200 mL) and extracted with tetrahydrofuran (50 mL×3). The combined organic layers were washed with brine (50 mL×3), dried over Na$_2$SO$_4$, filtered and concentrated under reduced pressure to give a residue. Ethyl acetate (50 mL) was added and the mixture was filtered to give (E)-2-chloro-N-(5-(2-(2-fluoropyrimidin-5-yl)vinyl)-6-methoxypyridin-2-yl)benzenesulfonamide (340 mg, 14.1% yield) as a yellow solid. $^1$H NMR (400 MHz, DMSO-d$_6$) δ 8.89 (br s, 2H), 8.19 (br d, J=6.6 Hz, 1H), 7.71 (br d, J=7.3 Hz, 1H), 7.61-7.46 (m, 4H), 7.29 (br d, J=17.4 Hz, 1H), 7.07-6.96 (m, 1H), 6.41 (br d, J=6.8 Hz, 1H), 3.50 (br s, 3H).

Step 5:
To a solution of (E)-2-chloro-N-(5-(2-(2-fluoropyrimidin-5-yl)vinyl)-6-methoxypyridin-2-yl)benzenesulfonamide (150 mg, 356.4 umol) in n-BuOH (4.0 mL) was added DIEA (138 mg, 1.0 mmol, 186.2 uL) and tert-butyl ((1r,4r)-4-aminocyclohexyl)(methyl)carbamate (122 mg, 534.6 umol). The mixture was stirred at 100° C. for 12 h. The reaction was concentrated under reduced pressure to give a residue. The residue was purified by column chromatography (SiO$_2$) to afford tert-butyl ((1r,4r)-4-((5-((E)-2-(6-((2-chlorophenyl)sulfonamido)-2-methoxypyridin-3-yl)vinyl)pyrimidin-2-yl)amino)cyclohexyl)(methyl)carbamate (100 mg, 24.8% yield) as a yellow solid. M+H$^+$=629.2 (LCMS).

Step 6:
To a solution of tert-butyl ((1r,4r)-4-((5-((E)-2-(6-((2-chlorophenyl)sulfonamido)-2-methoxypyridin-3-yl)vinyl)pyrimidin-2-yl)amino)cyclohexyl)(methyl)carbamate (100 mg, 158.9 umol) in DCM (2.0 mL) was added TFA (1.0 mL). The mixture was stirred at 25° C. for 0.5 h. The mixture was concentrated to give crude residue. The residue was dissolved in MeOH (2.0 mL) and basified pH to 8 with NH$_3$·H$_2$O (25% purity), and concentrated to give a residue. The residue was purified by prep-HPLC (FA condition) to give 2-chloro-N-(6-methoxy-5-((E)-2-(2-(((1r,4r)-4-(methylamino)cyclohexyl)amino)pyrimidin-5-yl)vinyl)pyridin-2-yl)benzenesulfonamide (39.5 mg, 41.7% yield, FA) as a pale yellow solid. M+H$^+$=529.1 (LCMS); $^1$H NMR (400 MHz, METHANOL-d$_4$) δ 8.54 (s, 1H), 8.40 (s, 2H), 8.28 (dd, J=1.3, 7.8 Hz, 1H), 7.73 (d, J=8.1 Hz, 1H), 7.61-7.46 (m, 3H), 7.04-6.96 (m, 1H), 6.93-6.85 (m, 1H), 6.53 (d, J=8.1 Hz, 1H), 3.85-3.73 (m, 1H), 3.68 (s, 3H), 3.04 (ddd, J=3.5, 8.0, 11.4 Hz, 1H), 2.70 (s, 3H), 2.18 (br d, J=9.9 Hz, 4H), 1.60-1.33 (m, 4H).

Example 20: Synthesis of 2-chloro-N-(6-ethyl-5-((E)-2-(2-(((1r,4r)-4-(methylamino)cyclohexyl)amino)pyrimidin-5-yl)vinyl)pyridin-2-yl)benzenesulfonamide (Compound 47)

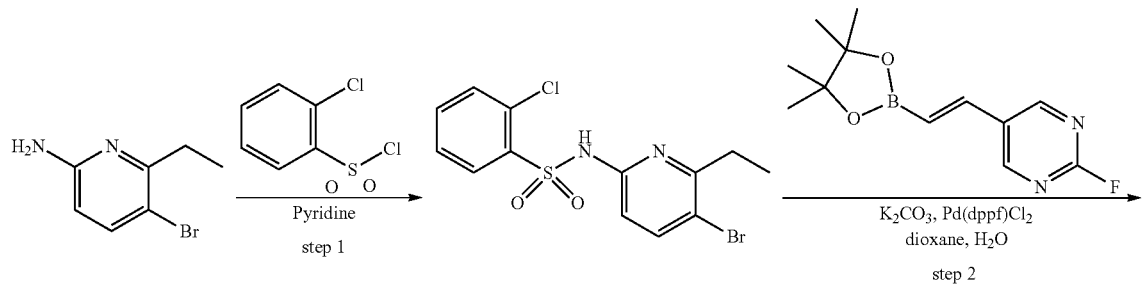

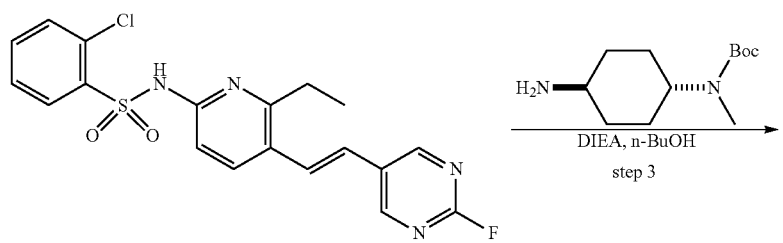

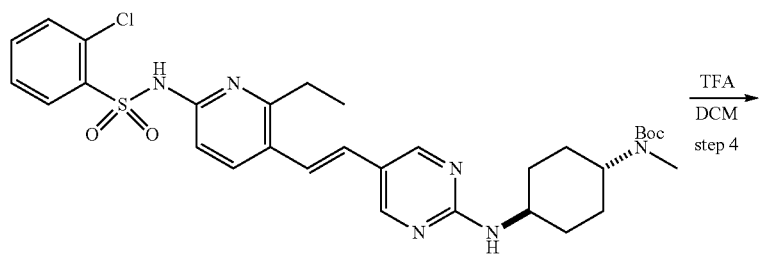

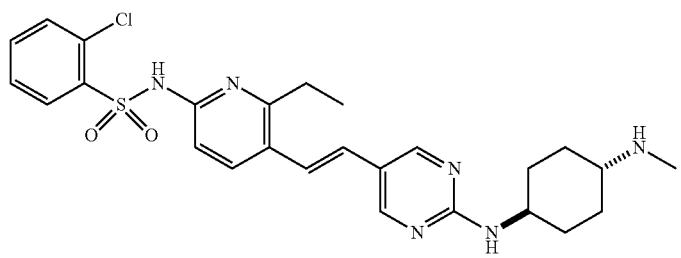

The title compound was synthesized in a similar manner as described in Example 19 to afford 2-chloro-N-(6-ethyl-5-((E)-2-(2-(((1r,4r)-4-(methylamino)cyclohexyl)amino)pyrimidin-5-yl)vinyl)pyridin-2-yl)benzenesulfonamide (28.5 mg, 26.6% yield, FA) as a yellow solid. M+H$^+$=527.2 (LCMS); $^1$H NMR (400 MHz, METHANOL-d$_4$) δ 8.47 (s, 2H), 8.37 (br s, 1H), 8.22-8.17 (m, 1H), 7.97 (d, J=9.3 Hz, 1H), 7.51 (d, J=3.5 Hz, 2H), 7.49-7.43 (m, 1H), 7.11 (d, J=9.3 Hz, 1H), 7.05 (d, J=16.3 Hz, 1H), 6.82 (d, J=16.3 Hz, 1H), 3.81 (ddd, J=3.6, 7.7, 11.1 Hz, 1H), 3.10-2.99 (m, 1H), 2.82 (q, J=7.5 Hz, 2H), 2.70 (s, 3H), 2.25-2.12 (m, 4H), 1.61-1.33 (m, 4H), 1.18 (t, J=7.6 Hz, 3H).

Example 21: Synthesis of 2-chloro-N-(5-((E)-2-(2-(((1r,4r)-4-(dimethylamino)cyclohexyl)amino)pyrimidin-5-yl)vinyl)-6-ethylpyridin-2-yl)benzenesulfonamide (Compound 29)

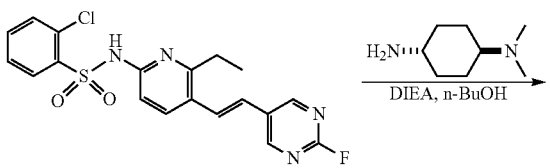

-continued

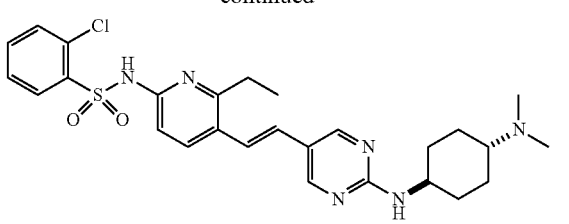

The title compound was synthesized in a similar manner as described in Example 19 to afford 2-chloro-N-(5-((E)-2-(2-(((1r,4r)-4-(dimethylamino)cyclohexyl)amino)pyrimidin-5-yl)vinyl)-6-ethylpyridin-2-yl)benzenesulfonamide (52.6 mg, 34.1% yield) as a pale yellow solid. M+H⁺=541.2 (LCMS); ¹H NMR (400 MHz, METHANOL-d₄) δ 8.46 (s, 2H), 8.24-8.16 (m, 1H), 8.00-7.92 (m, 1H), 7.57-7.41 (m, 3H), 7.12-7.02 (m, 2H), 6.83 (d, J=16.4 Hz, 1H), 3.81-3.70 (m, 1H), 2.82 (q, J=7.7 Hz, 2H), 2.43-2.29 (m, 7H), 2.13 (br d, J=12.0 Hz, 2H), 2.04-1.94 (m, 2H), 1.49-1.28 (m, 4H), 1.18 (t, J=7.6 Hz, 3H).

Example 22: Synthesis of N-(5-(2-(2-(((1r,4r)-4-aminocyclohexyl)amino)pyrimidin-5-yl)vinyl)-6-ethylpyridin-2-yl)-2-chlorobenzenesulfonamide (Compound 45)

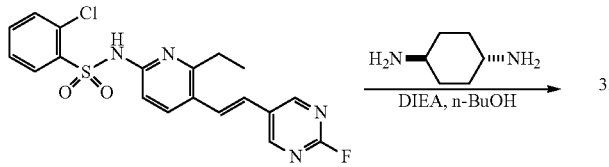

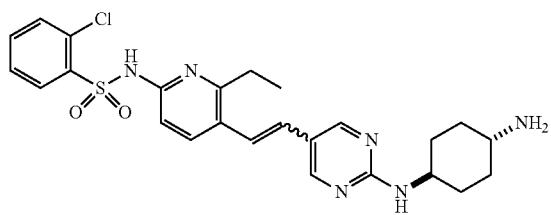

The title compound was synthesized in a similar manner as described in Example 19 to afford N-(5-(2-(2-(((1r,4r)-4-aminocyclohexyl)amino)pyrimidin-5-yl)vinyl)-6-ethylpyridin-2-yl)-2-chlorobenzenesulfonamide (17.7 mg, 16.5% yield, FA, cis and trans) as a pale yellow solid. M+H⁺=513.1 (LCMS); ¹H NMR (400 MHz, METHANOL-d₄) δ 8.55 (s, 1H), 8.47 (s, 2H), 8.22-8.16 (m, 1H), 7.94 (d, J=9.0 Hz, 1H), 7.53-7.48 (m, 2H), 7.48-7.42 (m, 1H), 7.12-7.04 (m, 2H), 6.82 (d, J=16.3 Hz, 1H), 3.83-3.74 (m, 1H), 3.06 (br s, 1H), 2.81 (q, J=7.6 Hz, 2H), 2.19-1.99 (m, 4H), 1.57-1.35 (m, 4H), 1.17 (t, J=7.5 Hz, 3H).

Example 23: Synthesis of 2-chloro-N-(4-((E)-2-(2-(((1r,4r)-4-(dimethylamino)cyclohexyl)amino)pyrimidin-5-yl)vinyl)-2-fluoro-5-methylphenyl)benzenesulfonamide (Compound 28)

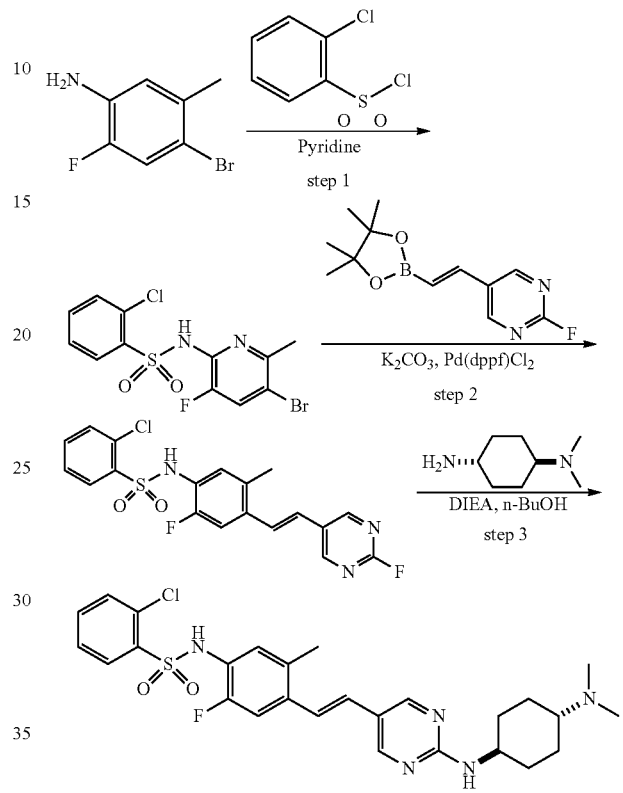

The title compound was synthesized in a similar manner as described in Example 19 to afford 2-chloro-N-(4-((E)-2-(2-(((1r,4r)-4-(dimethylamino)cyclohexyl)amino)pyrimidin-5-yl)vinyl)-2-fluoro-5-methylphenyl)benzenesulfonamide (14.8 mg, 37.1% yield) as a pale yellow solid. M+H⁺=544.2 (LCMS); ¹H NMR (400 MHz, DMSO-d₆) δ 8.50 (s, 2H), 7.90 (dd, J=1.4, 7.8 Hz, 1H), 7.59-7.45 (m, 2H), 7.44-7.36 (m, 1H), 7.31-7.21 (m, 2H), 7.06 (d, J=16.3 Hz, 1H), 6.96 (d, J=8.6 Hz, 1H), 6.80 (d, J=16.3 Hz, 1H), 3.68 (br dd, J=3.9, 7.6 Hz, 1H), 2.58-2.53 (m, 1H), 2.38 (s, 6H), 2.18 (s, 3H), 2.05-1.82 (m, 4H), 1.44-1.21 (m, 4H).

Example 24: Synthesis of 2-chloro-N-(4-((E)-2-(2-(((1r,4r)-4-(dimethylamino)cyclohexyl)amino)pyrimidin-5-yl)vinyl)-3-methylphenyl)benzenesulfonamide (Compound 26)

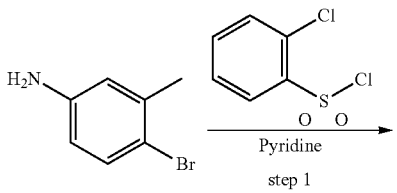

-continued

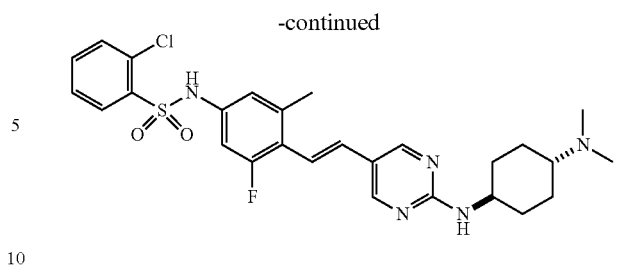

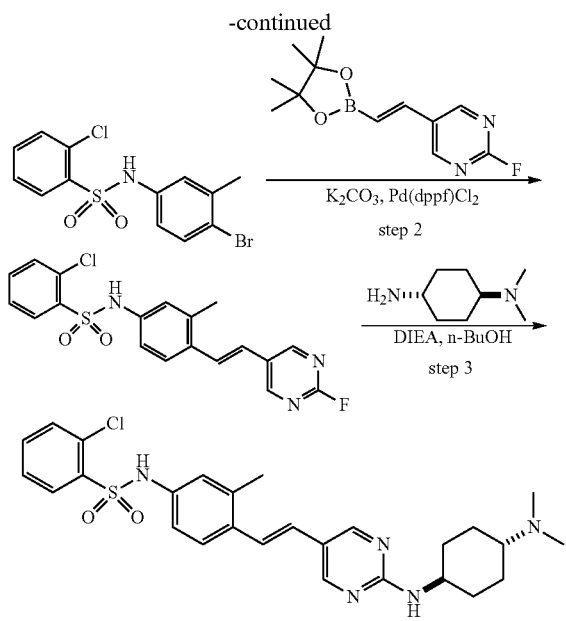

The title compound was synthesized in a similar manner as described in Example 19 to afford 2-chloro-N-(4-((E)-2-(2-(((1r,4r)-4-(dimethylamino)cyclohexyl)amino)pyrimidin-5-yl)vinyl)-3-methylphenyl)benzenesulfonamide (13.7 mg, 18.4% yield) as a pale yellow solid. M+H$^+$=526.2 (LCMS); $^1$H NMR (400 MHz, METHANOL-d$_4$) δ 8.42 (s, 2H), 8.09-8.02 (m, 1H), 7.57-7.48 (m, 2H), 7.45-7.37 (m, 2H), 7.11 (d, J=16.3 Hz, 1H), 7.00-6.91 (m, 2H), 6.72 (d, J=16.3 Hz, 1H), 3.80-3.68 (m, 1H), 2.49-2.30 (m, 7H), 2.28 (s, 3H), 2.12 (br d, J=9.3 Hz, 2H), 2.00 (br d, J=12.3 Hz, 2H), 1.49-1.27 (m, 4H).

Example 25: Synthesis of 2-chloro-N-(4-((E)-2-(2-(((1r,4r)-4-(dimethylamino)cyclohexyl)amino)pyrimidin-5-yl)vinyl)-3-fluoro-5-methylphenyl)benzenesulfonamide (Compound 27)

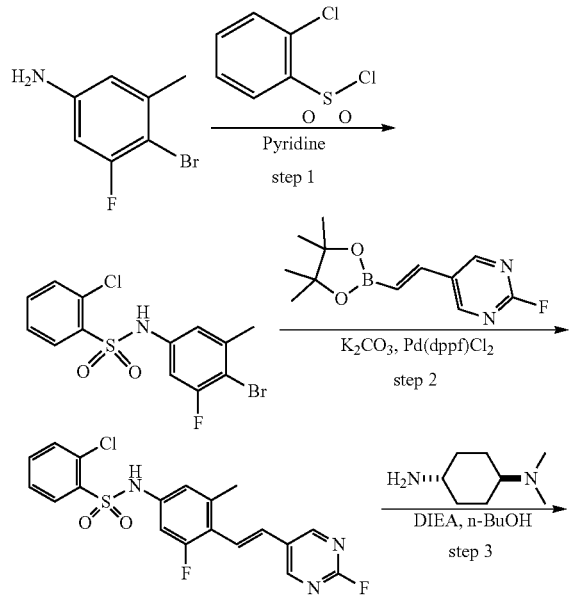

-continued

The title compound was synthesized in a similar manner as described in Example 19 to afford 2-chloro-N-(4-((E)-2-(2-(((1r,4r)-4-(dimethylamino)cyclohexyl)amino)pyrimidin-5-yl)vinyl)-3-fluoro-5-methylphenyl)benzenesulfonamide (4.8 mg, 16.4% yield) as a pale yellow solid. M+H$^+$=544.2 (LCMS); $^1$H NMR (400 MHz, METHANOL-d$_4$) δ 8.42 (s, 2H), 8.12 (d, J=7.5 Hz, 1H), 7.60-7.51 (m, 2H), 7.50-7.43 (m, 1H), 6.92-6.87 (m, 1H), 6.86-6.81 (m, 1H), 6.81-6.75 (m, 2H), 3.81-3.68 (m, 1H), 2.50-2.27 (m, 10H), 2.14 (br d, J=12.2 Hz, 2H), 2.05-1.97 (m, 2H), 1.51-1.28 (m, 4H).

Example 26: Synthesis of 2-chloro-N-(5-((E)-2-(2-(((1r,4r)-4-(dimethylamino)cyclohexyl)amino)pyrimidin-5-yl)vinyl)-3-fluoro-6-methoxypyridin-2-yl)benzenesulfonamide (Compound 50)

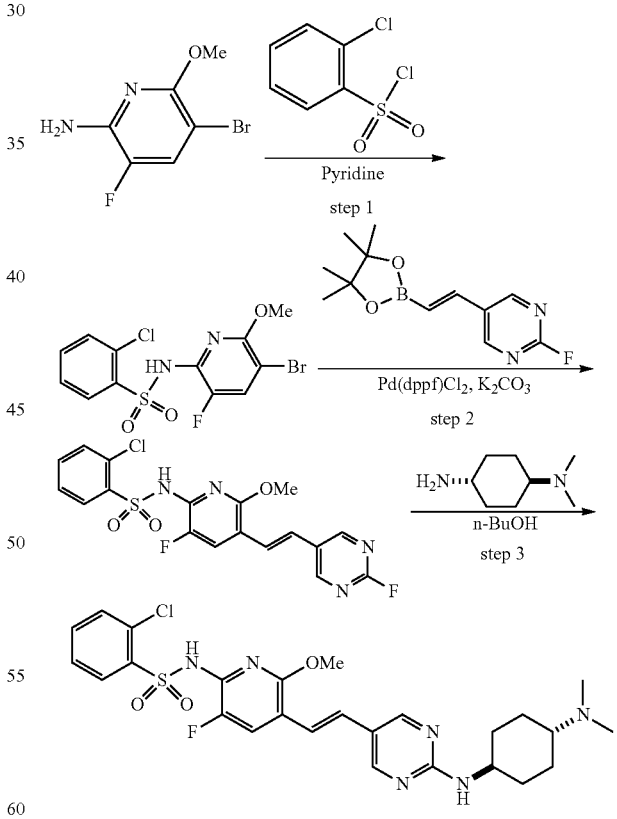

The title compound was synthesized in a similar manner as described in Example 19 to afford 2-chloro-N-(5-((E)-2-(2-(((1r,4r)-4-(dimethylamino)cyclohexyl)amino)pyrimidin-5-yl)vinyl)-3-fluoro-6-methoxypyridin-2-yl)benzenesulfonamide (440.3 mg, 23.8% yield) as a yellow solid. M+H$^+$=561.2 (LCMS); $^1$H NMR (400 MHz, DMSO-d$_6$) δ

8.36 (s, 2H), 8.12 (dd, J=2D, 5.2 Hz, 1H), 7.45-7.31 (m, 4H), 7.20 (br d, J=7.9 Hz, 1H), 6.89-6.81 (m, 1H), 6.72-6.64 (m, 1H), 3.76-3.63 (m, 1H), 3.23 (s, 3H), 3.09-2.98 (m, 1H), 2.67 (s, 6H), 1.99 (br t, J=14.7 Hz, 4H), 1.58-1.45 (m, 2H), 1.37-1.25 (m, 2H).

Example 27: Synthesis of 2-chloro-N-(5-((E)-2-(2-(((1r,4r)-4-(dimethylamino)cyclohexyl)amino)pyrimidin-5-yl)vinyl)-6-methylpyridin-2-yl)-3-fluorobenzenesulfonamide (Compound 33)

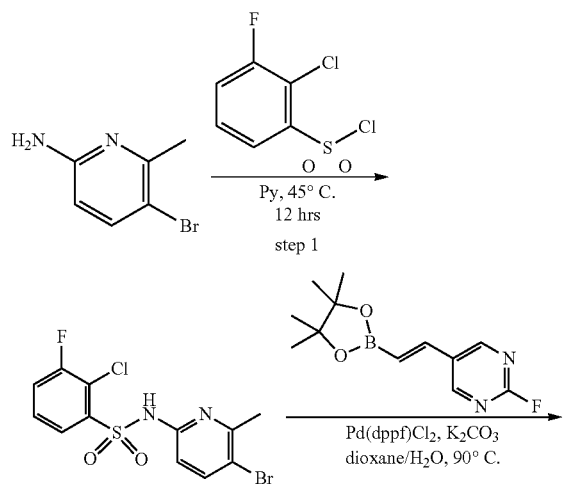

Example 28: Synthesis of 2-chloro-N-(5-((E)-2-(2-(((1r,4r)-4-(dimethylamino)cyclohexyl)amino)pyrimidin-5-yl)vinyl)-6-methoxypyridin-2-yl)-4-fluorobenzenesulfonamide (Compound 32)

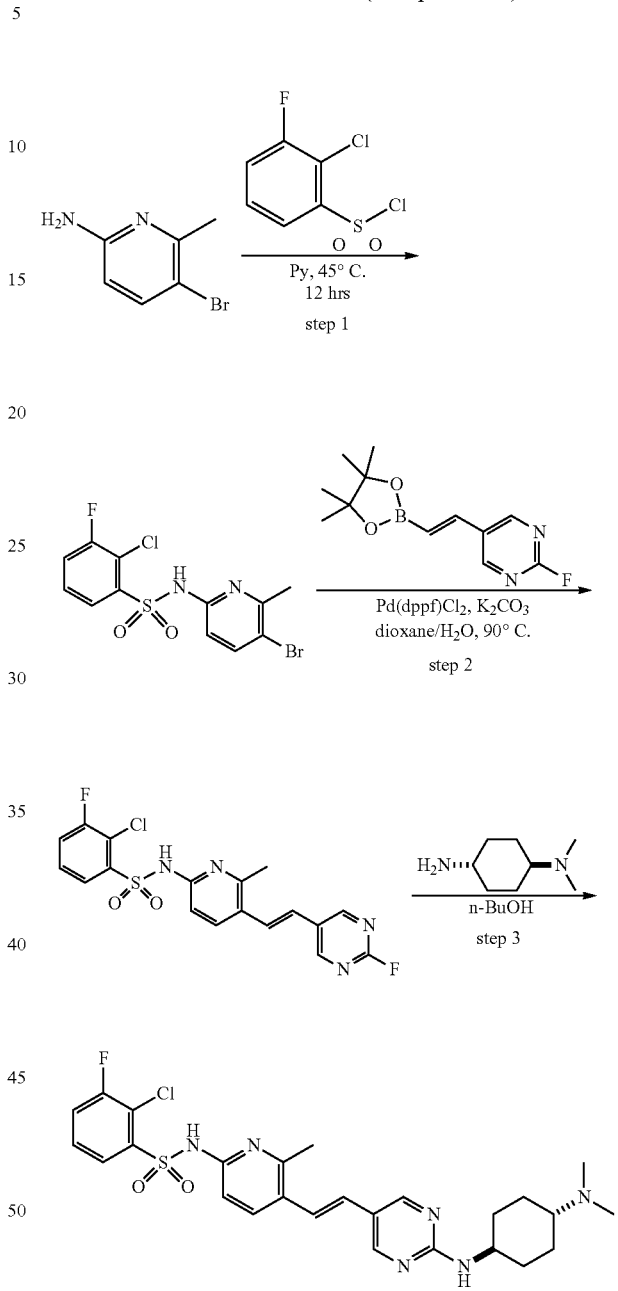

The title compound was synthesized in a similar manner as described in Example 19 to afford 2-chloro-N-(5-((E)-2-(2-(((1r,4r)-4-(dimethylamino)cyclohexyl)amino)pyrimidin-5-yl)vinyl)-6-methylpyridin-2-yl)-3-fluorobenzenesulfonamide (19.5 mg, 19.2% yield, FA) as a yellow solid. M+H$^+$=545.3; $^1$H NMR (400 MHz, METHANOL-d$_4$) δ 8.55 (s, 1H), 8.48 (s, 2H), 8.05-7.99 (m, 2H), 7.52-7.39 (m, 2H), 7.21 (d, J=9.0 Hz, 1H), 7.05 (d, J=16.3 Hz, 1H), 6.85 (d, J=16.3 Hz, 1H), 3.78 (br t, J=11.2 Hz, 1H), 2.82 (br s, 1H), 2.61 (s, 6H), 2.50 (s, 3H), 2.18 (br d, J=12.1 Hz, 2H), 2.08 (brd, J=11.0 Hz, 2H), 1.56 (br d, J=11.2 Hz, 2H), 1.46-1.32 (m, 2H).

The title compound was synthesized in a similar manner as described in Example 19 to afford 2-chloro-N-(5-((E)-2-(2-(((1r,4r)-4-(dimethylamino)cyclohexyl)amino)pyrimidin-5-yl)vinyl)-6-methoxypyridin-2-yl)-4-fluorobenzenesulfonamide (27.4 mg, 28.3% yield, FA) as a yellow solid. M+H$^+$=561.1; $^1$H NMR (400 MHz, METHANOL-d$_4$) δ 8.54 (s, 1H), 8.40 (s, 2H), 8.33 (dd, J=5.9, 8.9 Hz, 1H), 7.75 (d, J=8.1 Hz, 1H), 7.41 (dd, J=2.6, 8.4 Hz, 1H), 7.33-7.22 (m, 1H), 7.08-6.87 (m, 2H), 6.53 (d, J=8.1 Hz, 1H), 3.79 (tt, J=3.9, 11.6 Hz, 1H), 3.71 (s, 3H), 3.20-3.02 (m, 1H), 2.79 (s, 6H), 2.24-2.10 (m, 4H), 1.73-1.55 (m, 2H), 1.48-1.33 (m, 2H).

Example 29: Synthesis of 2-chloro-N-(5-((E)-2-(2-(((1r,4r)-4-(dimethylamino)cyclohexyl)amino)pyrimidin-5-yl)vinyl)-6-methylpyridin-2-yl)-4-fluorobenzenesulfonamide (Compound 31)

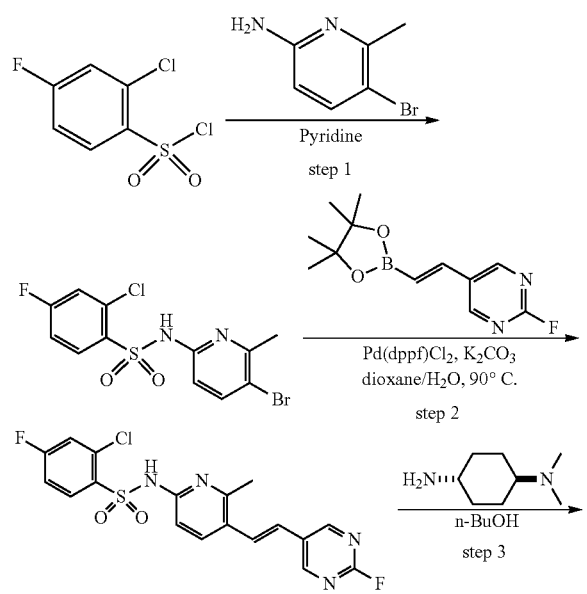

-continued

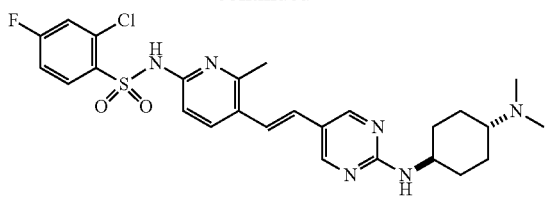

The title compound was synthesized in a similar manner as described in Example 19 to afford 2-chloro-N-(5-((E)-2-(2-(((1r,4r)-4-(dimethylamino)cyclohexyl)amino)pyrimidin-5-yl)vinyl)-6-methylpyridin-2-yl)-4-fluorobenzenesulfonamide (14.5 mg, 18.2% yield, FA) as a yellow solid. M+H$^+$=545.1 (LCMS); $^1$H NMR (400 MHz, METHANOL-d$_4$) δ 8.54 (br s, 1H), 8.48 (s, 2H), 8.24 (dd, J=6.2, 8.8 Hz, 1H), 8.00 (d, J=9.5 Hz, 1H), 7.36 (dd, J=2.3, 8.5 Hz, 1H), 7.23 (dt, J=2.4, 8.4 Hz, 1H), 7.16 (d, J=9.0 Hz, 1H), 7.05 (d, J=16.5 Hz, 1H), 6.83 (d, J=16.3 Hz, 1H), 3.86-3.71 (m, 1H), 2.95 (brt, J=11.9 Hz, 1H), 2.69 (s, 6H), 2.48 (s, 3H), 2.19 (br d, J=12.3 Hz, 2H), 2.09 (br d, J=11.9 Hz, 2H), 1.68-1.52 (m, 2H), 1.48-1.33 (m, 2H).

Example 30: Synthesis of 2-chloro-N-(5-((E)-2-(2-(((1r,4r)-4-(dimethylamino)cyclohexyl)amino)pyrimidin-5-yl)vinyl)-6-methylpyridin-2-yl)-3,4-difluorobenzenesulfonamide (Compound 38)

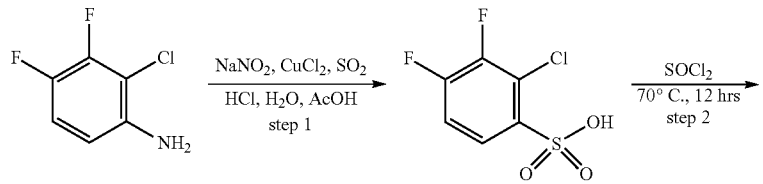

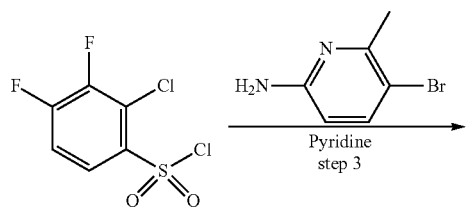

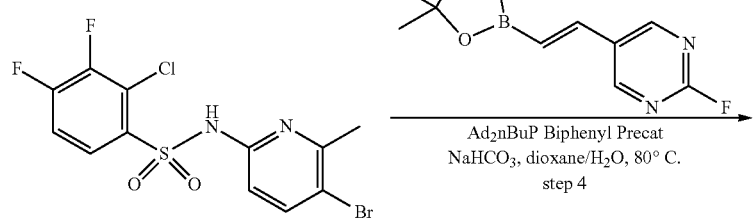

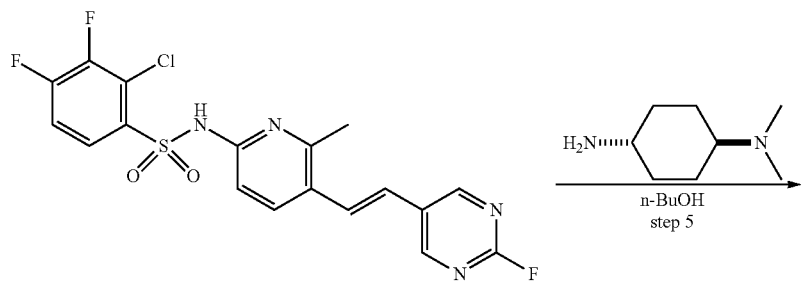

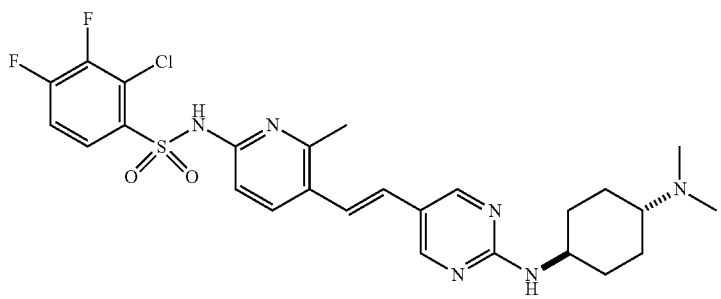

Step 1:

To a solution of 2-chloro-3,4-difluoro-aniline (500 mg, 3.1 mmol) in HCl (5.0 mL) was added NaNO$_2$ (2.5 g, 36.7 mmol) in H$_2$O (5.0 mL). The mixture was stirred at 0° C. for 30 min, then the mixture was poured into CuCl$_2$ (616 mg, 4.6 mmol) in AcOH (10.0 mL) and H$_2$O (1.0 mL). The mixture was stirred at 0° C. for 15 min under SO$_2$ (15 psi). The mixture was diluted with H$_2$O (10.0 mL) and extracted with ethyl acetate (10 mL×3). The combined organic layers were washed with brine (15 mL×2), dried over Na$_2$SO$_4$, filtered and concentrated under reduced pressure to give a residue. The residue was purified by column chromatography (SiO$_2$) to give 2-chloro-3,4-difluorobenzenesulfonic acid (600 mg, 54.1% yield) as a yellow oil. M−H$^+$=226.9 (LCMS).

Step 2:

To a solution of 2-chloro-3,4-difluorobenzenesulfonic acid (300 mg, 1.3 mmol) in SOCl$_2$ (2.0 mL) was added DMF (0.2 mL). The mixture was stirred at 70° C. for 12 h. The reaction mixture was concentrated under reduced pressure to give 2-chloro-3,4-difluorobenzenesulfonyl chloride (300 mg) as a yellow oil.

Step 3:

To a solution of 2-chloro-3,4-difluorobenzenesulfonyl chloride (300 mg, 1.2 mmol) in pyridine (2.0 mL) was added 5-bromo-6-methyl-pyridin-2-amine (113 mg, 607.2 umol). The mixture was stirred at 45° C. for 12 h. The reaction mixture was concentrated under reduced pressure. The residue was purified by column chromatography (SiO$_2$) to afford N-(5-bromo-6-methylpyridin-2-yl)-2-chloro-3,4-difluorobenzenesulfonamide (200 mg, 32.7% yield) as a brown oil. M+H$^+$=398.8 (LCMS).

Step 4:

A mixture of (E)-2-fluoro-5-(2-(4,4,5,5-tetramethyl-1,3,2-dioxaborolan-2-yl)vinyl)pyrimidine (125 mg, 503.0 umol), N-(5-bromo-6-methylpyridin-2-yl)-2-chloro-3,4-difluorobenzenesulfonamide (100 mg, 251.5 umol), [2-(2-aminophenyl)phenyl]-chloro-palladium; bis(1-adamantyl)-butyl-phosphane (16 mg, 25.2 umol), NaHCO$_3$ (63 mg, 754.5 umol) and H$_2$O (0.2 mL) in dioxane (2.0 mL) was degassed and purged with N$_2$ three times, and then the mixture was stirred at 80° C. for 12 h under N$_2$ atmosphere. The reaction mixture was concentrated under reduced pressure to give a residue. The residue was purified by prep-TLC (SiO$_2$) to afford (E)-2-chloro-3,4-difluoro-N-(5-(2-(2-fluoropyrimidin-5-yl)vinyl)-6-methylpyridin-2-yl)benzenesulfonamide (80 mg, 53.4% yield) as a brown oil. M+H$^+$=441.1 (LCMS).

Step 5:

To a solution of (E)-2-chloro-3,4-difluoro-N-(5-(2-(2-fluoropyrimidin-5-yl)vinyl)-6-methylpyridin-2-yl)benzenesulfonamide (80 mg, 181.5 umol) in n-BuOH (2.0 mL) was added DIEA (117 mg, 907.4 umol) and (1r,4r)-N$^1$,N$^1$-dimethylcyclohexane-1,4-diamine (64 mg, 363.0 umol, HCl). The mixture was stirred at 100° C. for 12 h. The reaction mixture was concentrated under reduced pressure to give a residue. The residue was purified by prep-HPLC (FA condition) to give 2-chloro-N-(5-((E)-2-(2-(((1r,4r)-4-(dimethylamino)cyclohexyl)amino)pyrimidin-5-yl)vinyl)-6-methylpyridin-2-yl)-3,4-difluorobenzenesulfonamide (14.5 mg, 12.5% yield, FA) as a pale yellow solid. M+H$^+$=563.2 (LCMS); $^1$H NMR (400 MHz, METHANOL-d$_4$) δ 8.50 (s, 3H), 8.09-8.01 (m, 2H), 7.46-7.37 (m, 1H), 7.23 (d, J=93 Hz, 1H), 7.06 (d, J=16.3 Hz, 1H), 6.90-6.83 (m, 1H), 3.82 (tt, J=4.1, 11.6 Hz, 1H), 3.27-3.17 (m, 1H), 2.86-2.84 (m, 6H), 2.51 (s, 3H), 2.28-2.10 (m, 4H), 1.76-1.61 (m, 2H), 1.53-1.36 (m, 2H).

Example 31: Synthesis of 2-chloro-N-(5-((E)-2-(2-(((1r,4r)-4-(dimethylamino)cyclohexyl)amino)pyrimidin-5-yl)vinyl)-6-methoxypyridin-2-yl)-3,4-difluorobenzenesulfonamide (Compound 41)

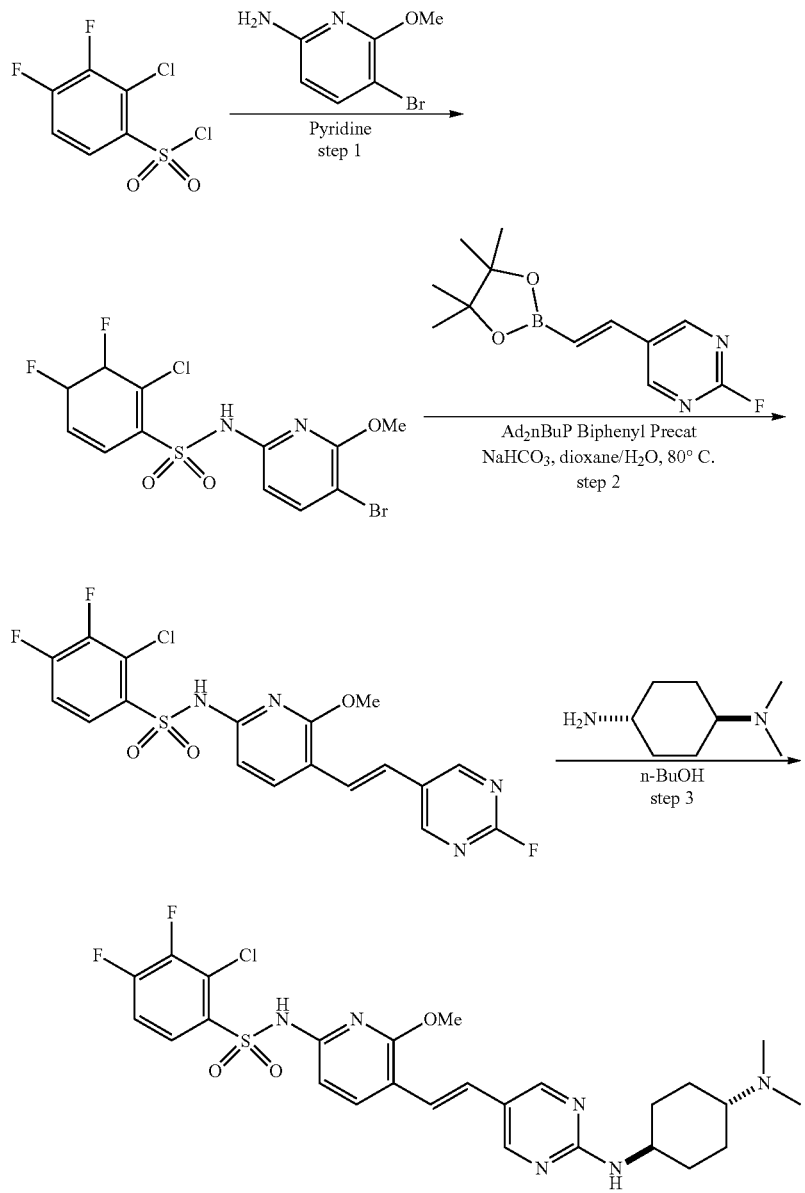

The title compound was synthesized in a similar manner as described in Example 30 to afford 2-chloro-N-(5-((E)-2-(2-(((1r,4r)-4-(dimethylamino)cyclohexyl)amino)pyrimidin-5-yl)vinyl)-6-methoxypyridin-2-yl)-3,4-difluorobenzenesulfonamide (12.6 mg, 10.6% yield) as a yellow solid. M+H$^+$=579.2 (LCMS) $^1$H NMR (400 MHz, METHANOL-d$_4$) δ 8.40 (s, 2H), 8.16-8.13 (br dd, J=5.2, 7.2 Hz, 1H), 7.75-7.73 (d, J=8.2 Hz, 1H), 7.49-7.47 (m, 1H), 7.04-6.87 (m, 2H), 6.51-6.49 (m, 1H), 3.81-3.75 (m, 1H), 3.69 (s, 3H), 3.13-3.08 (m, 1H), 2.79 (s, 6H), 2.22-2.10 (m, 4H), 1.68-1.59 (m, 2H), 1.46-1.37 (m, 2H).

Example 32: Synthesis of 2-chloro-N-(4-((E)-2-(2-(((1r,4r)-4-(dimethylamino)cyclohexyl)amino)pyrimidin-5-yl)vinyl)-2-fluorophenyl)benzenesulfonamide (Compound 35)

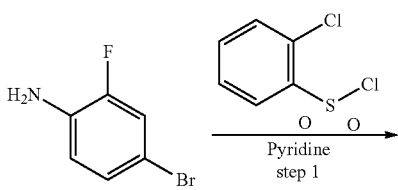

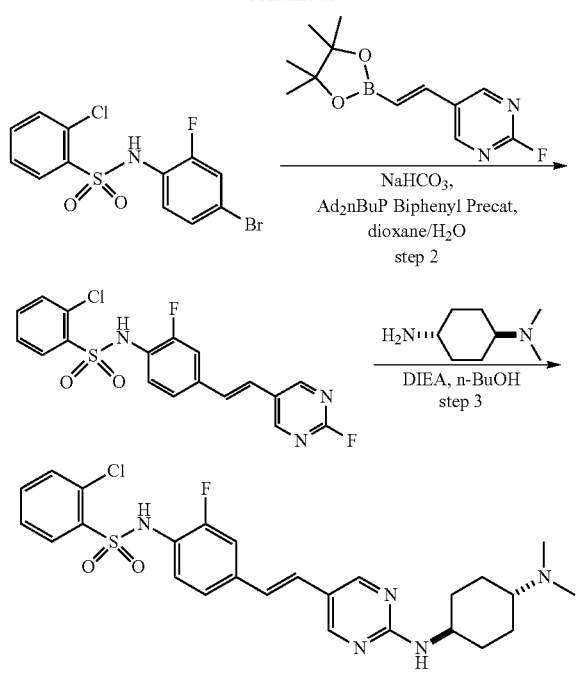

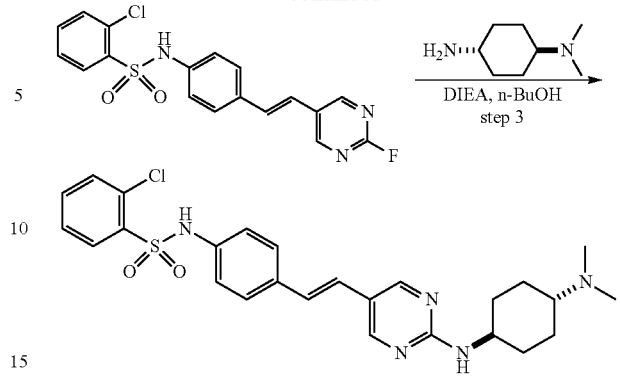

The title compound was synthesized in a similar manner as described in Example 30 to afford 2-chloro-N-(4-((E)-2-(2-(((1r,4r)-4-(dimethylamino)cyclohexyl)amino)pyrimidin-5-yl)vinyl)-2-fluorophenyl)benzenesulfonamide (15.0 mg, 8.2% yield) as a pale yellow solid. M+H$^+$=530.2 (LCMS); $^1$H NMR (400 MHz, METHANOL-d$_4$) δ 8.45 (s, 2H), 8.00 (dd, J=1.5, 7.9 Hz, 1H), 7.61-7.51 (m, 2H), 7.44-7.36 (m, 1H), 7.35-7.27 (m, 1H), 7.25-7.13 (m, 2H), 7.00-6.86 (m, 2H), 3.83-3.70 (m, 1H), 2.47-2.43 (m, 1H), 2.40 (s, 6H), 2.20-2.09 (m, 2H), 2.07-1.97 (m, 2H), 1.54-1.29 (m, 4H).

Example 33: Synthesis of 2-chloro-N-(4-((E)-2-(2-(((1r,4r)-4-(dimethylamino)cyclohexyl)amino)pyrimidin-5-yl)vinyl)phenyl)benzenesulfonamide (Compound 34)

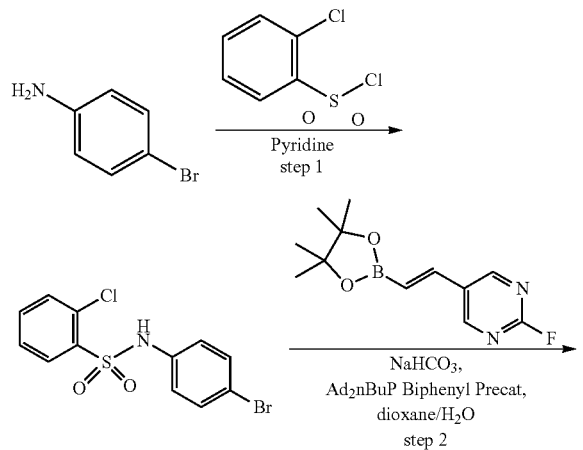

The title compound was synthesized in a similar manner as described in Example 30 to afford 2-chloro-N-(4-((E)-2-(2-(((1r,4r)-4-(dimethylamino)cyclohexyl)amino)pyrimidin-5-yl)vinyl)phenyl)benzenesulfonamide (3.7 mg, 3.3% yield, FA) as a pale yellow solid. M+H$^+$=512.1 (LCMS); $^1$H NMR (400 MHz, METHANOL-d$_4$) δ 8.56 (br s, 1H), 8.47-8.39 (m, 2H), 8.09-8.02 (m, 1H), 7.56-7.49 (m, 2H), 7.41 (ddd, J=2.3, 6.2, 8.1 Hz, 1H), 7.34 (d, J=8.7 Hz, 2H), 7.11 (d, J=8.7 Hz, 2H), 6.97-6.89 (m, 1H), 6.89-6.81 (m, 1H), 3.76 (tt, J=4.0, 11.4 Hz, 1H), 2.73-2.63 (m, 1H), 2.53 (s, 6H), 2.16 (br d, J=10.8 Hz, 2H), 2.04 (br d, J=12.7 Hz, 2H), 1.51 (dq, J=3.0, 12.4 Hz, 2H), 1.43-1.30 (m, 2H).

Example 34: Synthesis of 2-chloro-N-(5-((E)-2-(2-(((1r,4r)-4-(dimethylamino)cyclohexyl)amino)pyrimidin-5-yl)vinyl)pyridin-2-yl)benzenesulfonamide (Compound 36)

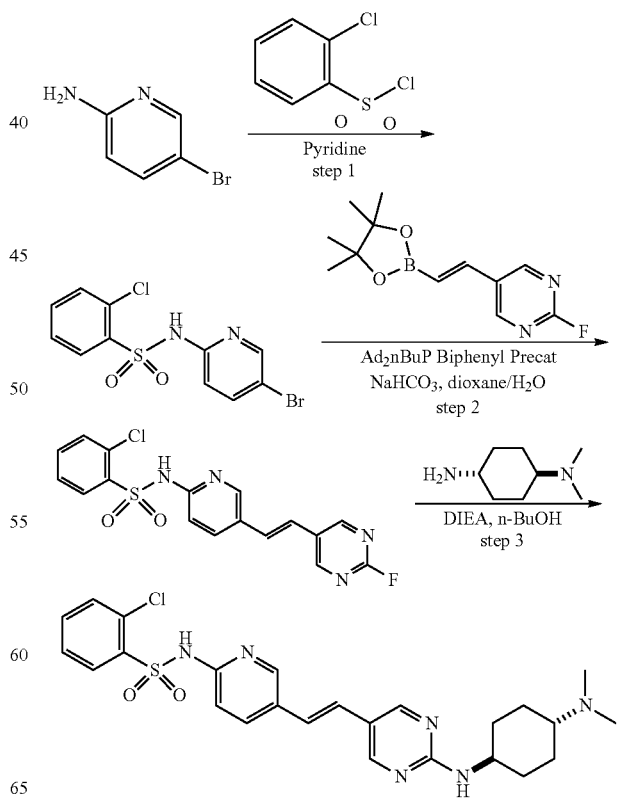

The title compound was synthesized in a similar manner as described in Example 30 to afford 2-chloro-N-(5-((E)-2-(2-(((1r,4r)-4-(dimethylamino)cyclohexyl)amino)pyrimidin-5-yl)vinyl)pyridin-2-yl)benzenesulfonamide (29.2 mg, 24.3% yield, FA) as a pale yellow solid. M+H$^+$=513.2 (LCMS); $^1$H NMR (400 MHz, DMSO-d$_6$) δ 8.44 (s, 2H), 8.23 (s, 1H), 8.14-8.05 (m, 1H), 7.98 (d, J=2.0 Hz, 1H), 7.90 (dd, J=2.2, 9.0 Hz, 1H), 7.60-7.44 (m, 3H), 7.29 (d, J=7.9 Hz, 1H), 7.06 (d, J=8.8 Hz, 1H), 7.00-6.85 (m, 2H), 2.35 (s, 6H), 1.96 (br d, J=11.7 Hz, 2H), 1.87 (brd, J=11.0 Hz, 2H), 1.46-1.16 (m, 4H).

Example 35: Synthesis of 2-chloro-N-(5-((E)-2-(2-(((1r,4r)-4-(dimethylamino)cyclohexyl)amino)pyrimidin-5-yl)vinyl)pyrazin-2-yl)benzenesulfonamide (Compound 37)

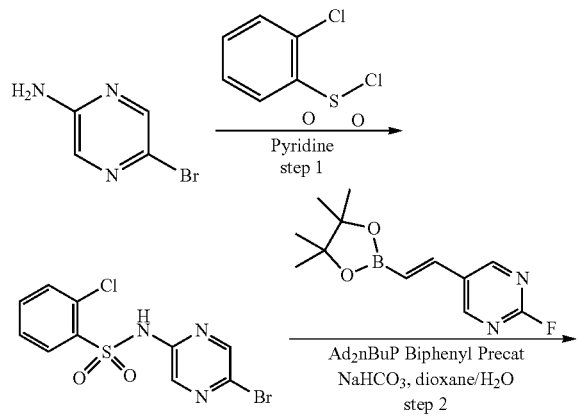

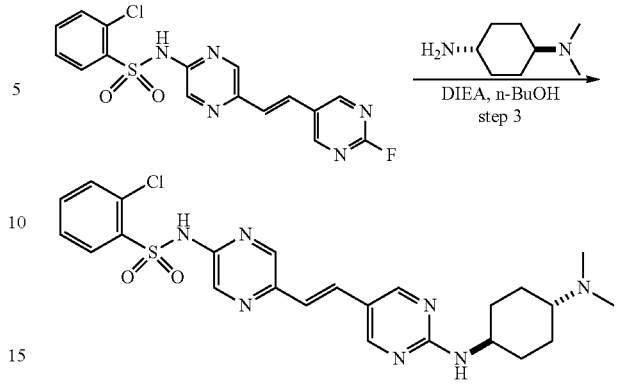

The title compound was synthesized in a similar manner as described in Example 30 to afford 2-chloro-N-(5-((E)-2-(2-(((1r,4r)-4-(dimethylamino)cyclohexyl)amino)pyrimidin-5-yl)vinyl)pyrazin-2-yl)benzenesulfonamide (18.0 mg, 11.0% yield, FA) as a light yellow solid. M+H$^+$=514.2 (LCMS); $^1$H NMR (400 MHz, DMSO-d$_6$) δ 8.49 (s, 2H), 8.15 (s, 1H), 8.06-7.98 (m, 1H), 7.91 (s, 1H), 7.84 (s, 1H), 7.43-7.33 (m, 3H), 7.28 (d, J=7.9 Hz, 1H), 7.14-7.06 (m, 1H), 7.01-6.92 (m, 1H), 3.72 (ddd, J=3.8, 7.7, 15.5 Hz, 1H), 3.07-2.98 (m, 1H), 2.69-2.64 (m, 6H), 2.09-1.91 (m, 4H), 1.60-1.44 (m, 2H), 1.41-1.25 (m, 2H).

Example 36: Synthesis of (E)-N-(5-(2-(2-((4-aminobicyclo[2.2.2]octan-1-yl)amino)pyrimidin-5-yl)vinyl)-6-methylpyridin-2-yl)-2-chlorobenzenesulfonamide (Compound 49)

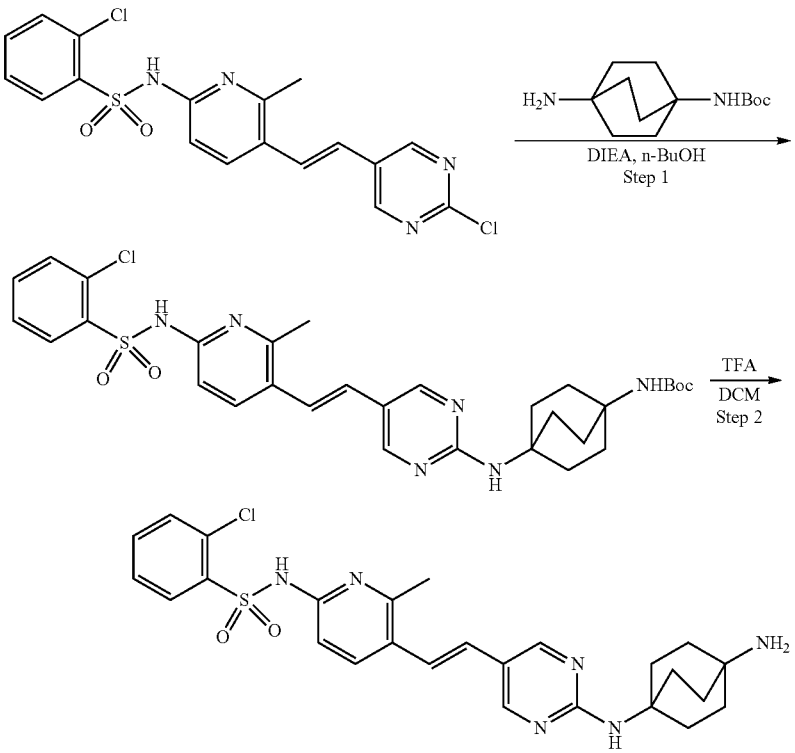

Step 1:

To a solution of (E)-2-chloro-N-(5-(2-(2-chloropyrimidin-5-yl)vinyl)-6-methylpyridin-2-yl)benzenesulfonamide (120 mg, 284.8 umol) in n-BuOH (2.0 mL) and DIEA (73 mg, 569.6 umol, 99.2 uL) was added tert-butyl (4-aminobicyclo[2.2.2]octan-1-yl)carbamate (68 mg, 284.8 umol). The mixture was stirred at 145° C. for 12 h under microwave. The mixture was concentrated to give a residue. The residue was purified by prep-TLC (SiO$_2$) to afford tert-butyl (E)-(4-((5-(2-(6-((2-chlorophenyl)sulfonamido)-2-methylpyridin-3-yl)vinyl)pyrimidin-2-yl)amino)bicyclo[2.2.2]octan-1-yl)carbamate (30 mg, 16.8% yield) as a yellow solid.

Step 2:

A solution of tert-butyl (E)-(4-((5-(2-(6-((2-chlorophenyl)sulfonamido)-2-methylpyridin-3-yl)vinyl)pyrimidin-2-yl)amino)bicyclo[2.2.2]octan-1-yl)carbamate (30 mg, 47.9 umol) in DCM (1.0 mL) and TFA (1.0 mL) was stirred at 25° C. for 10 min. The mixture was concentrated to give a residue. The residue was dissolved in MeOH (2.0 mL) and basified pH to 8 with NH$_3$·H$_2$O (25% purity), and concentrated to give a residue. The residue was purified by Prep-HPLC (FA condition) to afford (E)-N-(5-(2-(2-((4-aminobicyclo[2.2.2]octan-1-yl)amino)pyrimidin-5-yl)vinyl)-6-methylpyridin-2-yl)-2-chlorobenzenesulfonamide (7.9 mg, 28.1% yield, FA) as a pale yellow solid. M+H$^+$=525.2 (LCMS); $^1$H NMR (400 MHz, METHANOL-d$_4$) δ 8.55 (br s, 1H), 8.46 (s, 2H), 8.19 (br d, J=7.2 Hz, 1H), 7.98 (br d, J=10.1 Hz, 1H), 7.58-7.39 (m, 3H), 7.15 (br d, J=9.2 Hz, 1H), 7.05 (d, J=16.4 Hz, 1H), 6.82 (d, J=16.4 Hz, 1H), 2.48 (s, 3H), 2.26-2.10 (m, 6H), 1.98-1.82 (m, 6H).

Example 37: Synthesis of N-(5-((E)-2-(2-(((1r,4r)-4-aminocyclohexyl)amino)pyrimidin-5-yl)vinyl)-6-methylpyridin-2-yl)-2-chlorobenzenesulfonamide (Compound 46)

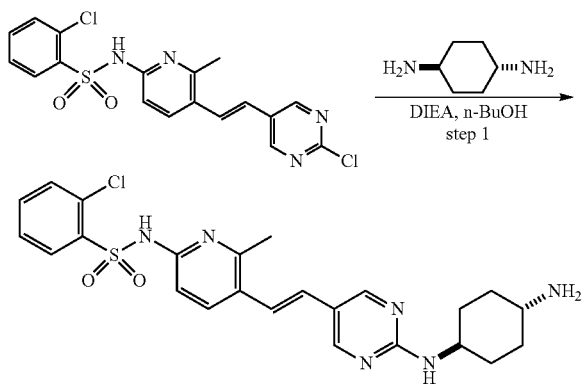

The title compound was synthesized in a similar manner as described in Example 36 to afford N-(5-((E)-2-(2-(((1r,4r)-4-aminocyclohexyl)amino)pyrimidin-5-yl)vinyl)-6-methylpyridin-2-yl)-2-chlorobenzenesulfonamide (40.0 mg, 28.7% yield, FA) as a yellow solid. M+H$^+$=499.1 (LCMS); $^1$H NMR (400 MHz, METHANOL-d$_4$) δ 8.52 (br s, 1H), 8.49 (s, 2H), 8.23-8.15 (m, 1H), 8.03-7.97 (m, 1H), 7.56-7.42 (m, 3H), 7.17 (d, J=9.2 Hz, 1H), 7.06 (d, J=16.4 Hz, 1H), 6.84 (d, J=16.4 Hz, 1H), 3.81 (tt, J=3.8, 11.3 Hz, 1H), 3.12 (tt, J=3.8, 11.5 Hz, 1H), 2.49 (s, 3H), 2.22-2.04 (m, 4H), 1.64-1.33 (m, 4H).

Example 38: Synthesis of 2-chloro-N-(6-methyl-5-((E)-2-(2-(((1r,4r)-4-(methylamino)cyclohexyl)amino)pyrimidin-5-yl)vinyl)pyridin-2-yl)benzenesulfonamide (Compound 44)

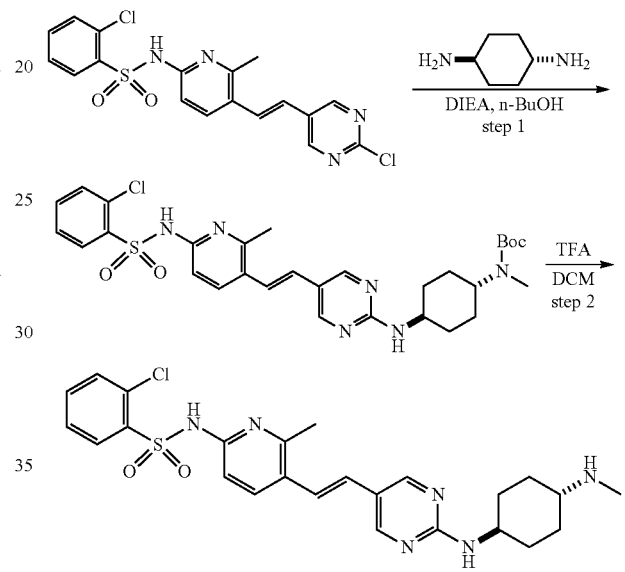

The title compound was synthesized in a similar manner as described in Example 36 to afford 2-chloro-N-(6-methyl-5-((E)-2-(2-(((1r,4r)-4-(methylamino)cyclohexyl)amino)pyrimidin-5-yl)vinyl)pyridin-2-yl)benzenesulfonamide (19.8 mg, 50.8% yield, FA) as a white solid. M+H$^+$=513.1 (LCMS); $^1$H NMR (400 MHz, METHANOL-d$_4$) δ 8.55 (br s, 1H), 8.49 (s, 2H), 8.26-8.12 (m, 1H), 8.07-7.94 (m, 1H), 7.56-7.42 (m, 3H), 7.17 (br d, J=9.2 Hz, 1H), 7.06 (d, J=16.4 Hz, 1H), 6.84 (d, J=16.4 Hz, 1H), 3.88-3.70 (m, 1H), 3.08-2.94 (m, 1H), 2.70 (s, 3H), 2.49 (s, 3H), 2.19 (br dd, J=2.2, 9.9 Hz, 4H), 1.61-1.29 (m, 4H).

Example 39: Synthesis of 2-chloro-N-(5-((E)-2-(2-(((1r,4r)-4-(diethylamino)cyclohexyl)amino)pyrimidin-5-yl)vinyl)-6-methylpyridin-2-yl)benzenesulfonamide (Compound 30)

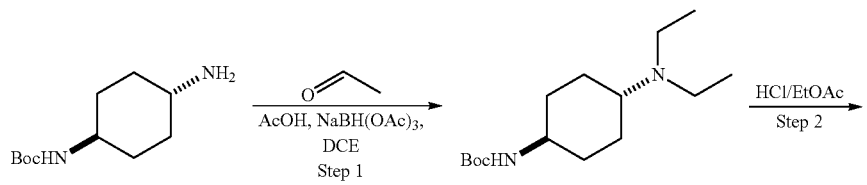

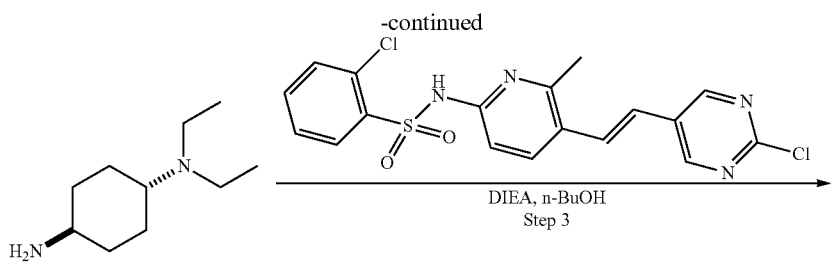

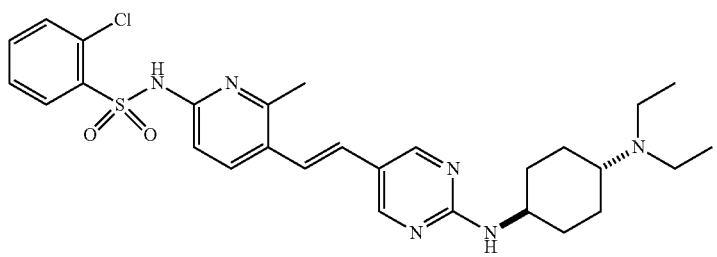

Step 1:

To a solution of tert-butyl ((1r,4r)-4-aminocyclohexyl)carbamate (2.0 g, 9.3 mmol) in DCE (100.0 mL) was added acetaldehyde (5 M, 18.6 mL) and AcOH (2.1 g, 34.9 mmol, 2.0 mL). The mixture was stirred at 0° C. for 1 h and then NaBH(OAc)$_3$ (5.9 g, 28.0 mmol) was added. The reaction mixture was stirred at 25° C. for 1 h. The reaction mixture was poured into NaHCO$_3$ (50.0 mL) and extracted with EtOAc (50 mL×3). The combined organic layers were washed with brine (50 mL×3), dried over Na$_2$SO$_4$, filtered, and concentrated under reduced pressure to give tert-butyl ((1r,4r)-4-(diethylamino)cyclohexyl)carbamate (1.0 g) as a red oil.

Step 2:

A solution of tert-butyl ((1r,4r)-4-(diethylamino)cyclohexyl)carbamate (1.0 g, 3.7 mmol) in HCl/EtOAc (10.0 mL, 4 M) was stirred at 25° C. for 10 min. The mixture was concentrated to give (1r,4r)-$N^1$,$N^1$-ethylcyclohexane-1,4-diamine (0.7 g, HCl salt) as a red oil.

Step 3:

To a solution of (E)-2-chloro-N-(5-(2-(2-chloropyrimidin-5-yl)vinyl)-6-methylpyridin-2-yl)benzenesulfonamide (0.5 g, 1.1 mmol) in n-BuOH (50.0 mL) was added DIEA (460 mg, 3.5 mmol, 620.1 uL) and (1r,4r)-$N^1$,$N^1$-ethylcyclohexane-1,4-diamine (613 mg, 2.9 mmol, HCl salt). The reaction mixture was stirred at 150° C. for 12 h under microwave. The reaction mixture was concentrated to get crude residue. The residue was purified by prep-HPLC (FA condition) and further purified by prep-HPLC (basic condition) to afford 2-chloro-N-(5-((E)-2-(2-(((1r,4r)-4-(diethylamino)cyclohexyl)amino)pyrimidin-5-yl)vinyl)-6-methylpyridin-2-yl)benzenesulfonamide (39.8 mg, 6.0% yield) as a pale yellow solid. M+H$^+$=555.2 (LCMS); $^1$H NMR (400 MHz, METHANOL-d$_4$) δ 8.48 (s, 2H), 8.19 (d, J=7.3 Hz, 1H), 7.98 (d, J=9.0 Hz, 1H), 7.53-7.49 (m, 2H), 7.49-7.42 (m, 1H), 7.15 (d, J=9.0 Hz, 1H), 7.05 (d, J=16.3 Hz, 1H), 6.83 (d, J=16.3 Hz, 1H), 3.80 (tt, J=4.1, 11.6 Hz, 1H), 3.22-3.02 (m, 5H), 2.48 (s, 3H), 2.25-2.14 (m, 2H), 2.06 (br d, J=12.3 Hz, 2H), 1.74-1.57 (m, 2H), 1.50-1.35 (m, 2H), 1.28 (t, J=7.3 Hz, 6H).

Example 40: Synthesis of 2-chloro-N-(5-((E)-2-(2-(((1r,4r)-4-(dimethylamino)cyclohexyl)amino)pyrimidin-5-yl)vinyl)-6-methoxypyridin-2-yl)-3-fluorobenzenesulfonamide (Compound 39)

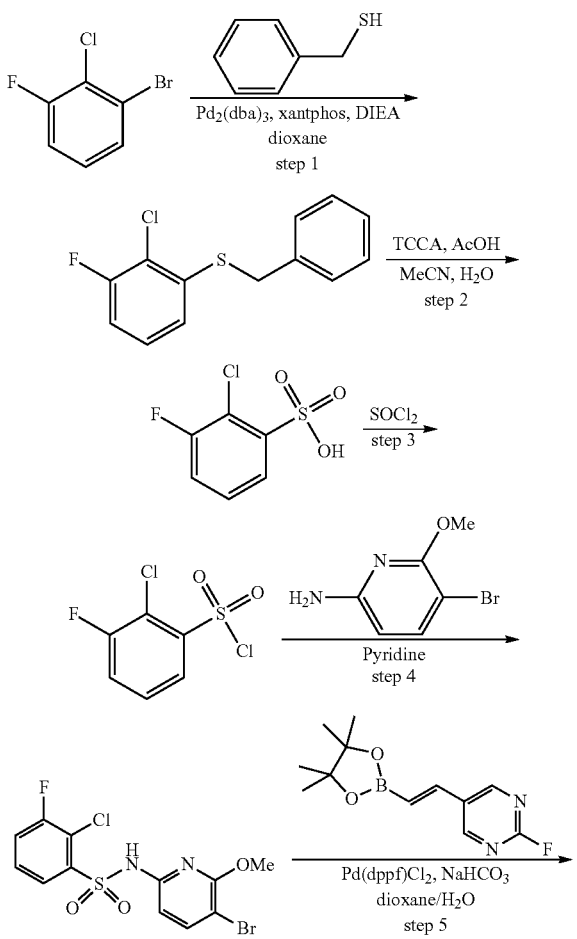

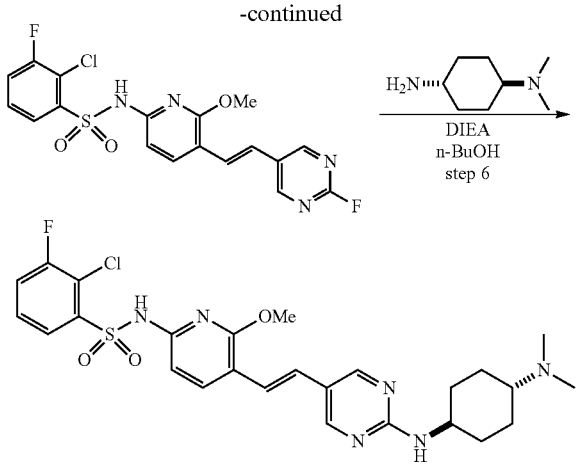

Step 1:

A mixture of 1-bromo-2-chloro-3-fluoro-benzene (2.0 g, 9.5 mmol), phenylmethanethiol (1.4 g, 11.4 mmol, 1.3 mL), Pd$_2$(dba)$_3$ (1.7 g, 1.9 mmol), DIEA (3.7 g, 28.6 mmol, 4.9 mL), and xantphos (1.1 g, 1.9 mmol) in dioxane (30.0 mL) was degassed and purged with N$_2$ three times, and then the mixture was stirred at 100° C. for 12 h under N$_2$ atmosphere. The reaction mixture was concentrated under reduced pressure. The residue was purified by column chromatography (SiO$_2$) to afford benzyl(2-chloro-3-fluorophenyl)sulfane (2.6 g, 76.2% yield) as a yellow oil. $^1$H NMR (400 MHz, CHLOROFORM-7) δ 7.49-7.25 (m, 5H), 7.21-7.11 (m, 1H), 7.06 (td, J=1.2, 7.9 Hz, 1H), 6.99 (dt, J=1.5, 8.4 Hz, 1H), 4.20 (s, 2H).

Step 2:

To a solution of benzyl(2-chloro-3-fluorophenyl)sulfane (1.6 g, 6.3 mmol) in MeCN (20.0 mL) was added H$_2$O (11 mg, 633.0 umol, 11.4 uL), AcOH (76 mg, 1.2 mmol, 72.4 uL). TCCA (1.7 g, 7.6 mmol) was then added at 0° C. The mixture was stirred at 0° C. for 2 h. The reaction mixture was quenched by addition of H$_2$O (20.0 mL), and then extracted with ethyl acetate (30.0 mL×3). The combined organic layers were washed with brine (30.0 mL×3), dried over Na$_2$SO$_4$, filtered, and concentrated under reduced pressure to give a residue. The residue was purified by flash silica gel chromatography to afford 2-chloro-3-fluorobenzenesulfonic acid (862 mg, 46.6% yield) as a pale yellow oil. M−H$^+$=209.0 (LCMS).

Step 3:

A solution of 2-chloro-3-fluorobenzenesulfonic acid (0.5 g, 2.3 mmol) in SOCl$_2$ (4 mL) was stirred at 70° C. for 36 h. The reaction mixture was concentrated under reduced pressure to give 2-chloro-3-fluorobenzenesulfonyl chloride (540 mg, crude) as a yellow oil.

Step 4:

To a solution of 2-chloro-3-fluorobenzenesulfonyl chloride (540 mg, 2.3 mmol) in pyridine (10 mL) was added 5-bromo-6-methoxypyridin-2-amine (239 mg, 1.1 mmol). The mixture was stirred at 45° C. for 12 h. The reaction mixture was concentrated under reduced pressure. The residue was purified by flash silica gel chromatography to afford N-(5-bromo-6-methoxypyridin-2-yl)-2-chloro-3-fluorobenzenesulfonamide (434 mg, 55.8% yield) as a yellow solid. M+H$^+$=396.6 (LCMS).

Step 5:

A mixture of N-(5-bromo-6-methoxypyridin-2-yl)-2-chloro-3-fluorobenzenesulfonamide (100 mg, 252.7 umol), (E)-2-fluoro-5-(2-(4,4,5,5-tetramethyl-1,3,2-dioxaborolan-2-yl)vinyl)pyrimidine (126 mg, 505.5 umol), Pd(dppf)Cl$_2$ (18 mg, 25.2 umol), and NaHCO$_3$ (63 mg, 758.2 umol, 29.4 uL) in dioxane (3.0 mL) and H$_2$O (0.3 mL) was degassed and purged with N$_2$ three times, and then the mixture was stirred at 80° C. for 12 h under N$_2$ atmosphere. The reaction mixture was concentrated under reduced pressure to give a residue. The residue was purified by column chromatography by prep-TLC (SiO$_2$) to give (E)-2-chloro-3-fluoro-N-(5-(2-(2-fluoropyrimidin-5-yl)vinyl)-6-methoxypyridin-2-yl)benzenesulfonamide (100 mg, 70.0% yield) as a yellow solid. M+H$^+$=439.0 (LCMS).

Step 6:

A a solution of (E)-2-chloro-3-fluoro-N-(5-(2-(2-fluoropyrimidin-5-yl)vinyl)-6-methoxypyridin-2-yl)benzenesulfonamide (100 mg, 227.8 umol) in n-BuOH (2 mL) was added DIEA (147 mg, 1.1 mmol, 198.4 uL) and (1r,4r)-N$^1$,N$^1$-methylcyclohexane-1,4-diamine (81 mg, 455.7 umol, HCl). The mixture was stirred at 100° C. for 12 h. The reaction mixture was concentrated under reduced pressure to give a residue. The residue was purified by prep-HPLC (FA condition) to give (E)-2-chloro-3-fluoro-N-(5-(2-(2-(fluoropyrimidin-5-yl)vinyl)-6-methoxypyridin-2-yl)benzenesulfonamide (16.7 mg, 11.3% yield, FA) as a yellow solid. M+H$^+$=561.2 (LCMS); $^1$H NMR (400 MHz, METHANOL-d$_4$) δ 8.56 (br s, 1H), 8.40 (s, 2H), 8.15-8.07 (m, 1H), 7.74 (d, J=8.1 Hz, 1H), 7.58-7.44 (m, 2H), 7.07-6.98 (m, 1H), 6.94-6.85 (m, 1H), 6.53 (d, J=8.1 Hz, 1H), 3.78 (tt, J=3.9, 11.5 Hz, 1H), 3.67 (s, 3H), 3.17-2.98 (m, 1H), 2.76 (s, 6H), 2.21 (br d, J=11.1 Hz, 2H), 2.12 (br d, J=12.2 Hz, 2H), 1.73-1.53 (m, 2H), 1.51-1.33 (m, 2H).

Example 41: Synthesis of 2-chloro-N-(5-(2-(2-(((1r,4r)-4-(dimethylamino)cyclohexyl)amino)pyrimidin-5-yl)vinyl)pyrimidin-2-yl)benzenesulfonamide (Compound 40)

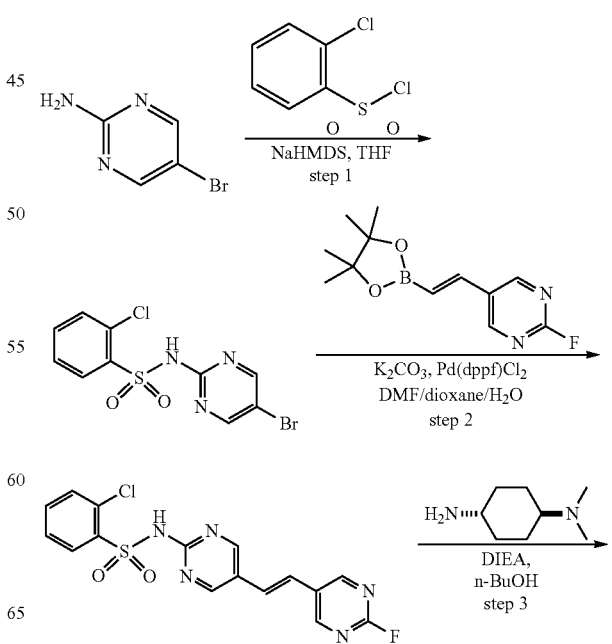

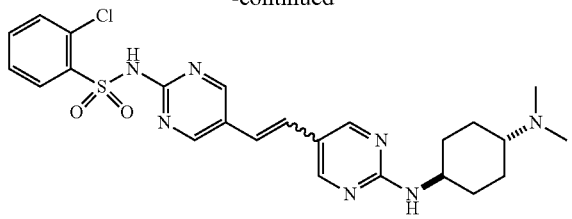

Step 1:
To a solution of 5-bromopyrimidin-2-amine (0.5 g, 2.8 mmol) in THF (10.0 mL) was added NaHMDS (1.0 M, 4.3 mL) at 0° C. The mixture was stirred at 0° C. for 10 min and then 2-chlorobenzene-1-sulfonyl chloride (909 mg, 4.3 mmol, 586.9 uL) was added to the mixture. The resulting mixture was stirred at 25° C. for 0.5 h. Saturated NH$_4$Cl (10.0 mL) and EtOAc (10.0 mL) were added into the reaction mixture. The resulting mixture was filtered and the cake was collected to afford N-(5-bromopyrimidin-2-yl)-2-chlorobenzenesulfonamide (0.3 g) as a white solid.

Step 2:
To a solution of N-(5-bromopyrimidin-2-yl)-2-chlorobenzenesulfonamide (70 mg, 200.8 umol) and K$_2$CO$_3$ (83 mg, 602.4 umol) in DMF (1.0 mL), dioxane (1.0 mL) and H$_2$O (0.2 mL) were added (E)-2-fluoro-5-(2-(4,4,5,5-tetramethyl-1,3,2-dioxaborolan-2-yl)vinyl)pyrimidine (75 mg, 301.2 umol) and Pd(dppf)Cl$_2$ (14 mg, 20.0 umol). The reaction mixture was stirred at 80° C. for 12 h under N$_2$. The reaction mixture was concentrated to get crude residue. The residue was purified by prep-TLC (SiO$_2$) to afford (E)-2-chloro-N-(5-(2-(2-fluoropyrimidin-5-yl)vinyl)pyrimidin-2-yl)benzenesulfonamide (40 mg, 50.8% yield) as a yellow solid.

Step 3:
To a solution of (E)-2-chloro-N-(5-(2-(2-fluoropyrimidin-5-yl)vinyl)pyrimidin-2-yl)benzenesulfonamide (40 mg, 102.0 umol) in n-BuOH (2.0 mL) was added DIEA (65 mg, 510.4 umol, 88.9 uL) and (1r,4r)-N$^1$,N$^1$-methylcyclohexane-1,4-diamine (54 mg, 306.2 umol, HCl). The mixture was stirred at 100° C. for 12 h. The reaction mixture was concentrated under reduced pressure to give a residue. The residue was purified by pre-HPLC (FA condition and basic condition) to give 2-chloro-N-(5-(2-(2-(((1r,4r)-4-(dimethylamino)cyclohexyl)amino)pyrimidin-5-yl)vinyl)pyrimidin-2-yl)benzenesulfonamide (3.1 mg, 5.8% yield) as a pale yellow solid. M+H$^+$=514.1 (LCMS); $^1$H NMR (400 MHz, DMSO-d$_6$) δ 8.44 (s, 1H), 8.36 (s, 1H), 8.14 (s, 1H), 8.11-7.99 (m, 2H), 7.45-7.33 (m, 3H), 7.28 (br d, J=7.9 Hz, 1H), 6.92-6.86 (m, 0.5H), 6.86-6.79 (m, 0.5H), 6.30-6.25 (m, 0.5H), 6.25-6.21 (m, 0.5H), 3.83-3.63 (m, 1H), 2.87 (br s, 1H), 2.60 (br d, J=13.9 Hz, 6H), 2.05-1.91 (m, 4H), 1.63-1.43 (m, 2H), 1.39-1.20 (m, 2H).

Example 42: Synthesis of 4-chloro-N-(5-((E)-2-(2-(((1r,4r)-4-(dimethylamino)cyclohexyl)amino)pyrimidin-5-yl)vinyl)-6-ethylpyridin-2-yl)pyridine-3-sulfonamide (Compound 42)

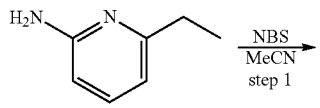

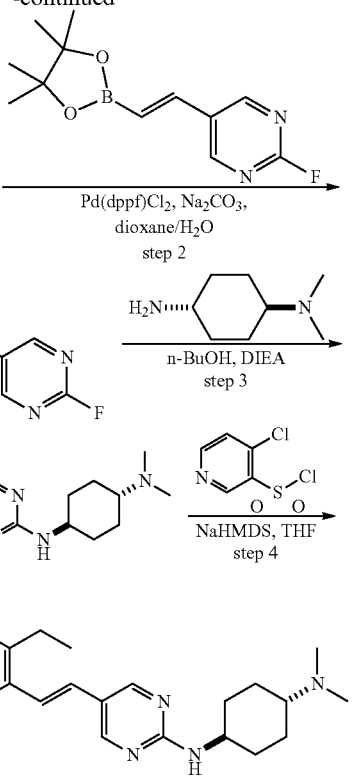

Step 1:
To a solution of 6-ethylpyridin-2-amine (2.0 g, 16.3 mmol) in MeCN (20.0 mL) was added NBS (2.9 g, 16.3 mmol) in batches at 0° C. The reaction mixture was stirred at 25° C. for 1 h. The reaction mixture was concentrated under reduced pressure. The reaction mixture was quenched by addition of H$_2$O (40.0 mL) and extracted with EtOAc (30.0 mL×3). The combined organic layers were washed with brine (30.0 mL×3), dried over Na$_2$SO$_4$, filtered and concentrated under reduced pressure to give a residue. The residue was purified by column chromatography (SiO$_2$) to afford 5-bromo-6-ethylpyridin-2-amine (2.7 g, 82.0% yield) as a pale yellow solid. $^1$H NMR (400 MHz, DMSO-d$_6$) δ 7.44 (d, J=8.6 Hz, 1H), 6.23 (d, J=8.6 Hz, 1H), 6.05 (s, 2H), 2.63 (q, J=7.5 Hz, 2H), 1.12 (t, J=IB Hz, 3H).

Step 2:
A mixture of 5-bromo-6-ethylpyridin-2-amine (500 mg, 2.4 mmol), (E)-2-fluoro-5-(2-(4,4,5,5-tetramethyl-1,3,2-dioxaborolan-2-yl)vinyl)pyrimidine (1.2 g, 4.9 mmol), Pd(dppf)Cl$_2$ (181 mg, 248.6 umol), and Na$_2$CO$_3$ (627 mg, 5.9 mmol) in dioxane (4.0 mL) and H$_2$O (0.4 mL) was degassed and purged with N$_2$ three times. The mixture was stirred at 80° C. for 12 h under N$_2$ atmosphere and concentrated. The residue was diluted with H$_2$O (30.0 mL) and extracted with ethyl acetate (20.0 mL×3). The combined organic layers were washed with saturated sodium chloride (20.0 mL×2), dried over anhydrous sodium sulfate, filtered, and concentrated under reduced pressure to give a residue. The residue was purified by column chromatography (SiO$_2$) to give (E)-6-ethyl-5-(2-(2-fluoropyrimidin-5-yl)vinyl)pyridin-2-amine (448 mg) as a yellow solid. M+H$^+$=245.1 (LCMS).

Step 3:
A mixture of (E)-6-ethyl-5-(2-(2-fluoropyrimidin-5-yl)vinyl)pyridin-2-amine (400 mg, 1.6 mmol), (1r,4r)-N$^1$,N$^1$- dimethylcyclohexane-1,4-diamine (585 mg, 3.2 mmol, HCl), and DIEA (1.0 g, 8.1 mmol, 1.4 mL) in n-BuOH (3.0 mL) was degassed and purged with $N_2$ three times. The mixture was stirred at 100° C. for 12 h under $N_2$ atmosphere. The reaction mixture was concentrated under reduced pressure to give a residue. The residue was purified by prep-HPLC (neutral condition) to give (1r,4r)-$N^1$-(5-((E)-2-(6-amino-2-ethylpyridin-3-yl)vinyl)pyrimidin-2-yl)-$N^4$,$N^4$-dimethylcyclohexane-1,4-diamine (380 mg, 63.3% yield) as a yellow solid. M+H$^+$=367.3 (LCMS).

Step 4:

To a solution of (1r,4r)-$N^1$-(5-((E)-2-(6-amino-2-ethylpyridin-3-yl)vinyl)pyrimidin-2-yl)-$N^4$,$N^4$-dimethylcyclohexane-1,4-diamine (140 mg, 381.9 umol) in THF (5.0 mL) was added NaHMDS (1M, 1.9 mL). The mixture was stirred at −20° C. for 30 min. 4-Chloropyridine-3-sulfonyl chloride (162 mg, 763.9 umol) was added and the reaction mixture was warmed to 25° C. over 1 h. The mixture was stirred at 25° C. for 1 h. The reaction mixture was quenched by addition of the solution of NH$_4$Cl (3.0 mL), concentrated under reduced pressure to give a residue. The residue was purified by prep-HPLC (FA condition) to afford 4-chloro-N-(5-((E)-2-(2-(((1r,4r)-4-(dimethylamino)cyclohexyl)amino)pyrimidin-5-yl)vinyl)-6-ethylpyridin-2-yl)pyridine-3-sulfonamide (51.3 mg, 22.7% yield, FA) as a yellow solid. M+H$^+$=542.2 (LCMS); $^1$H NMR (400 MHz, METHANOL-d$_4$) δ 9.22 (s, 1H), 8.60-8.56 (m, 1H), 8.55-8.52 (m, 1H), 8.49-8.45 (m, 2H), 8.02 (d, J=9.3 Hz, 1H), 7.17 (d, J=9.0 Hz, 1H), 7.07 (d, J=16.3 Hz, 1H), 6.85 (d, J=16.3 Hz, 1H), 3.85-3.72 (m, 1H), 3.04-2.91 (m, 1H), 2.82 (q, J=7.7 Hz, 2H), 2.69 (s, 6H), 2.18 (br d, J=12.1 Hz, 2H), 2.13-2.03 (m, 2H), 1.68-1.52 (m, 2H), 1.47-1.32 (m, 2H), 1.16 (t, J=7.6 Hz, 3H).

Example 43: Synthesis of 2-chloro-N-(1-(2-(((1r,4r)-4-(dimethylamino)cyclohexyl)amino)quinazolin-6-yl)-2-oxo-1,2-dihydropyridin-4-yl)benzenesulfonamide (Compound 43)

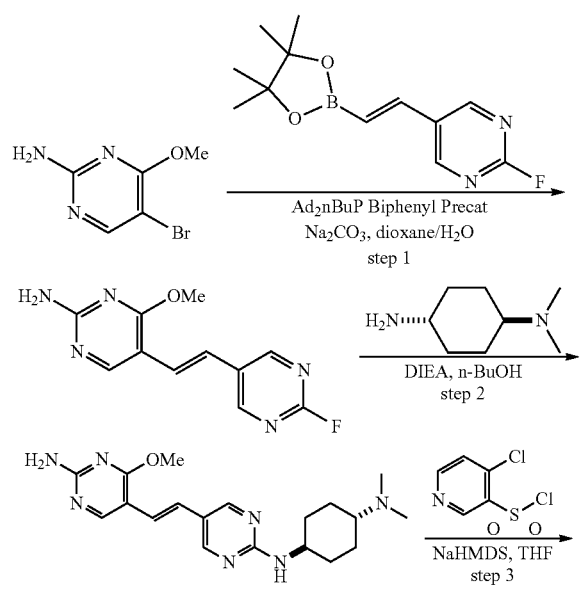

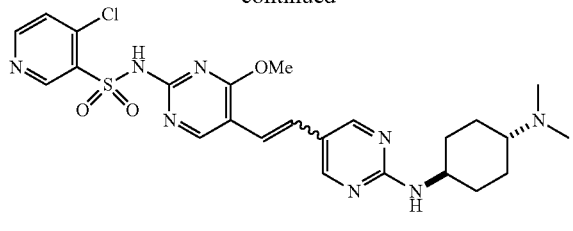

Step 1:

A mixture of 5-bromo-4-methoxypyrimidin-2-amine (500 mg, 2.4 mmol), (E)-2-fluoro-5-(2-(4,4,5,5-tetramethyl-1,3,2-dioxaborolan-2-yl)vinyl)pyrimidine (1.2 g, 4.9 mmol), Pd(dppf)Cl$_2$ (179 mg, 245.0 umol), and Na$_2$CO$_3$ (618 mg, 5.8 mmol) in dioxane (20.0 mL) and H$_2$O (2.0 mL) was degassed and purged with $N_2$ three times. The mixture was stirred at 80° C. for 12 h under $N_2$ atmosphere. The reaction mixture was diluted with H$_2$O (30.0 mL) and extracted with ethyl acetate (20.0 mL×3). The combined organic layer was washed with saturated sodium chloride (20.0 mL×2), dried over anhyrous sodium sulfate, filtered, and concentrated under reduced pressure to give a residue. The residue was purified by column chromatography (SiO$_2$) to afford (E)-5-(2-(2-fluoropyrimidin-5-yl)vinyl)-4-methoxypyrimidin-2-amine (173 mg, 16.8% yield) as a yellow solid. M+H$^+$=248.1 (LCMS).

Step 2:

A mixture of (E)-5-(2-(2-fluoropyrimidin-5-yl)vinyl)-4-methoxypyrimidin-2-amine (173 mg, 699.7 umol), (1r,4r)-$N^1$,$N^1$-dimethylcyclohexane-1,4-diamine (250 mg, 1.4 mmol, HCl), and DIEA (452 mg, 3.5 mmol, 609.4 uL) in n-BuOH (3.0 mL) was degassed and purged with $N_2$ three times, then the mixture was stirred at 100° C. for 12 h under $N_2$ atmosphere. The reaction mixture was concentrated under reduced pressure to give a residue. The residue was purified by prep-HPLC (neutral condition) to give (1r,4r)-N1-(5-((E)-2-(2-amino-4-methoxypyrimidin-5-yl)vinyl)pyrimidin-2-yl)-N4,N4-dimethylcyclohexane-1,4-diamine (80 mg, 30.9% yield) as a pale yellow solid. M+H$^+$=370.1 (LCMS); $^1$H NMR (400 MHz, METHANOL-d$_4$) δ 8.40 (s, 2H), 8.14 (s, 1H), 6.97-6.91 (m, 1H), 6.90-6.84 (m, 1H), 4.00 (s, 3H), 3.73 (tdd, J=3.8, 7.4, 14.7 Hz, 1H), 2.37-2.26 (m, 7H), 2.12 (br d, J=13.0 Hz, 2H), 1.99 (br d, J=12.3 Hz, 2H), 1.50-1.26 (m, 4H).

Step 3:

To a solution of (1r,4r)-N1-(5-((E)-2-(2-amino-4-methoxypyrimidin-5-yl)vinyl)pyrimidin-2-yl)-N4,N4-dimethylcyclohexane-1,4-diamine (70 mg, 189.4 umol) in THF (4.0 mL) was added NaHMDS (1 mol/L, 947.3 uL). The mixture was stirred at −20° C. for 0.5 h. 4-Chloropyridine-3-sulfonyl chloride (80 mg, 378.9 umol) was added and the reaction mixture was warmed to 25° C. over 1 h. The mixture was stirred at 25° C. for 1 h. The reaction mixture was quenched by addition of the solution of NH$_4$Cl (3.0 mL) and concentrated under reduced pressure to give a residue. The residue was purified by prep-HPLC (FA condition) and further purified by prep-HPLC (basic condition) to give 2-chloro-N-(1-(2-(((1r,4r)-4-(dimethylamino)cyclohexyl)amino)quinazolin-6-yl)-2-oxo-1,2-dihydropyridin-4-yl)benzenesulfonamide (12.2 mg, 10.6% yield) as a light yellow solid. M+H$^+$=545.2 (LCMS); $^1$H NMR (400 MHz, DMSO-d$_6$) δ 9.13 (s, 1H), 8.52 (d, J=5.3 Hz, 1H), 8.40 (s, 2H), 8.16 (s, 1H), 7.52 (d, J=5.3 Hz, 1H), 7.26 (d, J=8.2 Hz, 1H), 6.88-6.81 (m, 1H), 6.80-6.74 (m, 1H), 3.79-3.64 (m, 1H), 3.50 (s, 3H), 3.05-2.88 (m, 1H), 2.67-2.60 (m, 6H), 2.07-1.88 (m, 4H), 1.60-1.44 (m, 2H), 1.37-1.24 (m, 2H).

Example 44: Synthesis of 2,3-dichloro-N-(5-((E)-2-(2-(((1r,4r)-4-(dimethylamino)cyclohexyl)amino)pyrimidin-5-yl)vinyl)-6-methoxypyridin-2-yl)benzenesulfonamide (Compound 51)

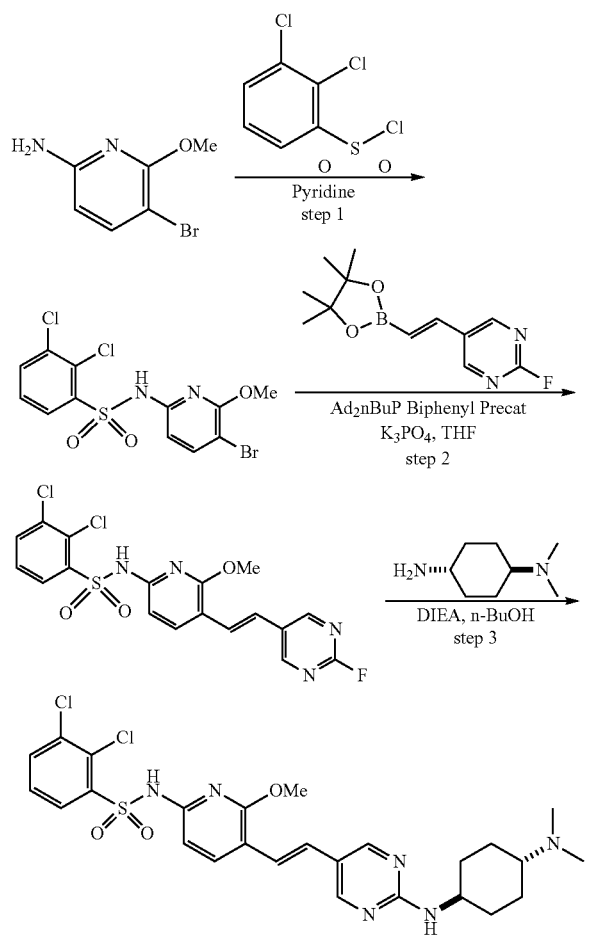

Step 1:
To a solution of 5-bromo-6-methoxypyridin-2-amine (1.0 g, 4.9 mmol) in pyridine (10.0 mL) was added 2,3-dichlorobenzenesulfonyl chloride (1.8 g, 7.3 mmol). The mixture was stirred at 45° C. for 12 h. The reaction mixture was concentrated under reduced pressure to give a residue. The residue was purified by column chromatography (SiO$_2$) to give N-(5-bromo-6-methoxypyridin-2-yl)-2,3-dichlorobenzenesulfonamide (1.6 g, 80.8% yield) as a yellow solid.

Step 2:
A mixture of N-(5-bromo-6-methoxypyridin-2-yl)-2,3-dichlorobenzenesulfonamide (825 mg, 2.0 mmol), (E)-2-fluoro-5-(2-(4,4,5,5-tetramethyl-1,3,2-dioxaborolan-2-yl)vinyl)pyrimidine (500 mg, 2.0 mmol), K$_3$PO$_4$ (0.5 M, 12.0 mL), and [2-(2-aminophenyl)phenyl]-chloro-palladium bis (1-adamantyl)-butyl-phosphane (66 mg, 100.1 umol) in THF (40.0 mL) was degassed and purged with N$_2$ three times, and then the mixture was stirred at 80° C. for 12 h under N$_2$ atmosphere. The reaction mixture was diluted with water (150.0 mL) and extracted with ethyl acetate (50.0 mL×3). The combined organic layer was washed with saturated sodium chloride (50.0 mL×3), dried over anhydrous sodium sulfate, filtered, and concentrated under reduced pressure to give a residue. The residue was purified by column chromatography (SiO$_2$) to give (E)-2,3-dichloro-N-(5-(2-(2-fluoropyrimidin-5-yl)vinyl)-6-methoxypyridin-2-yl)benzenesulfonamide (388 mg, 666.4 umol, 33.2% yield) as a yellow solid. M+H$^+$=454.9 (LCMS).

Step 3:
To a solution of (E)-2,3-dichloro-N-(5-(2-(2-fluoropyrimidin-5-yl)vinyl)-6-methoxypyridin-2-yl)benzenesulfonamide (388 mg, 852.2 umol) in n-BuOH (3.0 mL) was added (1r,4r)-N$^1$,N$^1$-methylcyclohexane-1,4-diamine (304 mg, 1.7 mmol, HCl) and DIEA (550 mg, 4.2 mmol, 742.1 uL). The mixture was stirred at 100° C. for 12 h. The reaction mixture was concentrated under reduced pressure to give a residue. The residue was purified by prep-HPLC (FA condition) to give 2,3-dichloro-N-(5-((E)-2-(2-(((1r,4r)-4-(dimethylamino)cyclohexyl)amino)pyrimidin-5-yl)vinyl)-6-methoxypyridin-2-yl)benzenesulfonamide (176.5 mg, 32.7% yield, FA) as a pale yellow solid. M+H$^+$=577.2 (LCMS); $^1$H NMR (400 MHz, METHANOL-d$_4$) δ 8.45 (s, 1H), 8.41 (s, 2H), 8.26 (dd, J=1.4, 8.0 Hz, 1H), 7.84-7.72 (m, 2H), 7.50 (t, J=7.9 Hz, 1H), 7.08-6.98 (m, 1H), 6.96-6.85 (m, 1H), 6.55 (d, J=8.2 Hz, 1H), 3.86-3.75 (m, 1H), 3.69 (s, 3H), 3.26-3.13 (m, 1H), 2.86 (s, 6H), 2.28-2.19 (m, 2H), 2.17-2.05 (m, 2H), 1.75-1.60 (m, 2H), 1.51-1.34 (m, 2H).

The compounds below were prepared by similar procedures as described in Examples 1-44 above.

| Compound No. | Structure | Name | MS [M + H]$^+$ |
|---|---|---|---|
| 1 | 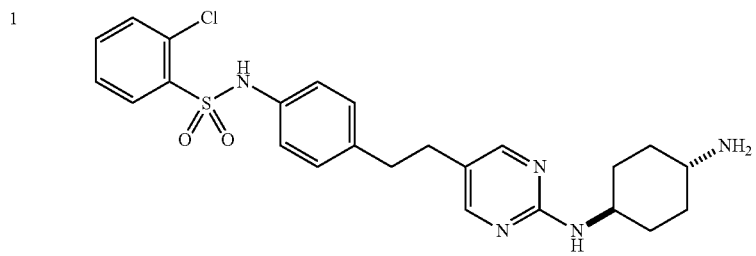 | N-(4-(2-(2-(((1r,4r)-4-aminocyclohexyl)amino)pyrimidin-5-yl)ethyl)phenyl)-2-chlorobenzenesulfonamide | 487.2 |

-continued

| Compound No. | Structure | Name | MS [M + H]+ |
|---|---|---|---|
| 2 | 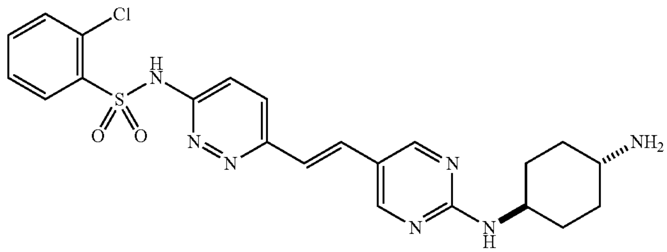 | N-(6-((E)-2-(2-(((1r,4r)-4-aminocyclohexyl)amino)pyrimidin-5-yl)vinyl)pyridazin-3-yl)-2-chlorobenzenesulfonamide | 487.0 |
| 3 | 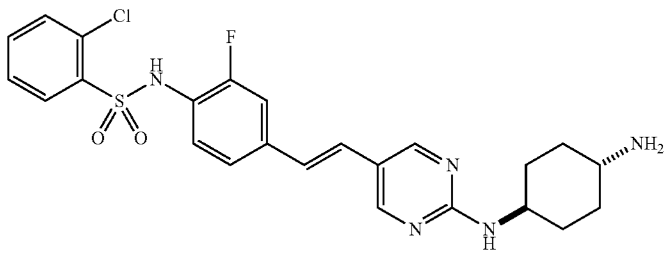 | N-(4-((E)-2-(2-(((1r,4r)-4-aminocyclohexyl)amino)pyrimidin-5-yl)vinyl)-2-fluorophenyl)-2-chlorobenzenesulfonamide | 503.0 |
| 4 | 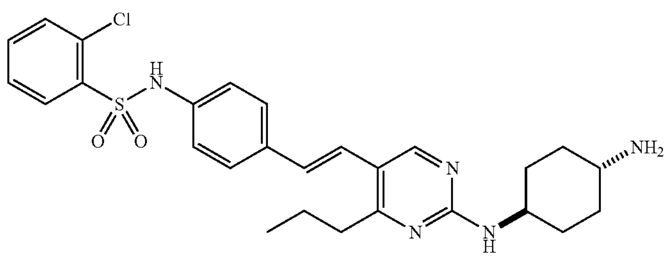 | N-(4-((E)-2-(2-(((1r,4r)-4-aminocyclohexyl)amino)-4-propylpyrimidin-5-yl)vinyl)phenyl)-2-chlorobenzenesulfonamide | 527.2 |
| 12 | 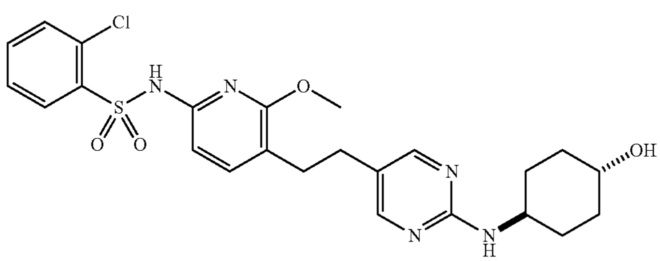 | 2-chloro-N-(5-(2-(2-(((1r,4r)-4-hydroxycyclohexyl)amino)pyrimidin-5-yl)ethyl)-6-methoxypyridin-2-yl)benzenesulfonamide | 519.2 |
| 13 | 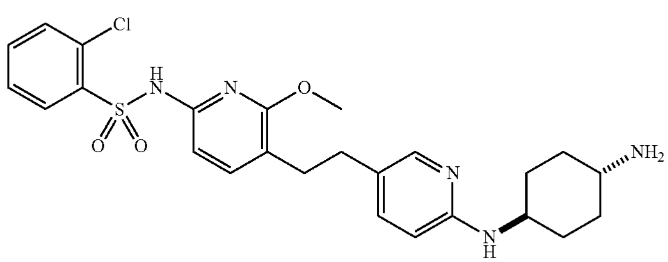 | N-(5-(2-(6-(((1r,4r)-4-aminocyclohexyl)amino)pyridin-3-yl)ethyl)-6-methoxypyridin-2-yl)-2-chlorobenzenesulfonamide | 517.1 |
| 22 | 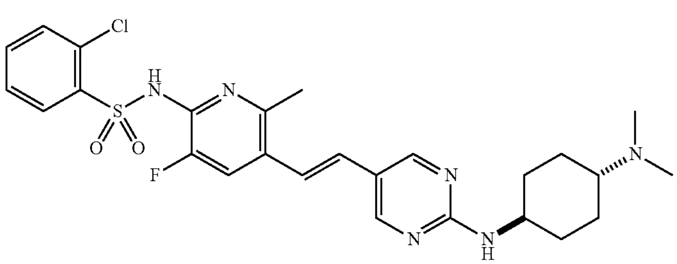 | 2-chloro-N-(5-((E)-2-(2-(((1r,4r)-4-(dimethylamino)cyclohexyl)amino)pyrimidin-5-yl)vinyl)-3-fluoro-6-methylpyridin-2-yl)benzenesulfonamide | 546.1 |

-continued

| Compound No. | Structure | Name | MS [M + H]+ |
|---|---|---|---|
| 52 | 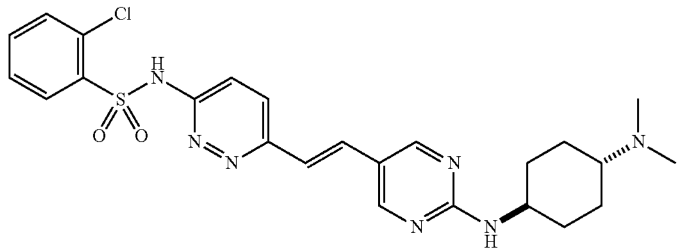 | 2-chloro-N-(6-((E)-2-(2-(((1r,4r)-4-(dimethylamino)cyclohexyl)amino)pyrimidin-5-yl)vinyl)pyridazin-3-yl)benzenesulfonamide | 515.2 |
| 53 | 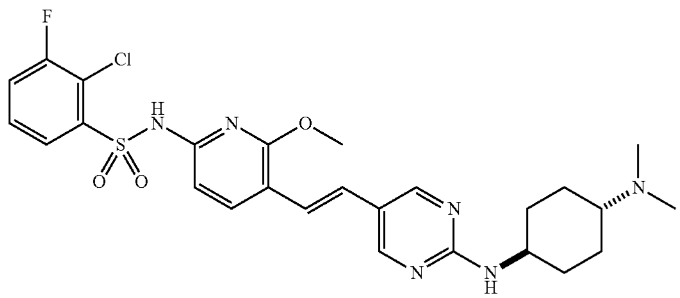 | 2-chloro-N-(5-((E)-2-(2-(((1r,4R)-4-(dimethylamino)cyclohexyl)amino)pyrimidin-5-yl)vinyl)-6-methoxypyridin-2-yl)-3-fluorobenzenesulfonamide | 564.2 |
| 54 | 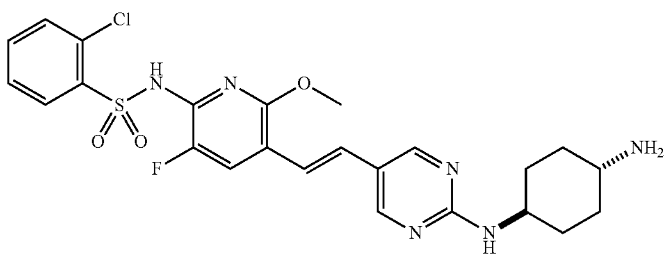 | N-(5-((E)-2-(2-(((1r,4r)-4-aminocyclohexyl)amino)pyrimidin-5-yl)vinyl)-3-fluoro-6-methoxypyridin-2-yl)-2-chlorobenzenesulfonamide | 534.2 |
| 55 | 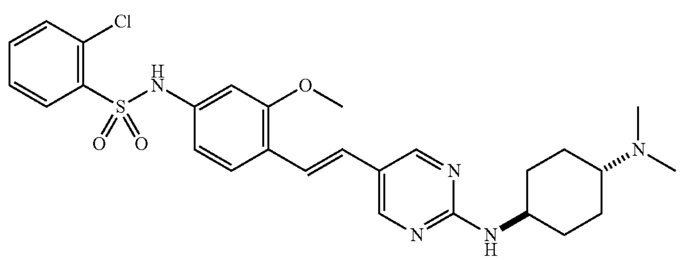 | 2-chloro-N-(4-((E)-2-(2-(((1r,4r)-4-(dimethylamino)cyclohexyl)amino)pyrimidin-5-yl)vinyl)-3-methoxyphenyl)benzenesulfonamide | 543.2 |
| 56 | 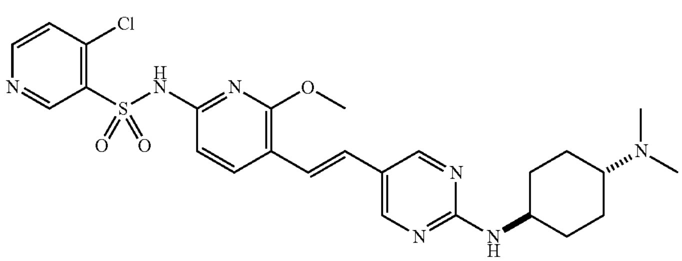 | 4-chloro-N-(5-((E)-2-(2-(((1r,4r)-4-(dimethylamino)cyclohexyl)amino)pyrimidin-5-yl)vinyl)-6-methoxypyridin-2-yl)pyridine-3-sulfonamide | 545.1 |
| 57 | 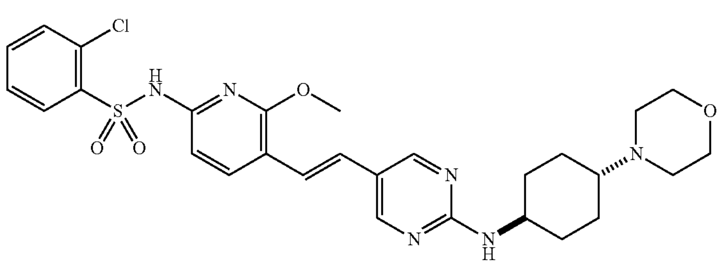 | 2-chloro-N-(6-methoxy-5-((E)-2-(2-(((1r,4r)-4-morpholinocyclohexyl)amino)pyrimidin-5-yl)vinyl)pyridin-2-yl)benzenesulfonamide | 586.2 |

| Compound No. | Structure | Name | MS [M + H]+ |
|---|---|---|---|
| 58 | 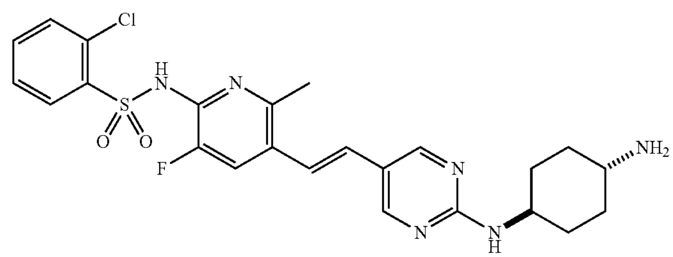 | N-(5-((E)-2-(2-(((1r,4r)-4-aminocyclohexyl)amino)pyrimidin-5-yl)vinyl)-3-fluoro-6-methylpyridin-2-yl)-2-chlorobenzenesulfonamide | 518.2 |
| 59 | 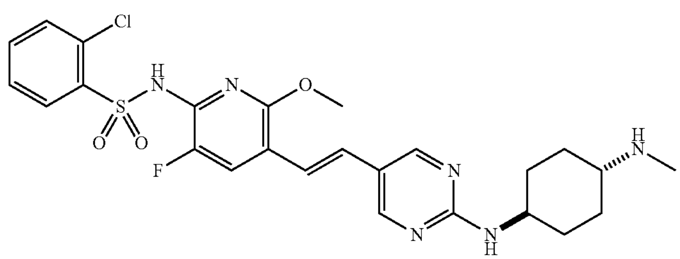 | 2-chloro-N-(3-fluoro-6-methoxy-5-((E)-2-(2-(((1r,4r)-4-(methylamino)cyclohexyl)amino)pyrimidin-5-yl)vinyl)pyridin-2-yl)benzenesulfonamide | 548.2 |
| 60 | 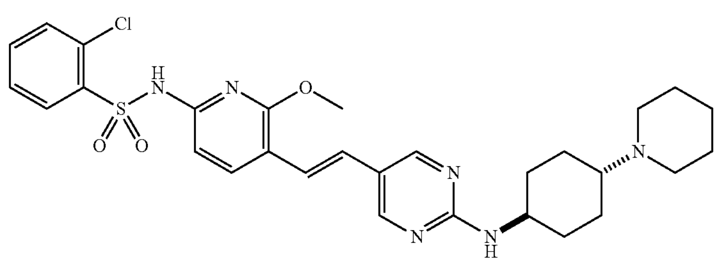 | 2-chloro-N-(6-methoxy-5-((E)-2-(2-(((1r,4r)-4-(piperidin-1-yl)cyclohexyl)amino)pyrimidin-5-yl)vinyl)pyridin-2-yl)benzenesulfonamide | 584.2 |
| 61 | 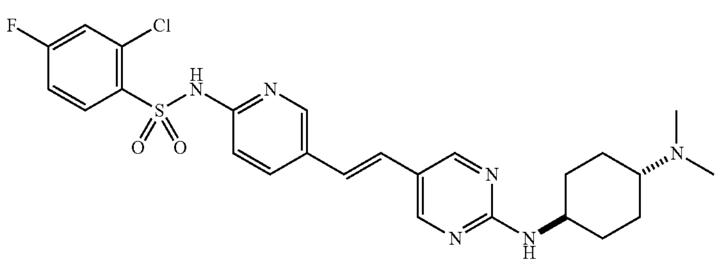 | 2-chloro-N-(5-((E)-2-(2-(((1r,4r)-4-(dimethylamino)cyclohexyl)amino)pyrimidin-5-yl)vinyl)pyridin-2-yl)-4-fluorobenzenesulfonamide | 532.2 |
| 62 | 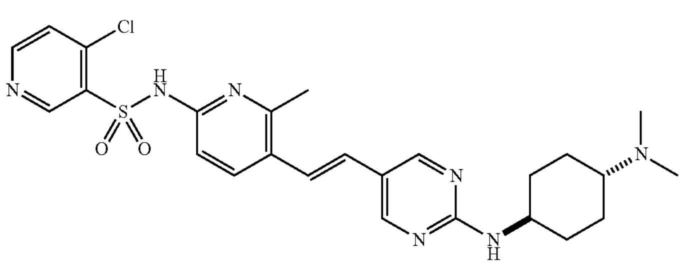 | 4-chloro-N-(5-(((E)-2-(2-(((1r,4r)-4-(dimethylamino)cyclohexyl)amino)pyrimidin-5-yl)vinyl)-6-methylpyridin-2-yl)pyridine-3-sulfonamide | 529.2 |

-continued

| Compound No. | Structure | Name | MS [M + H]+ |
|---|---|---|---|
| 63 | 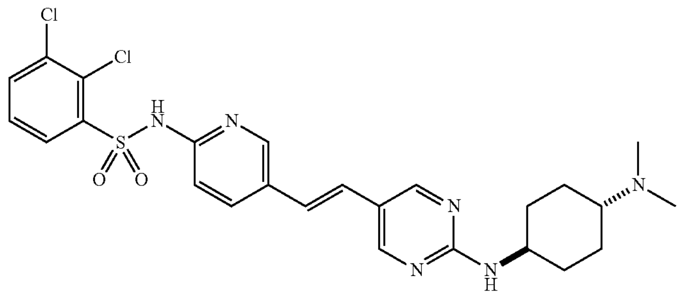 | 2,3-dichloro-N-(5-((E)-2-(2-(((1r,4r)-4-(dimethylamino)cyclohexyl)amino)pyrimidin-5-yl)vinyl)pyridin-2-yl)benzenesulfonamide | 548.0 |
| 64 | 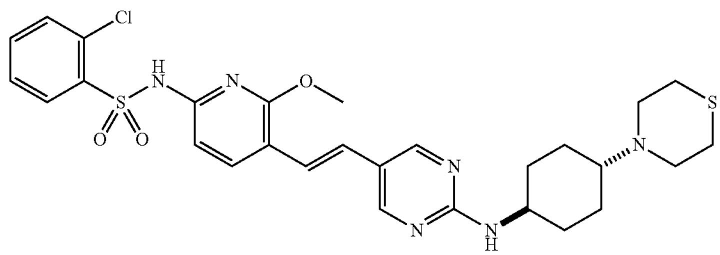 | 2-chloro-N-(6-methoxy-5-((E)-2-(2-(((1r,4r)-4-thiomorpholinocyclohexyl)amino)pyrimidin-5-yl)vinyl)pyridin-2-yl)benzenesulfonamide | 602.3 |
| 65 | 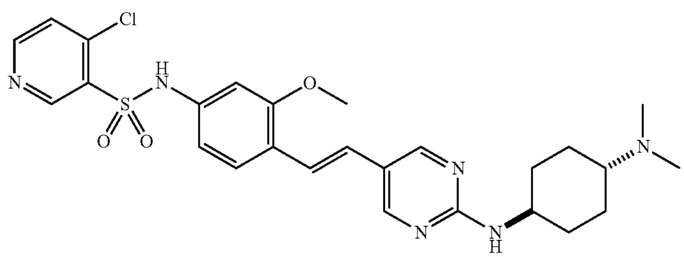 | 4-chloro-N-(4-((E)-2-(2-(((1r,4r)-4-(dimethylamino)cyclohexyl)amino)pyrimidin-5-yl)vinyl)-3-methoxyphenyl)pyridine-3-sulfonamide | 544.1 |
| 66 | 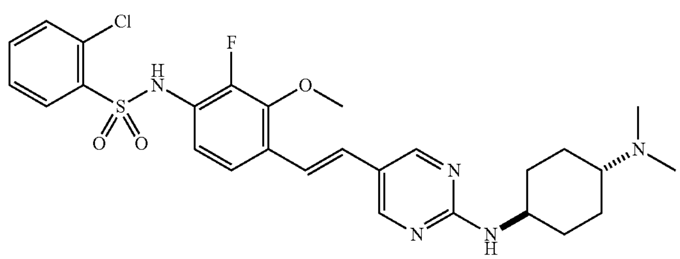 | 2-chloro-N-(4-((E)-2-(2-(((1r,4r)-4-(dimethylamino)cyclohexyl)amino)pyrimidin-5-yl)vinyl)-2-fluoro-3-methoxyphenyl)benzenesulfonamide | 561.1 |
| 67 | 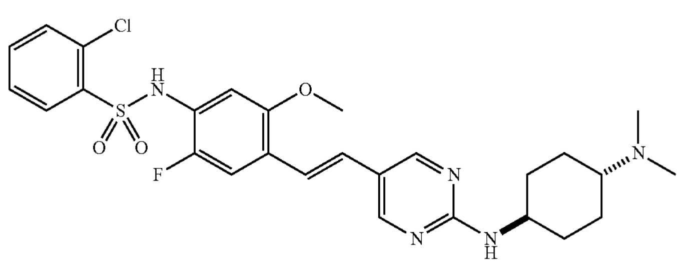 | 2-chloro-N-(4-((E)-2-(2-(((1r,4r)-4-(dimethylamino)cyclohexyl)amino)pyrimidin-5-yl)vinyl)-2-fluoro-5-methoxyphenyl)benzenesulfonamide | 561.1 |

-continued

| Compound No. | Structure | Name | MS [M + H]+ |
|---|---|---|---|
| 68 | 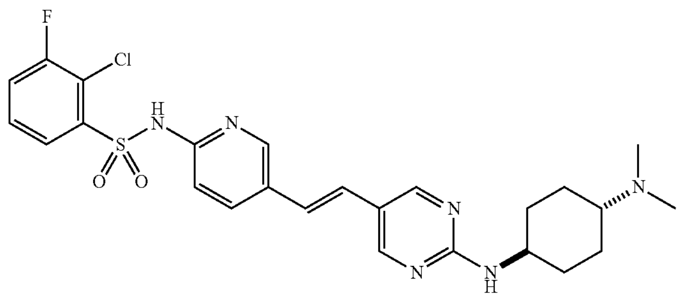 | 2-chloro-N-(5-((E)-2-(2-(((1r,4r)-4-(dimethylamino)cyclohexyl)amino)pyrimidin-5-yl)vinyl)pyridin-2-yl)-3-fluorobenzenesulfonamide | 532.1 |
| 69 | 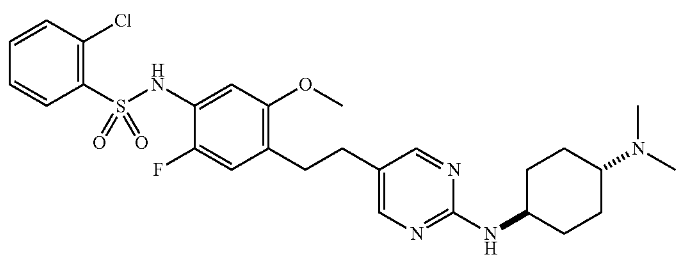 | 2-chloro-N-(4-(2-(2-(((1r,4r)-4-(dimethylamino)cyclohexyl)amino)pyrimidin-5-yl)ethyl)-2-fluoro-5-methoxyphenyl)benzenesulfonamide | 563.1 |
| 70 | 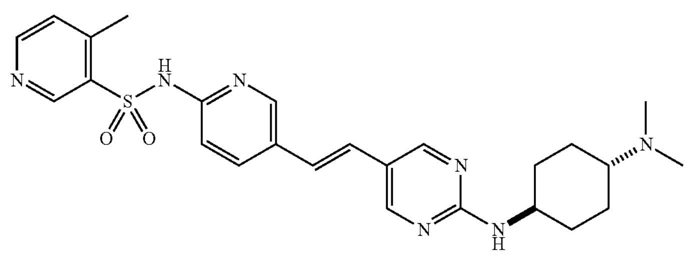 | N-(5-((E)-2-(2-(((1r,4r)-4-(dimethylamino)cyclohexyl)amino)pyrimidin-5-yl)vinyl)pyridin-2-yl)-4-methylpyridine-3-sulfonamide | 594.2 |
| 71 | 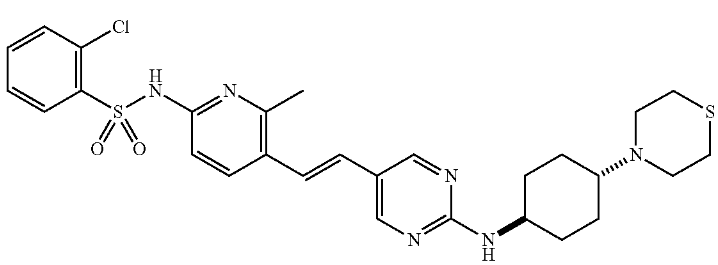 | 2-chloro-N-(6-methyl-5-((E)-2-(2-(((1r,4r)-4-thiomorpholinocyclohexyl)amino)pyrimidin-5-yl)vinyl)pyridin-2-yl)benzenesulfonamide | 586.2 |
| 72 | 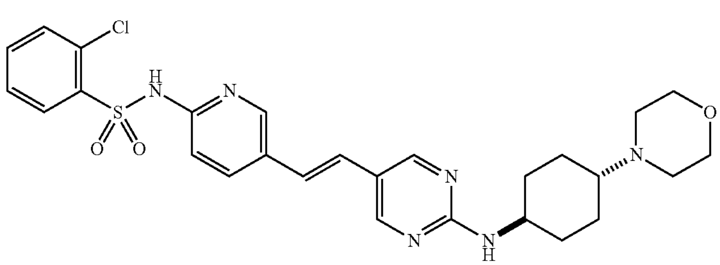 | 2-chloro-N-(5-((E)-2-(2-(((1r,4r)-4-morpholinocyclohexyl)amino)pyrimidin-5-yl)vinyl)pyridin-2-yl)benzenesulfonamide | 556.3 |

II. Biological Evaluation

Example 1: In Vitro FRET Assay

In vitro FRET assay was performed to evaluate the ability of select compounds to inhibit IRE1, the results of which are summarized in Table 3. To perform the in vitro FRET assay, 1× complete assay buffer (CAB; 1M DTT, 50 mM sodium citrate pH 7.15, 1 mM magnesium acetate, 0.02% tween 20) was used to dilute SignalChem IRE1α protein to a final concentration of 2 nM. Selected compounds were serially diluted with DMSO in a non-binding black 384-well plate for a total of 15 ul in each well. 2 ul of the serially diluted compound or DMSO control were then added to new wells containing 98 ul of 1×CAB, for a total volume of 100 ul, 10 ul of which were then transferred to wells of a new plate. 5 ul of the diluted IRE1α was then added to each well. 5 ul of a 400 mM XBP1 RNA probe was then added to each well. Fluorescence was then read over 30 minutes in kinetic mode (485/515 nm).

Two RNA probes were used, XBP1 wildtype (SEQ ID NO: 2) which is able to be spliced by active IRE1α or XBP1 mutant (SEQ ID NO: 3) which is unable to be spliced. Each probe contained a 5' 6-FAM modification and a 3' IOWA Black FQ modification.

A second FRET assay was performed to assess ATP-mediated inhibition. In this case, compounds and IRE1α were prepared and combined as discussed above, with the addition of ATP up to 1 mM final concentration. This mixture was incubated at room temperature for 60 minutes and then 5 ul of 400 nM XBP1 wildtype or mutant RNA probe was added. Plates were then read over 30 minutes in kinetic mode (485/515 nm) and rate of fluorescence increase calculated for different compound dilutions to determine $IC_{50}$ (Table 3).

TABLE 3

| Compound No. | Compound Name | Mean $IC_{50}$ |
| --- | --- | --- |
| 1 | N-(4-(2-(2-(((1r,4r)-4-aminocyclohexyl)amino)pyrimidin-5-yl)ethyl)phenyl)-2-chlorobenzenesulfonamide | A |
| 2 | N-(6-((E)-2-(2-(((1r,4r)-4-aminocyclohexyl)amino)pyrimidin-5-yl)vinyl)pyridazin-3-yl)-2-chlorobenzenesulfonamide | A+ |
| 3 | N-(4-((E)-2-(2-(((1r,4r)-4-aminocyclohexyl)amino)pyrimidin-5-yl)vinyl)-2-fluorophenyl)-2-chlorobenzenesulfonamide | A+ |
| 4 | N-(4-((E)-2-(2-(((1r,4r)-4-aminocyclohexyl)amino)-4-propylpyrimidin-5-yl)vinyl)phenyl)-2-chlorobenzenesulfonamide | A |
| 5 | N-(4-((E)-2-(2-(((1r,4r)-4-aminocyclohexyl)amino)pyrimidin-5-yl)vinyl)-3-methylphenyl)-2-chlorobenzenesulfonamide; formic acid | A+ |
| 6 | N-(4-(2-(2-(((1r,4r)-4-aminocyclohexyl)amino)pyrimidin-5-yl)ethyl)-3-methylphenyl)-2-chlorobenzenesulfonamide; formic acid | A+ |
| 7 | N-(6-(2-(2-(((1r,4r)-4-aminocyclohexyl)amino)pyrimidin-5-yl)ethyl)pyridazin-3-yl)-2-chlorobenzenesulfonamide; formic acid | A |
| 8 | N-(4-(2-(2-(((1r,4r)-4-aminocyclohexyl)amino)pyrimidin-5-yl)ethyl)-2-fluorophenyl)-2-chlorobenzenesulfonamide; formic acid | A+ |
| 9 | N-(5-((E)-2-(2-(((1r,4r)-4-aminocyclohexyl)amino)pyrimidin-5-yl)vinyl)-6-methoxypyridin-2-yl)-2-chlorobenzenesulfonamide; formic acid | A+ |
| 10 | N-(5-(2-(2-(((1r,4r)-4-aminocyclohexyl)amino)pyrimidin-5-yl)ethyl)-6-methoxypyridin-2-yl)-2-chlorobenzenesulfonamide | A+ |
| 11 | 2-Chloro-N-(5-((E)-2-(2-(((1r,4r)-4-hydroxycyclohexyl)amino)pyrimidin-5-yl)vinyl)-6-methoxypyridin-2-yl)benzenesulfonamide; formic acid | A |
| 12 | 2-chloro-N-(5-(2-(2-(((1r,4r)-4-hydroxycyclohexyl)amino)pyrimidin-5-yl)ethyl)-6-methoxypyridin-2-yl)benzenesulfonamide | B |
| 13 | N-(5-(2-(6-(((1r,4r)-4-aminocyclohexyl)amino)pyridin-3-yl)ethyl)-6-methoxypyridin-2-yl)-2-chlorobenzenesulfonamide; formic acid | A |
| 14 | N-(4-((E)-2-(2-(((1r,4r)-4-aminocyclohexyl)amino)pyrimidin-5-yl)vinyl)-3-methoxyphenyl)-2-chlorobenzenesulfonamide; formic acid | A+ |
| 15 | N-(4-(2-(2-(((1r,4r)-4-aminocyclohexyl)amino)pyrimidin-5-yl)ethyl)-3-methoxyphenyl)-2-chlorobenzenesulfonamide; formic acid | A+ |
| 16 | N-(6-(2-(2-(((1r,4r)-4-aminocyclohexyl)amino)pyrimidin-5-yl)ethyl)-5-ethylpyridin-3-yl)-2-chlorobenzenesulfonamide; formic acid | A+ |
| 17 | 2-Chloro-N-(5-((E)-2-(2-(((1r,4r)-4-(dimethylamino)cyclohexyl)amino)pyrimidin-5-yl)vinyl)-6-methoxypyridin-2-yl)benzenesulfonamide; formic acid | A+ |
| 18 | N-(6-(2-(2-(((1r,4r)-4-aminocyclohexyl)amino)pyrimidin-5-yl)ethyl)-5-methoxypyridin-3-yl)-2-chlorobenzenesulfonamide; formic acid | A+ |
| 19 | 2-Chloro-N-(5-(2-(2-(((1r,4r)-4-(dimethylamino)cyclohexyl)amino)pyrimidin-5-yl) ethyl)-6-methoxypyridin-2-yl)benzenesulfonamide; formic acid | A+ |
| 20 | 2-Chloro-N-(5-(2-(2-(((1r,4r)-4-hydroxycyclohexyl)amino)pyrimidin-5-yl)ethyl)-6-methylpyridin-2-yl)benzenesulfonamide; formic acid | D |
| 21 | 2-Chloro-N-(5-(2-(2-(((1r,4r)-4-(dimethylamino)cyclohexyl)amino)pyrimidin-5-yl)ethyl)-6-methylpyridin-2-yl)benzenesulfonamide; formic acid | A |
| 22 | 2-Chloro-N-(5-((E)-2-(2-(((1r,4r)-4-(dimethylamino)cyclohexyl)amino)pyrimidin-5-yl)vinyl)-3-fluoro-6-methylpyridin-2-yl)benzenesulfonamide; formic acid | A+ |
| 23 | 2-Chloro-N-(5-((E)-2-(2-(((1r,4r)-4-(dimethylamino)cyclohexyl)amino)pyrimidin-5-yl)vinyl)-6-methoxypyridin-2-yl)benzenesulfonamide; formic acid | A+ |
| 24 | 2-Chloro-N-(5-(2-(2-(((1r,4r)-4-(dimethylamino)cyclohexyl)amino)pyrimidin-5-yl)ethyl)-3-fluoro-6-methylpyridin-2-yl)benzenesulfonamide | A |
| 25 | 2-chloro-N-(5-((E)-2-(2-(((1r,4r)-4-(dimethylamino)cyclohexyl)amino)pyrimidin-5-yl)vinyl)-3-fluoro-6-methylpyridin-2-yl)benzenesulfonamide | A+ |

TABLE 3-continued

| Compound No. | Compound Name | Mean IC$_{50}$ |
|---|---|---|
| 26 | 2-chloro-N-(4-((E)-2-(2-(((1r,4r)-4-(dimethylamino)cyclohexyl)amino)pyrimidin-5-yl)vinyl)-3-methylphenyl)benzenesulfonamide | A+ |
| 27 | 2-chloro-N-(4-((E)-2-(2-(((1r,4r)-4-(dimethylamino)cyclohexyl)amino)pyrimidin-5-yl)vinyl)-3-methylphenyl)benzenesulfonamide | A+ |
| 28 | 2-chloro-N-(4-((E)-2-(2-(((1r,4r)-4-(dimethylamino)cyclohexyl)amino)pyrimidin-5-yl)vinyl)-2-fluoro-5-methylphenyl)benzenesulfonamide | A+ |
| 29 | 2-chloro-N-(5-((E)-2-(2-(((1r,4r)-4-(dimethylamino)cyclohexyl)amino)pyrimidin-5-yl)vinyl)-6-ethylpyridin-2-yl)benzenesulfonamide | A+ |
| 30 | 2-chloro-N-(5-((E)-2-(2-(((1r,4r)-4-(diethylamino)cyclohexyl)amino)pyrimidin-5-yl)vinyl)-6-methylpyridin-2-yl)benzenesulfonamide | A+ |
| 31 | 2-chloro-N-(5-((E)-2-(2-(((1r,4r)-4-(dimethylamino)cyclohexyl)amino)pyrimidin-5-yl)vinyl)-6-methylpyridin-2-yl)-4-fluorobenzenesulfonamide | A+ |
| 32 | 2-chloro-N-(5-((E)-2-(2-(((1r,4r)-4-(dimethylamino)cyclohexyl)amino)pyrimidin-5-yl)vinyl)-6-methoxypyridin-2-yl)-4-fluorobenzenesulfonamide | A+ |
| 33 | 2-chloro-N-(5-((E)-2-(2-(((1r,4r)-4-(dimethylamino)cyclohexyl)amino)pyrimidin-5-yl)vinyl)-6-methylpyridin-2-yl)-3-fluorobenzenesulfonamide | A+ |
| 34 | 2-chloro-N-(4-((E)-2-(2-(((1r,4r)-4-(dimethylamino)cyclohexyl)amino)pyrimidin-5-yl)vinyl)phenyl)benzenesulfonamide | A+ |
| 35 | 2-chloro-N-(4-((E)-2-(2-(((1r,4r)-4-(dimethylamino)cyclohexyl)amino)pyrimidin-5-yl)vinyl)-2-fluorophenyl)benzenesulfonamide | A+ |
| 36 | 2-chloro-N-(5-((E)-2-(2-(((1r,4r)-4-(dimethylamino)cyclohexyl)amino)pyrimidin-5-yl)vinyl)pyridin-2-yl)benzenesulfonamide | A+ |
| 37 | 2-chloro-N-(5-((E)-2-(2-(((1r,4r)-4-(dimethylamino)cyclohexyl)amino)pyrimidin-5-yl)vinyl)pyrazin-2-yl)benzenesulfonamide | A+ |
| 38 | 2-chloro-N-(5-((E)-2-(2-(((1r,4r)-4-(dimethylamino)cyclohexyl)amino)pyrimidin-5-yl)vinyl)-6-methylpyridin-2-yl)-3,4-difluorobenzenesulfonamide | A+ |
| 39 | 2-chloro-N-(5-((E)-2-(2-(((1r,4r)-4-(dimethylamino)cyclohexyl)amino)pyrimidin-5-yl)vinyl)-6-methoxypyridin-2-yl)-3-fluorobenzenesulfonamide | A+ |
| 40 | 2-chloro-N-(5-(2-(2-(((1r,4r)-4-(dimethylamino)cyclohexyl)amino)pyrimidin-5-yl)vinyl)pyrimidin-2-yl)benzenesulfonamide | A+ |
| 41 | 2-chloro-N-(5-((E)-2-(2-(((1r,4r)-4-(dimethylamino)cyclohexyl)amino)pyrimidin-5-yl)vinyl)-6-methoxypyridin-2-yl)-3,4-difluorobenzenesulfonamide | A+ |
| 42 | 4-chloro-N-(5-((E)-2-(2-(((1r,4r)-4-(dimethylamino)cyclohexyl)amino)pyrimidin-5-yl)vinyl)-6-ethylpyridin-2-yl)pyridine-3-sulfonamide | A+ |
| 43 | 4-chloro-N-(5-(2-(2-(((1r,4r)-4-(dimethylamino)cyclohexyl)amino)pyrimidin-5-yl)vinyl)-4-methoxypyrimidin-2-yl)pyridine-3-sulfonamide | A |
| 44 | 2-chloro-N-(6-methyl-5-(2-(2-(((1r,4r)-4-(methylamino)cyclohexyl)amino)pyrimidin-5-yl)vinyl)pyridin-2-yl)benzenesulfonamide | A+ |
| 45 | N-(5-(2-(2-(((1r,4r)-4-aminocyclohexyl)amino)pyrimidin-5-yl)vinyl)-6-ethylpyridin-2-yl)-2-chlorobenzenesulfonamide | A+ |
| 46 | N-(5-((E)-2-(2-(((1r,4r)-4-aminocyclohexyl)amino)pyrimidin-5-yl)vinyl)-6-methylpyridin-2-yl)-2-chlorobenzenesulfonamide | A+ |
| 47 | 2-chloro-N-(6-ethyl-5-((E)-2-(2-(((1r,4r)-4-(methylamino)cyclohexyl)amino)pyrimidin-5-yl)vinyl)pyridin-2-yl)benzenesulfonamide | A+ |
| 48 | 2-chloro-N-(6-methoxy-5-((E)-2-(2-(((1r,4r)-4-(methylamino)cyclohexyl)amino)pyrimidin-5-yl)vinyl)pyridin-2-yl)benzenesulfonamide | A+ |
| 49 | (E)-N-(5-(2-(2-((4-aminobicyclo[2.2.2]octan-1-yl)amino)pyrimidin-5-yl)vinyl)-6-methylpyridin-2-yl)-2-chlorobenzenesulfonamide | A+ |
| 50 | 2-chloro-N-(5-((E)-2-(2-(((1r,4r)-4-(dimethylamino)cyclohexyl)amino)pyrimidin-5-yl)vinyl)-3-fluoro-6-methoxypyridin-2-yl)benzenesulfonamide | A+ |
| 51 | 2,3-dichloro-N-(5-((E)-2-(2-(((1r,4r)-4-(dimethylamino)cyclohexyl)amino)pyrimidin-5-yl)vinyl)-6-methoxypyridin-2-yl)benzenesulfonamide | A+ |

TABLE 3-continued

| Compound No. | Compound Name | Mean IC$_{50}$ |
|---|---|---|
| 52 | 2-chloro-N-(6-((E)-2-(2-(((1r,4r)-4-(dimethylamino)cyclohexyl)amino)pyrimidin-5-yl)vinyl)pyridazin-3-yl)benzenesulfonamide | A+ |
| 53 | 2-chloro-N-(5-((E)-2-(2-(((1r,4r)-4-(dimethylamino)cyclohexyl)amino)pyrimidin-5-yl)vinyl)-6-methoxypyridin-2-yl)-3-fluorobenzenesulfonamide | A+ |
| 54 | N-(5-((E)-2-(2-(((1r,4r)-4-aminocyclohexyl)amino)pyrimidin-5-yl)vinyl)-3-fluoro-6-methoxypyridin-2-yl)-2-chlorobenzenesulfonamide | A+ |
| 55 | 2-chloro-N-(4-((E)-2-(2-(((1r,4r)-4-(dimethylamino)cyclohexyl)amino)pyrimidin-5-yl)vinyl)-3-methoxyphenyl)benzenesulfonamide | A+ |
| 56 | 4-chloro-N-(5-((E)-2-(2-(((1r,4r)-4-(dimethylamino)cyclohexyl)amino)pyrimidin-5-yl)vinyl)-6-methoxypyridin-2-yl)pyridine-3-sulfonamide | A+ |
| 57 | 2-chloro-N-(6-methoxy-5-((E)-2-(2-(((1r,4r)-4-morpholinocyclohexyl)amino)pyrimidin-5-yl)vinyl)pyridin-2-yl)benzenesulfonamide | A+ |
| 58 | N-(5-((E)-2-(2-(((1r,4r)-4-aminocyclohexyl)amino)pyrimidin-5-yl)vinyl)-3-fluoro-6-methylpyridin-2-yl)-2-chlorobenzenesulfonamide | A+ |
| 59 | 2-chloro-N-(3-fluoro-6-methoxy-5-((E)-2-(2-(((1r,4r)-4-(methylamino)cyclohexyl)amino)pyrimidin-5-yl)vinyl)pyridin-2-yl)benzenesulfonamide | A+ |
| 60 | 2-chloro-N-(6-methoxy-5-((E)-2-(2-(((1r,4r)-4-(piperidin-1-yl)cyclohexyl)amino)pyrimidin-5-yl)vinyl)pyridin-2-yl)benzenesulfonamide | A+ |
| 61 | 2-chloro-N-(5-((E)-2-(2-(((1r,4r)-4-(dimethylamino)cyclohexyl)amino)pyrimidin-5-yl)vinyl)pyridin-2-yl)-4-fluorobenzenesulfonamide | A+ |
| 62 | 4-chloro-N-(5-((E)-2-(2-(((1r,4r)-4-(dimethylamino)cyclohexyl)amino)pyrimidin-5-yl)vinyl)-6-methylpyridin-2-yl)pyridine-3-sulfonamide | A+ |
| 63 | 2,3-dichloro-N-(5-((E)-2-(2-(((1r,4r)-4-(dimethylamino)cyclohexyl)amino)pyrimidin-5-yl)vinyl)pyridin-2-yl)benzenesulfonamide | A+ |
| 64 | 2-chloro-N-(6-methoxy-5-((E)-2-(2-(((1r,4r)-4-thiomorpholinocyclohexyl)amino)pyrimidin-5-yl)vinyl)pyridin-2-yl)benzenesulfonamide | A+ |
| 65 | 4-chloro-N-(4-((E)-2-(2-(((1r,4r)-4-(dimethylamino)cyclohexyl)amino)pyrimidin-5-yl)vinyl)-3-methoxyphenyl)pyridine-3-sulfonamide | A+ |
| 66 | 2-chloro-N-(4-((E)-2-(2-(((1r,4r)-4-(dimethylamino)cyclohexyl)amino)pyrimidin-5-yl)vinyl)-2-fluoro-3-methoxyphenyl)benzenesulfonamide | A+ |
| 67 | 2-chloro-N-(4-((E)-2-(2-(((1r,4r)-4-(dimethylamino)cyclohexyl)amino)pyrimidin-5-yl)vinyl)-2-fluoro-5-methoxyphenyl)benzenesulfonamide | A+ |
| 68 | 2-chloro-N-(5-((E)-2-(2-(((1r,4r)-4-(dimethylamino)cyclohexyl)amino)pyrimidin-5-yl)vinyl)pyridin-2-yl)-3-fluorobenzenesulfonamide | A+ |
| 69 | 2-chloro-N-(4-(2-(2-(((1r,4r)-4-(dimethylamino)cyclohexyl)amino)pyrimidin-5-yl)ethyl)-2-fluoro-5-methoxyphenyl)benzenesulfonamide | NT |
| 70 | N-(5-((E)-2-(2-(((1r,4r)-4-(dimethylamino)cyclohexyl)amino)pyrimidin-5-yl)vinyl)pyridin-2-yl)-4-methylpyridine-3-sulfonamide | NT |
| 71 | 2-chloro-N-(6-methyl-5-((E)-2-(2-(((1r,4r)-4-thiomorpholinocyclohexyl)amino)pyrimidin-5-yl)vinyl)pyridin-2-yl)benzenesulfonamide | NT |
| 72 | 2-chloro-N-(5-((E)-2-(2-(((1r,4r)-4-morpholinocyclohexyl)amino)pyrimidin-5-yl)vinyl)pyridin-2-yl)benzenesulfonamide | NT |

Note:
Biochemical assay Mean IC$_{50}$ data are designated within the following ranges: A+: ≤1 nM A: >1 nM to ≤5 nM; B: >5 nM to ≤50 nM; C: >50 nM to ≤100 nM; and D: >100 nM to ≤1 uM; NT = not tested.

Example 2: In Vitro Luciferase Assay

Compounds disclosed herein were assessed for disruption of IRE-1 signaling using a IRE1α Endoribonuclease Nano-luciferase Assay. Briefly, 2.5×10$^6$ 293T cells were seeded in a 10 cm$^2$ tissue culture plate. About 24 hours later, the cells were transfected with Effectene. In a 15 mL Tube, the following was added: 2 μg XBP1 luciferase reporter plasmid (PGK-Luc2-P2A-XBP1u-Nanoluciferase-PEST); 300 μl EC buffer; and 16 μl Enhancer, followed by incubation at room temp for 5 minutes. Next, 60 μl Effectene (Qiagen 301427) was added, followed by incubation at room temperature for 10 minutes. 2.6 mL cDMEM media was added. Old media was aspirated from the cells, followed by addition of 7 mL fresh media. Full transfection mixture was added dropwise to cells. Cells were incubated for 6 hours, followed by trypsinization, centrifugation and resuspension in 11 mL media. 100 uL of cells were plated per a well in a 96 well plate. A day later, ER stressors of choice+/−inhibitors were added. To harvest, media was aspirated from cells completely, then 50 uL 1× passive lysis buffer (Promega: E1941) was added per well and put on shaker (300 rpm) for 30 minutes at room temperature. Cells were centrifuged, and 15 uL sample per well was added to a new, opaque white 384 well plate (Corning 3570). 15 uL OneGlo (nanoluciferase kit, Promega N1630) was added. Plates were spun down, placed on shaker (300 rpm) for 10 minutes. Plates were read on luminometer, 1000 ms integration time per well. 15 uL Stop and Glo (nanoluciferase kit) was added. Plates were spun down, placed on shaker (300 rpm) for 10 minutes. Plates were read on luminometer, 1000 ms second integration time per well. Recordings are provided below in Table 4

TABLE 4

| Compound No. | Compound Name | Mean $EC_{50}$ |
|---|---|---|
| 1 | N-(4-(2-(2-(((1r,4r)-4-aminocyclohexyl)amino)pyrimidin-5-yl)ethyl)phenyl)-2-chlorobenzenesulfonamide | C |
| 2 | N-(6-((E)-2-(2-(((1r,4r)-4-aminocyclohexyl)amino)pyrimidin-5-yl)vinyl)pyridazin-3-yl)-2-chlorobenzenesulfonamide | C |
| 3 | N-(4-((E)-2-(2-(((1r,4r)-4-aminocyclohexyl)amino)pyrimidin-5-yl)vinyl)-2-fluorophenyl)-2-chlorobenzenesulfonamide | A |
| 4 | N-(4-((E)-2-(2-(((1r,4r)-4-aminocyclohexyl)amino)-4-propylpyrimidin-5-yl)vinyl)phenyl)-2-chlorobenzenesulfonamide | C |
| 5 | N-(4-((E)-2-(2-(((1r,4r)-4-aminocyclohexyl)amino)pyrimidin-5-yl)vinyl)-3-methylphenyl)-2-chlorobenzenesulfonamide; formic acid | A |
| 6 | N-(4-(2-(2-(((1r,4r)-4-aminocyclohexyl)amino)pyrimidin-5-yl)ethyl)-3-methylphenyl)-2-chlorobenzenesulfonamide; formic acid | NT |
| 7 | N-(6-(2-(2-(((1r,4r)-4-aminocyclohexyl)amino)pyrimidin-5-yl)ethyl)pyridazin-3-yl)-2-chlorobenzenesulfonamide; formic acid | NT |
| 8 | N-(4-(2-(2-(((1r,4r)-4-aminocyclohexyl)amino)pyrimidin-5-yl)ethyl)-2-fluorophenyl)-2-chlorobenzenesulfonamide; formic acid | D |
| 9 | N-(5-((E)-2-(2-(((1r,4r)-4-aminocyclohexyl)amino)pyrimidin-5-yl)vinyl)-6-methoxypyridin-2-yl)-2-chlorobenzenesulfonamide; formic acid | A |
| 10 | tert-Butyl ((1r,4r)-4-((6-(6-(2-chlorophenylsulfonamido)-4-ethylpyridazin-3-yl)-8-ethylquinazolin-2-yl)amino)cyclohexyl)carbamate; formic acid | C |
| 11 | 2-Chloro-N-(5-((E)-2-(2-(((1r,4r)-4-hydroxycyclohexyl)amino)pyrimidin-5-yl)vinyl)-6-methoxypyridin-2-yl)benzenesulfonamide; formic acid | NT |
| 12 | 2-chloro-N-(5-(2-(2-(((1r,4r)-4-hydroxycyclohexyl)amino)pyrimidin-5-yl)ethyl)-6-methoxypyridin-2-yl)benzenesulfonamide | NT |
| 13 | N-(5-(2-(6-(((1r,4r)-4-aminocyclohexyl)amino)pyridin-3-yl)ethyl)-6-methoxypyridin-2-yl)-2-chlorobenzenesulfonamide; formic acid | NT |
| 14 | N-(4-((E)-2-(2-(((1r,4r)-4-aminocyclohexyl)amino)pyrimidin-5-yl)vinyl)-3-methoxyphenyl)-2-chlorobenzenesulfonamide; formic acid | A |
| 15 | N-(4-(2-(2-(((1r,4r)-4-aminocyclohexyl)amino)pyrimidin-5-yl)ethyl)-3-methoxyphenyl)-2-chlorobenzenesulfonamide; formic acid | D |
| 16 | N-(6-(2-(2-(((1r,4r)-4-aminocyclohexyl)amino)pyrimidin-5-yl)ethyl)-5-ethylpyridin-3-yl)-2-chlorobenzenesulfonamide; formic acid | D |
| 17 | 2-Chloro-N-(5-((E)-2-(2-(((1r,4r)-4-(dimethylamino)cyclohexyl)amino)pyrimidin-5-yl)vinyl)-6-methoxypyridin-2-yl)benzenesulfonamide; formic acid | A |
| 18 | N-(6-(2-(2-(((1r,4r)-4-aminocyclohexyl)amino)pyrimidin-5-yl)ethyl)-5-methoxypyridin-3-yl)-2-chlorobenzenesulfonamide; formic acid | NT |
| 19 | 2-Chloro-N-(5-(2-(2-(((1r,4r)-4-(dimethylamino)cyclohexyl)amino)pyrimidin-5-yl) ethyl)-6-methoxypyridin-2-yl)benzenesulfonamide; formic acid | B |
| 20 | 2-Chloro-N-(5-(2-(2-(((1r,4r)-4-hydroxycyclohexyl)amino)pyrimidin-5-yl)ethyl)-6-methylpyridin-2-yl)benzenesulfonamide; formic acid | NT |
| 21 | 2-Chloro-N-(5-(2-(2-(((1r,4r)-4-(dimethylamino)cyclohexyl)amino)pyrimidin-5-yl)ethyl)-6-methylpyridin-2-yl)benzenesulfonamide; formic acid | NT |
| 22 | 2-Chloro-N-(5-((E)-2-(2-(((1r,4r)-4-(dimethylamino)cyclohexyl)amino)pyrimidin-5-yl)vinyl)-3-fluoro-6-methylpyridin-2-yl)benzenesulfonamide; formic acid | A |
| 23 | 2-Chloro-N-(5-((E)-2-(2-(((1r,4r)-4-(dimethylamino)cyclohexyl)amino)pyrimidin-5-yl)vinyl)-6-methylpyridin-2-yl)benzenesulfonamide; formic acid | A |
| 24 | 2-Chloro-N-(5-(2-(2-(((1r,4r)-4-(dimethylamino)cyclohexyl)amino)pyrimidin-5-yl)ethyl)-3-fluoro-6-methylpyridin-2-yl)benzenesulfonamide | NT |
| 25 | 2-chloro-N-(5-((E)-2-(2-(((1r,4r)-4-(dimethylamino)cyclohexyl)amino)pyrimidin-5-yl)vinyl)-3-fluoro-6-methylpyridin-2-yl)benzenesulfonamide | B |
| 26 | 2-chloro-N-(4-((E)-2-(2-(((1r,4r)-4-(dimethylamino)cyclohexyl)amino)pyrimidin-5-yl)vinyl)-3-methylphenyl)benzenesulfonamide | A |
| 27 | 2-chloro-N-(4-((E)-2-(2-(((1r,4r)-4-(dimethylamino)cyclohexyl)amino)pyrimidin-5-yl)vinyl)-3-fluoro-5-methylphenyl)benzenesulfonamide | A |
| 28 | 2-chloro-N-(4-((E)-2-(2-(((1r,4r)-4-(dimethylamino)cyclohexyl)amino)pyrimidin-5-yl)vinyl)-2-fluoro-5-methylphenyl)benzenesulfonamide | A |
| 29 | 2-chloro-N-(5-((E)-2-(2-(((1r,4r)-4-(dimethylamino)cyclohexyl)amino)pyrimidin-5-yl)vinyl)-6-ethylpyridin-2-yl)benzenesulfonamide | A |

TABLE 4-continued

| Compound No. | Compound Name | Mean EC$_{50}$ |
|---|---|---|
| 30 | 2-chloro-N-(5-((E)-2-(2-(((1r,4r)-4-(diethylamino)cyclohexyl)amino)pyrimidin-5-yl)vinyl)-6-methylpyridin-2-yl)benzenesulfonamide | A |
| 31 | 2-chloro-N-(5-((E)-2-(2-(((1r,4r)-4-(dimethylamino)cyclohexyl)amino)pyrimidin-5-yl)vinyl)-6-methylpyridin-2-yl)-4-fluorobenzenesulfonamide | A |
| 32 | 2-chloro-N-(5-((E)-2-(2-(((1r,4r)-4-(dimethylamino)cyclohexyl)amino)pyrimidin-5-yl)vinyl)-6-methoxypyridin-2-yl)-4-fluorobenzenesulfonamide | A |
| 33 | 2-chloro-N-(5-((E)-2-(2-(((1r,4r)-4-(dimethylamino)cyclohexyl)amino)pyrimidin-5-yl)vinyl)-6-methylpyridin-2-yl)-3-fluorobenzenesulfonamide | A |
| 34 | 2-chloro-N-(4-((E)-2-(2-(((1r,4r)-4-(dimethylamino)cyclohexyl)amino)pyrimidin-5-yl)vinyl)phenyl)benzenesulfonamide | A |
| 35 | 2-chloro-N-(4-((E)-2-(2-(((1r,4r)-4-(dimethylamino)cyclohexyl)amino)pyrimidin-5-yl)vinyl)-2-fluorophenyl)benzenesulfonamide | B |
| 36 | 2-chloro-N-(5-((E)-2-(2-(((1r,4r)-4-(dimethylamino)cyclohexyl)amino)pyrimidin-5-yl)vinyl)pyridin-2-yl)benzenesulfonamide | A |
| 37 | 2-chloro-N-(5-((E)-2-(2-(((1r,4r)-4-(dimethylamino)cyclohexyl)amino)pyrimidin-5-yl)vinyl)pyrazin-2-yl)benzenesulfonamide | B |
| 38 | 2-chloro-N-(5-((E)-2-(2-(((1r,4r)-4-(dimethylamino)cyclohexyl)amino)pyrimidin-5-yl)vinyl)-6-methylpyridin-2-yl)-3,4-difluorobenzenesulfonamide | B |
| 39 | 2-chloro-N-(5-((E)-2-(2-(((1r,4r)-4-(dimethylamino)cyclohexyl)amino)pyrimidin-5-yl)vinyl)-6-methoxypyridin-2-yl)-3-fluorobenzenesulfonamide | A |
| 40 | 2-chloro-N-(5-(2-(2-(((1r,4r)-4-(dimethylamino)cyclohexyl)amino)pyrimidin-5-yl)vinyl)pyrimidin-2-yl)benzenesulfonamide | NT |
| 41 | 2-chloro-N-(5-((E)-2-(2-(((1r,4r)-4-(dimethylamino)cyclohexyl)amino)pyrimidin-5-yl)vinyl)-6-methoxypyridin-2-yl)-3,4-difluorobenzenesulfonamide | B |
| 42 | 4-chloro-N-(5-((E)-2-(2-(((1r,4r)-4-(dimethylamino)cyclohexyl)amino)pyrimidin-5-yl)vinyl)-6-ethylpyridin-2-yl)pyridine-3-sulfonamide | B |
| 43 | 4-chloro-N-(5-(2-(2-(((1r,4r)-4-(dimethylamino)cyclohexyl)amino)pyrimidin-5-yl)vinyl)-4-methoxypyrimidin-2-yl)pyridine-3-sulfonamide | NT |
| 44 | 2-chloro-N-(6-methyl-5-(2-(2-(((1r,4r)-4-(methylamino)cyclohexyl)amino)pyrimidin-5-yl)vinyl)pyridin-2-yl)benzenesulfonamide | B |
| 45 | N-(5-(2-(2-(((1r,4r)-4-aminocyclohexyl)amino)pyrimidin-5-yl)vinyl)-6-ethylpyridin-2-yl)-2-chlorobenzenesulfonamide | B |
| 46 | N-(5-((E)-2-(2-(((1r,4r)-4-aminocyclohexyl)amino)pyrimidin-5-yl)vinyl)-6-methylpyridin-2-yl)-2-chlorobenzenesulfonamide | B |
| 47 | 2-chloro-N-(6-ethyl-5-((E)-2-(2-(((1r,4r)-4-(methylamino)cyclohexyl)amino)pyrimidin-5-yl)vinyl)pyridin-2-yl)benzenesulfonamide | B |
| 48 | 2-chloro-N-(6-methoxy-5-((E)-2-(2-(((1r,4r)-4-(methylamino)cyclohexyl)amino)pyrimidin-5-yl)vinyl)pyridin-2-yl)benzenesulfonamide | A |
| 49 | (E)-N-(5-(2-(2-((4-aminobicyclo[2.2.2]octan-1-yl)amino)pyrimidin-5-yl)vinyl)-6-methylpyridin-2-yl)-2-chlorobenzenesulfonamide | D |
| 50 | 2-chloro-N-(5-((E)-2-(2-(((1r,4r)-4-(dimethylamino)cyclohexyl)amino)pyrimidin-5-yl)vinyl)-3-fluoro-6-methoxypyridin-2-yl)benzenesulfonamide | B |
| 51 | 2,3-dichloro-N-(5-((E)-2-(2-(((1r,4r)-4-(dimethylamino)cyclohexyl)amino)pyrimidin-5-yl)vinyl)-6-methoxypyridin-2-yl)benzenesulfonamide | A |
| 52 | 2-chloro-N-(6-((E)-2-(2-(((1r,4r)-4-(dimethylamino)cyclohexyl)amino)pyrimidin-5-yl)vinyl)pyridazin-3-yl)benzenesulfonamide | B |
| 53 | 2-chloro-N-(5-((E)-2-(2-(((1r,4r)-4-(dimethylamino)cyclohexyl)amino)pyrimidin-5-yl)vinyl)-6-methoxypyridin-2-yl)-3-fluorobenzenesulfonamide | C |
| 54 | N-(5-((E)-2-(2-(((1r,4r)-4-aminocyclohexyl)amino)pyrimidin-5-yl)vinyl)-3-fluoro-6-methoxypyridin-2-yl)-2-chlorobenzenesulfonamide | C |
| 55 | 2-chloro-N-(4-((E)-2-(2-(((1r,4r)-4-(dimethylamino)cyclohexyl)amino)pyrimidin-5-yl)vinyl)-3-methoxyphenyl)benzenesulfonamide | A |

TABLE 4-continued

| Compound No. | Compound Name | Mean EC$_{50}$ |
|---|---|---|
| 56 | 4-chloro-N-(5-((E)-2-(2-(((1r,4r)-4-(dimethylamino)cyclohexyl)amino)pyrimidin-5-yl)vinyl)-6-methoxypyridin-2-yl)pyridine-3-sulfonamide | C |
| 57 | 2-chloro-N-(6-methoxy-5-((E)-2-(2-(((1r,4r)-4-morpholinocyclohexyl)amino)pyrimidin-5-yl)vinyl)pyridin-2-yl)benzenesulfonamide | A |
| 58 | N-(5-((E)-2-(2-(((1r,4r)-4-aminocyclohexyl)amino)pyrimidin-5-yl)vinyl)-3-fluoro-6-methylpyridin-2-yl)-2-chlorobenzenesulfonamide | C |
| 59 | 2-chloro-N-(3-fluoro-6-methoxy-5-((E)-2-(2-(((1r,4r)-4-(methylamino)cyclohexyl)amino)pyrimidin-5-yl)vinyl)pyridin-2-yl)benzenesulfonamide | C |
| 60 | 2-chloro-N-(6-methoxy-5-((E)-2-(2-(((1r,4r)-4-(piperidin-1-yl)cyclohexyl)amino)pyrimidin-5-yl)vinyl)pyridin-2-yl)benzenesulfonamide | A |
| 61 | 2-chloro-N-(5-((E)-2-(2-(((1r,4r)-4-(dimethylamino)cyclohexyl)amino)pyrimidin-5-yl)vinyl)pyridin-2-yl)-4-fluorobenzenesulfonamide | A |
| 62 | 4-chloro-N-(5-((E)-2-(2-(((1r,4r)-4-(dimethylamino)cyclohexyl)amino)pyrimidin-5-yl)vinyl)-6-methylpyridin-2-yl)pyridine-3-sulfonamide | C |
| 63 | 2,3-dichloro-N-(5-((E)-2-(2-(((1r,4r)-4-(dimethylamino)cyclohexyl)amino)pyrimidin-5-yl)vinyl)pyridin-2-yl)benzenesulfonamide | A |
| 64 | 2-chloro-N-(6-methoxy-5-((E)-2-(2-(((1r,4r)-4-thiomorpholinocyclohexyl)amino)pyrimidin-5-yl)vinyl)pyridin-2-yl)benzenesulfonamide | A |
| 65 | 4-chloro-N-(4-((E)-2-(2-(((1r,4r)-4-(dimethylamino)cyclohexyl)amino)pyrimidin-5-yl)vinyl)-3-methoxyphenyl)pyridine-3-sulfonamide | A |
| 66 | 2-chloro-N-(4-((E)-2-(2-(((1r,4r)-4-(dimethylamino)cyclohexyl)amino)pyrimidin-5-yl)vinyl)-2-fluoro-3-methoxyphenyl)benzenesulfonamide | A |
| 67 | 2-chloro-N-(4-((E)-2-(2-(((1r,4r)-4-(dimethylamino)cyclohexyl)amino)pyrimidin-5-yl)vinyl)-2-fluoro-5-methoxyphenyl)benzenesulfonamide | A |
| 68 | 2-chloro-N-(5-((E)-2-(2-(((1r,4r)-4-(dimethylamino)cyclohexyl)amino)pyrimidin-5-yl)vinyl)pyridin-2-yl)-3-fluorobenzenesulfonamide | A |
| 69 | 2-chloro-N-(4-(2-(2-(((1r,4r)-4-(dimethylamino)cyclohexyl)amino)pyrimidin-5-yl)ethyl)-2-fluoro-5-methoxyphenyl)benzenesulfonamide | NT |
| 70 | N-(5-((E)-2-(2-(((1r,4r)-4-(dimethylamino)cyclohexyl)amino)pyrimidin-5-yl)vinyl)pyridin-2-yl)-4-methylpyridine-3-sulfonamide | NT |
| 71 | 2-chloro-N-(6-methyl-5-((E)-2-(2-(((1r,4r)-4-thiomorpholinocyclohexyl)amino)pyrimidin-5-yl)vinyl)pyridin-2-yl)benzenesulfonamide | NT |
| 72 | 2-chloro-N-(5-((E)-2-(2-(((1r,4r)-4-morpholinocyclohexyl)amino)pyrimidin-5-yl)vinyl)pyridin-2-yl)benzenesulfonamide | NT |

Note:
Biochemical assay Mean EC$_{50}$ data are designated within the following ranges: A: ≤5 nM; B: >5 nM to ≤50 nM; C: >50 nM to ≤100 nM; and D: >100 nM to ≤10 uM; NT: not tested.

Example 3: qPCR Assay

Figure 3A:
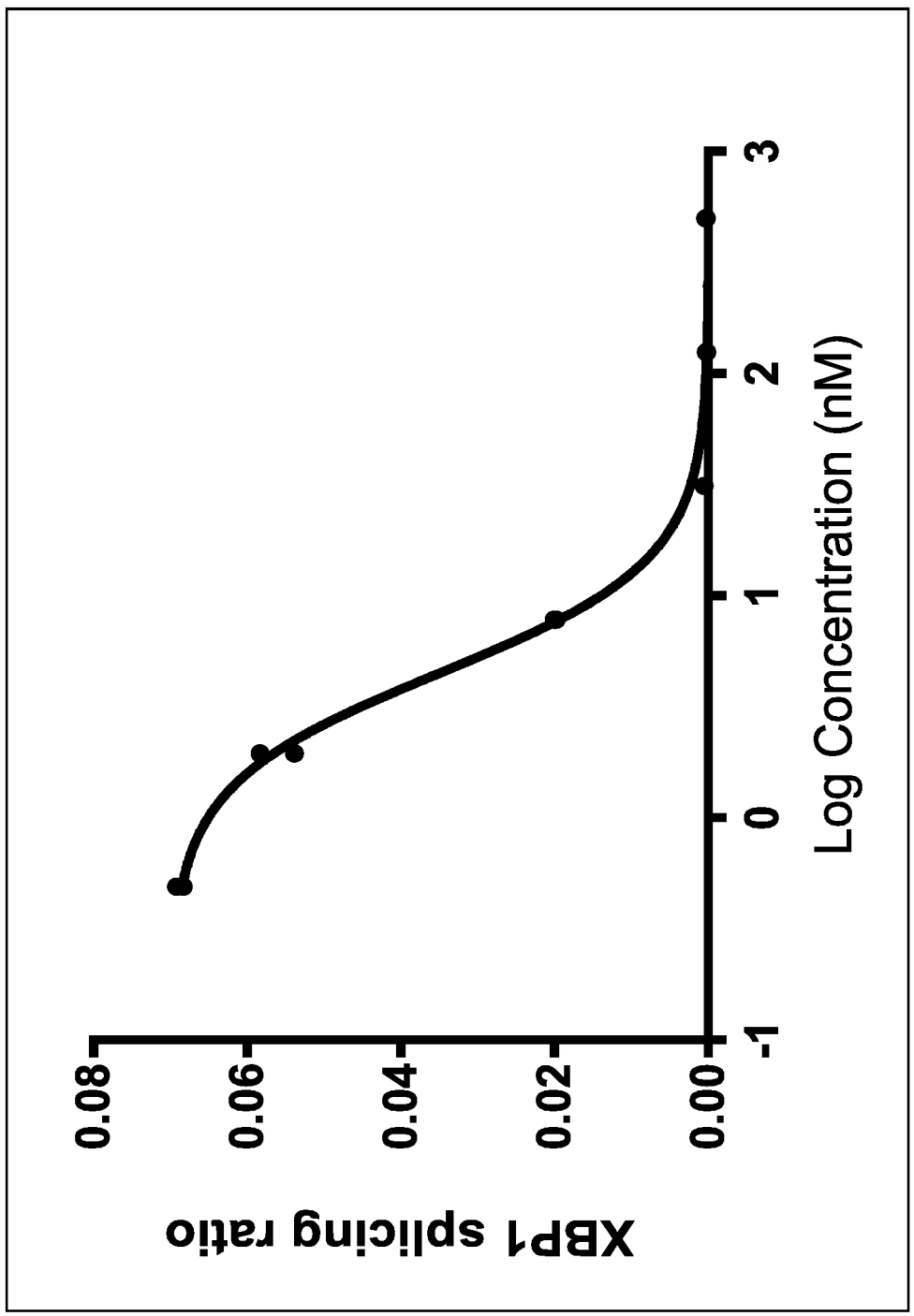
FIG. 3A depicts a plot from a quantitative PCR splicing assay of a XBP1 splicing event occurrence in 293T cells treated with compound 17.
Figure 3B:
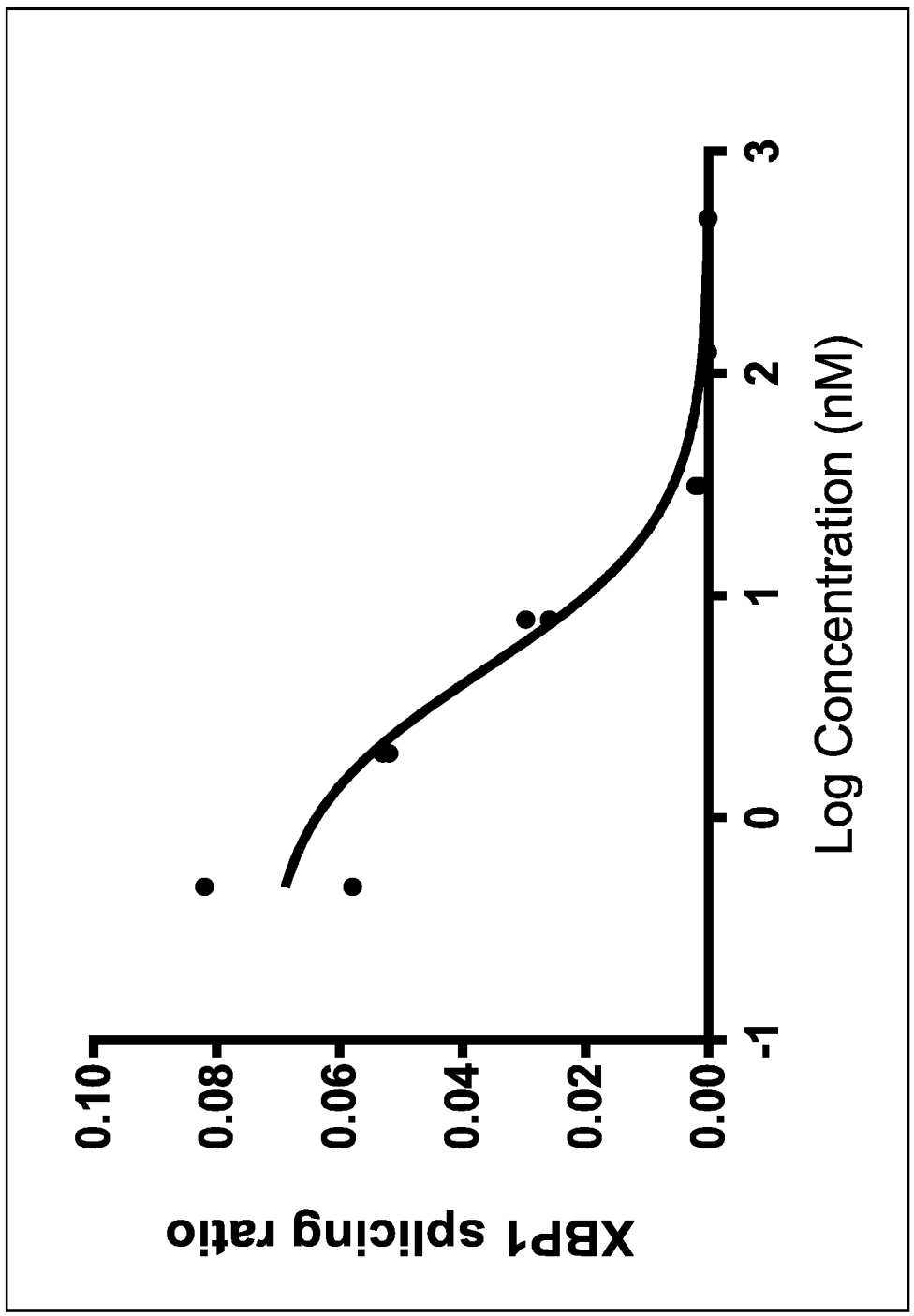
FIG. 3B depicts a plot from a quantitative PCR splicing assay of a XBP1 splicing event occurrence in 293T cells treated with compound 23.

A quantitative PCR (qPCR) assay was performed to evaluate the ability of compound 17 and compound 23 to inhibit IRE1. To perform the qPCR assay, 50,000 293T cells were plated in each well of a flat-bottomed 96 well plates in duplicate. Test compounds or DMSO control were diluted to 4× their final concentration and 50 microliters were added to the cells. Compounds were incubated for 1 hour, then 50 microliters of 4× concentrated tunicamycin (8 ug/mL) were added to the cells to induce ER stress. ER stress was allowed to accumulate for 6 hours, after which the supernatant was removed and the cells were lysed with 150 uL of RLT lysis buffer (Qiagen). Samples were frozen at −80 degrees Celsius until RNA was isolated with the RNeasy 96 kit (Qiagen) according to the manufacturer's recommended protocol. The samples were used for subsequent RT-qPCR analysis of beta-actin, XBP1s, total XBP1 and SEC24D. Gene expression was evaluated by quantitative PCR for XBP1s, total XBP1 and SEC24D transcripts using the $2^{(-\Delta CT)}$ method for calculating normalized gene expression. Gene expression levels were normalized to ACTB transcripts. XBP1 splicing is calculated as XBP1s expression divided by total XBP1 expression. IC$_{50}$ is 4.95 nM for compound 17 and 4.39 nM for compound 23. See FIG. 3A (Compound 17) and FIG. 3B (Compound 23).

Example 4: Growth Assay

A growth assay is performed to evaluate the compounds disclosed in Table 1 for cytotoxicity. Briefly, 5,000,000 293T cells are resuspended in 18 mL of cDMEM for a final concentration of 277,777 cells/mL. 180 μL (50,000 cells) cDMEM was seeded per well in 96 well flat bottom plate, with some wells left unfilled. In a 96 well plate, 199 L cDMEM and 1 uL of any one of the compounds disclosed herein. 133.3 uL cDMEM is added to wells 1, 2, 3, 5, 6, 7, 9, 10, and 11 of row A. Wells are serially diluted with 66.7 uL (highest concentration on right, lowest on left) to the total concentrations shown below. 20 uL of each dilution is transferred in duplicate to the cells plated in the 96-well plate. The plate is then placed in a humidified chamber for a 2 day incubation, and then photographed (media is more yellow in wells with potent cell growth). Absorbance is then measured at ~535 nM (lower for more acidic media) and ~450 nM (higher for more acidic media).

The vast majority of compounds tested had percentage growth at 5 uM greater than 75% (compounds 1, 2, 3, 8, 10, 17, 19, 22, 23, 24, 25, 28-39, 41, 45, 47, 810, and 81-49). Compound 27 had percentage growth at 5 uM greater than 50% and compound 3, 14 and 26 had percentage growth at 5 uM greater than 35%.

Example 5: Microsome Stability Assay

The formic acid salt of a compound from Table 1 is tested under the microsome stability assay outlined below. Test compounds are incubated at 37° C. with liver microsomes (pooled from multiple donors) at 1 μM in the presence of a NADPH regenerating system at 0.5 mg/ml microsomal protein. Positive controls included Testosterone (3A4 substrate), Propafenone (2D6) and Diclofenac (2C9), which are incubated with microsomes in the presence of an NADPH regenerating system. At time points (0, 5, 10, 20, 30 and 60 minutes), samples are removed and immediately mixed with cold acetonitrile containing internal standard (IS). Test compounds incubated with microsomes without the NADPH regenerating system for 60 min is also included. A single point for each test condition (n=1) is obtained, and samples are analyzed by LC/MS/MS. Disappearance of the test compound is assessed based on peak area ratios of analyte/IS (no standard curve). A number of compounds showed good stability in human and mouse liver microsomes with a T½ of over 2 hrs and low microsome clearance. Select compounds had 50% or more of parent compound remaining after a 60 minute incubation.

Example 6: Suppression of XBP1 Splicing

Mice are injected with 0.25 mg/kg tunicamycin dissolved in DMSO:PBS at a ratio of 1:3. After 2 hours, the mice are injected with 10 mg/kg of an IRE1α inhibitor compound from Table 1 dissolved in water or water alone as a vehicle control. After an additional 4 hours, the animals are euthanized, livers dissected out, and 2-3 mm$^3$ liver pieces are flash frozen on dry ice. Liver pieces are then thawed in Trizol on ice, homogenized for 3 minutes with a bead mill at medium-high speed. RNA is then extracted from the Trizol solution according to the manufacturer's recommendation. Gene expression analysis is also performed via Reverse Transcription quantitative PCR (RT-qPCR) using a Stratagene Mx3005 instrument and SYBR green I (Life Technologies). Gene expression is measured of the spliced Xbp1s transcript, a primer set measuring all Xbp1 transcripts, Xbp1s target genes including Sec24d and general ER stress response markers Hspa5 (BiP) and Ddit3 (CHOP).

TABLE 5

| Species | Gene | Oligo name | Sequence 5'-3' | SEQ ID NO | Purpose |
|---|---|---|---|---|---|
| Mouse | Xbp1 | Xbp1-SA-F | ACACGTTTGGGAATGGACAC | 8 | Splicing Assay |
|  |  | Xbp1-SA-F | CCATGGGAAGATGTTCTGGG | 9 |  |
| Mouse | Actb | actb1083 | CTCAGGAGGAGCAATGATCTTGAT | 10 | RT-qPCR |
|  |  | actb987 | TACCACCATGTACCCAGGCA | 11 |  |
| Mouse | Xbp1 | Xbp1.total-F | GACAGAGAGTCAAACTAACGTGG | 12 | RT-qPCR |
|  |  | Xbp1.total-R | GTCCAGCAGGCAAGAAGGT | 13 |  |
| Mouse | Xbp1s | XBPsA406F | AAGAACACGCTTGGGAATGG | 14 | RT-qPCR |
|  |  | XBPsAa518R | CTGCACCTGCTGCGGAC | 15 |  |
| Mouse | Xbp1 (exon 2) | XBP1WT205-F | CCTGAGCCCGGAGGAGAA | 16 | RT-qPCR |
|  |  | XBP1WT272-R | CTCGAGCAGTCTGCGCTG | 17 |  |
| Mouse | Dnajb9/Erdj4 | ERdj4-F | TAAAAGCCCTGATGCTGAAGC | 18 | RT-qPCR |
|  |  | ERdj4-R | TCCGACTATTGGCATCCGA | 19 |  |
| Mouse | Sec61a1 | Sec61a1-F | CTATTTCCAGGGCTTCCGAGT | 20 | RT-qPCR |
|  |  | Sec61a1-R | AGGTGTTGTACTGGCCTCGGT | 21 |  |
| Mouse | Edem1 | EDEM-F | AAGCCCTCTGGAACTTGCG | 22 | RT-qPCR |
|  |  | EDEM-R | AACCCAATGGCCTGTCTGG | 23 |  |
| Mouse | Hspa5/BiP | Grp78-F | TCATCGGACGCACTTGGAA | 24 | RT-qPCR |
|  |  | Grp78-R | CAACCACCTTGAATGGCAAGA | 25 |  |
| Mouse | Ddit3/CHOP | CHOP-F | GTCCCTAGCTTGGCTGACAGA | 26 | RT-qPCR |
|  |  | CHOP-R | TGGAGAGCGAGGGCTTTG | 27 |  |
| Mouse | Agpat6 | Agpat6-F | AGCTTGATTGTCAACCTCCTG | 28 | RT-qPCR |

Protein analysis of XBP1S is performed by Western blot or intracellular flow cytometric analysis of sDCs and T cells from naïve mice, sDCs and T cells from parental ID8 mice and ID8-Defb29/Vegf-A mice, and tDCs, tumor cells and tumor-infiltrating T cells from parental ID8 mice and ID8-Defb29/Vegf-A mice administered either vehicle or a compound from Table 1. Briefly, for Western blotting 5×10$^6$ sDCs, tumor cells, T cells, or tDCs are washed twice in 1× cold PBS and nuclear proteins are purified using the Nuclear Extraction Kit (Life Technologies). Proteins are quantified using the BCA method (Pierce) and 15-20 pg of nuclear proteins are separated via SDS-PAGE and are transferred onto nitrocellulose membranes. Anti-mouse XBP1s (GL Biochem) is raised in rabbit using a peptide corresponding to the XBP1s C-terminus, and is used at a 1:500 dilution for immunoblotting. Goat anti-mouse Lamin B (Santa Cruz) is used at 1:2000. HRP-conjugated secondary antibodies to rabbit and mouse (Santa Cruz) are used at a 1:2000 dilution. SuperSignal West Femto (Pierce) is used as Chemiluminescent Substrate and blots are imaged using a FluorChemE instrument (ProteinSimple). For intracellular flow cytometry of XBP1s protein, 1-2 million splenocytes or dissociated cells from solid tumors or ascites are washed in cold PBS and stained with the Ghost Dye 510 fixable viability dye diluted 1:1000 in PBS for 30 minutes on ice. The staining reaction is quenched with 2 mL of FACS buffer (PBS with 2% fetal bovine serum and 1 mM EDTA), cells pelleted by centrifugation at 300×g for 5 minutes, and then surface stained with antibodies directed at key lineage defining markers such as CD45/CD3/CD4/CD8 (for T cells) or CD45/CD11c/MHC-II (for DCs) for 30 minutes in FACS buffer on ice. Cells are washed twice with FACS buffer and then fixed and permeabilized for 30 minutes with the eBioscience FoxP3 nuclear staining kit according to the manufacturer's protocol. Cells are washed twice with 1× permeabilization buffer, then Fc receptors are blocked with Truestain FcX anti-mouse CD16/32 (Biolegend) for 15 minutes at room temperature. Finally, 5 microliters of XBP1s antibody (clone Q3-695) or an equivalent amount of isotype control antibody are added directly to cells and stained for 30 minutes at room temperature protected from light. Cells are washed twice with 1× permeabilization buffer and resuspended in FACS buffer, then analyzed on a flow cytometer such as the BD LSRII.

Example 7: IC$_{50}$ Measurements for hERG Potassium Ion Channel

Blockade of the cardiac ion channel coded by the hERG gene can lead to cardiac arrhythmia. Many small compounds have been found to bind to the hERG gene leading to problems in the QT response. To determine the viability of the compounds disclosed herein as pharmacological agents that would not affect the hERG channel blockade, a standard automated planar clamp method is employed to determine the IC$_{50}$ for various test compounds on their inhibition of the channel. An electrophysiological assay is prepared to measure the electric current passing through the hERG channel expressed in a stable CHO cell line by applying the planar clamp method. This assay is performed using the automated QPatch platform (Sophion, Denmark) which allows fast and accurate electrophysiological characterization of the hERG ion channel and the determination of IC$_{50}$ values for the compounds from Table 1. This assay was performed on select compounds and they did not inhibit hERG when tested in concentrations up to 30 uM.

Example 8: Pharmacokinetic Studies

Compounds are tested in a pharmacokinetic ("PK") study to determine the half-life (T$_{1/2}$) in mice. A compound from Table 1 is dissolved in a vehicle to make a test antibiotic composition. The vehicle might be, for example, a water or a 25% PEG400 in saline solution Administration to each mouse is performed via intravenous (IV) cannulation of the tail vein. Blood is collected over K2-EDTA anticoagulant from the submandibular or saphenous vein at predetermined time points. Following collection, the blood samples are stored at −70° C. until analysis by LC-MS and comparison to a standard calibration curve results in the T$_{1/2}$ for each compound. Compounds tested had a IV T½ of 2-4 hours and showed a measured oral bioavailability of 7-90%.

Alternatively, on study day, the animals (fasted) usually receive a compound from Table 1 (typically 10 or 30 mg/kg) by IP injection (typically 10 mL/kg). The IP dose is typically delivered via a bolus into the IP space for mice. All dosages are expressed as target dose in mg free base/acid equivalent/kg; actual doses are calculated for each individual animal and are recorded. The plasma samples are then collected as above and plasma levels determined.

Example 9: Protein Binding—Plasma Protein Binding Assay—HTD Method

The plasma protein binding is determined according to the following steps. Frozen plasma or freshly prepared plasma from various subjects are used as test matrix. They are purchased from commercial vendors or prepared in house from animals. Warfarin is used as a positive control. Other control compound(s) may be used according to specific requirement. One or more compounds from Table 1 are spiked into blank matrix at the final concentration of 2 μM (or other test concentrations based on specific requirement). Final organic solvent concentration is ≤1%. If plasma samples are collected from in-life studies, they are used as test matrix without spiking compounds. An appropriate volume of spiked plasma solution is removed before incubation for recovery calculation. An aliquot (e.g., 150 μL) of matrix sample is added to one side of the chamber (donor chamber) in a 96-well equilibrium dialyzer plate (HTD dialysis device) and an equal volume of dialysis buffer is added to the other side of the chamber (receiver chamber). Triplicate incubations are performed (or other replicate number according to specific requirement). The dialyzer plate is placed into a humidified incubator with 5% CO$_2$ and incubated at 37° C. for 4 to 6 hours. After incubation, samples are taken from the donor chamber as well as the receiver chamber. The plasma sample is matched with an appropriate volume of blank buffer; and buffer samples are matched with an appropriate volume of blank plasma. The matrix-matched samples are quenched with stop solution containing internal standard. Samples are analyzed by LC/MS/MS. Test compound concentrations in donor and receiver samples are expressed as peak area ratios of analyte/internal standard. If a quantitative analysis is needed, a set of calibration curve and quality controls could be included. Compounds tested had moderate to high human plasma protein binding of 90-98%.

Example 10: Kinase Panel Selectivity

Several compounds were sent to Reaction Biology Corp. for profiling in their wild type kinase profiling panel of 369 kinases. The compounds showed good selectivity for IRE1 vs other kinases. Compounds were evaluated for the percentage of kinases inhibited greater than 50% when tested at 1 uM. The tested compounds inhibited about 4-14% of the panel when using this criteria and demonstrated the greatest amount of inhibition for IRE1.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

SEQ ID NO: 1
MPARRLLLLLTLLLPGLGIFGSTSTVTLPETLLFVSTLDGSLHAVSKRTGS
IKWTLKEDPVLQVPTHVEEPAFLPDPNDGSLYTLGSKNNEGLTKLPFTIPE
LVQASPCRSSDGILYMGKKQDIWYVIDLLTGEKQQTLSSAFADSLCPSTSL
LYLGRTEYTITMYDTKTRELRWNATYFDYAASLPEDDVDYKMSHFVSNGDG
LVVTVDSESGDVLWIQNYASPVVAFYVWQREGLRKVMHINVAVETLRYLTF
MSGEVGRITKWKYPFPKETEAKSKLTPTLYVGKYSTSLYASPSMVHEGVAV
VPRGSTLPLLEGPQTDGVTIGDKGECVITPSTDVKFDPGLKSKNKLNYLRN
YWLLIGHHETPLSASTKMLERFPNNLPKHRENVIPADSEKKSFEEVINLVD
QTSENAPTTVSRDVEEKPAHAPARPEAPVDSMLKDMATIILSTFLLIGWVA
FIITYPLSMHQQQQLQHQQFQKELEKIQLLQQQQQQLPFHPPGDTAQDGEL
LDTSGPYSESSGTSSPSTSPRASNHSLCSGSSASKAGSSPSLEQDDGDEET
SVVIVGKISFCPKDVLGHGAEGTIVYRGMFDNRDVAVKRILPECFSFADRE
VQLLRESDEHPNVIRYFCTEKDRQFQYIAIELCAATLQEYVEQKDFAHLGL
EPITLLQQTTSGLAHLHSLNIVHRDLKPHNILISMPNAHGKIKAMISDFGL
CKKLAVGRHSFSRRSGVPGTEGWIAPEMLSEDCKENPTYTVDIFSAGCVFY
YVISEGSHPFGKSLQRQANILLGACSLDCLHPEKHEDVIARELIEKMIAMD
PQKRPSAKHVLKHPFFWSLEKQLQFFQDVSDRIEKESLDGPIVKQLERGGR
AVVKMDWRENITVPLQTDLRKFRTYKGGSVRDLLRAMRNKKHHYRELPAEV
RETLGSLPDDFVCYFTSRFPHLLAHTYRAMELCSHERLFQPYYFHEPPEPQ
PPVTPDAL

SEQ ID NO: 2
CAUGUCCGCAGCACAUG

SEQ ID NO: 3
CAUGUCCCCAGCACAUG

---

What is claimed is:

1. A compound of Formula (I), or a pharmaceutically acceptable salt, or solvate thereof:

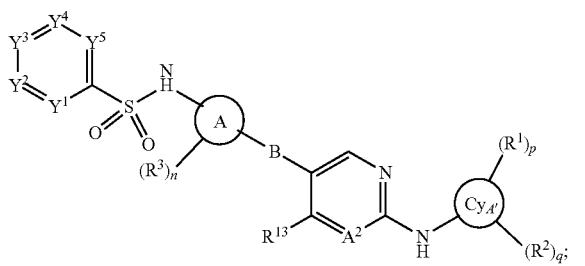

Formula (I)

wherein

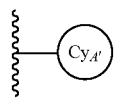

is $C_3$-$C_{10}$cycloalkyl;

each R1 is independently —$OR^{6a}$, —$SR^{6a}$, —S(=O)$R^7$, —S(=O)$_2R^7$, or —N($R^{6b}$)$_2$;

each $R^2$ is independently halogen, —CN, —$OR^{8a}$, —$SR^{8a}$, —S(=O)$R^9$, —S(=O)$_2R^9$, —S(=O)$_2$N($R^{8b}$)$_2$, —$NR^{8a}$S(=O)$_2R^9$, —C(=O)$R^9$, —OC(=O)$R^9$, —CO$_2R^{8a}$, —OCO$_2R^9$, —N($R^{8b}$)$_2$, —OC(=O)N($R^{8b}$)$_2$, —$NR^{8a}$C(=O)$R^9$, —$NR^{8a}$C(=O)OR$^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$Y^5$ is $CR^4$;

$Y^1$, $Y^2$, $Y^3$, and $Y^4$ are each independently selected from N and $CR^5$ with the proviso that no more than two of $Y^1$, $Y^2$, $Y^3$, and $Y^4$ are N;

each $R^{6a}$ is independently H, optionally substituted $C_1$-$C_4$alkyl, optionally substituted $C_1$-$C_4$heteroalkyl, optionally substituted $C_1$-$C_4$fluoroalkyl, —X-optionally substituted $C_1$-$C_4$alkyl, —X-optionally substituted $C_1$-$C_4$heteroalkyl, —X-optionally substituted $C_1$-$C_4$fluoroalkyl, optionally substituted $C_3$-$C_6$cycloalkyl, optionally substituted $C_3$-$C_4$cycloalkyl$C_1$-$C_3$alkyl, optionally substituted $C_2$-$C_{10}$heterocycloalkyl, optionally substituted aryl, or optionally substituted heteroaryl;

each $R^{6b}$ is independently H, optionally substituted $C_1$-$C_4$alkyl, optionally substituted $C_1$-$C_4$heteroalkyl, optionally substituted $C_1$-$C_4$fluoroalkyl, —X-optionally substituted $C_1$-$C_4$alkyl, —X-optionally substituted $C_1$-$C_4$heteroalkyl, —X-optionally substituted $C_1$-$C_4$fluoroalkyl, optionally substituted $C_3$-$C_6$cycloalkyl, optionally substituted $C_3$-$C_4$cycloalkyl$C_1$-$C_3$alkyl, optionally substituted $C_2$-$C_{10}$heterocycloalkyl, optionally substituted aryl, or optionally substituted heteroaryl;

or two $R^{6b}$ are taken together with the N atom to which they are attached to form an optionally substituted heterocycle;

X is —C(=O)—;

each $R^7$ is independently optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

each $R^{8a}$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

each $R^{8b}$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

or two $R^{8b}$ are taken together with the N atom to which they are attached to form an optionally substituted heterocycle;

each $R^9$ is independently optionally substituted $C_1$-$C_4$alkyl, optionally substituted $C_1$-$C_4$heteroalkyl, or optionally substituted $C_1$-$C_4$fluoroalkyl, optionally substituted $C_1$-$C_4$cycloalkyl, optionally substituted $C_2$-$C_{10}$heterocycloalkyl, optionally substituted aryl, or optionally substituted heteroaryl;

$A^2$ is N or $CR^A$;

$R^A$ is H, halogen, optionally substituted $C_1$-$C_4$alkyl, optionally substituted $C_1$-$C_4$fluoroalkyl, optionally substituted aryl, or —$OR^{10}$;

$R^{A1}$, $R^{A2}$, $R^{A3}$ and $R^{A4}$ are each independently H, optionally substituted $C_1$-$C_4$alkyl, optionally substituted $C_1$-$C_4$fluoroalkyl, or optionally substituted aryl;

$R^{10}$ is independently H, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

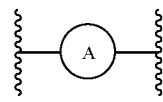

is phenylene or a 6-membered heteroarylene ring comprising 1 or 2 nitrogen atoms in the ring;

B is

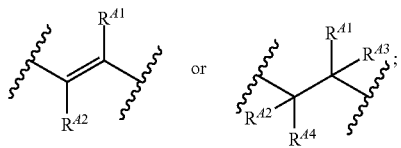

each $R^3$ is independently halogen, —CN, —$OR^{11}$, —$SR^{11}$, —$N(R^{11})_2$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

each $R^{11}$ is independently H, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

n is 0, 1, 2, 3, or 4;

p is 1, 2, or 3;

q is 0, 1, 2, or 3;

$R^4$ and each $R^5$ are each independently H, halogen, —CN, —$OR^{12}$, —$SR^{12}$, —$N(R^{12})_2$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$ heterocycloalkyl, optionally substituted aryl, or optionally substituted heteroaryl; and $R^{12}$ is independently H, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl.

2. The compound of claim 1, or a pharmaceutically acceptable salt, or solvate thereof, wherein $R^{A1}$ is H.

3. The compound of claim 1, or a pharmaceutically acceptable salt, or solvate thereof, wherein $R^{A2}$ is Ff.

4. The compound of claim 1, or a pharmaceutically acceptable salt, or solvate thereof, wherein each $R^1$ is —$N(R^{6b})_2$.

5. The compound of claim 1, or a pharmaceutically acceptable salt, or solvate thereof, wherein

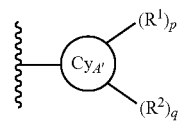

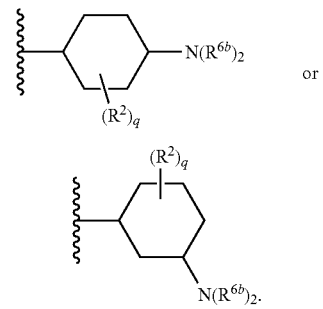

6. The compound of claim 1, or a pharmaceutically acceptable salt, or solvate thereof, wherein each $R^{6b}$ is independently H or optionally substituted —$C_1$-$C_3$alkyl.

7. The compound of claim 1, or a pharmaceutically acceptable salt, or solvate thereof, wherein two $R^{6b}$ are taken together with the N atom to which they are attached to form an optionally substituted heterocycle.

8. The compound of <s> any one of </s> claim 1, or a pharmaceutically acceptable salt, or solvate thereof, wherein q is 0.

9. The compound of claim 1, or a pharmaceutically acceptable salt, or solvate thereof, wherein $A^2$ is N.

10. The compound of claim 1, or a pharmaceutically acceptable salt, or solvate thereof, wherein $A^2$ is $CR^A$, and $R^A$ is H.

11. The compound of claim 1, or a pharmaceutically acceptable salt, or solvate thereof, wherein:

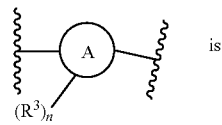 is

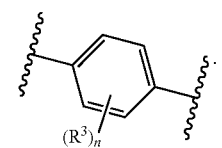

12. The compound of claim 1, or a pharmaceutically acceptable salt, or solvate thereof, wherein:

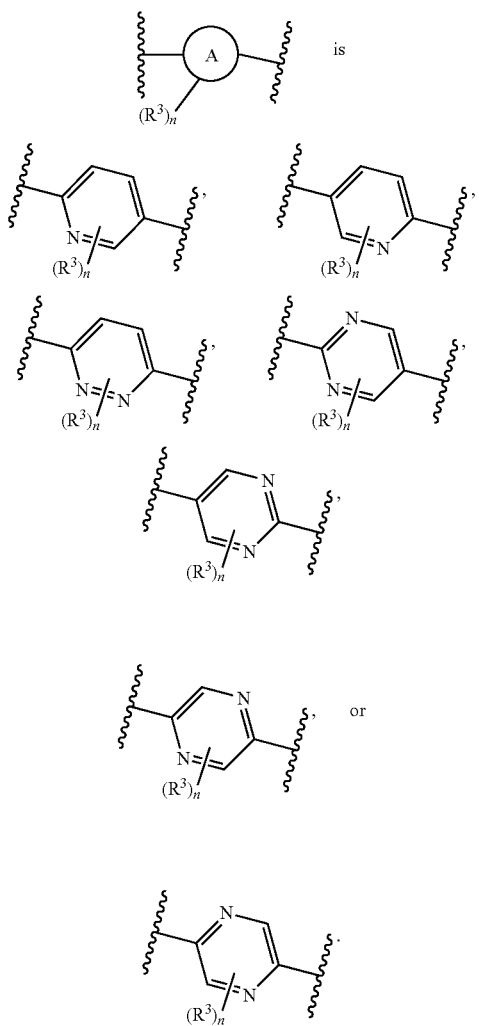

13. The compound of claim 1, or a pharmaceutically acceptable salt, or solvate thereof, wherein n is 1.

14. The compound of claim 1, or a pharmaceutically acceptable salt, or solvate thereof, wherein each $R^3$ is independently —$OR^{11}$, optionally substituted $C_1$-$C_4$alkyl, or optionally substituted $C_1$-$C_4$fluoroalkyl; and $R^{11}$ is methyl, ethyl, propyl, or butyl.

15. The compound of claim 1, or a pharmaceutically acceptable salt, or solvate thereof, wherein $R^4$ is halogen, or optionally substituted $C_1$-$C_4$alkyl.

16. The compound of claim 1, or a pharmaceutically acceptable salt, or solvate thereof, wherein each $R^5$ is independently H, halogen, or optionally substituted $C_1$-$C_4$alkyl.

17. The compound of claim 1, or a pharmaceutically acceptable salt, or solvate thereof, wherein one of $Y^1$, $Y^2$, $Y^3$, and $Y^4$ is N.

18. The compound of claim 1, or a pharmaceutically acceptable salt, or solvate thereof, wherein none of $Y^1$, $Y^2$, $Y^3$, and $Y^4$ is N.

19. The compound of claim 1, or a pharmaceutically acceptable salt, or solvate thereof, wherein the compound has the structure of any one of formula (Ia)-(Ip)

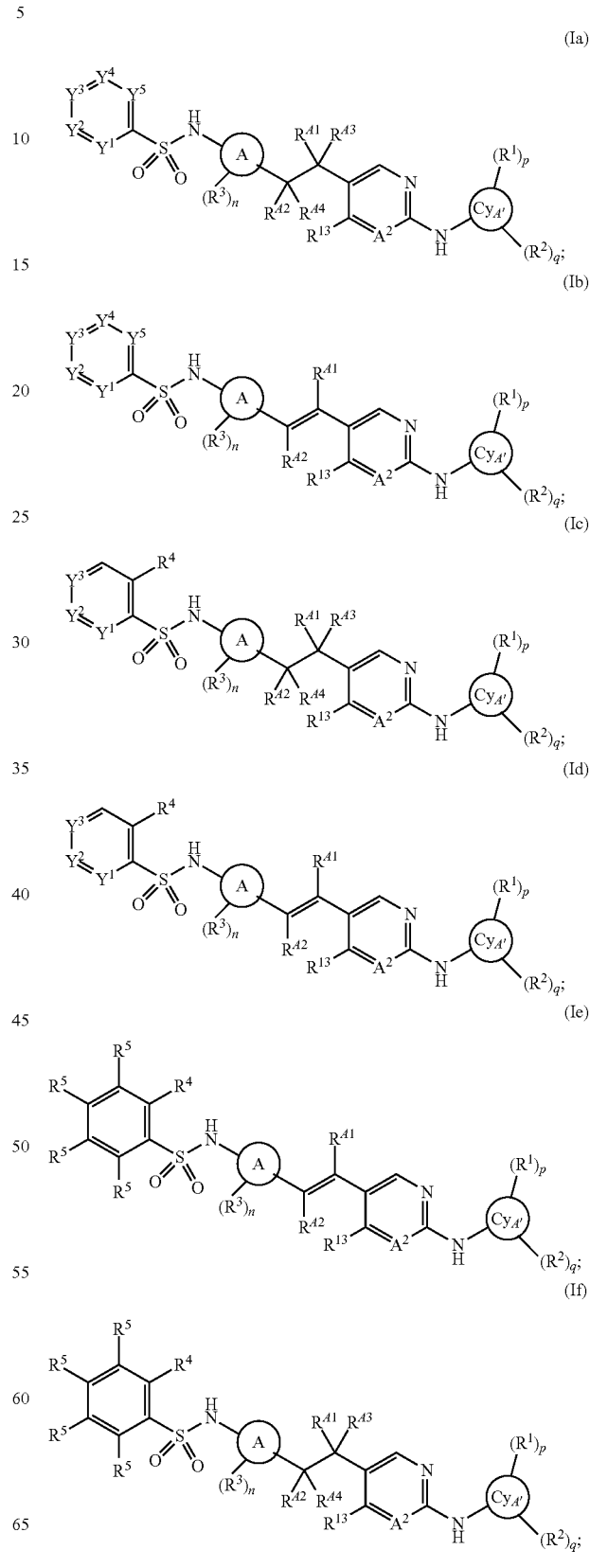

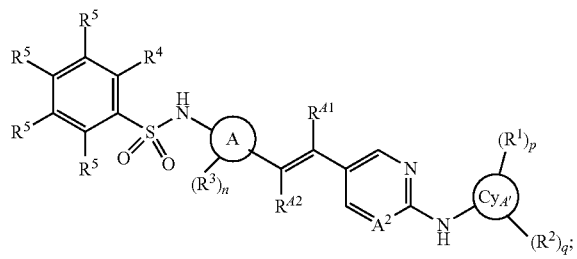
(Ig)
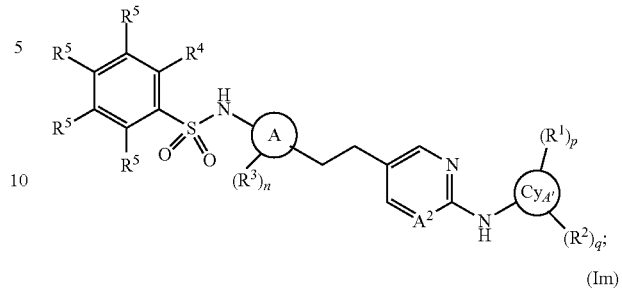
(Il)
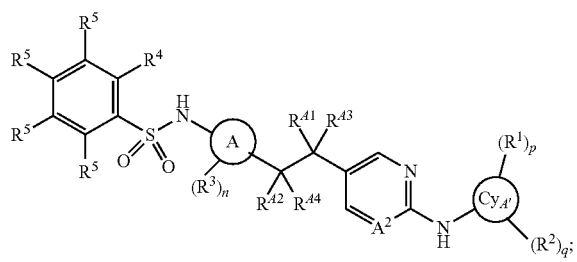
(Ih)
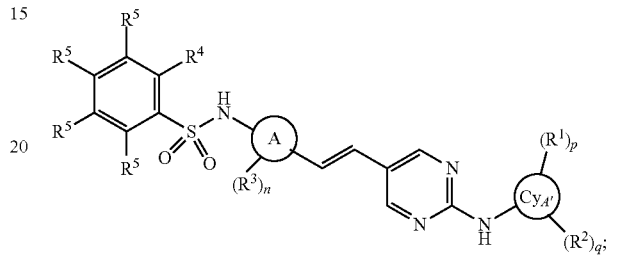
(Im)
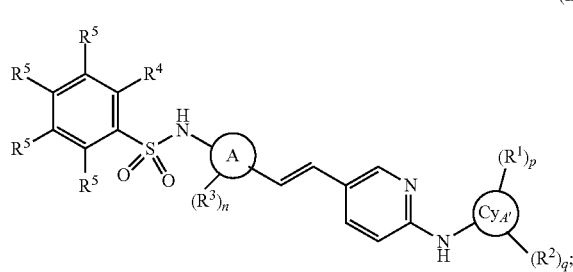
(Ii)
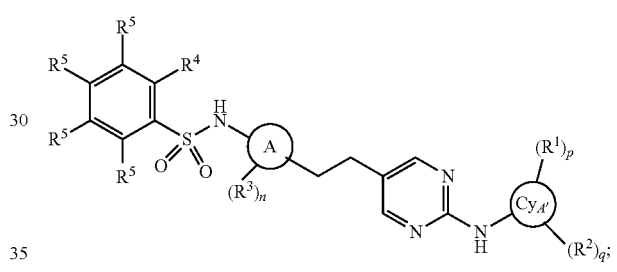
(In)
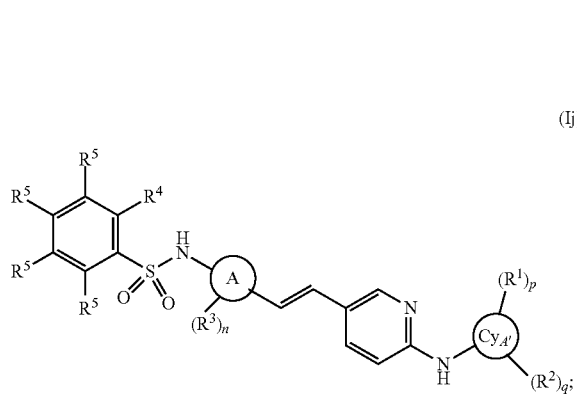
(Ij)
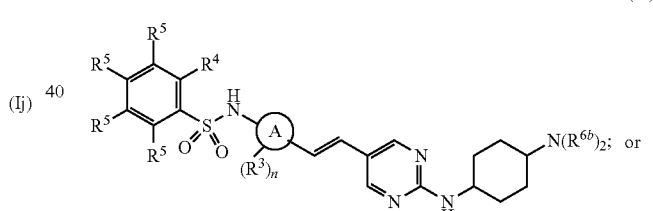
(Io)
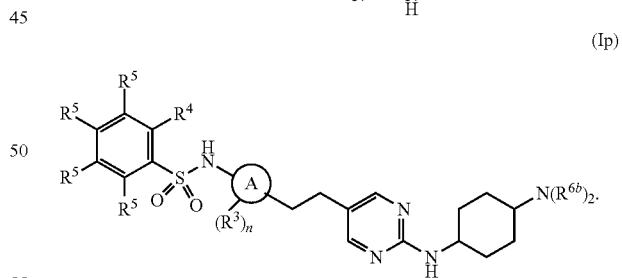
(Ip)
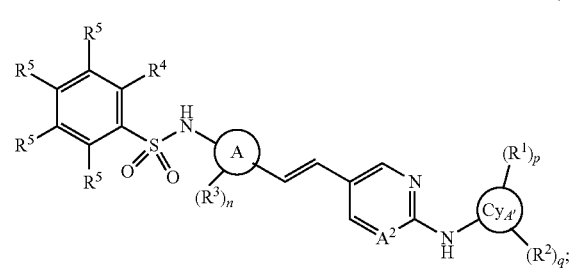
(Ik)
20. The compound of claim 19, or a pharmaceutically acceptable salt, or solvate thereof, wherein
R4 is chlorine;
each R6b is independently selected from hydrogen, —CH$_3$, or —CH$_2$CH$_3$;
each R$^5$ is independently selected from hydrogen, fluorine, or chlorine;
each R$^3$ is independently selected from —CH$_3$, —OCH$_3$, —CH$_2$CH$_3$, or fluorine;

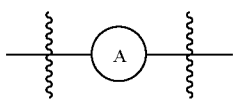

is phenylene, pyridazinyl, pyrimidinyl, pyrazinyl, or pyridinyl; and n is 0, 1, or 2.

21. A compound, or a pharmaceutically acceptable salt, or solvate thereof, wherein the compound is:

N-(4-(2-(2-(((1r,4r)-4-aminocyclohexyl)amino)pyrimidin-5-yl)ethyl)phenyl)-2-chlorobenzenesulfonamide;

N-(6-((E)-2-(2-(((1r,4r)-4-aminocyclohexyl)amino)pyrimidin-5-yl)vinyl)pyridazin-3-yl)-2-chlorobenzenesulfonamide, N-(4-((E)-2-(2-(((1r,4r)-4-aminocyclohexyl)amino)pyrimidin-5-yl)vinyl)-2-fluorophenyl)-2-chlorobenzenesulfonamide;

N-(4-((E)-2-(2-(((1r,4r)-4-aminocyclohexyl)amino)-4-propylpyrimidin-5-yl)vinyl)phenyl)-2-chlorobenzenesulfonamide;

N-(4-((E)-2-(2-(((1r,4r)-4-aminocyclohexyl)amino)pyrimidin-5-vi)vinyl)-3-methylphenyl)-2-chlorobenzenesulfonamide;

N-(4-(2-(2-(((1r,4r)-4-aminocyclohexyl)amino)pyrimidin-5-yl)ethyl)-3-methylphenyl)-2-chlorobenzenesulfonamide;

N-(6-(2-(2-(((1r,4r)-4-aminocyclohexyl)amino)pyrimidin-5-yl)ethyl)pyridazin-3-yl)-2-chlorobenzenesulfonamide;

N-(4-(2-(2-(((1r,4r)-4-aminocyclohexyl)amino)pyrimidin-5-yl)ethyl)-2-fluorophenyl)-2-chlorobenzenesulfonamide;

N-(5-((E)-2-(2-(((1r,4r)-4-aminocyclohexyl)amino)pyrimidin-5-yl)vinyl)-6-methoxypyridin-2-yl)-2-chlorobenzenesulfonamide;

N-(5-(2-(2-(((1r,4r)-4-aminocyclohexyl)amino)pyrimidin-5-yl)ethyl)-6-methoxypyridin-2-yl)-2-chlorobenzenesulfonamide;

-chloro-N-(5-((E)-2-(2-(((1r,4r)-4-hydroxycyclohexyl)amino) pyrimidin-5-yl)vinyl)-6-methoxypyridin-2-yl)benzenesulfonamide;

2-chloro-N-(5-(2-(2-(((1r,4r)-4-hydroxycyclohexyl)amino)pyrimidin-5-yl)ethyl)-6-methoxypyridin-2-yl)benzenesulfonamide;

N-(5-(2-(6-(((1r,4r)-4-aminocyclohexyl)amino)pyridin-3-yl)ethyl)-6-methoxypyridin-2-yl)-2-chlorobenzenesulfonamide;

N-(4-((E)-2-(2-(((1r,4r)-4-aminocyclohexyl)amino)pyrimidin-5-yl)vinyl)-3-methoxyphenyl)-2-chlorobenzenesulfonamide;

N-(4-(2-(2-(((1r,4r)-4-aminocyclohexyl)amino)pyrimidin-5-yl)ethyl)-3-methoxyphenyl)-2-chlorobenzenesulfonamide;

N-(6-(2-(2-(((1r,4r)-4-aminocyclohexyl)amino)pyrimidin-5-yl)ethyl)-5-ethylpyridin-3-yl)-2-chlorobenzenesulfonamide;

2-chloro-N-(5-((E)-2-(2-4(1r,4r)-4-(dimethylamino)cyclohexyl)amino)pyrimidin-5-yl)vinyl)-6-methoxypyridin-2-yl)benzenesulfonamide;

N-(6-(2-(2-(((1r,4r)-4-aminocyclohexyl)amino)pyrimidin-5-yl)ethyl)-5-methoxypyridin-3-yl)-2-chlorobenzenesulfonamide;

2-chloro-N-(5-(2-(2-4(1r,4r)-4-(dimethylamino)cyclohexyl)amino) pyrimidin-5-yl)ethyl)-6-methoxypyridin-2-yl)benzenesulfonamide;

2-chloro-N-(5-(2-(2-4(1r,4r)-4-hydroxycyclohexyl) amino)pyrimidin-5-yl)ethyl-6-methylpyridin-2-yl)benzenesulfonamide;

2-chloro-N-(5-(2-(2-(((1r,4r)-4-(dimethylamino)cyclohexyl)amino)pyrimidin-5-yl)ethyl)-6-methylpyridin-2-yl)benzenesulfonamide;

2-chloro-N-(5-((E)-2-(2-4(1r,4r)-4-(dimethylamino)cyclohexyl)amino)pyrimidin-5-yl)vinyl)-3-fluoro-6-methylpyridin-2-yl)benzenesulfonamide;

2-chloro-N-(5-((E)-2-(2-(((1r,4r)-4-(dimethylamino)cyclohexyl)amino)pyrimidin-5-yl)-vinyl)-6-methylpyridin-2-yl)benzenesulfonamide;

2-chloro-N-(5-(2-(2-4(1r,4r)-4-(dimethylamino)cyclohexyl)amino)pyrimidin-5-yl)ethyl-3-fluoro-6-methylpyridin-2-yl)benzenesulfonamide;

2-chloro-N-(5-((E)-2-(2-(((1r,4r)-4-(dimethylamino)cyclohexyl)amino)pyrimidin-5-yl)vinyl)-3-fluoro-6-methylpyridin-2-yl)benzenesulfonamide;

2-chloro-N-(4-((E)-2-(2-(((1r,4r)-4-(dimethylamino)cyclohexylamino)pyrimidin-5-yl)vinyl)-3-methylphenyl)benzenesulfonamide;

2-chloro-N-(4-((E)-2-(2-(1r,4r)-4-(dimethylamino)cyclohexyl)amino)pyrimidin-5-yl)vinyl)-3-fluoro-5-methylphenyl)benzenesulfonamide;

2-chloro-N-(4-((E)-2-(2-(((1r,4r)-4-(dimethylamino)cyclohexyl)amino)pyrimidin-5-yl)vinyl)-2-fluoro-5-methylphenyl)benzenesulfonamide;

2-chloro-N-(5-((E)-2-(2-(((1r,4r)-4-(dimethylaminocyclohexyl)amino)pyrimidin-5-yl)vinyl)-6-ethylpyridin-2-yl)benzenesulfonamide;

2-chloro-N-(5-((E)-2-(2-(((1r,4r)-4-(diethylamino)cyclohexyl)amino)pyrimidin-5-yl)vinyl)-6-methylpyridin-2-yl)benzenesulfonamide;

2-chloro-N-(5-((E)-2-(2-(((1r,4r)-4-(dimethylamino)cyclohexyl)amino)pyrimidin-5-yl)vinyl)-6-methylpyridin-2-yl)-4-fluorobenzenesulfonamide;

2-chloro-N-(5-((E)-2-(2-(((1r,4r)-4-(dimethylamino)cyclohexyl)amino)pyrimidin-5-yl)vinyl)-6-methoxypyridin-2-yl)-4-fluorobenzenesulfonamide;

2-chloro-N-(5-((E)-2-(2-(((1r,4r)-4-(dimethylamino)cyclohexyl)amino)pyrimidin-5-yl)vinyl)-6-methylpyridin-2-yl)-3-fluorobenzenesulfonamide;

2-chloro-N-(4-((E)-2-(2-(((1r,4r)-4-(dimethylamino)cyclohexyl)amino)pyrimidin-5-yl)vinyl)phenyl)benzenesulfonamide;

2-chloro-N-(4-((E)-2-(2-(((1r,4r)-4-(dimethylamino)cyclohex)amino)pyrimidin-5-yl)vinyl)-2-fluorophenyl)benzenesulfonamide;

2-chloro-N-(5-((E)-2-(2-(((1r,4r)-4-(dimethylamino)cyclohexyl)amino)pyrimidin-5-yl)vinyl)pyridin-2-yl)benzenesulfonamide;

2-chloro-N-(5-((E)-2-(2-4(1r,4r)-4-(dimethylaminohexyl)amino)pyrimidin-5-yl)vinyl)pyrazin-2-yl)benzenesulfonamide;

2-chloro-N-(5-((E)-2-(2-(((1r,4)-4-(dimethylamino)cyclohexyl)amino)pyrimidin-5-yl)-vinyl)-6-methylpyridin-2-yl)-3,4-difluorobenzenesulfonamide;

2-chloro-N-(5-((E)-2-(2-(((1r,4r)-4-(dimethylamino)cyclohexyl)amino)pyrimidin-5-yl)vinyl)-6-methoxypyridin-2-yl)-3-fluorobenzenesulfonamide;

2-chloro-N-(5-(2-(2-(((1r,4r)-4-(dimethylamino)cyclohexyl)amino)pyrimidin-5-yl)vinyl)pyrimidin-2-yl)benzenesulfonamide;

2-chloro-N-(5-((E)-2-(2-(((1r,4r)-4-(dimethylamino)cyclohexyl)amino)pyrimidin-5-yl)vinyl)-6-methoxypyridin-2-yl)-3,4-difluorobenzenesulfonamide;

4-chloro-N-(5-((E)-2-(2-(((1r,4r)-4-(dimethylamino)cyclohexyl)amino)pyrimidin-5-yl)vinyl)-6-ethylpyridin-2-yl)pyridine-3-sulfonamide;

4-chloro-N-(5-(2-(2-(((1r,4r)-4-(dimethylamino)cyclohexyl)amino)pyrimidin-5-yl)vinyl)-4-methoxypyrimidin-2-yl)pyridine-3-sulfonamide, 2-chloro-N(6-methyl-5-(2-(2-(((1r,4r)-4-(methylamino)cyclohexyl)amino)pyrimidin-5-yl)vinyl)pyridin-2-yl)benzenesulfonamide;

N-(5-(2-(2-(((1r,4r)-4-aminocyclohexyl)amino)pyrimidin-5-yl)vinyl)-6-ethylpyridin-2-yl)-2-chlorobenzenesulfonamide;

N-(5-((E)-2-(2-(((1r,4r)-4-aminocyclohexyl)amino)pyrimidin-5-yl)vinyl)-6-methylpyridin-2-yl)-2-chlorobenzenesulfonamide;

2-chloro-N-(6-ethyl-5-((E)-2-(2-(((1r,4r)-4-(methylamino)cyclohexyl)amino)pyrimidin-5-yl)vinyl)pyridin-2-yl)benzenesulfonamide, 2-chloro-N-(6-methoxy-5-((E)-2-(2-(((1r,4r)-4-(methylamino)cyclohexyl)amino)pyrimidin-5-yl)vinyl)pyridin-2-yl)benzenesulfonamide;

(E)-N-(5-(2-(2-((4-aminobicyclo[2.2.2]octan-1-yl)amino)pyrimidin-5-yl)vinyl)-6-methylpyridin-2-yl)-2-chlorobenzenesulfonamide;

2-chloro-N-(5-((E)-2-(2-(((1r,4r)-4-(dimethylamino)cyclohexyl)amino)pyrimidin-5-yl)vinyl)-3-fluoro-6-methoxypyridin-2-yl)benzenesulfonamide; or 2,3-dichloro-N-(5-((E)-2-(2-(1r,4r)-4-(dimethylamino)cyclohexyl)amino)pyrimidin-5-yl)vinyl)-6-methoxypyridin-2-yl)benzenesulfonamide.

22. A pharmaceutical composition comprising a compound according to any one of claim 1, or a pharmaceutically acceptable salt or solvate thereof.

* * * * *

UNITED STATES PATENT AND TRADEMARK OFFICE
CERTIFICATE OF CORRECTION

| | | |
|---|---|---|
| PATENT NO. | : 11,945,784 B2 | Page 1 of 3 |
| APPLICATION NO. | : 17/296771 | |
| DATED | : April 2, 2024 | |
| INVENTOR(S) | : Vacca et al. | |

It is certified that error appears in the above-identified patent and that said Letters Patent is hereby corrected as shown below:

In the Claims

In Column 201, Line 40, in Claim 1, delete "wherein" and insert --wherein,-- therefor In Column 201, Line 49, in Claim 1, delete "R1" and insert --$R^1$-- therefor In Column 204, Line 2, in Claim 3, delete "Ff." and insert --H.-- therefor In Column 204, Line 41, in Claim 8, after "of", delete "<s> any one of </s>"

In Column 205, Line 54, in Claim 15, after "is", insert --H,--

In Column 208, Line 60, in Claim 20, delete "R4" and insert --$R^4$-- therefor

In Column 208, Line 61, in Claim 20, delete "R6b" and insert --$R^{6b}$-- therefor In Column 209, Lines 14-16, in Claim 21, delete "N-(6-((E)-2-(2-(((1 r,4r)-4-aminocyclohexyl)amino)pyrimidin-5-yl)vinyl)pyridazin-3-yl)-2-chlorobenzenesulfonamide," and insert --N-(6-((E)-2-(2-(((1r,4r)-4-aminocyclohexyl)amino)pyrimidin-5-yl)vinyl)pyridazin-3-yl)-2-chlorobenzenesulfonamide;-- therefor In Column 209, Lines 24-26, in Claim 21, delete "N-(4-((E)-2-(2-(((1r,4r)-4-aminocyclohexyl)amino)pyrimidin-5-vi)vinyl)-3-methylphenyl)-2-chlorobenzenesulfonamide;" and insert --N-(4-((E)-2-(2-(((1r,4r)-4-aminocyclohexyl)amino)pyrimidin-5-vl)vinyl)-3-methylphenyl)-2-chlorobenzenesulfonamide;-- therefor In Column 209, Line 43-45, in Claim 21, delete "-chloro-N-(5-((E)-2-(2-(((1 r,4 r)-4-hydroxycyclohexyl)amino) pyrimidin-5-yl)vinyl)-6-methoxypyridin-2-yl)benzenesulfonamide;" and insert --2-chloro-N-(5-((E)-2-(2-(((1 r,4 r)-4-hydroxycyclohexyl)amino)pyrimidin-5-yl)vinyl)-6-methoxypyridin-2-yl)benzenesulfonamide;-- therefor Signed and Sealed this
Twenty-first Day of October, 2025

John A. Squires
*Director of the United States Patent and Trademark Office*

CERTIFICATE OF CORRECTION (continued)
U.S. Pat. No. 11,945,784 B2

Page 2 of 3

In Column 209, Lines 62-64, in Claim 21, delete "2-chloro-N-(5-((E)-2-(2-4(1r,4r)-4-(dimethylamino)cyclohexyl)amino)pyrimidin-5-yl)vinyl)-6-methoxypyridin-2-yl)benzenesulfonamide;" and insert --2-chloro-N-(5-((E)-2-(2-4(((1r,4r)-4-(dimethylamino)cyclohexyl)amino)pyrimidin-5-yl)vinyl)-6-methoxypyridin-2-yl)benzenesulfonamide;-- therefor In Column 210, Lines 1-3, in Claim 21, delete "2-chloro-N-(5-(2-(2-4(1r,4r)-4-(dimethylamino)cyclohexyl)amino) pyrimidin-5-yl)ethyl)-6-methoxypyridin-2-yl)benzenesulfonamide;" and insert --2-chloro-N-(5-(2-(2-4(1r,4r)-4-(dimethylamino)cyclohexyl)amino)pyrimidin-5-yl)ethyl)-6-methoxypyridin-2-yl)benzenesulfonamide;-- therefor In Column 210, Lines 4-6, in Claim 21, delete "2-chloro-N-(5-(2-(2-4(1r,4r)-4-hydroxycyclohexyl)amino)pyrimidin-5-yl)ethyl-6-methylpyridin-2-yl)benzenesulfonamide;" and insert --2-chloro-N-(5-(2-(2-4(((1r,4r)-4-hydroxycyclohexyl)amino)pyrimidin-5-yl)ethyl-6-methylpyridin-2-yl)benzenesulfonamide;-- therefor In Column 210, Lines 10-12, in Claim 21, delete "2-chloro-N-(5-((E)-2-(2-4(1r,4r)-4-(dimethylamino)cyclohexyl)amino)pyrimidin-5-yl)vinyl)-3-fluoro-6-methylpyridin-2-yl)benzenesulfonamide;" and insert --2-chloro-N-(5-((E)-2-(2-4(((1r,4r)-4-(dimethylamino)cyclohexyl)amino)pyrimidin-5-yl)vinyl)-3-fluoro-6-methylpyridin-2-yl)benzenesulfonamide;-- therefor In Column 210, Lines 17-19, in Claim 21, delete "2-chloro-N-(5-(2-(2-4(1r,4r)-4-(dimethylamino)cyclohexyl)amino)pyrimidin-5-yl)ethyl-3-fluoro-6-methylpyridin-2-yl)benzenesulfonamide;" and insert --2-chloro-N-(5-(2-(2-4(((1r,4r)-4-(dimethylamino)cyclohexyl)amino)pyrimidin-5-yl)ethyl-3-fluoro-6-methylpyridin-2-yl)benzenesulfonamide;-- therefor In Column 210, Lines 26-28, in Claim 21, delete "2-chloro-N-(4-((E)-2-(2-(1r,4r)-4-(dimethylamino)cyclohexyl)amino)pyrimidin-5-yl)vinyl)-3-fluoro-5-methylphenyl)benzenesulfonamide;" and insert --2-chloro-N-(4-((E)-2-(2-(((1r,4r)-4-(dimethylamino)cyclohexyl)amino)pyrimidin-5-yl)vinyl)-3-fluoro-5-methylphenyl)benzenesulfonamide;-- therefor In Column 210, Lines 32-34, in Claim 21, delete "2-chloro-N-(5-((E)-2-(2-(((1r,4r)-4-(dimethylaminocyclohexyl)amino)pyrimidin-5-yl)vinyl)-6-ethylpyridin-2-yl)benzenesulfonamide;" and insert --2-chloro-N-(5-((E)-2-(2-(((1r,4r)-4-(dimethylamino)cyclohexyl)amino)pyrimidin-5-yl)vinyl)-6-ethylpyridin-2-yl)benzenesulfonamide;-- therefor In Column 210, Lines 50-52, in Claim 21, delete "2-chloro-N-(4-((E)-2-(2-(((1r,4r)-4-(dimethylamino)cyclohex)amino)pyrimidin-5-yl)vinyl)-2-fluorophenyl)benzenesulfonamide;" and insert --2-chloro-N-(4-((E)-2-(2-(((1r,4r)-4-(dimethylamino)cyclohexyl)amino)pyrimidin-5-yl)vinyl)-2-fluorophenyl)benzenesulfonamid;-- therefor

CERTIFICATE OF CORRECTION (continued)
U.S. Pat. No. 11,945,784 B2

In Column 210, Lines 56-58, in Claim 21, delete "2-chloro-N-(5-((E)-2-(2-4(1r,4r)-4-(dimethylaminohexyl)amino)pyrimidin-5-yl)vinyl)pyrazin-2-yl)benzenesulfonamide;" and insert --2-chloro-N-(5-((E)-2-(2-4(((1r,4r)-4-(dimethylaminohexyl)amino)pyrimidin-5-yl)vinyl)pyrazin-2-yl)benzenesulfonamide;-- therefor In Column 210, Lines 59-61, in Claim 21, delete "2-chloro-N-(5-((E)-2-(2-(((1r,4)-4-(dimethylamino)cyclohexyl)amino)pyrimidin-5-yl)-vinyl)-6-methylpyridin-2-yl)-3,4-difluorobenzenesulfonamide;" and insert --2-chloro-N-(5-((E)-2-(2-(((1r,4r)-4-(dimethylamino)cyclohexyl)amino)pyrimidin-5-yl)-vinyl)-6-methylpyridin-2-yl)-3,4-difluorobenzenesulfonamide;-- therefor In Column 211, Lines 7-9, in Claim 21, delete "4-chloro-N-(5-(2-(2-(((1r,4r)-4-(dimethylamino)cyclohexyl)amino)pyrimidin-5-yl)vinyl)-4-methoxypyrimidin-2-yl)pyridine-3-sulfonamide," and insert --4-chloro-N-(5-(2-(2-(((1r,4r)-4-(dimethylamino)cyclohexyl)amino)pyrimidin-5-yl)vinyl)-4-methoxypyrimidin-2-yl)pyridine-3-sulfonamide;-- therefor In Column 211, Lines 10-12, in Claim 21, delete "2-chloro-N(6-methyl-5-(2-(2-(((1r,4r)-4-(methyamino)cyclohexyl)amino)pyrimidin-5-yl)vinyl)pyridin-2-yl)benzenesulfonamide;" and insert --2-chloro-N-(6-methyl-5-(2-(2-(((1r,4r)-4-(methyamino)cyclohexyl)amino)pyrimidin-5-yl)vinyl)pyridin-2-yl)benzenesulfonamide;-- therefor In Column 211, Lines 13-15, in Claim 21, delete "N-(5-(2-(2-(((1 r,4r)-4-aminocyclohexyl)amino)pyrimidin-5-yl)vinyl)-6-ethylpyridin-2-yl)-2-chlorobenzenesulfonamide;" and insert --N-(5-(2-(2-(((1r,4r)-4-aminocyclohexyl)amino)pyrimidin-5-yl)vinyl)-6-ethylpyridin-2-yl)-2-chlorobenzenesulfonamide;-- therefor In Column 212, Lines 1-3, in Claim 21, delete "2-chloro-N-(6-ethyl-5-((E)-2-(2-(((1r,4r)-4-(methylamino)cyclohexyl)amino)pyrimidin-5-yl)vinyl)pyridin-2-yl)benzenesulfonamide," and insert --2-chloro-N-(6-ethyl-5-((E)-2-(2-(((1r,4r)-4-(methylamino)cyclohexyl)amino)pyrimidin-5-yl)vinyl)pyridin-2-yl)benzenesulfonamide;-- therefor In Column 212, Lines 13-15, in Claim 21, delete "2,3-dichloro-N-(5-((E)-2-(2-(1r,4r)-4-(dimethylamino)cyclohexyl)amino)pyrimidin-5-yl)vinyl)-6-methoxypyridin-2-yl)benzenesulfonamide." and insert --2,3-dichloro-N-(5-((E)-2-(2-(((1r,4r)-4-(dimethylamino)cyclohexyl)amino)pyrimidin-5-yl)vinyl)-6-methoxypyridin-2-yl)benzenesulfonamide.-- therefor In Column 212, Line 17, in Claim 22, after "according to", delete "any one of"

SEQUENCE LISTING

<160> NUMBER OF SEQ ID NOS: 28

<210> SEQ ID NO 1
<211> LENGTH: 977
<212> TYPE: PRT
<213> ORGANISM: Homo sapiens

<400> SEQUENCE: 1

Met Pro Ala Arg Arg Leu Leu Leu Leu Leu Thr Leu Leu Leu Pro Gly
1               5                   10                  15

Leu Gly Ile Phe Gly Ser Thr Ser Thr Val Thr Leu Pro Glu Thr Leu
            20                  25                  30

Leu Phe Val Ser Thr Leu Asp Gly Ser Leu His Ala Val Ser Lys Arg
        35                  40                  45

Thr Gly Ser Ile Lys Trp Thr Leu Lys Glu Asp Pro Val Leu Gln Val
    50                  55                  60

Pro Thr His Val Glu Glu Pro Ala Phe Leu Pro Asp Pro Asn Asp Gly
65                  70                  75                  80

Ser Leu Tyr Thr Leu Gly Ser Lys Asn Asn Glu Gly Leu Thr Lys Leu
                85                  90                  95

Pro Phe Thr Ile Pro Glu Leu Val Gln Ala Ser Pro Cys Arg Ser Ser
            100                 105                 110

Asp Gly Ile Leu Tyr Met Gly Lys Lys Gln Asp Ile Trp Tyr Val Ile
        115                 120                 125

Asp Leu Leu Thr Gly Glu Lys Gln Gln Thr Leu Ser Ser Ala Phe Ala
    130                 135                 140

Asp Ser Leu Cys Pro Ser Thr Ser Leu Leu Tyr Leu Gly Arg Thr Glu
145                 150                 155                 160

-continued

```
Tyr Thr Ile Thr Met Tyr Asp Thr Lys Thr Arg Glu Leu Arg Trp Asn
                165                 170                 175
Ala Thr Tyr Phe Asp Tyr Ala Ala Ser Leu Pro Glu Asp Val Asp
            180                 185                 190
Tyr Lys Met Ser His Phe Val Ser Asn Gly Asp Gly Leu Val Val Thr
        195                 200                 205
Val Asp Ser Glu Ser Gly Asp Val Leu Trp Ile Gln Asn Tyr Ala Ser
210                 215                 220
Pro Val Val Ala Phe Tyr Val Trp Gln Arg Glu Gly Leu Arg Lys Val
225                 230                 235                 240
Met His Ile Asn Val Ala Val Glu Thr Leu Arg Tyr Leu Thr Phe Met
                245                 250                 255
Ser Gly Glu Val Gly Arg Ile Thr Lys Trp Lys Tyr Pro Phe Pro Lys
            260                 265                 270
Glu Thr Glu Ala Lys Ser Lys Leu Thr Pro Thr Leu Tyr Val Gly Lys
        275                 280                 285
Tyr Ser Thr Ser Leu Tyr Ala Ser Pro Ser Met Val His Glu Gly Val
    290                 295                 300
Ala Val Val Pro Arg Gly Ser Thr Leu Pro Leu Leu Glu Gly Pro Gln
305                 310                 315                 320
Thr Asp Gly Val Thr Ile Gly Asp Lys Gly Glu Cys Val Ile Thr Pro
                325                 330                 335
Ser Thr Asp Val Lys Phe Asp Pro Gly Leu Lys Ser Lys Asn Lys Leu
            340                 345                 350
Asn Tyr Leu Arg Asn Tyr Trp Leu Leu Ile Gly His His Glu Thr Pro
        355                 360                 365
Leu Ser Ala Ser Thr Lys Met Leu Glu Arg Phe Pro Asn Asn Leu Pro
    370                 375                 380
Lys His Arg Glu Asn Val Ile Pro Ala Asp Ser Glu Lys Lys Ser Phe
385                 390                 395                 400
Glu Glu Val Ile Asn Leu Val Asp Gln Thr Ser Glu Asn Ala Pro Thr
                405                 410                 415
Thr Val Ser Arg Asp Val Glu Glu Lys Pro Ala His Ala Pro Ala Arg
            420                 425                 430
Pro Glu Ala Pro Val Asp Ser Met Leu Lys Asp Met Ala Thr Ile Ile
        435                 440                 445
Leu Ser Thr Phe Leu Leu Ile Gly Trp Val Ala Phe Ile Ile Thr Tyr
    450                 455                 460
Pro Leu Ser Met His Gln Gln Gln Leu Gln His Gln Gln Phe Gln
465                 470                 475                 480
Lys Glu Leu Glu Lys Ile Gln Leu Leu Gln Gln Gln Gln Gln Leu
                485                 490                 495
Pro Phe His Pro Pro Gly Asp Thr Ala Gln Asp Gly Glu Leu Leu Asp
            500                 505                 510
Thr Ser Gly Pro Tyr Ser Glu Ser Gly Thr Ser Ser Pro Ser Thr
        515                 520                 525
Ser Pro Arg Ala Ser Asn His Ser Leu Cys Ser Gly Ser Ala Ser
530                 535                 540
Lys Ala Gly Ser Ser Pro Ser Leu Glu Gln Asp Asp Gly Asp Glu Glu
545                 550                 555                 560
Thr Ser Val Val Ile Val Gly Lys Ile Ser Phe Cys Pro Lys Asp Val
                565                 570                 575
Leu Gly His Gly Ala Glu Gly Thr Ile Val Tyr Arg Gly Met Phe Asp
```

```
                  580                 585                 590
Asn Arg Asp Val Ala Val Lys Arg Ile Leu Pro Glu Cys Phe Ser Phe
            595                 600                 605

Ala Asp Arg Glu Val Gln Leu Leu Arg Glu Ser Asp Glu His Pro Asn
            610                 615                 620

Val Ile Arg Tyr Phe Cys Thr Glu Lys Asp Arg Gln Phe Gln Tyr Ile
625                 630                 635                 640

Ala Ile Glu Leu Cys Ala Ala Thr Leu Gln Glu Tyr Val Glu Gln Lys
            645                 650                 655

Asp Phe Ala His Leu Gly Leu Glu Pro Ile Thr Leu Leu Gln Gln Thr
            660                 665                 670

Thr Ser Gly Leu Ala His Leu His Ser Leu Asn Ile Val His Arg Asp
            675                 680                 685

Leu Lys Pro His Asn Ile Leu Ile Ser Met Pro Asn Ala His Gly Lys
            690                 695                 700

Ile Lys Ala Met Ile Ser Asp Phe Gly Leu Cys Lys Lys Leu Ala Val
705                 710                 715                 720

Gly Arg His Ser Phe Ser Arg Arg Ser Gly Val Pro Gly Thr Glu Gly
                725                 730                 735

Trp Ile Ala Pro Glu Met Leu Ser Glu Asp Cys Lys Glu Asn Pro Thr
                740                 745                 750

Tyr Thr Val Asp Ile Phe Ser Ala Gly Cys Val Phe Tyr Tyr Val Ile
            755                 760                 765

Ser Glu Gly Ser His Pro Phe Gly Lys Ser Leu Gln Arg Gln Ala Asn
            770                 775                 780

Ile Leu Leu Gly Ala Cys Ser Leu Asp Cys Leu His Pro Glu Lys His
785                 790                 795                 800

Glu Asp Val Ile Ala Arg Glu Leu Ile Glu Lys Met Ile Ala Met Asp
                805                 810                 815

Pro Gln Lys Arg Pro Ser Ala Lys His Val Leu Lys His Pro Phe Phe
            820                 825                 830

Trp Ser Leu Glu Lys Gln Leu Gln Phe Phe Gln Asp Val Ser Asp Arg
            835                 840                 845

Ile Glu Lys Glu Ser Leu Asp Gly Pro Ile Val Lys Gln Leu Glu Arg
850                 855                 860

Gly Gly Arg Ala Val Val Lys Met Asp Trp Arg Glu Asn Ile Thr Val
865                 870                 875                 880

Pro Leu Gln Thr Asp Leu Arg Lys Phe Arg Thr Tyr Lys Gly Gly Ser
                885                 890                 895

Val Arg Asp Leu Leu Arg Ala Met Arg Asn Lys Lys His His Tyr Arg
            900                 905                 910

Glu Leu Pro Ala Glu Val Arg Glu Thr Leu Gly Ser Leu Pro Asp Asp
            915                 920                 925

Phe Val Cys Tyr Phe Thr Ser Arg Phe Pro His Leu Leu Ala His Thr
            930                 935                 940

Tyr Arg Ala Met Glu Leu Cys Ser His Glu Arg Leu Phe Gln Pro Tyr
945                 950                 955                 960

Tyr Phe His Glu Pro Pro Glu Pro Gln Pro Pro Val Thr Pro Asp Ala
                965                 970                 975

Leu

<210> SEQ ID NO 2
<211> LENGTH: 17
```

```
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 2
cauguccgca gcacaug                                                    17

<210> SEQ ID NO 3
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 3
caugucccca gcacaug                                                    17

<210> SEQ ID NO 4
<211> LENGTH: 434
<212> TYPE: PRT
<213> ORGANISM: Saccharomyces cerevisiae

<400> SEQUENCE: 4
```

Ser Arg Ile Ala Asn Ile Pro Asn Phe Glu Gln Ser Leu Lys Asn Leu
1               5                   10                  15

Val Val Ser Glu Lys Ile Leu Gly Tyr Gly Ser Ser Gly Thr Val Val
            20                  25                  30

Phe Gln Gly Ser Phe Gln Gly Arg Pro Val Ala Val Lys Arg Met Leu
        35                  40                  45

Ile Asp Phe Cys Asp Ile Ala Leu Met Glu Ile Lys Leu Leu Thr Glu
    50                  55                  60

Ser Asp His Pro Asn Val Ile Arg Tyr Tyr Cys Ser Glu Thr Thr
65                  70                  75                  80

Asp Arg Phe Leu Tyr Ile Ala Leu Glu Leu Cys Asn Leu Asn Leu Gln
                85                  90                  95

Asp Leu Val Glu Ser Lys Asn Val Ser Asp Glu Asn Leu Lys Leu Gln
            100                 105                 110

Lys Glu Tyr Asn Pro Ile Ser Leu Leu Arg Gln Ile Ala Ser Gly Val
        115                 120                 125

Ala His Leu His Ser Leu Lys Ile Ile His Arg Asp Leu Lys Pro Gln
    130                 135                 140

Asn Ile Leu Val Ser Thr Ser Ser Arg Phe Thr Ala Asp Gln Gln Thr
145                 150                 155                 160

Gly Ala Glu Asn Leu Arg Ile Leu Ile Ser Asp Phe Gly Leu Cys Lys
                165                 170                 175

Lys Leu Asp Ser Gly Gln Ser Ser Phe Arg Thr Asn Leu Asn Asn Pro
            180                 185                 190

Ser Gly Thr Ser Gly Trp Arg Ala Pro Glu Leu Leu Glu Glu Ser Asn
        195                 200                 205

Asn Leu Gln Thr Lys Arg Arg Leu Thr Arg Ser Ile Asp Ile Phe Ser
    210                 215                 220

Met Gly Cys Val Phe Tyr Tyr Ile Leu Ser Lys Gly Lys His Pro Phe
225                 230                 235                 240

Gly Asp Lys Tyr Ser Arg Glu Ser Asn Ile Ile Arg Gly Ile Phe Ser
                245                 250                 255

```
Leu Asp Glu Met Lys Cys Leu His Asp Arg Ser Leu Ile Ala Glu Ala
            260                 265                 270

Thr Asp Leu Ile Ser Gln Met Ile Asp His Asp Pro Leu Lys Arg Pro
        275                 280                 285

Thr Ala Met Lys Val Leu Arg His Pro Leu Phe Trp Pro Lys Ser Lys
    290                 295                 300

Lys Leu Glu Phe Leu Leu Lys Val Ser Asp Arg Leu Glu Ile Glu Asn
305                 310                 315                 320

Arg Asp Pro Pro Ser Ala Leu Leu Met Lys Phe Asp Ala Gly Ser Asp
                325                 330                 335

Phe Val Ile Pro Ser Gly Asp Trp Thr Val Lys Phe Asp Lys Ile Phe
            340                 345                 350

Met Asp Asn Leu Glu Arg Tyr Arg Lys Tyr His Ser Ser Lys Leu Met
        355                 360                 365

Asp Leu Leu Arg Ala Leu Arg Asn Lys Tyr His His Phe Met Asp Leu
    370                 375                 380

Pro Glu Asp Ile Ala Glu Leu Met Gly Pro Val Pro Asp Gly Phe Tyr
385                 390                 395                 400

Asp Tyr Phe Ile Lys Arg Phe Pro Asn Leu Leu Ile Gly Val Tyr Met
                405                 410                 415

Ile Val Lys Glu Asn Leu Ser Asp Asp Gln Ile Leu Arg Glu Phe Leu
            420                 425                 430

Tyr Ser

<210> SEQ ID NO 5
<211> LENGTH: 424
<212> TYPE: PRT
<213> ORGANISM: Homo sapiens

<400> SEQUENCE: 5

Asp Asp Gly Asp Glu Glu Thr Ser Val Val Ile Val Gly Lys Ile Ser
1               5                   10                  15

Phe Cys Pro Lys Asp Val Leu Gly His Gly Ala Glu Gly Thr Ile Val
            20                  25                  30

Tyr Arg Gly Met Phe Asp Asn Arg Asp Val Ala Val Lys Arg Ile Leu
        35                  40                  45

Pro Glu Cys Phe Ser Phe Ala Asp Arg Glu Val Gln Leu Leu Arg Glu
    50                  55                  60

Ser Asp Glu His Pro Asn Val Ile Arg Tyr Phe Cys Thr Glu Lys Asp
65                  70                  75                  80

Arg Gln Phe Gln Tyr Ile Ala Ile Glu Leu Cys Ala Ala Thr Leu Gln
                85                  90                  95

Glu Tyr Val Glu Gln Lys Asp Cys Phe Ala His Leu Gly Leu Glu Pro
            100                 105                 110

Ile Thr Leu Leu Gln Gln Thr Thr Ser Gly Leu Ala His Leu His Ser
        115                 120                 125

Leu Asn Ile Val His Arg Asp Leu Lys Pro His Asn Ile Leu Ile Ser
    130                 135                 140

Met Pro Asn Ala His Gly Lys Ile Lys Ala Met Ile Ser Asp Phe Gly
145                 150                 155                 160

Leu Cys Lys Lys Leu Ala Val Gly Arg His Ser Phe Ser Arg Arg Ser
                165                 170                 175

Gly Val Pro Gly Thr Glu Gly Trp Ile Ala Pro Glu Met Leu Ser Glu
            180                 185                 190
```

```
Asp Cys Lys Glu Asn Pro Thr Tyr Thr Val Asp Ile Phe Ser Ala Gly
            195                 200                 205

Cys Val Phe Tyr Tyr Val Val Ser Glu Gly Ser His Pro Phe Gly Lys
    210                 215                 220

Ser Leu Gln Arg Gln Ala Asn Ile Leu Leu Gly Ala Cys Ser Leu Asp
225                 230                 235                 240

Cys Leu His Pro Glu Lys His Glu Asp Val Ile Ala Arg Glu Leu Ile
                245                 250                 255

Glu Lys Met Ile Ala Met Asp Pro Gln Lys Arg Pro Ser Ala Asn Asp
                260                 265                 270

Val Leu Lys His Pro Phe Phe Trp Ser Leu Glu Lys Gln Leu Gln Phe
                275                 280                 285

Phe Gln Asp Val Ser Asp Arg Ile Glu Lys Glu Ser Leu Asp Gly Pro
    290                 295                 300

Ile Val Lys Gln Leu Glu Arg Gly Gly Arg Ala Val Val Lys Met Asp
305                 310                 315                 320

Trp Arg Glu Asn Ile Thr Asp Pro Leu Gln Thr Asp Leu Arg Lys Phe
                325                 330                 335

Arg Thr Tyr Lys Gly Gly Ser Val Arg Asp Leu Leu Arg Ala Met Arg
                340                 345                 350

Asn Lys Lys His His Tyr Arg Asp Leu Pro Glu Glu Val Arg Glu Thr
                355                 360                 365

Leu Gly Thr Leu Pro Asp Asp Phe Val Cys Tyr Phe Thr Ser Arg Phe
    370                 375                 380

Pro His Leu Leu Ala His Thr Tyr Arg Ala Met Glu Leu Cys Ser His
385                 390                 395                 400

Glu Arg Leu Phe Gln Pro Tyr Tyr Phe His Glu Pro Glu Pro Gln
                405                 410                 415

Pro Pro Val Thr Pro Asp Ala Leu
                420

<210> SEQ ID NO 6
<211> LENGTH: 423
<212> TYPE: PRT
<213> ORGANISM: Mus musculus

<400> SEQUENCE: 6

Asp Asp Glu Asp Glu Thr Arg Met Val Ile Val Gly Lys Ile Ser
1               5                   10                  15

Phe Cys Pro Lys Asp Val Leu Gly His Gly Ala Glu Gly Thr Ile Val
                20                  25                  30

Tyr Lys Gly Met Phe Asp Asn Arg Asp Val Ala Val Lys Arg Ile Leu
            35                  40                  45

Pro Glu Cys Phe Ser Phe Ala Asp Arg Glu Val Gln Leu Leu Arg Glu
    50                  55                  60

Ser Asp Glu His Pro Asn Val Ile Arg Tyr Phe Cys Thr Glu Lys Asp
65                  70                  75                  80

Arg Gln Phe Gln Tyr Ile Ala Ile Glu Leu Cys Ala Ala Thr Leu Gln
                85                  90                  95

Glu Tyr Val Glu Gln Lys Asp Phe Ala His Leu Gly Leu Glu Pro Ile
                100                 105                 110

Thr Leu Leu His Gln Thr Thr Ser Gly Leu Ala His Leu His Ser Leu
            115                 120                 125

Asn Ile Val His Arg Asp Leu Lys Pro His Asn Ile Leu Leu Ser Met
            130                 135                 140
```

Pro Asn Ala His Gly Arg Ile Lys Ala Met Ile Ser Asp Phe Gly Leu
145                 150                 155                 160

Cys Lys Lys Leu Ala Val Gly Arg His Ser Phe Ser Arg Arg Ser Gly
            165                 170                 175

Val Pro Gly Thr Glu Gly Trp Ile Ala Pro Glu Met Leu Ser Glu Asp
        180                 185                 190

Cys Lys Asp Asn Pro Thr Tyr Thr Val Asp Ile Phe Ser Ala Gly Cys
        195                 200                 205

Val Phe Tyr Tyr Val Ile Ser Glu Gly Asn His Pro Phe Gly Lys Ser
    210                 215                 220

Leu Gln Arg Gln Ala Asn Ile Leu Leu Gly Ala Cys Asn Leu Asp Cys
225                 230                 235                 240

Phe His Ser Asp Lys His Glu Asp Val Ile Ala Arg Glu Leu Ile Glu
                245                 250                 255

Lys Met Ile Ala Met Asp Pro Gln Gln Arg Pro Ser Ala Lys His Val
                260                 265                 270

Leu Lys His Pro Phe Phe Trp Ser Leu Glu Lys Gln Leu Gln Phe Phe
            275                 280                 285

Gln Asp Val Ser Asp Arg Ile Glu Lys Glu Ala Leu Asp Gly Pro Ile
290                 295                 300

Val Arg Gln Leu Glu Arg Gly Gly Arg Ala Val Val Lys Met Asp Trp
305                 310                 315                 320

Arg Glu Asn Ile Thr Val Pro Leu Gln Thr Asp Leu Arg Lys Phe Arg
                325                 330                 335

Thr Tyr Lys Gly Gly Ser Val Arg Asp Leu Leu Arg Ala Met Arg Asn
            340                 345                 350

Lys Lys His His Tyr Arg Glu Leu Pro Ala Glu Val Gln Glu Thr Leu
            355                 360                 365

Gly Ser Ile Pro Asp Asp Phe Val Arg Tyr Phe Thr Ser Arg Phe Pro
370                 375                 380

His Leu Leu Ser His Thr Tyr Gln Ala Met Glu Leu Cys Arg His Glu
385                 390                 395                 400

Arg Leu Phe Gln Thr Tyr Tyr Trp His Glu Pro Thr Glu Pro Gln Pro
                405                 410                 415

Pro Val Ile Pro Tyr Ala Leu
                420

<210> SEQ ID NO 7
<211> LENGTH: 423
<212> TYPE: PRT
<213> ORGANISM: Rattus norvegicus

<400> SEQUENCE: 7

Asp Asp Glu Asp Glu Glu Thr Arg Met Val Ile Val Gly Lys Ile Ser
1               5                   10                  15

Phe Cys Pro Lys Asp Val Leu Gly His Gly Ala Glu Gly Thr Ile Val
            20                  25                  30

Tyr Lys Gly Met Phe Asp Asn Arg Asp Val Ala Val Lys Arg Ile Leu
        35                  40                  45

Pro Glu Cys Phe Ser Phe Ala Asp Arg Glu Val Gln Leu Leu Arg Glu
    50                  55                  60

Ser Asp Glu His Pro Asn Val Ile Arg Tyr Phe Cys Thr Glu Lys Asp
65                  70                  75                  80

Arg Gln Phe Gln Tyr Ile Ala Ile Glu Leu Cys Ala Ala Thr Leu Gln 85                  90                  95
Glu Tyr Val Glu Gln Lys Asp Phe Ala His Leu Gly Leu Glu Pro Ile
            100                 105                 110

Thr Leu Leu His Gln Thr Thr Ser Gly Leu Ala His Leu His Ser Leu
        115                 120                 125

Asn Ile Val His Arg Asp Leu Lys Pro His Asn Ile Leu Leu Ser Met
130                 135                 140

Pro Asn Ala His Gly Arg Ile Lys Ala Met Ile Ser Asp Phe Gly Leu
145                 150                 155                 160

Cys Lys Lys Leu Ala Val Gly Arg His Ser Phe Ser Arg Arg Ser Gly
            165                 170                 175

Val Pro Gly Thr Glu Gly Trp Ile Ala Pro Glu Met Leu Ser Glu Asp
        180                 185                 190

Cys Lys Glu Asn Pro Thr Tyr Thr Val Asp Ile Phe Ser Ala Gly Cys
    195                 200                 205

Val Phe Tyr Tyr Val Ile Ser Glu Gly Asn His Pro Phe Gly Lys Ser
210                 215                 220

Leu Gln Arg Gln Ala Asn Ile Leu Leu Gly Ala Cys Ser Leu Asp Cys
225                 230                 235                 240

Phe His Ser Asp Lys His Glu Asp Val Ile Ala Arg Glu Leu Ile Glu
            245                 250                 255

Lys Met Ile Ala Met Asp Pro Gln Gln Arg Pro Ser Ala Lys His Val
        260                 265                 270

Leu Lys His Pro Phe Phe Trp Ser Leu Glu Lys Gln Leu Gln Phe Phe
    275                 280                 285

Gln Asp Val Ser Asp Arg Ile Glu Lys Glu Ser Leu Asp Gly Pro Ile
290                 295                 300

Val Arg Gln Leu Glu Arg Gly Arg Ala Val Val Lys Met Asp Trp
305                 310                 315                 320

Arg Glu Asn Ile Thr Val Pro Leu Gln Thr Asp Leu Arg Lys Phe Arg
            325                 330                 335

Thr Tyr Lys Gly Gly Ser Val Arg Asp Leu Leu Arg Ala Met Arg Asn
        340                 345                 350

Lys Arg His His Tyr Arg Glu Leu Pro Leu Glu Val Gln Glu Thr Leu
    355                 360                 365

Gly Ser Ile Pro Asp Asp Phe Val Arg Tyr Phe Thr Ser Arg Phe Pro
370                 375                 380

His Leu Leu Ser His Thr Tyr Arg Ala Met Glu Leu Cys Arg His Glu
385                 390                 395                 400

Arg Leu Phe Gln Thr Tyr Tyr Trp His Glu Pro Thr Glu Ala Gln Pro
            405                 410                 415

Pro Gly Ile Pro Asp Ala Leu
            420

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
acacgtttgg gaatggacac                                              20

-continued

```
<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
ccatgggaag atgttctggg                                                  20

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
ctcaggagga gcaatgatct tgat                                             24

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
taccaccatg tacccaggca                                                  20

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
gacagagagt caaactaacg tgg                                              23

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
gtccagcagg caagaaggt                                                   19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
aagaacacgc ttgggaatgg                                                  20

<210> SEQ ID NO 15
```

```
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
ctgcacctgc tgcggac                                                    17

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
cctgagcccg gaggagaa                                                   18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
ctcgagcagt ctgcgctg                                                   18

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
taaaagccct gatgctgaag c                                               21

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
tccgactatt ggcatccga                                                  19

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
ctatttccag ggcttccgag t                                               21

<210> SEQ ID NO 21
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
aggtgttgta ctggcctcgg t                                              21

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
aagccctctg gaacttgcg                                                 19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
aacccaatgg cctgtctgg                                                 19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
tcatcggacg cacttggaa                                                 19

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
caaccacctt gaatggcaag a                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
gtccctagct tggctgacag a                                              21

<210> SEQ ID NO 27
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 27
tggagagcga gggctttg                                                  18

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
agcttgattg tcaacctcct g                                              21
```